US010106833B2

(12) United States Patent
Kahne et al.

(10) Patent No.: US 10,106,833 B2
(45) Date of Patent: Oct. 23, 2018

(54) METHODS AND COMPOUNDS FOR IDENTIFYING GLYCOSYLTRANSFERASE INHIBITORS

(71) Applicant: President and Fellows of Harvard College, Cambridge, MA (US)

(72) Inventors: Daniel Evan Kahne, Brookline, MA (US); Suzanne Walker Kahne, Brookline, MA (US); Christian M. Gampe, Brighton, MA (US); Hirokazu Tsukamoto, Sendai (JP)

(73) Assignee: President and Fellows of Harvard College, Cambridge, MA (US)

( * ) Notice: Subject to any disclaimer, the term of this patent is extended or adjusted under 35 U.S.C. 154(b) by 293 days.

(21) Appl. No.: 14/390,857

(22) PCT Filed: Mar. 13, 2013

(86) PCT No.: PCT/US2013/030800
§ 371 (c)(1),
(2) Date: Oct. 6, 2014

(87) PCT Pub. No.: WO2013/151697
PCT Pub. Date: Oct. 10, 2013

(65) Prior Publication Data
US 2015/0079618 A1 Mar. 19, 2015

Related U.S. Application Data

(60) Provisional application No. 61/621,229, filed on Apr. 6, 2012.

(51) Int. Cl.
*C07H 11/04* (2006.01)
*C12Q 1/48* (2006.01)
*C07H 13/12* (2006.01)
*C07H 15/26* (2006.01)

(52) U.S. Cl.
CPC .............. *C12Q 1/48* (2013.01); *C07H 11/04* (2013.01); *C07H 13/12* (2013.01); *C07H 15/26* (2013.01); *G01N 2333/91091* (2013.01); *G01N 2500/04* (2013.01); *G01N 2500/20* (2013.01)

(58) Field of Classification Search
CPC ........ C07H 11/04; C07H 15/10; C07H 13/00; C07H 13/04; C12P 19/18; C12P 19/44; Y02P 20/52
USPC ................. 536/16.8, 4.1, 55.1; 435/194, 74; 514/25, 54, 61
IPC ............... A61K 31/7028,31/715; C07H 13/00, 15/10, 5/06, 14/00; C12P 19/44
See application file for complete search history.

(56) References Cited

U.S. PATENT DOCUMENTS

| | | |
|---|---|---|
| 3,949,070 A | 4/1976 | Arai et al. |
| 3,992,263 A | 11/1976 | Dietrich et al. |
| 4,270,537 A | 6/1981 | Romaine |
| 4,522,811 A | 6/1985 | Eppstein et al. |
| 4,596,556 A | 6/1986 | Morrow et al. |
| 4,684,626 A | 8/1987 | Welzel et al. |
| 4,790,824 A | 12/1988 | Morrow et al. |
| 4,842,857 A | 6/1989 | Meyers et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,206,405 A | 4/1993 | Aretz et al. |
| 5,260,051 A | 11/1993 | Cho |
| 5,260,206 A | 11/1993 | Aretz et al. |
| 5,312,335 A | 5/1994 | McKinnon et al. |
| 5,315,038 A | 5/1994 | Aretz et al. |
| 5,316,929 A | 5/1994 | Aretz et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,454,971 A | 10/1995 | Sakai et al. |
| 5,466,220 A | 11/1995 | Brenneman |
| 5,480,381 A | 1/1996 | Weston |
| 5,503,627 A | 4/1996 | McKinnon et al. |
| 5,506,140 A | 4/1996 | Aretz et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |

(Continued)

FOREIGN PATENT DOCUMENTS

| | | |
|---|---|---|
| EP | 0 652 205 A2 | 5/1995 |
| EP | 1 069 130 A1 | 1/2001 |

(Continued)

OTHER PUBLICATIONS

Ostash et al., "Moenomycin family antibiotics: chemical synthesis, biosynthesis, and biological activity" Natural Product Reports (2010) vol. 27 pp. 1594-1617.*

(Continued)

*Primary Examiner* — Eric Olson

(74) *Attorney, Agent, or Firm* — Wolf, Greenfield & Sacks, P.C.

(57) ABSTRACT

The present invention provides moenomycin-based probe compounds of Formula (I) for use in screening inhibitors of bacterial glycosyltransferases. The present invention also provides bacterial glycosyltransferase screening assays using compounds of Formula (I).

17 Claims, 15 Drawing Sheets

(56) References Cited

U.S. PATENT DOCUMENTS

| | | | |
|---|---|---|---|
| 5,649,912 | A | 7/1997 | Peterson |
| 5,704,911 | A | 1/1998 | Parsons |
| 5,736,533 | A | 4/1998 | Simon et al. |
| 5,888,721 | A | 3/1999 | Rothstein et al. |
| 5,893,397 | A | 4/1999 | Peterson et al. |
| 5,986,089 | A | 11/1999 | Vertesy |
| 5,993,412 | A | 11/1999 | Deily et al. |
| 6,077,830 | A | 6/2000 | Vertesy et al. |
| 6,114,309 | A | 9/2000 | Allanson et al. |
| 6,153,381 | A | 11/2000 | Rothstein |
| 6,207,820 | B1 | 3/2001 | Allanson et al. |
| 6,242,424 | B1 | 6/2001 | Riess et al. |
| 6,274,716 | B1 | 8/2001 | Allanson et al. |
| 6,461,829 | B1 | 10/2002 | Kahne |
| 6,534,278 | B1 | 3/2003 | Rothstein |
| 6,911,318 | B2 | 6/2005 | Kahne |
| 6,913,895 | B1 | 7/2005 | Goldman et al. |
| 7,129,229 | B2 | 10/2006 | Raddatz et al. |
| 7,186,813 | B1 | 3/2007 | Schweitzer et al. |
| 8,604,004 | B2 | 12/2013 | Kahne et al. |
| 9,115,358 | B2 | 8/2015 | Walker et al. |
| 14,833,905 | * | 8/2015 | Kahne et al. .......... C07H 11/04 356/437 |
| 9,273,084 | B2 * | 3/2016 | Kahne ................. C07F 9/65586 |
| 2003/0108969 | A1 | 6/2003 | DeSousa et al. |
| 2003/0129683 | A1 | 7/2003 | Kahne |
| 2003/0158093 | A1 | 8/2003 | Sun et al. |
| 2004/0018582 | A1 | 1/2004 | Eggert et al. |
| 2004/0042981 | A1 | 3/2004 | Vertesy et al. |
| 2004/0127403 | A1 | 7/2004 | Parenti et al. |
| 2004/0147441 | A1 | 7/2004 | Leach et al. |
| 2005/0026214 | A1 * | 2/2005 | Biton ...................... C12Q 1/48 435/7.1 |
| 2005/0106555 | A1 | 5/2005 | Desousa |
| 2005/0186653 | A1 | 8/2005 | Heimann et al. |
| 2005/0287181 | A1 | 12/2005 | Murthy |
| 2005/0287198 | A1 | 12/2005 | Murthy |
| 2005/0287200 | A1 | 12/2005 | Murthy |
| 2005/0287219 | A1 | 12/2005 | Murthy |
| 2005/0287220 | A1 | 12/2005 | Murthy |
| 2006/0040891 | A1 | 2/2006 | Jiang et al. |
| 2006/0093632 | A1 | 5/2006 | Murthy |
| 2006/0094669 | A1 | 5/2006 | Murthy |
| 2006/0142217 | A1 | 6/2006 | Meutermans et al. |
| 2007/0060506 | A1 | 3/2007 | Walsh et al. |
| 2010/0279980 | A1 | 11/2010 | Walker et al. |
| 2011/0136759 | A1 * | 6/2011 | Kahne ..................... C07H 11/04 514/61 |
| 2015/0119354 | A1 | 4/2015 | Kahne et al. |
| 2015/0119561 | A1 | 4/2015 | Kahne et al. |
| 2015/0166594 | A1 | 6/2015 | Kahne et al. |
| 2016/0280732 | A1 | 9/2016 | Kahne et al. |
| 2017/0081690 | A1 | 3/2017 | Kahne et al. |

FOREIGN PATENT DOCUMENTS

| | | |
|---|---|---|
| WO | WO 97/13537 A1 | 4/1997 |
| WO | WO 97/37705 A1 | 10/1997 |
| WO | WO99/26956 * | 6/1999 ............... C07H 1/00 |
| WO | WO 99/26956 A1 | 6/1999 |
| WO | WO 99/34850 A1 | 7/1999 |
| WO | WO 00/52035 A1 | 9/2000 |
| WO | WO 00/64915 A1 | 11/2000 |
| WO | WO 03/020962 A2 | 3/2003 |
| WO | WO 2007/023348 A2 | 3/2007 |
| WO | WO 2008/021367 A2 | 2/2008 |
| WO | WO 2009/046314 A2 | 4/2009 |
| WO | WO 2013/151697 A1 | 10/2013 |
| WO | WO 2013/152277 A2 | 10/2013 |
| WO | WO 2013/152279 A1 | 10/2013 |

OTHER PUBLICATIONS

Daghish et al., "Tetrafunctional Photoaffinity Labels Based on Nakanishi's m-Nitroalkoxy-Substituted Phenyltrifluoromethylhydrazine" Angew Chem Int Ed (2002) vol. 41 No. 13 pp. 2293-2297.*
Ferse et al., "Acceptor Site Recognition of Transglycosylase Inhibitors A [beta-D-glucopyranosyl-(1,2)-alpha-D-glucopyranuronamide-derived Moenomycin Analogue" Tetrahedron (1999) vol. 55 pp. 3749-3766.*
Trofimenko et al., "Two Tests for Detecgin Nitriles nad Maides" Analytical Chemistry (1958) vol. 30 No. 8 pp. 1432-1434.*
Halliday et al., "Targeting the forgotten transglycosylases" Biochemical Pharmacology vol. 71 pp. 957-967 (Year: 2006).*
Hansske et al., Deficiency of UDP-galactose:N-acetylglucosamine beta-1,4-galactosyltransferase I causes the congenital disorder of glycosylation type IId. J Clin Invest. Mar. 2002;109(6):725-33.
Schneider et al., Isolation and analysis of moenomycin and its biosynthetic intermediates from Streptomyces ghanaensis (ATCC 14672) wildtype and selected mutants. Z Naturforsch C. Mar.-Apr. 1997;52(3-4):217-26. Abstract Only.
Vogel et al., Moenomycin analogues with long-chain amine lipid parts from reductive aminations. Tetrahedron. 2001;57:4147-60.
Extended European Search Report, dated Jul. 2, 2013, in connection with Application No. EP 08834841.2.
International Search Report and Written Opinion, dated Mar. 10, 2009, in connection with Application No. PCT/US2008/078771.
International Preliminary Report on Patentability dated Apr. 15, 2010, in connection with Application No. PCT/US2008/078771.
Invitation to Pay Additional Fees dated Jun. 10, 2013, in connection with Application No. PCT/US2013/035416.
International Search Report and Written Opinion, dated Oct. 15, 2013, in connection with Application No. PCT/US2013/035416.
International Preliminary Report on Patentability, dated Oct. 16, 2014, in connection with Application No. PCT/US2013/035416.
International Search Report and Written Opinion, dated Jun. 18, 2013, in connection with Application No. PCT/US2013/030800.
International Preliminary Report on Patentability, dated Oct. 16, 2014, in connection with Application No. PCT/US2013/030800.
International Search Report and Written Opinion, dated Sep. 30, 2008, in connection with Application No. PCT/US2007/017999.
International Preliminary Report on Patentability, dated Feb. 26, 2009, in connection with Application No. PCT/US2007/017999.
International Search Report and Written Opinion, dated Jun. 28, 2013, in connection with Application No. PCT/US2013/035427.
International Preliminary Report on Patentability, dated Oct. 16, 2014, in connection with Application No. PCT/US2013/035427.
Genbank Submission; NIH/NCBI, Accession No. AAF24002; Belanger et al.; Jan. 12, 2000.
Genbank Submission; NIH/NCBI, Accession No. AAG34163; Yoo et al.; Mar. 6, 2001.
Genbank Submission; NIH/NCBI, Accession No. AAO06921; Rascher et al.; Feb. 21, 2003.
Genbank Submission; NIH/NCBI, Accession No. AAU93096; Ward et al.; Nov. 21, 2011.
Genbank Submission; NIH/NCBI, Accession No. AAX98210; McAlpine et al.; Apr. 25, 2005.
Genbank Submission; NIH/NCBI, Accession No. AY240962; Petricek et al.; Jul. 5, 2006.
Genbank Submission; NIH/NCBI, Accession No. BAC68501; Omura et al.; Dec. 21, 2007.
Genbank Submission; NIH/NCBI, Accession No. BAC68502; Omura et al.; Dec. 21, 2007.
Genbank Submission; NIH/NCBI, Accession No. BAC70368; Omura et al.; Dec. 21, 2007.
Genbank Submission; NIH/NCBI, Accession No. CAA22758; Bentley et al.; Oct. 23, 2008.
Genbank Submission; NIH/NCBI, Accession No. CAC01594; Bentley et al.; Oct. 23, 2008.
Genbank Submission; NIH/NCBI, Accession No. CAC37544; Bentley et al.; Oct. 23, 2008.
Genbank Submission; NIH/NCBI, Accession No. CAC37545; Bentley et al.; Oct. 23, 2008.
Genbank Submission; NIH/NCBI, Accession No. CAI08539; Rabus et al.; Sep. 11, 2009.

(56) References Cited

OTHER PUBLICATIONS

Genbank Submission; NIH/NCBI, Accession No. EAM38951; Jun. 15, 2005.
Genbank Submission; NIH/NCBI, Accession No. EAO07657; Jul. 26, 2005.
Genbank Submission; NIH/NCBI, Accession No. EAS11435; Apr. 9, 2007.
Genbank Submission; NIH/NCBI, Accession No. EAS23724; Mar. 22, 2006.
Genbank Submission; NIH/NCBI, Accession No. EAS99725; Apr. 18, 2006.
Genbank Submission; NIH/NCBI, Accession No. JC7965; Nemoto et al.; Mar. 15, 2004.
Genbank 2012. Submission; NIH/NCBI, Accession No. NP_142754; Kawarabayasi et al.; Jan. 19, 2012.
Genbank Submission; NIH/NCBI, Accession No. NP_220145; Griffiths et al.; Sep. 15, 2011.
Genbank Submission; NIH/NCBI, Accession No. NP_630535; Hsiao et al.; Jan. 19, 2012.
Genbank Submission; NIH/NCBI, Accession No. YP_074610; Ueda et al.; Jan. 23, 2012.
Genbank Submission; NIH/NCBI, Accession No. YP_075255; Ueda et al.; Jan. 23, 2012.
Genbank Submission; NIH/NCBI, Accession No. YP_075256; Ueda et al.; Jan. 23, 2012.
Genbank Submission; NIH/NCBI, Accession No. ZP_00616987; Heuts et al.; Jun. 28, 2007.
Adachi et al., Degradation and reconstruction of moenomycin A and derivatives: dissecting the function of the isoprenoid chain. J Am Chem Soc. Nov. 1, 2006;128(43):14012-3.
Arai et al., Pholipomycin, a new member of phosphoglycolipid antibiotics. I. Taxonomy of producing organism and fermentation and isolation of pholipomycin. J Antibiot (Tokyo). Dec. 1977;30(12):1049-54.
Baizman et al., Antibacterial activity of synthetic analogues based on the disaccharide structure of moenomycin, an inhibitor of bacterial transglycosylase. Microbiology. Dec. 2000;146 Pt 12:3129-40.
Banker et al., Modern Pharmacetuics. 3rd ed. Marcel Dekker, New York, 1996, p. 596.
Bardone et al., Teichomycins, new antibiotics from *Actinoplanes teichomyceticus* nov. sp. II. Extraction and chemical characterization. J Antibiot (Tokyo). Mar. 1978;31(3):170-7.
Barrett et al., Kinetic characterization of the glycosyltransferase module of *Staphylococcus aureus* PBP2. J Bacteriol. Mar. 2005;187(6):2215-7.
Belanger et al., Functional analysis of genes responsible for the synthesis of the B-band O antigen of Pseudomonas aeruginosa serotype O6 lipopolysaccharide. Microbiology. Dec. 1999;145 (Pt 12):3505-21.
Bentley et al., Complete genome sequence of the model actinomycete Streptomyces coelicolor A3(2). Nature. May 9, 2002;417(6885):141-7.
Berge et al., Pharmaceutical salts. J Pharm Sci. Jan. 1977;66(1):1-19.
Bibb, Regulation of secondary metabolism in streptomycetes. Curr Opin Microbiol. Apr. 2005;8(2):208-15.
Bierman et al., Plasmid cloning vectors for the conjugal transfer of DNA from *Escherichia coli* to *Streptomyces* spp. Gene. Jul. 1, 1992;116(1):43-9.
Blackman et al., Tetrazine ligation: fast bioconjugation based on inverse-electron-demand Diels-Alder reactivity. J Am Chem Soc. Oct. 15, 2008;130(41):13518-9. Epub Sep. 18, 2008.
Blondelet-Rouault et al., Antibiotic resistance gene cassettes derived from the omega interposon for use in *E. coli* and Streptomyces. Gene. May 6, 1997;190(2):315-7.
Castro-Palomino et al., N-Tetrachlorophthaloyl-Protected Trichloroacetimidate of Glucosamine as Glycosyl Donor in Oligosaccharide Synthesis. Tetrahedron Lett. 1995;36:5343-46.
Chaffin et al., CpsK of *Streptococcus agalactiae* exhibits alpha2,3-sialyltransferase activity in Haemophilus ducreyi. Mol Microbiol. Jul. 2002;45(1):109-22.
Chang, Multidrug resistance ABC transporters. FEBS Lett. Nov. 27, 2003;555(1):102-5.
Chater, Streptomyces inside-out: a new perspective on the bacteria that provide us with antibiotics. Philos Trans R Soc Lond B Biol Sci. May 29, 2006;361(1469):761-8.
Chen et al., Vancomycin analogues active against vanA-resistant strains inhibit bacterial transglycosylase without binding substrate. Proc Natl Acad Sci U S A. May 13, 2003;100(10):5658-63. Epub Apr. 24, 2003.
Cheng et al., Domain requirement of moenomycin binding to bifunctional transglycosylases and development of high-throughput discovery of antibiotics. Proc Natl Acad Sci U S A. Jan. 15, 2008;105(2):431-6. Epub Jan. 8, 2008.
Coates et al., Stereoselective Synthesis of Moenocinol and Assignment of Its Carbon-13 Nuclear Magnetic Resonance Spectrum. J Org Chem. 1980;45:2685-97.
Crich et al., Are Glycosyl Triflates Intermediates in the Sulfoxide Glycosylation Method? A Chemical and 1H, 13C, and 19F NMR Spectroscopic Investigation. J Am Chem Soc. 1997;119:11217-23.
Crich et al., Chapter 2. Gylcosylation with Sulfoxides and Sulfinates as Donors or Promoters. Org React. 2004;64:115-251.
Crich et al., Why are the hydroxy groups of partially protected N-acetylglucosamine derivatives such poor glycosyl acceptors, and what can be done about it? A comparative study of the reactivity of N-acetyl-, N-phthalimido-, and 2-azido-2-deoxy-glucosamine derivatives in glycosylation. 2-Picolinyl ethers as reactivity-enhancing replacements for benzyl ethers. J Am Chem Soc. Jul. 18, 2001;123(28):6819-25.
Daghish et al., Tetrafunctional photoaffinity labels based on Nakanishi's m-nitroalkoxy-substituted phenyltrifluoromethyldiazirine. Angew Chem Int Ed Engl. Jul. 2, 2002;41(13):2293-7.
Dairi, Studies on biosynthetic genes and enzymes of isoprenoids produced by actinomycetes. J Antibiot (Tokyo). Apr. 2005;58(4):227-43.
Datsenko et al., One-step inactivation of chromosomal genes in *Escherichia coli* K-12 using PCR products. Proc Natl Acad Sci U S A. Jun. 6, 2000;97(12):6640-5.
Debenham et al., Two New Orthogonal Amine-Protecting Groups That Can Be Cleaved under Mild or Neutral Conditions. J Am Chem Soc. 1995;117:3302-03.
Decker et al., A general approach for cloning and characterizing dNDP-glucose dehydratase genes from actinomycetes. FEMS Microbiol Lett. Aug. 1, 1996;141(2-3):195-201.
Dirksen et al., Rapid oxime and hydrazone ligations with aromatic aldehydes for biomolecular labeling. Bioconjug Chem. Dec. 2008;19(12):2543-8.
Du et al., Identification and functional analysis of dTDP-glucose-4,6-dehydratase gene and its linked gene cluster in an aminoglycoside antibiotics producer of Streptomyces tenebrarius H6. Curr Microbiol. Aug. 2004;49(2):99-107.
Durr et al., Biosynthesis of the terpene phenalinolactone in Streptomyces sp. Tü6071: analysis of the gene cluster and generation of derivatives. Chem Biol. Apr. 2006;13(4):365-77.
Ebenezer, Colabomycin Co-Metabolites. Synthesis of 2880-II, A Metabolite Related to Ferulic Acid. J Synth Commun. 1991;21:351-58.
Eichhorn et al., Characterization of moenomycin antibiotics from medicated chicken feed by ion-trap mass spectrometry with electrospray ionization. Rapid Commun Mass Spectrom. 2005;19(15):2179-86.
El-Abadla et al., Moenomycin A: The Role of the Methyl Group in the Moenuronamide Unit and a General Discussion of Structure-Activity Relationships. Tetrahedron. 1999;55(3):699-722.
Ellervik et al., A High Yielding Chemical Synthesis of Sialyl Lewis x Tetrasaccharide and Lewis x Trisaccharide; Examples of Regio-and Stereodifferentiated Glycosylations. J Org Chem. 1998;63:9314-22.
Fehlhaber et al., Moenomycin A: A Structural Revision and New Structure-Activity Relations. Tetrahedron. 1990;46(5):1557-68.

(56) References Cited

OTHER PUBLICATIONS

Feng et al., Structure of the Shigella dysenteriae 7 O antigen gene cluster and identification of its antigen specific genes. Microb Pathog. Feb. 2004;36(2):109-15.
Flett et al., High efficiency intergeneric conjugal transfer of plasmid DNA from *Escherichia coli* to methyl DNA-restricting streptomycetes. FEMS Microbiol Lett. Oct. 15, 1997;155(2):223-9.
Fuse et al., Functional and Structural Analysis of a Key Region of the Cell Wall Inhibitor Moenomycin. ACS Chem Biol. 2010;5(7):701-711.
Gampe et al., Tuning the moenomycin pharmacophore to enable discovery of bacterial cell wall synthesis inhibitors. J Am Chem Soc. Mar. 13, 2013;135(10):3776-9. doi: 10.1021/ja4000933. Epub Mar. 4, 2013.
Garegg et al., Formation of Internucleotidic Bonds via Phosphonate Intermediates. Chem Scr. 1985;25:280-82.
Garneau et al., Synthesis of mono- and disaccharide analogs of moenomycin and lipid II for inhibition of transglycosylase activity of penicillin-binding protein 1b. Bioorg Med Chem. Dec. 15, 2004;12(24):6473-94.
Gildersleeve et al., Scavenging Byproducts in the Sulfoxide Glycosylation Reaction: Application to the Synthesis of Ciclamycin 0. J Am Chem Soc. 1999;121:6176-82.
Gildersleeve et al., Sulfenate Intermediates in the Sulfoxide Glycosylation Reaction. J Am Chem Soc. 1998;120:5961-69.
Goldman et al., Differential antibacterial activity of moenomycin analogues on gram-positive bacteria. Bioorg Med Chem Lett. Oct. 16, 2000;10(20):2251-4.
Goldman et al., Inhibition of transglycosylation involved in bacterial peptidoglycan synthesis. Curr Med Chem. Aug. 2000;7(8):801-20.
Gromyko et al., Generation of Streptomyces globisporus SMY622 strain with increased landomycin E production and it's initial characterization. J Antibiot (Tokyo). Jun. 2004;57(6):383-9.
Gust et al., PCR-targeted Streptomyces gene replacement identifies a protein domain needed for biosynthesis of the sesquiterpene soil odor geosmin. Proc Natl Acad Sci U S A. Feb. 18, 2003;100(4):1541-6. Epub Jan. 31, 2003.
Halliday et al., Targeting the forgotten transglycosylases. Biochem Pharmacol. Mar. 30, 2006;71(7):957-67. Epub Nov. 18, 2005.
Hang et al., Probing Glycosyltransferase Activities with the Staudinger Ligation. J Am Chem Soc. 2004;126(1):6-7.
Hang et al., Small molecule inhibitors of mucin-type O-linked glycosylation from a uridine-based library. Chem Biol. Mar. 2004;11(3):337-45.
Hang et al., The chemistry and biology of mucin-type O-linked glycosylation. Bioorg Med Chem. Sep. 1, 2005;13(17):5021-34.
He et al., Isolation and structural elucidation of AC326-alpha, a new member of the moenomycin group. J Antibiot (Tokyo). Feb. 2000;53(2):191-5.
Hebler-Klintz et al., The First Moenomycin Antibiotic Without the Methyl-Branched Uronic Acid Constituent.—Unexpected Structure Activity Relations. Tetrahedron. 1993;35:7667-78.
Hernández-Torres et al., Temperature-controlled regioselectivity in the reductive cleavage of p-methoxybenzylidene acetals. J Org Chem. Oct. 15, 2004;69(21):7206-11.
Hodgson, Primary metabolism and its control in streptomycetes: a most unusual group of bacteria. Adv Microb Physiol. 2000;42:47-238.
Hong et al., A signal transduction system in Streptomyces coelicolor that activates the expression of a putative cell wall glycan operon in response to vancomycin and other cell wall-specific antibiotics. Mol Microbiol. Jun. 2002;44(5):1199-1211.
Hong et al., Inactivation of the carbamoyltransferase gene refines post-polyketide synthase modification steps in the biosynthesis of the antitumor agent geldanamycin. J Am Chem Soc. Sep. 15, 2004;126(36):11142-3.
Hopwood, Soil to genomics: the Streptomyces chromosome. Annu Rev Genet. 2006;40:1-23.
Ishikawa et al., FramePlot: a new implementation of the frame analysis for predicting protein-coding regions in bacterial DNA with a high G+C content. FEMS Microbiol Lett. May 15, 1999;174(2):251-3.
Iyobe et al., Sex pili mutants isolated by macarbomycin treatment. Antimicrob Agents Chemother. May 1973;3(5):614-20.
Jabbouri et al., Involvement of nodS in N-methylation and nodU in 6-O-carbamoylation of *Rhizobium* sp. NGR234 nod factors. J Biol Chem. Sep. 29, 1995;270(39):22968-73.
Jansson et al., 2-(Trimethylsilyl)ethyl Glycosides. Synthesis, Anomeric Deblocking, and Transformation into 1,2-Trans 1-O-Acyl Sugars. J Org Chem. 1988;53:5629-47.
Kahne et al., Glycosylation of Unreactive Substrates. J Am Chem Soc. 1989;111:6881-82.
Kaplan et al., Genes involved in the synthesis and degradation of matrix polysaccharide in Actinobacillus actinomycetemcomitans and Actinobacillus pleuropneumoniae biofilms. J Bacteriol. Dec. 2004;186(24):8213-20.
Kartha et al., Iodine: A Versatile Reagent in Carboyhydrate Chemistry III. Efficient Activation of Glycosyl Halides in Combination with DDQ1. Tetrahedron Lett. 1996;37:8807-10.
Kaur, Expression and characterization of DrrA and DrrB proteins of Streptomyces peucetius in *Escherichia coli*: DrrA is an ATP binding protein. J Bacteriol. Feb. 1997;179(3):569-75.
Kawasaki et al., Biosynthesis of a natural polyketide-isoprenoid hybrid compound, furaquinocin A: identification and heterologous expression of the gene cluster. J Bacteriol. Feb. 2006;188(4):1236-44.
Kawasaki et al., Interconversion of the product specificity of type I eubacterial farnesyl diphosphate synthase and geranylgeranyl diphosphate synthase through one amino acid substitution. J Biochem. Jan. 2003;133(1):83-91.
Khidekel et al., A chemoenzymatic approach toward the rapid and sensitive detection of O-GlcNAc posttranslational modifications. J Am Chem Soc. Dec. 31, 2003;125(52):16162-3.
Knirel et al., Somatic antigens of Shigella: structure of the O-specific polysaccharide chain of the Shigella dysenteriae type 7 lipopolysaccharide. Carbohydr Res. Aug. 15, 1988;179:51-60.
Kudo et al., A new family of glucose-1-phosphate/glucosamine-1-phosphate nucleotidylyltransferase in the biosynthetic pathways for antibiotics. J Am Chem Soc. Feb. 16, 2005;127(6):1711-8.
Kuiper et al., A Selective and Mild Synthetic Route to Dialkyl Phosphates. Synthesis. 2003;5:695-98.
Lay et al., Synthesis of N-acetylglucosamine containing Lewis A and Lewis X building blocks based on N-tetrachlorophthaloyl protection—synthesis of Lewis X pentasaccharide. Carbohydr Res. Aug. 1998;310(3):157-71.
Lehtovaara et al., A new method for random mutagenesis of complete genes: enzymatic generation of mutant libraries in vitro. Protein Eng. Apr. 1988;2(1):63-8.
Leimkuhler et al., Differential inhibition of *Staphylococcus aureus* PBP2 by lycopeptides antibiotics. J Am Chem Soc. Mar. 16, 2005;127(10):3250-1.
Leskiw et al., Accumulation of bldA-specified tRNA is temporally regulated in Streptomyces coelicolor A3(2). J Bacteriol. Apr. 1993;175(7):1995-2005.
Leskiw et al., TTA codons in some genes prevent their expression in a class of developmental, antibiotic-negative, Streptomyces mutants. Proc Natl Acad Sci U S A. Mar. 15, 1991;88(6):2461-5.
Lin et al., Sequence analysis and molecular characterization of genes required for the biosynthesis of type 1 capsular polysaccharide in *Staphylococcus aureus*. J Bacteriol. Nov. 1994;176(22):7005-16.
Linnett et al., Additional antibiotic inhibitors of peptidoglycan synthesis. Antimicrob Agents Chemother. Sep. 1973;4(3):231-6.
Liu et al., Acceptor specificity and inhibition of the bacterial cell-wall glycosyltransferase MurG. Chembiochem. Jul. 7, 2003;4(7):603-9.
Lombo et al., The mithramycin gene cluster of Streptomyces argillaceus contains a positive regulatory gene and two repeated DNA sequences that are located at both ends of the cluster. J Bacteriol. Jan. 1999;181(2):642-7.

(56) References Cited

OTHER PUBLICATIONS

Lovering et al., Structural insight into the transglycosylation step of bacterial cell-wall biosynthesis. Science. Mar. 9, 2007;315(5817):1402-5.
Luning et al., Moenomycin-Type Transglycosylase Inhibitors: Inhibiting Activity vs. Topology around the Phosphoric Acid Diester Group. Tetrahedron Lett. 1994;35(12):1859-62.
Luzhetskii et al., [Interspecies conjugation of *Escherichia coli*-Streptomyces globisporus 1912 using integrative plasmid pSET152 and its derivatives]. Genetika. Oct. 2001;37(10):1340-7. Russian.
Luzhetskyy et al., Iteratively acting glycosyltransferases involved in the hexasaccharide biosynthesis of landomycin A. Chem Biol. Jul. 2005;12(7):725-9.
Marzian et al., Moenomycin A: Reactions at the Lipid Part. New Structure-Activity Relations. Tetrahedron. 1994;50:5299-308.
McAlpine et al., Microbial genomics as a guide to drug discovery and structural elucidation: ECO-02301, a novel antifungal agent, as an example. J Nat Prod. Apr. 2005;68(4):493-6.
McKeegan et al., The structure and function of drug pumps: an update. Trends Microbiol. Jan. 2003;11(1):21-9.
Men et al., Substrate Synthesis and Activity Assay for MurG. J. Am. Chem. Soc. Feb. 1998;120(10):2484-2485.
Mendez et al., The role of ABC transporters in antibiotic-producing organisms: drug secretion and resistance mechanisms. Res Microbiol. Apr.-May 2001;152(3-4):341-50.
Metten et al., The First Enzymatic Degradation Products of the Antibiotic Moenomycin A. Tetrahedron. 1992;48:8401-18.
Meyers et al., The Diumycins. New Members of an Antibiotic Family Having Prolonged In Vivo Activity. J Antibiot. 1969;22:490-93.
Müller et al., Utility of Glycosyl Phosphites as Glycosyl Donors-Fructofuranosyl and 2-Deoxyhexopyranosyl Phosphites in Glycoside Bond Formation. Tetrahedron Lett. 1994;35:4763-66.
Murrell et al., Biochemical characterization of the SgcA1 alpha-D-glucopyranosyl-1-phosphate thymidylyltransferase from the enediyne antitumor antibiotic C-1027 biosynthetic pathway and overexpression of sgcA1 in Streptomyces globisporus to improve C-1027 production. J Nat Prod. Feb. 2004;67(2):206-13.
Muth et al., A vector sytem with temperature-sensitive replication for gene disruption and mutational cloning in streptomycetes. Mol Gen Genet. 1989;219:341-48.
Nakagawa et al., Biosynthesis of asukamycin. Formation of the 2-amino-3-hydroxycyclopent-2-enone-moiety. J Chem Soc Chem Commun. 1985:519-21.
Nemoto et al., Purification and characterization of geranylgeranylglyceryl phosphate synthase from a thermoacidophilic archaeon, Thermoplasma acidophilum. J Biochem. May 2003;133(5):651-7.
Neundorf et al., Evidence for the combined participation of a C10 and a C15 precursor in the biosynthesis of moenocinol, the lipid part of the moenomycin antibiotics. Chembiochem. Nov. 7, 2003;4(11):1201-5.
Oh et al., Denaturation of circular or linear DNA facilitates targeted integrative transformation of Streptomyces coelicolor A3(2): possible relevance to other organisms. J Bacteriol. Jan. 1997;179(1):122-7.
Ostash et al., A streamlined metabolic pathway for the biosynthesis of moenomycin A. Chem Biol. Mar. 2007;14(3):257-67.
Ostash et al., Bacterial transglycosylase inhibitors. Curr Opin Chem Biol. Oct. 2005;9(5):459-66.
Ostash et al., Complete characterization of the seventeen step moenomycin biosynthetic pathway. Biochemistry. Sep. 22, 2009;48(37):8830-41.
Pacholec et al., Characterization of the aminocoumarin ligase SimL from the simocyclinone pathway and tandem incubation with NovM,P,N from the novobiocin pathway. Biochemistry. May 29, 2005;44(12):4949-56.
Paton et al., Molecular characterization of the locus encoding biosynthesis of the lipopolysaccharide O antigen of *Escherichia coli* serotype O113. Infect Immun. Nov. 1999;67(11):5930-7.

Paulsen, Advances in Selective Chemical Syntheses of Complex Oligosaccharides. Angew Chem Int Ed Engl. 1982;21:155-73.
Petricek et al., Occurrence of two 5-aminolevulinate biosynthetic pathways in *Streptomyces nodosus* subsp. Asukaensis is linked with the production of asukamycin. J Bacteriol. Jul. 2006;188(14):5113-23.
Pfaller, Flavophospholipol use in animals: positive implications for antimicrobial resistance based on its microbiologic properties. Diagn Microbiol Infect Dis. Oct. 2006;56(2):115-21. Epub May 15, 2006.
Ramakrishnan et al., alpha-Lactalbumin (LA) stimulates milk beta-1,4-galactosyltransferase I (beta 4Gal-T1) to transfer glucose from UDP-glucose to N-acetylglucosamine. Crystal structure of beta 4Gal-T1 x LA complex with UDP-Glc. J Biol Chem. Oct. 5, 2001;276(40):37665-71. Epub Aug. 2, 2001.
Ramakrishnan et al., Structure-based design of beta 1,4-galactosyltransferase I (beta 4Gal-T1) with equally efficient N-acetylgalactosaminyltransferase activity: point mutation broadens beta 4Gal-T1 donor specificity. J Biol Chem. Jun. 7, 2002;277(23):20833-9. Epub Mar. 26, 2002.
Rascher et al., Cloning and characterization of a gene cluster for geldanamycin production in Streptomyces hygroscopicus NRRL 3602. FEMS Microbiol Lett. Jan. 28, 2003;218(2):223-30.
Rebets et al., Expression of the regulatory protein LndI for landomycin E production in Streptomyces globisporus 1912 is controlled by the availability of tRNA for the rare UUA codon. FEMS Microbiol Lett. Mar. 2006;256(1):30-7.
Redenbach et al., The Streptomyces lividans 66 chromosome contains a 1 MB deletogenic region flanked by two amplifiable regions. Mol Gen Genet. Nov. 1993;241(3-4):255-62.
Riedel et al., Synthesis and Transglycosylase-Inhibiting Properties of a Disaccharide Analogue of Moenomycin A Lacking Substitution at C-4 of Unit f. Tetrahedron. 1999;55(7):1921-36.
Riedl et al., Impact of flavophospholipol and vancomycin on conjugational transfer of vancomycin resistance plasmids. Antimicrob Agents Chemother. Nov. 2000;44(11):3189-92.
Ritzeler et al., Search for new moenomycin structure-activity relationships Synthesis of a trisaccharide precursor of a moenomycin analogue. Tetrahedron. 1997;53:1665-74.
Rose et al., Consensus-degenerate hybrid oligonucleotide primers for amplification of distantly related sequences. Nucleic Acids Res. Apr. 1, 1998;26(7):1628-35.
Rühl et al., A trifunctional reagent for photoaffinity labeling. Tetrahedron Lett. 2000;41(23):4555-58.
Schmidt et al., Nitriles as Solvents in Glycosylation Reactions: Highly Selective β-Glycoside Synthesis. Synlett. 1990;11:694-96.
Schurer et al., Fluorescence correlation spectroscopy as a new method for the investigation of aptamer/target interactions. Biol Chem. Mar. 2001;382(3):479-81.
Schuricht et al., Studies on the Biosynthesis of the Antibiotic Moenomycin A. J Prakt Chem. 2000;342(8):761-72.
Schuricht et al., The Biosynthesis of Moenocinol, the Lipid Part of the Moenomycin Antibiotics. Tetrahedron Lett. 2001;42:3835-37.
Sekurova et al., In vivo analysis of the regulatory genes in the nystatin biosynthetic gene cluster of Streptomyces noursei ATCC 11455 reveals their differential control over antibiotic biosynthesis. J Bacteriol. Mar. 2004;186(5):1345-54.
Shin et al., Total synthesis and structure of the ramoplanin A1 and A3 aglycons: two minor components of the ramoplanin complex. Proc Natl Acad Sci U S A. Aug. 17, 2004;101(33):11977-9. Epub Jun. 2, 2004.
Sletten et al., A bioorthogonal quadricyclane ligation. J Am Chem Soc. Nov. 9, 2011;133(44):17570-3. Epub Oct. 17, 2011.
Slusarchyk et al., The Structure of a Novel Lipid from the Antibiotic Diumycin. J Am Chem Soc. 1970;92:4486-88.
Slusarchyk et al., The structure of the lipid portion of the antibiotic prasinomycin. Tetrahedron Lett. Feb. 1969;8:659-62.
Smith et al., The cps genes of Streptococcus suis serotypes 1, 2, and 9: development of rapid serotype-specific PCR assays. J Clin Microbiol. Oct. 1999;37(10):3146-52.
Soderberg et al., Geranylgeranylglyceryl phosphate synthase. Characterization of the recombinant enzyme from Methanobacterium thermoautotrophicum. Biochemistry. Dec. 11, 2001;40(49):14847-54.

(56) References Cited

OTHER PUBLICATIONS

Sosio et al., The gene cluster for the biosynthesis of the glycopeptide antibiotic A40926 by nonomuraea species. Chem Biol. Jun. 2003;10(6):541-9.

Srivastava et al., Combined chemical-enzymic synthesis of deoxygenated oligosaccharide analogs: transfer of deoxygenated D-GlcpNAc residues from their UDP-GlcpNAc derivatives using N-acetylglucosaminyltransferase I. Carbohydr Res. Oct. 25, 1990;207(2):259-76.

Stawinski, Chapter 8. Some Aspects of H-Phosphonate Chemistry. In: Handbook of Organophosphorus Chemistry. R. Engel ed. Marcel Dekker, New York. 1992:377-434.

Stumpp et al., Synthesis of Moenocinol. Tetrahedron. 1986;42:5941-48.

Subramaniam-Niehaus et al., Isolation and analysis of moenomycin and its biosynthetic intermediates from Streptomyces ghanaensis (ATCC 14672) wildtype and selected mutants. Z Naturforsch C. Mar.-Apr. 1997;52(3-4):217-26.

Tachibana et al., Novel prenyltransferase gene encoding farnesylgeranyl diphosphate synthase from a hyperthermophilic archaeon, Aeropyrum pernix. Molecular evolution with alteration in product specificity. Eur J Biochem. Jan. 2000;267(2):321-8.

Tahlan et al., Three unlinked gene clusters are involved in clavam metabolite biosynthesis in Streptomyces clavuligerus. Can J Microbiol. Oct. 2004;50(10):803-10.

Tai et al., Parallel identification of O-GlcNAc-modified proteins from cell lysates. J Am Chem Soc. Sep. 1, 2004;126(34):10500-1.

Takahashi et al., A two-stage one-pot enzymatic synthesis of TDP-L-mycarose from thymidine and glucose-1-phosphate. J Am Chem Soc. Feb. 8, 2006;128(5):1432-3.

Takahashi et al., Macarbomycin, a new antibiotic containing phosphorus. J Antibiot (Tokyo). Jan. 1970;23(1):48-50.

Taylor et al., The total synthesis of moenomycin A. J Am Chem Soc. Nov. 29, 2006;128(47):15084-5.

Thuy et al., Functional characterizations of novWUS involved in novobiocin biosynthesis from Streptomyces spheroides. Arch Biochem Biophys. Apr. 1, 2005;436(1):161-7.

Tirado et al., Stereochemistry of the Iodocarbonation of cis- and trans-3-Methyl-4-pentene-1,2-diols: The Unusual Formation of Several Anti Iodo Carbonates. J Org Chem. 1993;58:5666-73.

Trepanier et al., The positive activator of cephamycin C and clavulanic acid production in Streptomyces clavuligerus is mistranslated in a bldA mutant. Microbiology. Mar. 2002;148(Pt 3):643-56.

Tschesche et al., Uber den Lipoidteil Moenocinol des Antibiotikums Moenomycin. Tetrahedron Letters. 1968;24:2905-09.

Van Heijenoort, Formation of the glycan chains in the synthesis of bacterial peptidoglycan. Glycobiology. Mar. 2001;11(3):25R-36R.

Vocadlo et al., A chemical approach for identifying O-GlcNAc-modified proteins in cells. Proc Natl Acad Sci U S A. Aug. 5, 2003;100(16):9116-21. Epub Jul. 21, 2003.

Vocadlo et al., A strategy for functional proteomic analysis of glycosidase activity from cell lysates. Angew Chem Int Ed Engl. Oct. 11, 2004;43(40):5338-42.

Vogel et al. Moenomycin analogues with modified lipid side chains from indium-mediated Barbier-type reaction. Tetrahedron. 2001;57:4139-46.

Vogel et al., Some selective reactions of moenomycin A. Bioorg Med Chem Lett. Sep. 4, 2000;10(17):1963-5.

Volke et al., Characterisation of antibiotic moenomycin A interaction with phospholipid model membranes. Chem Phys Lipids. Feb. 28, 1997;85(2):115-23.

Volke et al., On Penicillin-Binding Protein 1b Affinity-Labeling Reagents. Helvetica Chimica Acta. 2003;86(12):4214-32.

Wallhausser et al., Moenomycin, a new antibiotic. I. Fermentation and isolation. Antimicrob Agents Chemother (Bethesda). 1965;5:734-6.

Wang et al., The pgaABCD locus of Escherichia coli promotes the synthesis of a polysaccharide adhesin required for biofilm formation. J Bacteriol. May 2004;186(9):2724-34.

Wang et al., Primer preactivation of peptidoglycan polymerases. J Am Chem Soc. Jun. 8, 2011;133(22):8528-30. doi: 10.1021/ja2028712. Epub May 17, 2011.

Weber et al., Exploiting the genetic potential of polyketide producing streptomycetes. J Biotechnol. Dec. 19, 2003;106(2-3):221-32.

Weisenborn et al., The prasinomycins: antibiotics containing phosphorus. Nature. Mar. 18, 1967;213(5081):1092-4.

Welzel et al., [Moenomycin A: Spaltung Des Antibiotikums Mit Trifluoressigsaure/2-Propanol Und Bestimmung Der Verknupfung Von D-Glucose Und 2-Acetamido-2-Desoxy-D-Glucose.] Tetrahedron. 1981;37:97-104. German.

Welzel et al., [Zur Struktur Eines 2-Amino-Cyclopentandion-1,3, Galakturonsaure and Chinovos-Amin Enthaltenden Hydrolyseruchstucks Des Antibiotikums Moenomycin A.] Tetrahedron Lett. 1973;3:227-30. German.

Welzel et al., Moenomycin A: Minimum Structural Requirements for Biological Activity. Tetrahedron. 1987;43:585-98.

Welzel, Syntheses around the transglycosylation step in peptidoglycan biosynthesis. Chem Rev. Dec. 2005;105(12):4610-60.

Welzel, Transglycosylase Inhibition. In: Antibiotics and antiviral compounds—chemical synthesis and modification. Krohn et al., eds. Weinheim, Germany. 1993:373-78.

Westerduin et al., Synthesis of the Fragment GlcNAc-α(1-P-6)-GlcNac of the Cell Wall Polymer of Staphylococcus lactis Having Repeating N-Acetyl-D-Glucosamine Phosphate Units. Tetrahedron Lett. 1986;27:6271-74.

Westrich et al., Cloning and characterization of a gene cluster from Streptomyces cyanogenus S136 probably involved in landomycin biosynthesis. FEMS Microbiol Lett. Jan. 15, 1999;170(2):381-7.

White et al., New oligomeric catalyst for the hydrolytic kinetic resolution of terminal epoxides under solvent-free conditions. Tetrahedron Asymm. 2003;14:3633-38.

Wilen et al., Strategies in Optical Resolutions. Tetrahedron. 1977;33:2725-36.

Wilen, Tables of Resolving Agents and Optical Resolutions. E.L. Eliel, ed. Universtify of Notre Dame Press, Notre Dame, IN. 1972:268-98.

Wilson et al., Molecular analysis of tlrB, an antibiotic-resistance gene from tylosin-producing Streptomyces fradiae, and discovery of a novel resistance mechanism. J Antibiot (Tokyo). Mar. 1999;52(3):288-96.

Wolff, Burger's Medicinal Chemistry. 5th ed., Part 1. John Wiley & Sons, 1995, pp. 975-977.

Xiang et al., The crystal structure of Escherichia coli MoeA and its relationship to the multifunctional protein gephyrin. Structure. Apr. 4, 2001;9(4):299-310.

Ye et al., Better substrates for bacterial transglycosylases. J Am Chem Soc. Apr. 4, 2001;123(13):3155-6.

Yu et al., The biosynthetic gene cluster of the maytansinoid antitumor agent ansamitocin from Actinosynnema pretiosum. Proc Natl Acad Sci U S A. Jun. 11, 2002;99(12):7968-73.

Yuan et al., Crystal structure of a peptidoglycan glycosyltransferase suggests a model for processive glycan chain synthesis. Proc Natl Acad Sci U S A. Mar. 27, 2007;104(13):5348-53. Epub Mar. 8, 2007.

Zalkin et al., Enzymes utilizing glutamine as an amide donor. Adv Enzymol Relat Areas Mol Biol. 1998;72:87-144.

Zehl et al., Characterization of moenomycin antibiotic complex by multistage MALDI-IT/RTOF-MS and ESI-IT-MS. J Am Soc Mass Spectrom. Aug. 2006;17(8):1081-90. Epub May 30, 2006.

Zhang et al., A Simple Statistical Parameter for Use in Evaluation and Validation of High Throughput Screening Assays. J Biomol Screen. 1999;4(2):67-73.

Zhang et al., Molecular and chemical characterization of the lipopolysaccharide O-antigen and its role in the virulence of Yersinia enterocolitica serotype O:8. Mol Microbiol. Jan. 1997;23(1):63-76.

Zhu et al., Identification of the function of gene lndM2 encoding a bifunctional oxygenase-reductase involved in the biosynthesis of the antitumor antibiotic landomycin E by Streptomyces globisporus 1912 supports the originally assigned structure for landomycinone. J Org Chem. Jan. 21, 2005;70(2):631-8.

U.S. Appl. No. 15/057,019, filed Feb. 29, 2016, Kahne et al.
U.S. Appl. No. 14/833,905, filed Aug. 25, 2015, Walker et al.

(56) References Cited

OTHER PUBLICATIONS

Dube et al., Chemical tools to discover and target bacterial glycoproteins. Chem Commun (Camb). Jan. 7, 2011:47(1):87-101. doi: 10.1039/c0cc01557a. Epub Aug. 23, 2010.

Havel et al., Isopentenoid synthesis in isolated embryonic *Drosophila* cells. Possible regulation of 3-hydroxy-3-methylglutaryl coenzyme A reductase activity by shunted mevalonate carbon. J Biol Chem. Aug. 5, 1986;261(22):10150-6.

Hu et al., Site-specific interplay between O-GlcNAcylation and phosphorylation in cellular regulation. FEBS Lett. Jun. 18, 2010;584(12):2526-38. doi: 10.1016/j.febslet.2010.04.044. Epub Apr. 22, 2010.

\* cited by examiner positive control (152)

Enzyme concentrations:
E. coli: 0.15 uM
E. faecalis: 0.40 uM
sgtB: 0.2 uM

| Indicates concentration of library compounds positive control (152)

ZE-Farneyl-Moenomycin A

IC$_{50}$ (*E. coli* PBP1b): 12 nM
MIC (*E. coli* NR698): 0.9 mg/mL

Enzyme concentrations:
E. coli: 0.15 uM
E. faecalis: 0.40 uM
SgtB: 0.2 uM

| Indicates concentration of library compounds

METHODS AND COMPOUNDS FOR IDENTIFYING GLYCOSYLTRANSFERASE INHIBITORS

RELATED APPLICATIONS

The present application is a national stage filing under 35 U.S.C. § 371 of international PCT application, PCT/US2013/030800, filed Mar. 13, 2013, which claims priority under 35 U.S.C. § 119(e) to U.S. provisional patent application U.S. Ser. No. 61/621,229, filed Apr. 6, 2012, each of which is incorporated herein by reference.

GOVERNMENT FUNDING

This invention was made with U.S. Government support under GM066174 and GM076710, awarded by National Institutes of Health. The U.S. Government has certain rights in the invention.

BACKGROUND OF THE INVENTION

Bacteria have the ability to generate resistance to antibiotics through lateral gene transfer, mutation of enzymes, or the expression of enzymes which actively pump the antibiotic out of the cell or break it down. Over the past 10 years, resistance to existing antibiotics has become a significant problem. Vancomycin is currently the drug of last resort to combat multidrug-resistant Gram-positive bacteria. In many places vancomycin-resistant *Staphylococcus aureus* and *Enterococci* (VRE) have been discovered. There is thus a desperate need for new antibiotics to replace this drug of last resort.

A host of cytoplasmic targets have been used in the development of new antibiotics, such as gyrase inhibitors, protein synthesis inhibitors, muramyl cascade inhibitors, and many more. The major hurdle in designing such drugs is that in addition to enzyme based activity these drugs need to cross the bacterial cell wall to exert their antibacterial effect. On the other hand, enzymes involved in synthesis of the bacterial cell wall exist on the cell wall exterior, and therefore drugs inhibiting these enzymes can exert their bactericidal or bacteriostatic effect without having to cross the cell wall. For example, penicillins, cephalosporins, and moenomycin are antibiotics that interact with bacterial transpeptidase enzymes. Vancomycin does not interact with bacterial transpeptidase enzymes, but rather sequesters the substrate of the enzyme.

Moenomycin is a natural product that directly inhibits the synthesis of bacterial peptidoglycan (PG). The biological activity of moenomycin is remarkable compared with that of most other natural antibiotics: it is 10-1000 times more potent than vancomycin against Gram-positive organisms. See, e.g., Ostash and Walker, *Curr. Opin. Chem. Biol.* (2005) 9:459-466; Goldman et al., *Curr. Med. Chem.* (2000) 7:801-820. Structure-activity relationship studies of moenomycin analogs conducted on the saccharide portion of the molecule have revealed that moenomycin analogs with at least three carbohydrate units (C, E, and F) are active in vivo against Gram-positive bacteria. See, e.g., Garneau et al., *Bioorganic & Medicinal Chemistry* (2004) 12:6473-6494. Furthermore, while the phosphoryl group and the carboxylate group of the phosphoglycerate linker are now considered important for bioactivity, the moenocinol chain is also considered to be an important structural component of the molecule and probably contributes to target binding both by direct interactions with the hydrophobic funnel that leads to the membrane and by membrane anchoring. See, e.g., Fuse et al., *Chemical Biology* (2010) 5:701-711. However, at the same time, the moenocinol chain is also credited with poor pharmacokinetic properties and high serum binding of moenomycin, e.g., its absorption upon oral administration is relatively poor. See, e.g., van Heijenoort, *Glycobiology* (2001) 11:25 R-36R.

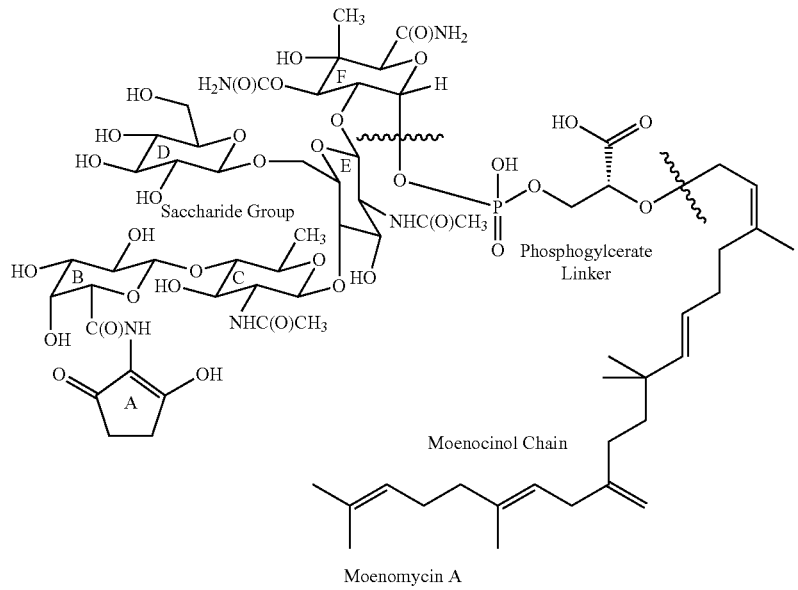

Moenomycin A

SUMMARY OF THE INVENTION

Moenomycin A and related compounds are potent inhibitors of glycosyltransferase enzymes in bacteria (Ostash et al. *Curr. Opin. Chem. Biol.* 9:459-466 (2005)). Previous work has established that, although $C_{10}$ analogues of the moenocinol chain are too short to retain biological activity, the $C_{25}$ moenocinol chain of moenomycin A is longer than required for activity. See, e.g., Ostash et al., *Biochemistry* (2009) 48:8830-8841.

The present invention provides assays for identification of other glycosyltransferase inhibitors. In certain embodiments, provided assays can be in high-throughput format, allowing for rapid identification of glycosyltransferase inhibitors. Moenomycin-based probe compounds are useful in such assays.

In one aspect, the present invention provides a moenomycin analog labeled with a detectable moiety. In certain embodiments, the detectable moiety is fluorescent. The detectable moiety can be attached to the moenomycin analog, optionally through a linker, anywhere on the compound (e.g., on one of the saccharides, on the phosphoglycerate linker, or on the moenocinol chain). The probe compound may be moenomycin A labeled with a detectable moiety, or it may be an analog of moenomycin.

In another aspect, the present invention provides moenomycin-based probes of Formula (I):

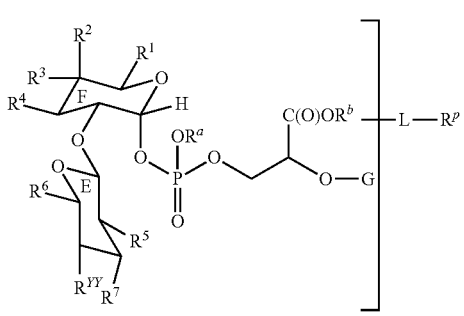

or a salt thereof, wherein $R^1$, $R^2$, $R^3$, $R^4$, $R^5$, $R^6$, $R^7$, $R^{YY}$, $R^a$, $R^b$, G, L, and $R^P$ are as described herein.

It will be understood by one of ordinary skill in the art that when a formula is shown in brackets with -L-$R^P$ straddling the bracket, -L-$R^P$ can be attached anywhere on the molecule, i.e., a hydrogen radical on the compound is replaced with -L-$R^P$.

In some embodiments, a probe compound according to the present invention is of Formula (Ia):

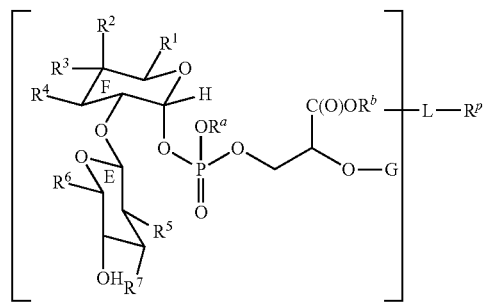

or a salt thereof, wherein $R^1$, $R^2$, $R^3$, $R^4$, $R^5$, $R^6$, $R^7$, $R^a$, $R^b$, G, L, and $R^P$ are as described herein.

In some embodiments, a probe compound according to the present invention is of Formula (Ib):

(Ib)

or a salt thereof, wherein $R^1$, $R^2$, $R^3$, $R^4$, $R^5$, $R^6$, $R^7$, $R^{11}$, $R^{12}$, $R^{13}$, $R^{14}$, $R^{19a}$, $R^{19b}$, $R^a$, $R^b$, G, L, and $R^P$ are as described herein.

In some embodiments, a probe compound according to the present invention is of Formula (Ic):

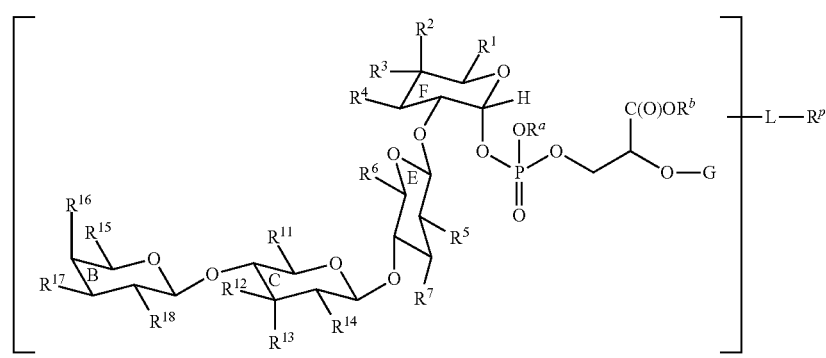

or a salt thereof, wherein $R^1$, $R^2$, $R^3$, $R^4$, $R^5$, $R^6$, $R^7$, $R^{11}$, $R^{12}$, $R^{13}$, $R^{14}$, $R^{15}$, $R^{16}$, $R^{17}$, $R^{18}$, $R^a$, $R^b$, G, L, and $R^P$ are as described herein.

In some embodiments, a probe compound according to the present invention is of Formula (Id):

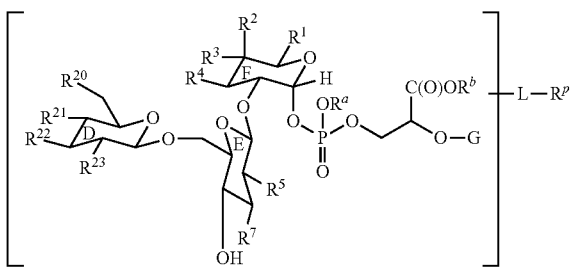

(Id)

or a salt thereof, wherein $R^1$, $R^2$, $R^3$, $R^4$, $R^5$, $R^7$, $R^{20}$, $R^{21}$, $R^{22}$, $R^{23}$, $R^a$, $R^b$, G, L, and $R^P$ are as described herein.

In some embodiments, a probe compound according to the present invention is of Formula (Ie):

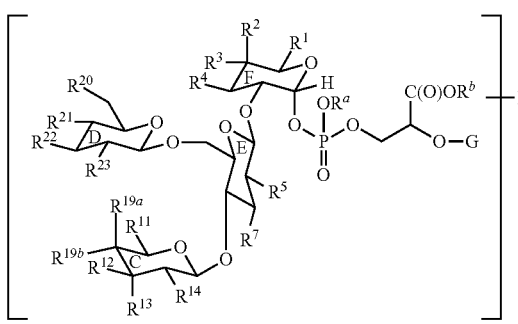

(Ie)

or a salt thereof, wherein $R^1$, $R^2$, $R^3$, $R^4$, $R^5$, $R^7$, $R^{11}$, $R^{12}$, $R^{13}$, $R^{14}$, $R^{19a}$, $R^{19b}$, $R^{20}$, $R^{21}$, $R^{22}$, $R^{23}$, $R^a$, $R^b$, G, L, and $R^P$ are as described herein.

In some embodiments, a probe compound according to the present invention is of Formula (If):

or a salt thereof, wherein $R^1$, $R^2$, $R^3$, $R^4$, $R^5$, $R^7$, $R^{11}$, $R^{12}$, $R^{13}$, $R^{14}$, $R^{15}$, $R^{16}$, $R^{17}$, $R^{18}$, $R^{20}$, $R^{21}$, $R^{22}$, $R^{23}$, $R^a$, $R^b$, G, L, and $R^P$ are as described herein.

In some embodiments, a probe compound according to the present invention is of Formula (Ib-xxiv):

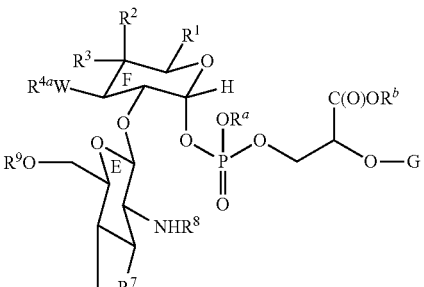

(Ib-xxiv)

or a salt thereof, wherein $R^1$, $R^2$, $R^3$, $R^{4a}$, $R^7$, $R^8$, $R^9$, $R^{11}$, $R^{12}$, $R^{13}$, $R^{19a}$, $R19^b$, $R^a$, $R^b$, W, G, L, and $R^P$ are as described herein.

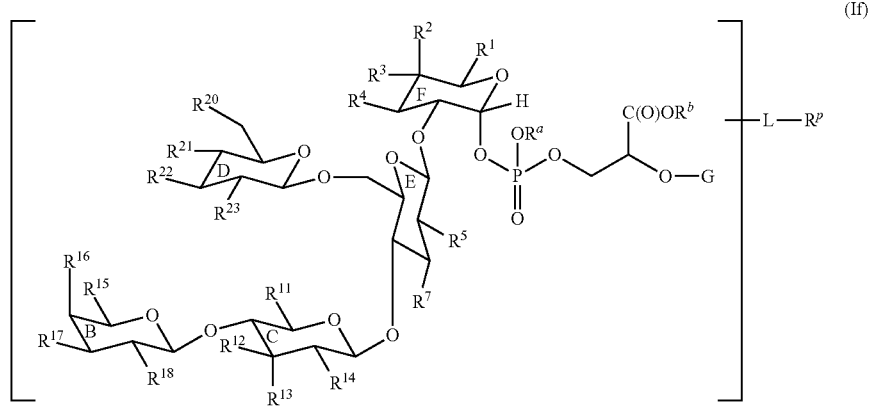

(If)

In certain embodiments, the present invention provides

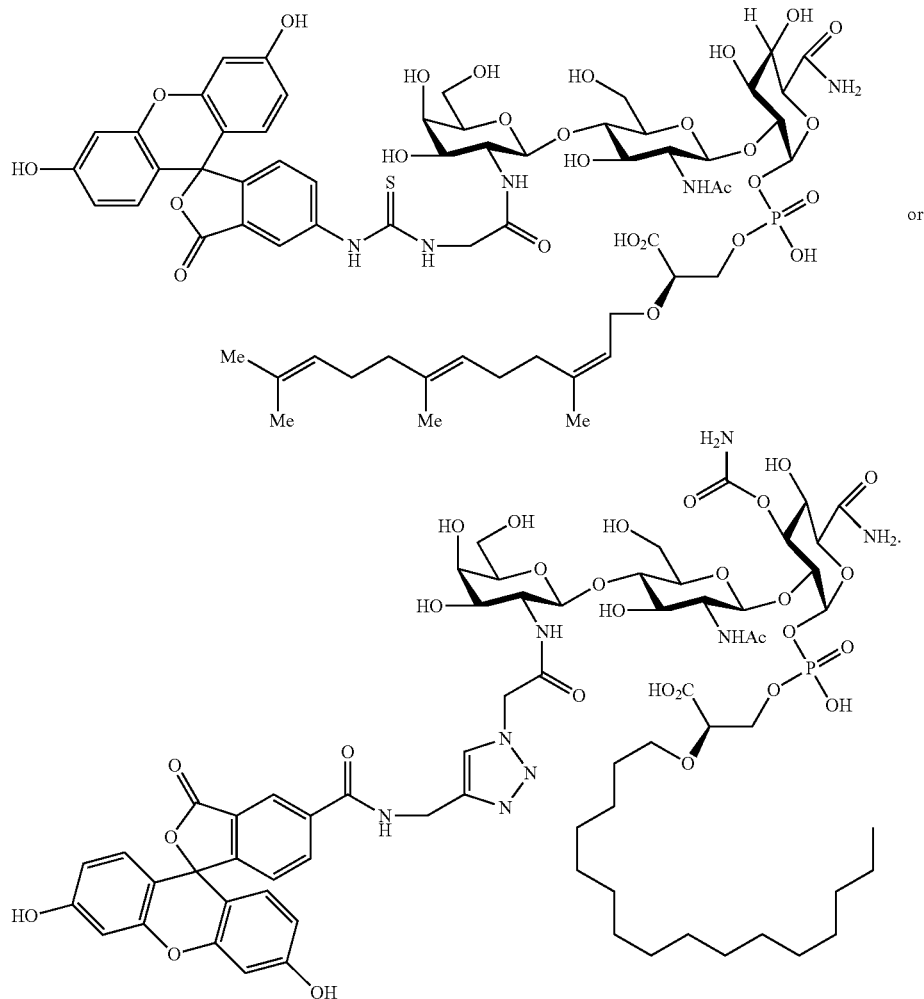

or

In another aspect, the present invention provides methods of identifying glycosyltransferase inhibitors. Identification of inhibitors of bacterial glycosyltransferases is important in developing new antibiotic compounds. In certain embodiments, a method of the present invention comprises incubating a glycosyltransferase protein with a probe compound described herein; measuring fluorescence polarization of the probe compound in the presence of the glycosyltransferase protein; adding a test compound; and measuring a change in fluorescence polarization after addition of the test compound. A decrease in fluorescence polarization indicates that the test compound binds to the same binding site as the probe compound and liberates the probe compound from the glycosyltransferase. In certain embodiments, a probe compound used in the methods of the present invention is of intermediate activity against the glycosyltransferase of interest.

In another aspect, the invention provides a kit comprising a probe compound of the present invention and glycosyltransferase protein. In some embodiments, the kit further comprises a buffer. In some embodiments, the kit further comprises instructions for use.

These and other aspects of the invention will be described in further detail in connection with the detailed description of the invention.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer and may also be referred to as "optically enriched." "Optically enriched," as used herein, means that the compound is made up of a significantly greater proportion of one enantiomer. In certain embodiments, the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw Hill, NY, 1962); Wilen, S. H. *Tables of Resolving Agents and Optical Resolutionsi*, p. 268 (E. L. Eliel, Ed., Univ. of Notre Dame Press, Notre Dame, Ind. 1972).

When a range of values is listed, it is intended to encompass each value and sub-range within the range. For example, an "alkyl group having from 1 to 6 carbons" (also referred to herein as "$C_{1-6}$ alkyl") is intended to encompass 1 ($C_1$ alkyl), 2 ($C_2$ alkyl), 3 ($C_3$ alkyl), 4 ($C_4$ alkyl), 5 ($C_5$ alkyl) and 6 ($C_6$ alkyl) carbons, and a range of 1 to 6 ($C_{1-6}$ alkyl), 1 to 5 ($C_{1-5}$ alkyl), 1 to 4 ($C_{1-4}$ alkyl), 1 to 3 ($C_{1-3}$ alkyl), 1 to 2 ($C_{1-2}$ alkyl), 2 to 6 ($C_{2-6}$ alkyl), 2 to 5 ($C_{2-5}$ alkyl), 2 to 4 ($C_{2-4}$ alkyl), 2 to 3 ($C_{2-3}$ alkyl), 3 to 6 ($C_{3-6}$ alkyl), 3 to 5 ($C_{3-5}$ alkyl), 3 to 4 ($C_{3-4}$ alkyl), 4 to 6 ($C_{4-6}$ alkyl), 4 to 5 ($C_{4-5}$ alkyl), and 5 to 6 ($C_{5-6}$ alkyl) carbons.

The term "aliphatic," as used herein, refers to a monoradical of a nonaromatic, saturated or unsaturated, unbranched ("straight-chain") or branched, substituted or unsubstituted, acyclic hydrocarbon having 1-50 carbon atoms (i.e., $C_{1-50}$ aliphatic). Thus, as used herein, the term "aliphatic" encompasses the groups "alkyl", "alkynyl", and "alkenyl" as defined herein. In certain embodiments, aliphatic refers to a $C_2$-$C_{30}$ aliphatic group. In certain embodiments, aliphatic refers to a $C_5$-$C_{25}$ aliphatic group. In certain embodiments, aliphatic refers to a $C_1$-$C_{10}$ aliphatic group. In certain embodiments, aliphatic refers to a $C_{10}$-$C_{20}$ aliphatic group. In certain embodiments, aliphatic refers to a $C_{11}$-$C_{15}$ aliphatic group. Unless otherwise specified, each instance of aliphatic is independently unsubstituted ("unsubstituted aliphatic") or substituted ("substituted aliphatic") with 1, 2, 3, 4, 5, 6, 7, 8, 9, 10, or more substituents as described herein. Aliphatic group substituents include, but are not limited to, any of the monovalent or divalent substituents described herein, that result in the formation of a stable moiety.

The term "alkyl," as used herein, refers to a monoradical of a nonaromatic, saturated, unbranched ("straight-chain") or branched, substituted or unsubstituted, acyclic hydrocarbon having 1-50 carbon atoms (i.e., $C_{1-50}$ alkyl). In certain embodiments, alkyl refers to a $C_2$-$C_{30}$ alkyl group. In certain embodiments, alkyl refers to a $C_5$-$C_{25}$ alkyl group. In certain embodiments, alkyl refers to a $C_{10}$-$C_{20}$ alkyl group. In certain embodiments, alkyl refers to a $C_1$-$C_{10}$ alkyl group. In certain embodiments, alkyl refers to a $C_{11}$-$C_{15}$ alkyl group. Exemplary alkyl groups include, without limitation, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, tridecyl, tetradecyl, pentadecyl, hexadecyl, heptadecyl, octadecyl, nonadecyl, eicosyl, and the like, which may bear one or more substitutents. Unless otherwise specified, each instance of alkyl is independently unsubstituted ("unsubstituted alkyl") or substituted ("substituted alkyl") with 1, 2, 3, 4, 5, 6, 7, 8, 9, 10, or more substituents as described herein. Alkyl group substituents include, but are not limited to, any of the monovalent or divalent substituents described herein, that result in the formation of a stable moiety.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene," a bivalent aryl ring is "arylene," a bivalent benzene ring is "phenylene," a bivalent heterocycle is "heterocyclylene," a bivalent heteroaryl ring is "heteroarylene," a bivalent alkyl chain is "alkylene," a bivalent cycloalkyl group is "cycloalkylene," a bivalent alkenyl chain is "alkenylene," a bivalent alkynyl chain is "alkynylene," a bivalent heteroalkyl chain is "heteroalkylene," a bivalent heteroalkenyl chain is "heteroalkenylene," a bivalent heteroalkynyl chain is "heteroalkynylene," and so forth.

The term "fluoroalkyl," as used herein, refers to an alkyl group having from 1 to 50 carbon atoms wherein at least one hydrogen is replaced with a fluorine atom ("$C_{1-50}$ fluoroalkyl"). In certain embodiments, the fluoroalkyl group has 1 to 8 carbon atoms ("$C_{1-8}$ fluoroalkyl"). In certain embodiments, the fluoroalkyl group has 1 to 6 carbon atoms ("$C_{1-6}$ fluoroalkyl"). In certain embodiments, the fluoroalkyl group has 1 to 4 carbon atoms ("$C_{1-4}$ fluoroalkyl"). In certain embodiments, the fluoroalkyl group has 1 to 3 carbon atoms ("$C_{1-3}$ fluoroalkyl"). In certain embodiments, the fluoroalkyl group has 1 to 2 carbon atoms ("$C_{1-2}$ fluoroalkyl"). In certain embodiments, one hydrogen atom is replaced with a fluorine atom. In certain embodiments, two hydrogen atoms are replaced with fluorine atoms. In certain embodiments, three hydrogen atoms are replaced with fluorine atoms. In certain embodiments, four hydrogen atoms are replaced with fluorine atoms. In certain embodiments, five hydrogen atoms are replaced with fluorine atoms. In certain embodiments, all of the hydrogen atoms are replaced with fluorine atoms (also referred to as a "perfluoroalkyl" group). Exemplary fluoroalkyl groups include, but are not limited to, —CH$_2$F, —CF$_2$H, —CF$_3$, —CH$_2$CF$_3$, —CF$_2$CF$_3$, —CH$_2$CH$_2$CF$_3$, —CH$_2$CF$_2$CF$_3$, —CF$_2$CF$_2$CF$_3$, and the like.

The term "alkenyl," as used herein, refers to a monoradical of a non-aromatic, unbranched ("straight-chain") or branched, substituted or unsubstituted, acyclic hydrocarbon having at least one carbon-carbon double bond, having zero carbon-carbon triple bonds, and having 2-50 carbon atoms (i.e., $C_{2-50}$ alkenyl). In certain embodiments, alkenyl refers to a $C_5$-$C_{25}$ alkenyl group. In certain embodiments, alkenyl refers to a $C_{10}$-$C_{20}$ alkenyl group. In certain embodiments, alkenyl refers to a $C_2$-$C_{10}$ alkenyl group. In certain embodiments, alkenyl refers to a $C_{11}$-$C_{15}$ alkenyl group. Exemplary alkenyl groups include, without limitation, ethenyl, propenyl, butenyl, 1-methyl-2-buten-1-yl, and the like, which may bear one or more substituents. Unless otherwise specified, each instance of alkenyl is independently unsubstituted ("unsubstituted alkenyl") or substituted ("substituted alkenyl") with 1, 2, 3, 4, 5, 6, 7, 8, 9, 10, or more substituents as described herein. Alkenyl group substituents include, but are not limited to, any of the monovalent or divalent substituents described herein, that result in the formation of a stable moiety.

The term "alkynyl," as used herein, refers to a monoradical of a non-aromatic, unbranched ("straight-chain") or branched, substituted or unsubstituted, acyclic hydrocarbon having at least one carbon-carbon triple bond, optionally containing one or more carbon-carbon double bonds, and having 2-50 carbon atoms (i.e., $C_{2-50}$ alkynyl). In certain embodiments, alkynyl refers to a $C_5$-$C_{25}$ alkynyl group. In certain embodiments, alkynyl refers to a $C_2$-$C_{10}$ alkynyl group. In certain embodiments, alkynyl refers to a $C_{10}$-$C_{20}$ alkynyl group. In certain embodiments, alkynyl refers to a $C_{11}$-$C_{15}$ alkynyl group. Exemplary alkynyl groups include, without limitation, ethynyl, 2-propynyl (propargyl), 1-propynyl, and the like, which may bear one or more substituents. Unless otherwise specified, each instance of alkynyl is independently unsubstituted ("unsubstituted alkynyl") or substituted ("substituted alkynyl") with 1, 2, 3, 4, 5, 6, 7, 8, 9, 10, or more substituents as described herein. Alkynyl group substituents include, but are not limited to, any of the monovalent or divalent substituents described herein, that result in the formation of a stable moiety.

The term "heteroaliphatic," as used herein, refers to a $C_{1-50}$ aliphatic group wherein one, two or three methylene units of the hydrocarbon chain are independently replaced with one or more oxygen, sulfur or nitrogen atoms. Thus, as used herein, the term "heteroaliphatic" encompasses the groups "heteroalkyl", "heteroalkynyl", and "heteroalkenyl" as defined herein. Unless otherwise specified, each instance of heteroaliphatic is independently unsubstituted ("unsubstituted heteroaliphatic") or substituted ("substituted heteroaliphatic") with 1, 2, 3, 4, 5, 6, 7, 8, 9, 10, or more substituents as described herein. Heteroaliphatic group substituents include, but are not limited to, any of the monovalent or divalent substituents described herein, that result in the formation of a stable moiety.

The term "heteroalkyl," as used herein, refers to a $C_{1-50}$ alkyl group wherein one, two or three methylene units of the hydrocarbon chain are independently replaced with one or more oxygen, sulfur or nitrogen atoms. Unless otherwise specified, each instance of heteroalkyl is independently unsubstituted ("unsubstituted heteroalkyl") or substituted ("substituted heteroalkyl") with 1, 2, 3, 4, 5, 6, 7, 8, 9, 10, or more substituents as described herein. Heteroalkyl group substituents include, but are not limited to, any of the monovalent or divalent substituents described herein, that result in the formation of a stable moiety.

The term "heteroalkenyl," as used herein, refers to a $C_{2-50}$ alkenyl group wherein one, two or three methylene units of the hydrocarbon chain are independently replaced with one or more oxygen, sulfur or nitrogen atoms. Unless otherwise specified, each instance of heteroalkenyl is independently unsubstituted ("unsubstituted heteroalkenyl") or substituted ("substituted heteroalkenyl") with 1, 2, 3, 4, 5, 6, 7, 8, 9, 10, or more substituents as described herein. Heteroalkenyl group substituents include, but are not limited to, any of the monovalent or divalent substituents described herein, that result in the formation of a stable moiety.

The term "heteroalkynyl," as used herein, refers to a $C_{2-50}$ alkynyl group wherein one, two or three methylene units of the hydrocarbon chain are independently replaced with one or more oxygen, sulfur or nitrogen atoms. Unless otherwise specified, each instance of heteroalkynyl is independently unsubstituted ("unsubstituted heteroalkynyl") or substituted ("substituted heteroalkynyl") with 1, 2, 3, 4, 5, 6, 7, 8, 9, 10, or more substituents as described herein. Heteroalkynyl group substituents include, but are not limited to, any of the monovalent or divalent substituents described herein, that result in the formation of a stable moiety.

The terms "carbocyclic" or "carbocyclyl," as used herein, refer to a monoradical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$-carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$) and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$-carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$) and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups, as defined herein, wherein the point of attachment is on the carbocyclyl ring; in such instances, the number of carbons continues to designate the number of carbons in the carbocyclic ring system. Unless otherwise specified, each instance of a carbocyclyl group is independently unsubstituted ("unsubstituted carbocyclyl") or substituted ("substituted carbocyclyl") with 1, 2, 3, 4, 5, 6, 7, 8, 9, 10, or more substituents as described herein. Carbocyclyl group substituents include, but are not limited to, any of the monovalent or divalent substituents described herein, that result in the formation of a stable moiety.

In certain embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$cycloalkyl"). In some embodiments, a cycloalkyl group has 3 to 6 ring carbon atoms ("$C_{3-6}$cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{5-6}$ cycloalkyl groups include, without limitation, cyclopentyl ($C_5$) and cyclohexyl ($C_5$). Exemplary $C_{3-6}$ cycloalkyl groups include, without limitation, the aforementioned $C_{5-6}$ cycloalkyl groups as well as cyclopropyl ($C_3$) and cyclobutyl ($C_4$). Exemplary $C_{3-8}$ cycloalkyl groups include, without limitation, the aforementioned $C_{3-6}$ cycloalkyl groups as well as cycloheptyl ($C_7$) and cyclooctyl ($C_8$). Unless otherwise specified, each instance of a cycloalkyl group is independently unsubstituted ("unsubstituted cycloalkyl") or substituted ("substituted cycloalkyl") with 1, 2, 3, 4, 5, 6, 7, 8, 9, 10, or more substituents as described herein. Cycloalkyl group substituents include, but are not limited to, any of the monovalent or divalent substituents described herein, that result in the formation of a stable moiety.

The terms "heterocyclic" or "heterocyclyl," as used herein, refer to a radical of a 3- to 14-membered nonaromatic ring system having ring carbon atoms and 1 to 4 ring heteroatoms, wherein each heteroatom is independently selected from the group consisting of nitrogen, oxygen and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" includes ring systems wherein the heterocycyl ring, as defined above, is fused with one or more carbocycyl groups wherein the point of attachment is either on the carbocycyl or heterocyclyl ring; in such instances, the number of ring members continues to designate the number of ring members in the heterocyclyl ring system. Heterocycyl also includes ring systems wherein the heterocyclyl ring, as defined above, is fused with one or more aryl or heteroaryl groups, wherein the point of attachment is on the heterocyclyl ring; in such instances, the number of ring members continues to designate the number of ring members in the heterocyclyl ring system. In some embodiments, a heterocyclyl group is a 5-10 membered non-aromatic ring system having ring carbon atoms and 1-4 ring heteroatoms, wherein each heteroatom is independently selected from the group consisting of nitrogen, oxygen and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from the group consisting of nitrogen, oxygen and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from the group consisting of nitrogen, oxygen and sulfur ("5-6 membered heterocyclyl"). In some embodiments, the 5-6 membered heterocyclyl has 1-3 ring heteroatoms selected from the group consisting of nitrogen, oxygen and sulfur. In some embodiments, the 5-6 membered heterocyclyl has 1-2 ring heteroatoms selected from the group consisting of nitrogen, oxygen and sulfur. In some embodiments, the 5-6 membered heterocyclyl has 1 ring heteroatom selected from the group consisting of nitrogen, oxygen and sulfur. Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like. Unless otherwise specified, each instance of heterocyclyl is independently unsubstituted ("unsubstituted heterocyclyl") or substituted ("substituted heterocyclyl") with 1, 2, 3, 4, 5, 6, 7, 8, 9, 10, or more substituents as described herein. Heterocyclyl group substituents include, but are not limited to, any of the monovalent or divalent substituents described herein, that result in the formation of a stable moiety.

The term "aryl," as used herein, refers to a radical of a monocyclic or polycyclic (e.g., bicyclic or tricyclic) aromatic ring system (e.g., having 6, 10 or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring; in such instances, the number of carbon atoms continues to designate the number of carbon atoms in the aryl ring system. Unless otherwise specified, each instance of an aryl group is independently unsubstituted ("unsubstituted aryl") or substituted ("substituted aryl") with 1, 2, 3, 4, 5, 6, 7, 8, 9, 10, or more substituents as described herein. Aryl group substituents include, but are not limited to, any of the monovalent substituents described herein, that result in the formation of a stable moiety.

The terms "aralkyl" or "arylalkyl" are a subset of "alkyl" and refer to an alkyl group, as defined herein, substituted by an aryl group, as defined herein, wherein the point of attachment is on the alkyl moiety.

The term "heteroaryl," as used herein, refers to a radical of a 5-14 membered monocyclic or polycyclic (e.g., bicyclic or tricyclic) aromatic ring system (e.g., having 6, 10 or 14π electrons shared in a cyclic array) having ring carbon atoms and 1-4 ring heteroatoms provided in the aromatic ring system, wherein each heteroatom is independently selected from the group consisting of nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocycyl or heterocycyl groups wherein the point of attachment is on the heteroaryl ring; in such instances, the number of ring members continues to designate the number of ring members in the heteroaryl ring system. "Heteroaryl" also includes ring systems wherein the heteroaryl ring, as defined above, is fused with one or more aryl groups wherein the point of attachment is either on the aryl or on the heteroaryl ring; in such instances, the number of ring members designates the number of ring members in the fused polycyclic (aryl/heteroaryl) ring system. For example, polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen, and sulfur ("5-6 membered heteroaryl"). In some embodiments, the 5-6 membered heteroaryl has 1-3 ring heteroatoms selected from the group consisting of nitrogen, oxygen and sulfur. In some embodiments, the 5-6 membered heteroaryl has 1-2 ring heteroatoms selected from the group consisting of nitrogen, oxygen and sulfur. In some embodiments, the 5-6 membered heteroaryl has 1 ring heteroatom selected from the group consisting of nitrogen, oxygen and sulfur. Exemplary 5-membered heteroaryls containing 1 heteroatom include, without limitation, pyrrolyl, furanyl, and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, thiadiazolyl. Exemplary 5-membered heteroaryls containing 4 heteroatoms include, without limitation, tetrazolyl. Exemplary 6-membered heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Exemplary tricyclic heteroaryls include, without limitation, phenanthridinyl, dibenzofuranyl, carbazolyl, acridinyl, phenothiazinyl, phenoxazinyl and phenazinyl. Unless otherwise specified, each instance of a heteroaryl group is independently unsubstituted ("unsubstituted heteroaryl") or substituted ("substituted heteroaryl") 1, 2, 3, 4, 5, 6, 7, 8, 9, 10, or more substituents as described herein. Heteroaryl group substituents include, but are not limited to, any of the monovalent substituents described herein, that result in the formation of a stable moiety.

The terms "heteroarylalkyl" or "heteroaralkyl" are a subset of "alkyl" and refer to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as defined herein.

In some embodiments, aliphatic (e.g., alkyl, alkenyl, alkynyl), heteroaliphatic (e.g., heteroalkyl, heteroalkenyl, heteroalkynyl), carbocyclyl, heterocyclyl, aryl and heteroaryl groups, as defined herein, are optionally substituted (e.g., "substituted" or "unsubstituted" aliphatic, "substituted" or "unsubstituted" alkyl, "substituted" or "unsubstituted" alkenyl, "substituted" or "unsubstituted" alkynyl, "substituted" or "unsubstituted" heteroaliphatic, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl, or "substituted" or "unsubstituted" heteroaryl group). In general, the term "substituted" means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Exemplary monovalent carbon atoms substituents include, but are not limited to, halo/halogen (i.e., —F, —Br, —Cl, —I), —NC, —CN, —NO$_2$, —N$_3$, —CO$_2$H, —CHO, —SO$_2$H, —SO$_3$H, —S(=O)OH, acyl (e.g., —C(=O)R$^A$, —CO$_2$R$^A$, —C(=O)—O—C(=O)R$^A$, —C(=O)SR$^A$, —C(=O)N(R$^B$)$_2$, —C(=O)NR$^B$SO$_2$R$^A$, —C(=NR$^B$)R$^A$, —C(=NR$^B$)OR$^A$, —C(=NR$^B$)N(R$^B$)$_2$, —C(=S)R$^A$, —C(=S)N(R$^A$)$_2$, —C(=S)SR$^A$), amino (e.g., —NH$_2$, —N(OR$^B$)R$^B$, —N(R$^B$)$_2$, —NR$^B$SO$_2$R$^A$, —NR$^B$C(=O)R$^A$, —NR$^B$CO$_2$R$^A$, —NR$^B$C(=O)N(R$^B$)$_2$, —NR$^B$C(=NR$^B$)N(R$^B$)$_2$, thio (e.g., —SH, —SR$^A$, —SSR$^B$), oxy (e.g., —OH, —OR$^A$, —ON(R$^B$)$_2$, —OSO$_2$R$^A$, —OS(=O)R$^A$, —OC(=O)R$^A$, —OCO$_2$R$^A$, —OC(=O)N(R$^B$)$_2$, —OC(=NR$^B$)R$^A$, —OC(=NR$^B$)OR$^A$, —C(=NR$^B$)N(R$^B$)$_2$), sulfonyl (e.g., —SO$_2$R$^A$, —SO$_2$OR$^A$, —SO$_2$N(R$^B$)$_2$), sulfinyl (e.g., —S(=O)R$^A$), silyl (e.g., —Si(R$^A$)$_3$), C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each aliphatic, heteroaliphatic, carbocyclyl, heterocyclyl, aryl, and heteroaryl is independently substituted with 0, 1, 2, 3, 4, or 5 R$^D$ groups;

each instance of R$^A$ is, independently, selected from the group consisting of C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, $C_{6-14}$ aryl, and 5-14 membered heteroaryl, wherein each aliphatic, heteroaliphatic, carbocyclyl, heterocyclyl, aryl, and heteroaryl is independently substituted with 0, 1, 2, 3, 4, or 5 $R^D$ groups;

each instance of $R^B$ is, independently, selected from the group consisting of hydrogen, —OH, —OR$^A$, —N(R$^C$)$_2$, —CN, —C(=O)R$^A$, —C(=O)N(R$^C$)$_2$, —CO$_2$R$^A$, —SO$_2$R$^A$, —C(=NR$^C$)OR$^A$, —C(=NR$^C$)N(R$^C$)$_2$, —SO$_2$N(R$^C$)$_2$, —SO$_2$R$^C$, —SO$_2$OR$^C$, —SOR$^A$, —C(=S)N(R$^C$)$_2$, —C(=O)SR$^C$, —C(=S)SR$^C$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^B$ groups attached to an N atom are joined to form a 3-14 membered heterocyclyl or 5-14 membered heteroaryl ring, wherein each aliphatic, heteroaliphatic, carbocyclyl, heterocyclyl, aryl, and heteroaryl is independently substituted with 0, 1, 2, 3, 4, or 5 $R^D$ groups;

each instance of $R^C$ is, independently, selected from the group consisting of hydrogen, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^C$ groups attached to an N atom are joined to form a 3-14 membered heterocyclyl or 5-14 membered heteroaryl ring, wherein each aliphatic, heteroaliphatic, carbocyclyl, heterocyclyl, aryl, and heteroaryl is independently substituted with 0, 1, 2, 3, 4, or 5 $R^D$ groups; and each instance of $R^D$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$alkyl), —OC(=NH)OC$_{1-6}$ alkyl, —C(=NH)N(C$_{1-6}$alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —S(=O)C$_{1-6}$ alkyl, $C_{1-6}$ alkyl, $C_{1-6}$ fluoroalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^D$ substituents are joined to form =O, =S or =NR$^B$.

Exemplary divalent carbon atom substituents include, but are not limited to =O, =S, and =NR$^B$, wherein $R^B$ is as defined herein.

Nitrogen atoms can be substituted or unsubstituted as valency permits, and include primary, secondary, tertiary and quarternary nitrogen atoms. Exemplary nitrogen atom substitutents include, but are not limited to, =NR$^B$, —CHO, —C(=O)R$^A$, —CO$_2$R$^A$, —C(=O)SR$^A$, —C(=O)N(R$^B$)$_2$, —C(=O)NR$^B$SO$_2$R$^A$, —C(=NR$^B$)R$^A$, —C(=NR$^B$)OR$^A$, —C(=NR$^B$)N(R$^B$)$_2$, —C(=S)R$^A$, —C(=S)N(R$^A$)$_2$, —C(=S)SR$^A$, —NH$_2$, —N(OR$^B$)R$^B$, —N(R$^B$)$_2$, —NR$^B$SO$_2$R$^A$, —NR$^B$C(=O)R$^A$, —NR$^B$CO$_2$R$^A$, —NR$^B$C(=O)N(R$^B$)$_2$, —NR$^B$C(=NR$^B$)N(R$^B$)$_2$, —OH, —OR$^A$, —SO$_2$R$^A$, —SO$_2$OR$^A$, —SO$_2$N(R$^B$)$_2$, —S(=O)R$^A$), —Si(R$^A$)$_3$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups.

In certain embodiments, nitrogen atom substituents, as described above, are also referred to as "amino protecting groups" or "nitrogen protecting groups". Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

Exemplary amino protecting groups include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Exemplary oxygen substituents, include, but are not limited to, $-C(=O)R^A$, $-CO_2R^A$, $-C(=O)-O-C(=O)R^A$, $-C(=O)SR^A$, $-C(=O)N(R^B)_2$, $-C(=O)NR^BSO_2R^A$, $-C(=NR^B)R^A$, $-C(=NR^B)OR^A$, $-C(=NR^B)N(R^B)_2$, $-C(=S)R^A$, $-C(=S)N(R^A)_2$, $-C(=S)SR^A$, $-SO_2R^A$, $-SO_2OR^A$, $-SO_2N(R^B)_2$, $-S(=O)R^A$, $-Si(R^A)_3$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups.

In certain embodiments, oxygen atom substituents, as described above, are also referred to as "hydroxyl protecting groups" or "oxygen protecting groups". Hydroxyl protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference.

Exemplary hydroxyl protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, N,N,N',N'-tetramethylphosphorodiamidate, N-phenylcarbamate, dimethylphosphinothioyl, 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In certain embodiments, a compound of the present invention is provided as a salt. Salts are well known in the art. For example, Berge et al., describe pharmaceutically acceptable salts in detail in *J. Pharmaceutical Sciences*, 1977, 66, 1-19, incorporated herein by reference. Salts of the compounds of this invention include those derived from suitable inorganic and organic acids and bases. Examples include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further salts include, when appropriate, ammonium, quaternary ammonium, and amine cations formed using counterions such as halide, hydroxide, carboxylate, sulfate, phosphate, nitrate, loweralkyl sulfonate and aryl sulfonate.

As used herein "inhibition," "inhibiting," and "inhibit", refer to the ability of a compound to reduce, slow, halt or prevent activity of a particular biological process in a cell relative to vehicle. In certain embodiments, the biological process is in vitro (e.g., cellular assay). In certain embodiments, the biological process is in vivo. In certain embodiments, a probe compound of the present invention inhibits a glycosyltransferase protein.

As used herein, the term "effective amount" refers to the amount of a substance, compound, molecule, agent or composition that elicits the relevant response in vitro or in vivo. For example, in the case of a probe compound of the present invention used in an assay of the present invention, an effective amount of probe compound is an amount of probe compound that elicits the desired response, e.g., binding to a desired protein.

The term "independently" is used herein to indicate that the groups can be identical or different.

The terms "labeled", "labeled with a detectable agent", and "labeled with a detectable moiety" are used herein interchangeably. "Label" and "detectable moiety" are also used interchangeably herein. When used in reference to a probe compound, these terms specify that the probe compound can be detected or visualized. In certain embodiments, a label is selected such that it generates a signal which can be measured and whose intensity is related to the amount of probe compound bound to a protein (e.g., in a sample). A label may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Labels suitable for use in the present invention may be detectable by any of a variety of means including, but not limited to, spectroscopic, photochemical, biochemical, immunochemical, electrical, optical or chemical means. Suitable labels include, but are not limited to, various ligands, radionuclides, fluorescent dyes, chemiluminescent agents, microparticles, enzymes, calorimetric labels, magnetic labels, and haptens.

The terms "fluorophore", "fluorescent moiety" and "fluorescent dye" are used herein interchangeably. They refer to a molecule which, in solution and upon excitation with light of appropriate wavelength, emits light back, generally at a longer wavelength. Numerous fluorescent dyes of a wide variety of structures and characteristics are suitable for use in the practice of the present invention. In choosing a fluorophore, it is often desirable that the molecule absorbs light and emits fluorescence with high efficiency (i.e., the fluorescent molecule has a high molar extinction coefficient at the excitation wavelength and a high fluorescence quantum yield, respectively) and is photostable (i.e., the fluorescent molecule does not undergo significant degradation upon light excitation within the time necessary to perform the detection). Examples of fluorescent labels include, but are not limited to: Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (e.g., BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), aminomethylcoumarin, carbocyanine, carboxyrhodamine 6G, carboxy-X- rhodamine (ROX), Cascade Blue, Cascade Yellow, coumarin, coumarin 343, cyanine dyes (e.g., Cy3, Cy5, Cy3.5, Cy5.5), dansyl, dapoxyl, dialkylaminocoumarin, 4',5'-dichloro-2',7'-dimethoxyfluorescein, DM-NERF, eosin, erythrosin, fluorescein, FAM, hydroxycoumarin, IRDyes (e.g., IRD40, IRD 700, IRD 800), JOE, lissamine rhodamine B, Marina Blue, merocyanine, methoxycoumarin, naphthofluorescein, Oregon Green 488, Oregon Green 500, Oregon Green 514, oxonol dyes, Pacific Blue, phycoerythrin, PyMPO, pyrene, rhodamine B, rhodamine 6G, rhodamine green, rhodamine red, rhodol green, styryl dyes, 2',4',5',7'-tetrabromosulfone-fluorescein, tetramethyl-rhodamine (TMR), carboxytetramethylrhodamine (TAMRA), Texas Red, Texas Red-X, 5(6)-carboxyfluorescein, 2,7-dichlorofluorescein, N,N-bis(2,4,6-trimethylphenyl)-3,4,9,10-perylenebis(dicarboximide), HPTS, ethyl eosin, DY-490XL MegaStokes, DY-485XL MegaStokes, Adirondack Green 520, ATTO 465, ATTO 488, ATTO 495, Y0Y0-1,5-FAM, BCECF, dichlorofluorescein, rhodamine 110, rhodamine 123, YO-PRO-I, SYTOX Green, Sodium Green, SYBR Green I, Alexa Fluor 500, FITC, Fluo-3, Fluo-4, fluoro-emerald, YoYo-I ssDNA, YoYo-I dsDNA, YoYo-I, SYTO RNASelect, Diversa Green-FP, Dragon Green, EvaGreen, Surf Green EX, Spectrum Green, Spectrum Red, NeuroTrace 500525, NBD-X, MitoTracker Green FM, LysoTracker Green DND-26, CBQCA, PA-GFP (post-activation), WEGFP (post-activation), FLASH-CCXXCC, Azami Green monomeric, Azami Green, green fluorescent protein (GFP), EGFP, Kaede Green, 7-benzylamino-4-nitrobenz-2-oxa-1,3-diazole, BexI, doxorubicin, Lumio Green, and SuperGlo GFP. For more examples of suitable fluorescent dyes and methods for coupling fluorescent dyes to other chemical entities see, for example, "The Handbook of Fluorescent Probes and Research Products", 9th Ed., Molecular Probes, Inc., Eugene, Oreg.

As used herein, the term "glycosyltransferase" refers to an enzyme that catalyzes transfer of a monosaccharide unit from an activated sugar (glycosyl donor) to a glycosyl acceptor molecule. In certain embodiments, a glycosyltransferase described herein is a peptidoglycan glycosyltransferase.

DETAILED DESCRIPTION OF CERTAIN EMBODIMENTS

Figure 1:
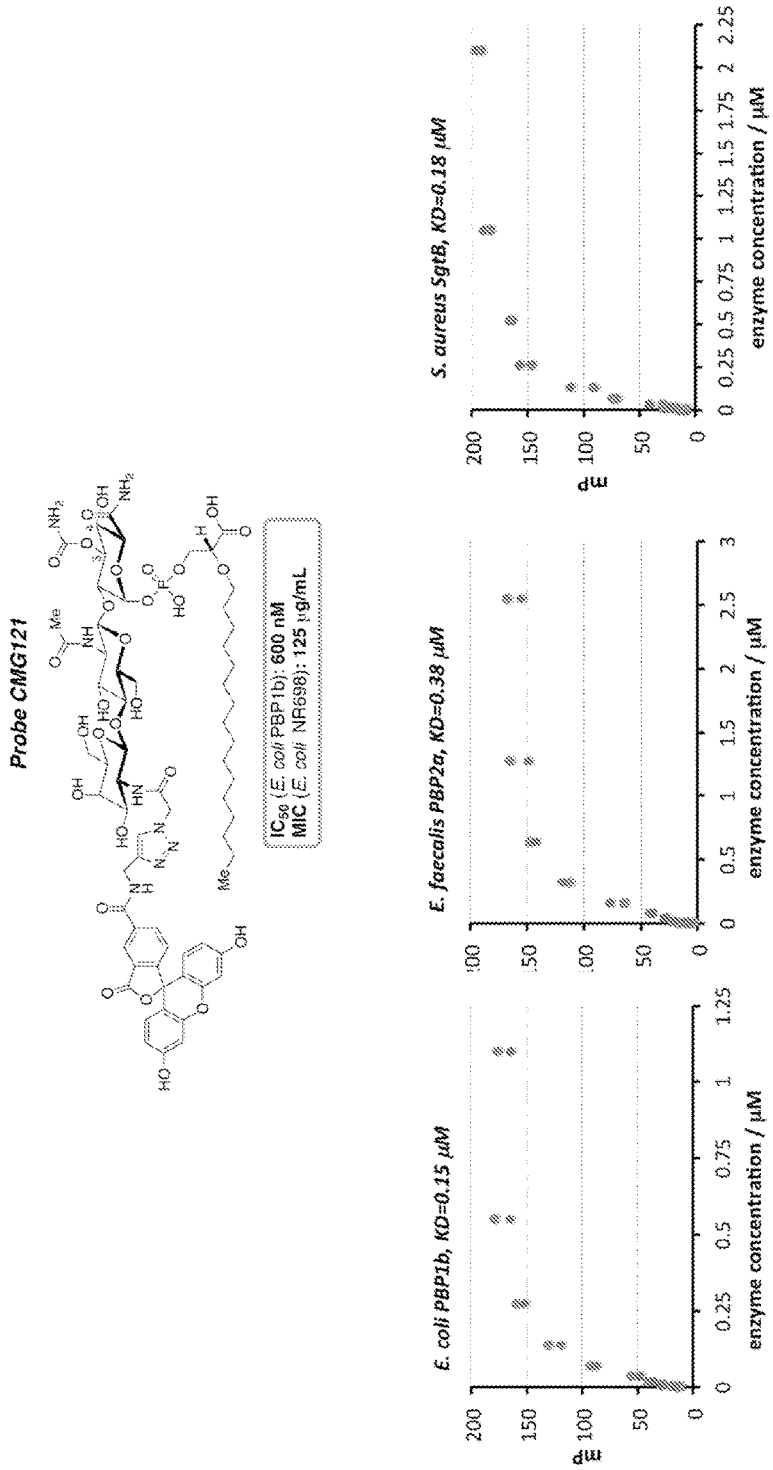
FIG. 1 shows titration of a probe compound of Formula (I) with the enzymes E. coli PBP1b, E. faecalis PBP2a, and S. aureus SgtB. Binding of the probe to the enzyme results in an increase in fluorescence polarization.
Figure 2:
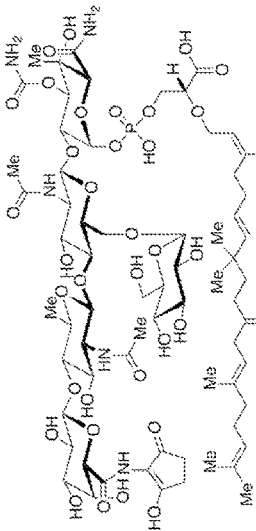
FIG. 2 depicts a decrease in fluorescence polarization of the probe compound when moenomycin A is added. This result indicates a displacement of the probe by moenomycin and suggests competition of both compounds for the same binding site on the enzyme.
Figure 2:
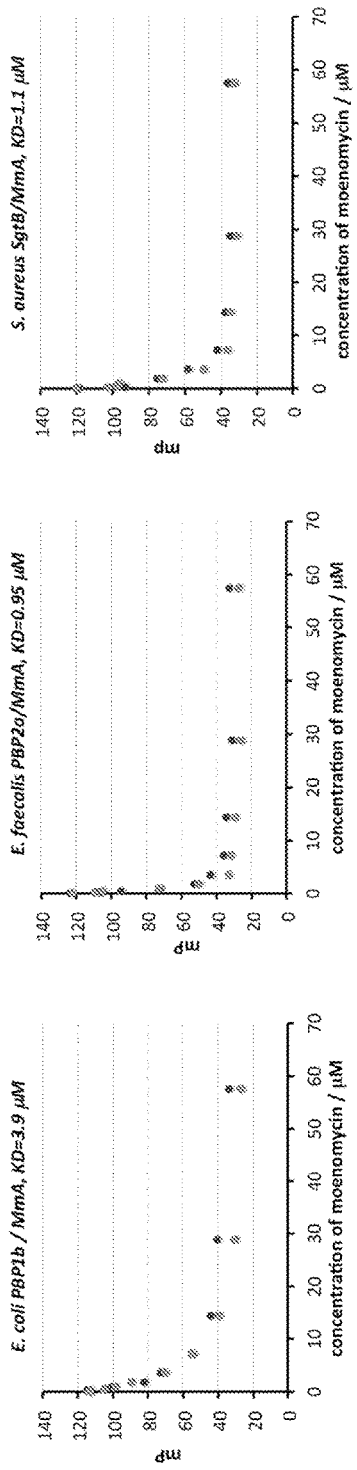
Figure 3:
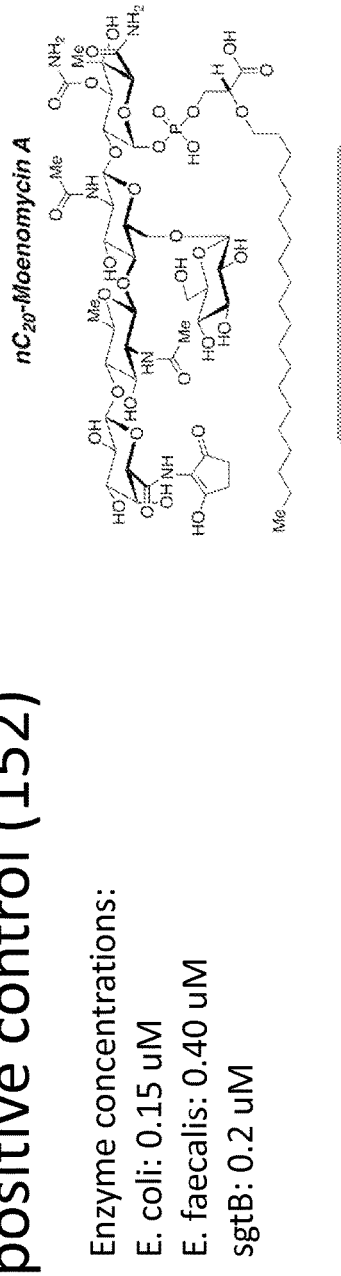
FIG. 3 depicts a decrease in fluorescence polarization of the probe compound when $nC_{20}$-moenomycin A is added and likewise indicates competitive displacement of the probe by $nC_{20}$-moenomycin A.
Figure 3:
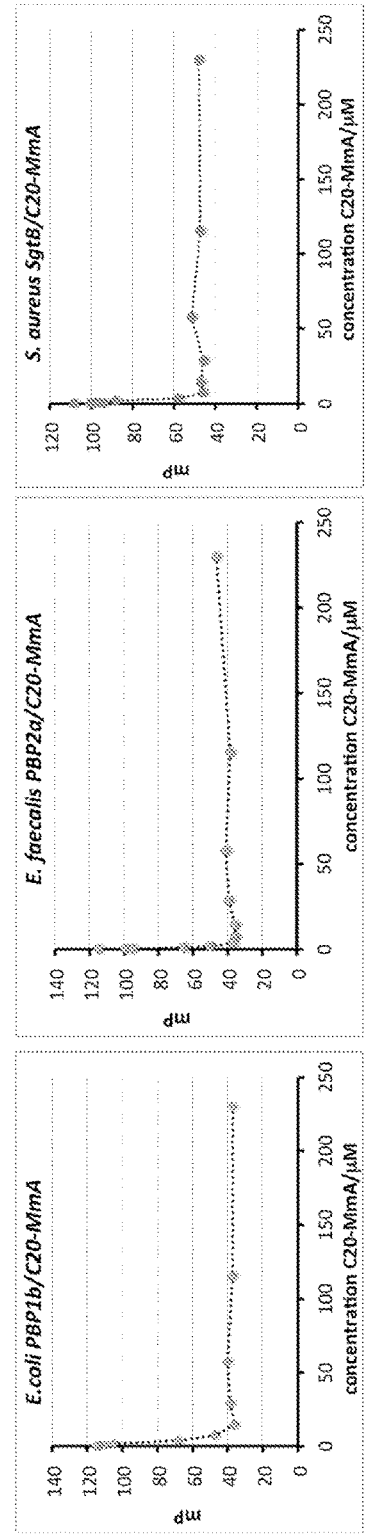
Figure 4:
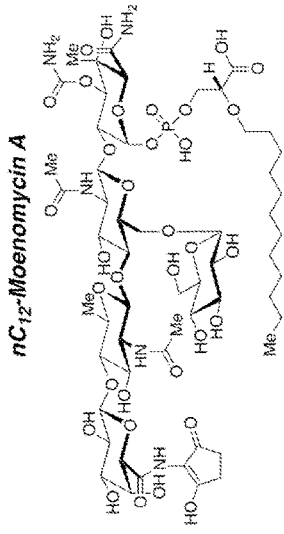
FIG. 4 depicts a decrease in fluorescence polarization of the probe compound when $nC_{12}$-moenomycin A is added.
Figure 4:
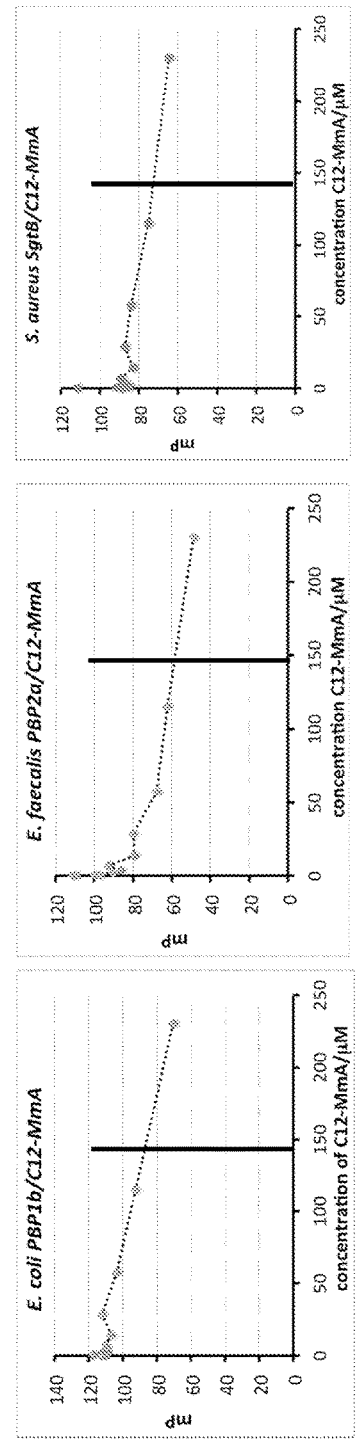
Figure 5:
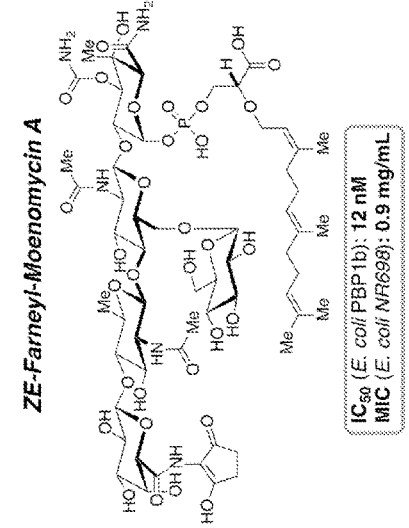
FIG. 5 depicts a decrease in fluorescence polarization of the probe compound when ZE-farnesyl-moenomycin A is added.
Figure 5:
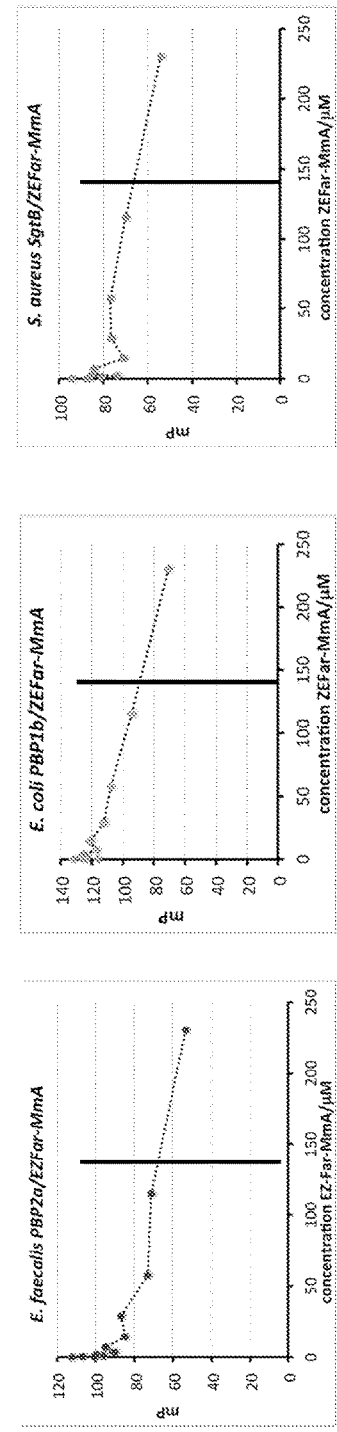
Figure 6:
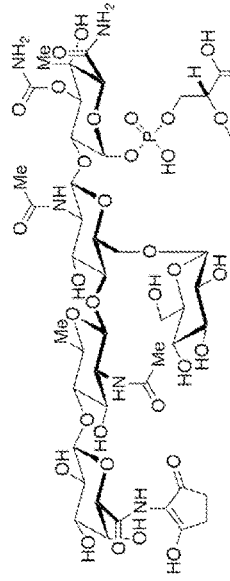
FIG. 6 depicts a decrease in fluorescence polarization of the probe compound when neryl-moenomycin A is added.
Figure 6:
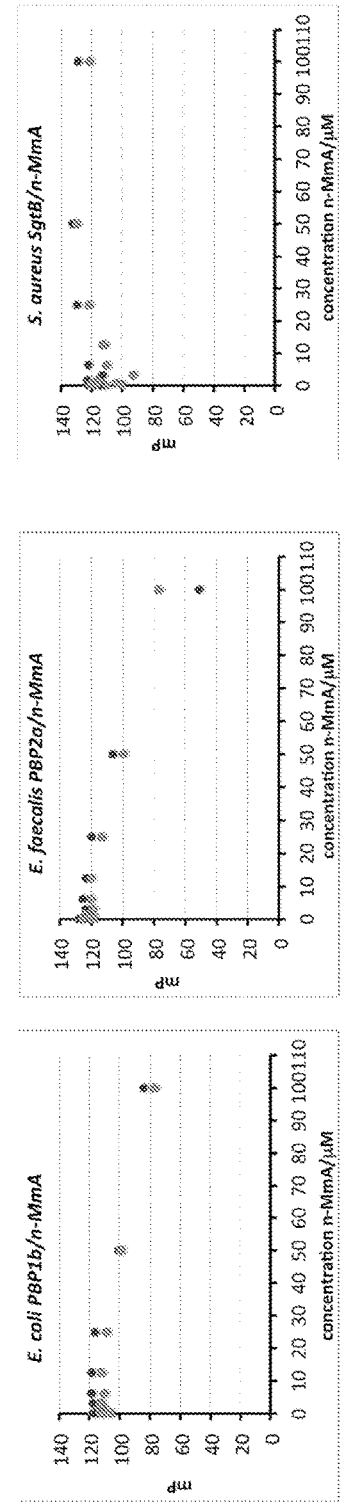
Figure 7:
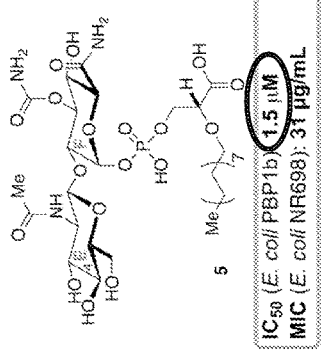
FIG. 7 depicts a decrease in fluorescence polarization of the probe compound when a disaccharide moenomcyin analog 5 (also disaccharide S15) is added. The disaccharide moenomycin analog exhibited a drastically reduced bioactivity compared with moenomycin A ($IC_{50}$ disaccharide E. coli PBP1b=1.5 µM; $IC_{50}$ moenomycin A E. coli PBP1b=12 nM) but was still able to displace the probe from the enzyme. This result suggests that compounds with low µM binding affinity can be successfully identify by the assays described herein.
Figure 7:
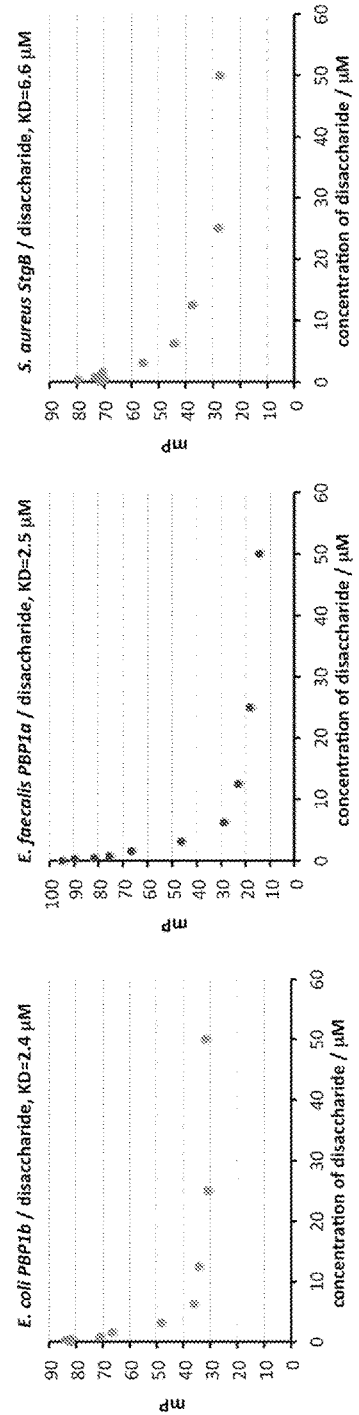
Figure 8:
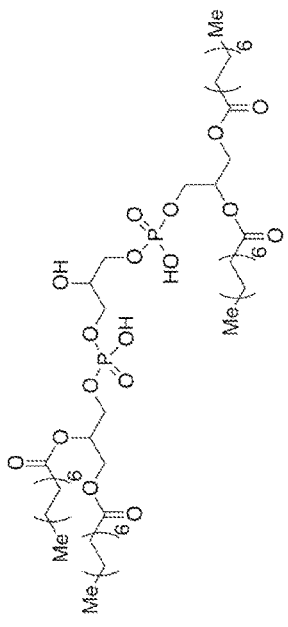
FIG. 8 depicts partial displacement of the probe compound with tetramystryl cardiolipin. Cardiolipin possesses structural similarity to both moenomycin A and probe compounds of Formula I in the phosphoglycerate portion of the molecules. This result confirms the importance of the phosphoglycerate unit in the binding of moenomycin to the target enzymes and shows that the assays described herein can identify non-saccharide compounds that are potential glycosyltransferase inhibitors.
Figure 8:
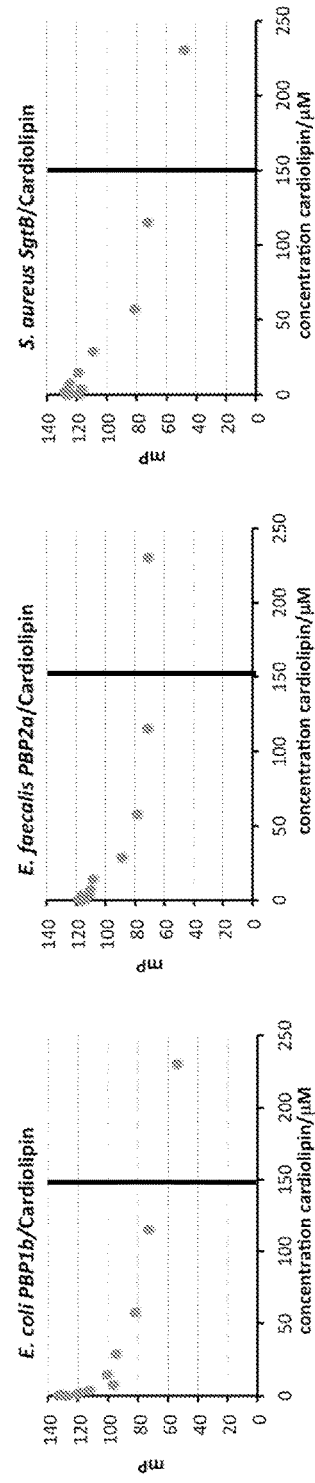
Figure 9:
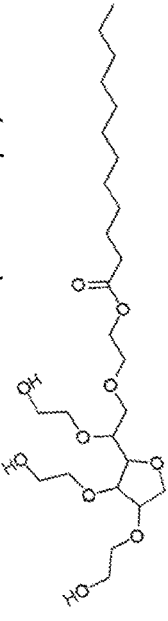
FIG. 9 shows that Tween-20 detergent does not displace the probe compound. This results shows that the assays described herein are selective for compounds that can compete with a probe compound described herein for binding to the active site of the enzyme, and that detergents do not generate false positives.
Figure 9:
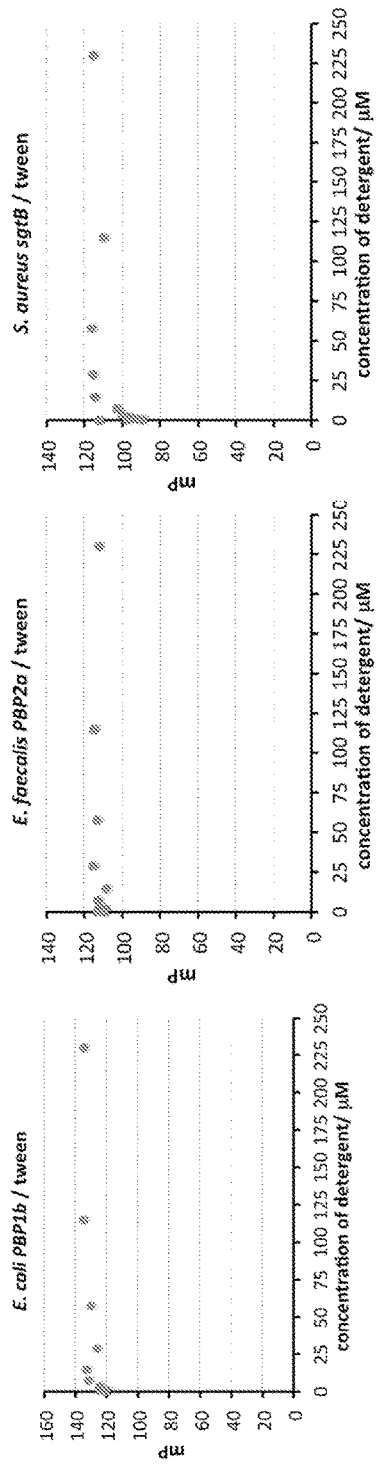
Figure 10:
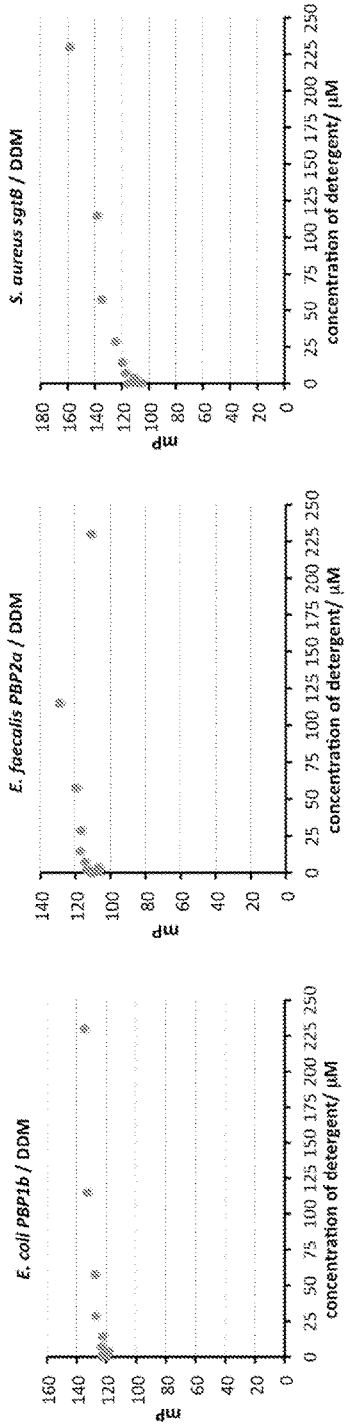
FIG. 10 shows that dodecyl-β-D-maltoside does not displace the probe compound. This result shows that the assays described herein are selective for compounds that can compete with a probe compound described herein for binding to the active site of the enzyme, and that detergents do not generate false positives.
Figure 10:
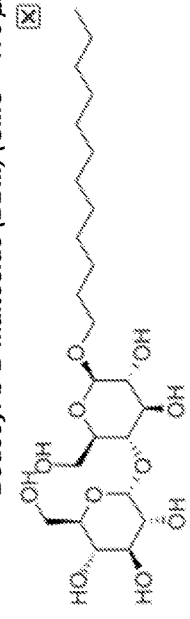
Figure 11:
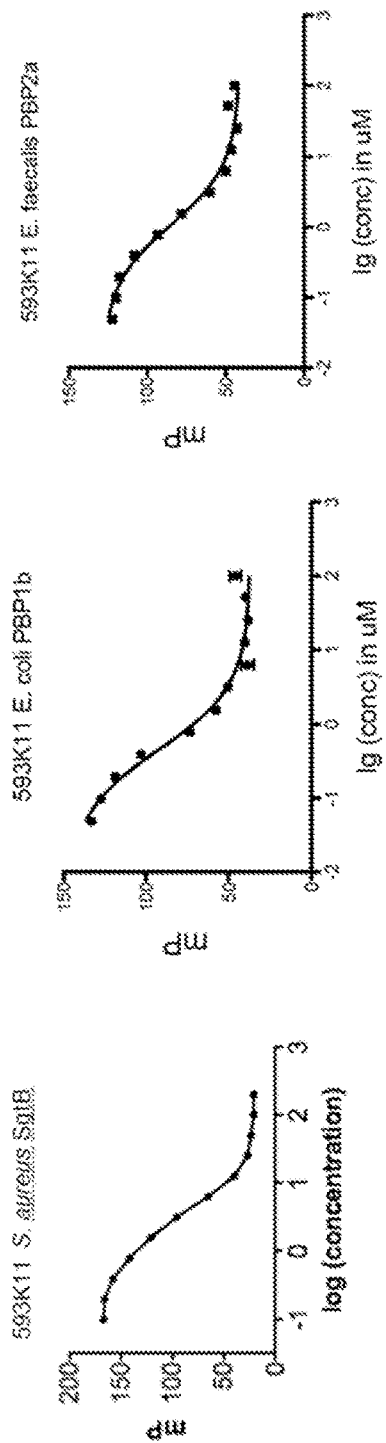
FIG. 11 shows treatment of the probe-PGT complex with 593K11 (75 nM S16, 10 mM TRIS pH=8, 100 mM NaCl, S. aureus ΔTM SgtB: 1.5 µM; E. coli PBP1b: 0.05 µM; E. faecalis PBP2a: 0.5 µM). $K_i$ (593K11 S. aureus SgtB)=2.6 µM, $K_i$ (593K11 E. coli PBP1b)=94 µM, $K_i$ (593K11 E. faecalis PBP2a)=0.90 µM.
Figure 12:
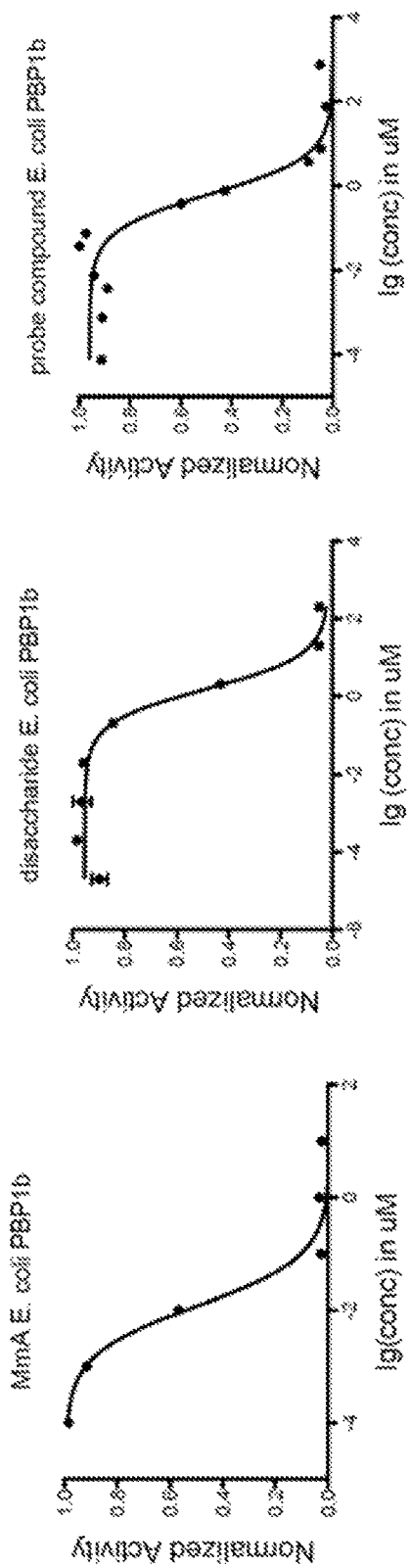
FIG. 12 shows dose-response curve for inhibition of PG formation by E. coli PBP1b (50 nM) from lipid II (4 µM). $IC_{50}$ were determined as follows: Moenomycin: 12.0 nM (left); disaccharide S15: 1.54 µM (middle); probe compound CMG12: 650 nM (right).
Figure 13:
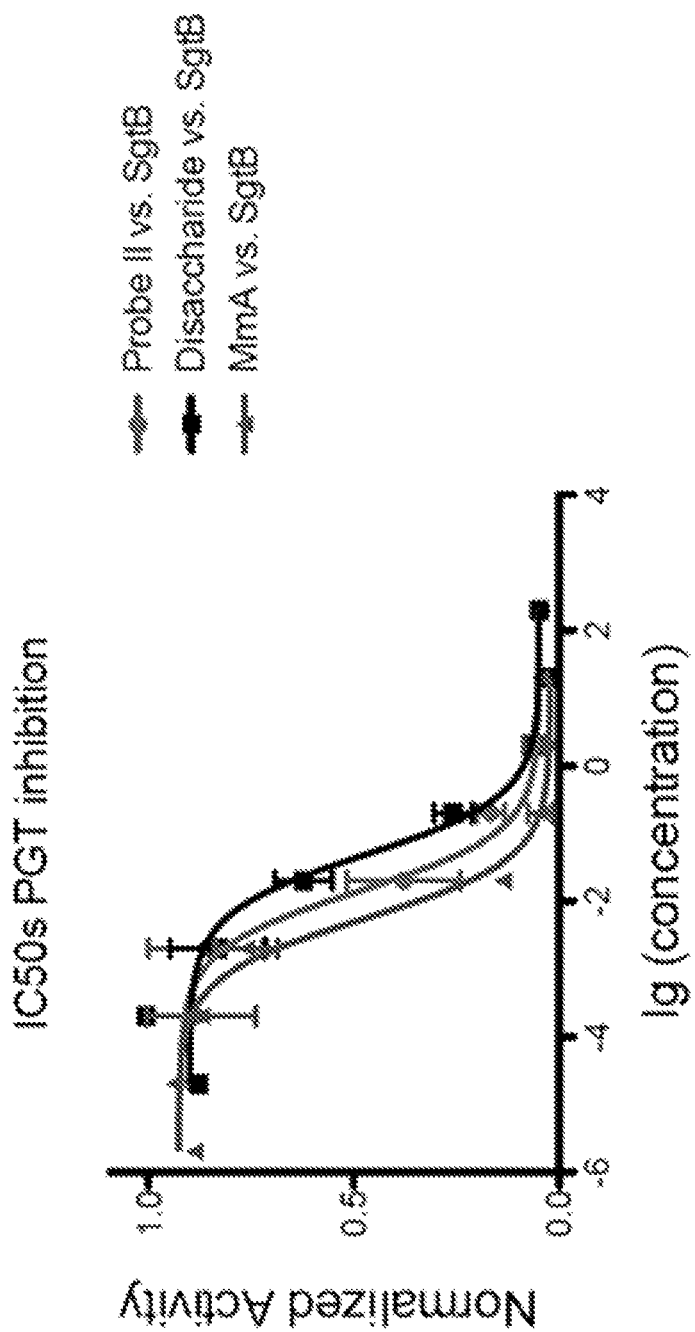
FIG. 13 shows dose-response curve for inhibition of PG formation by S. aureus SgtB (50 nM) from lipid II (4 µM). $IC_{50}$ were determined as follows: Moenomycin: 6.0 nM (blue); disaccharide S15: 48 nM (black); probe compound CMG121: 14 nM (red).
Figure 14:
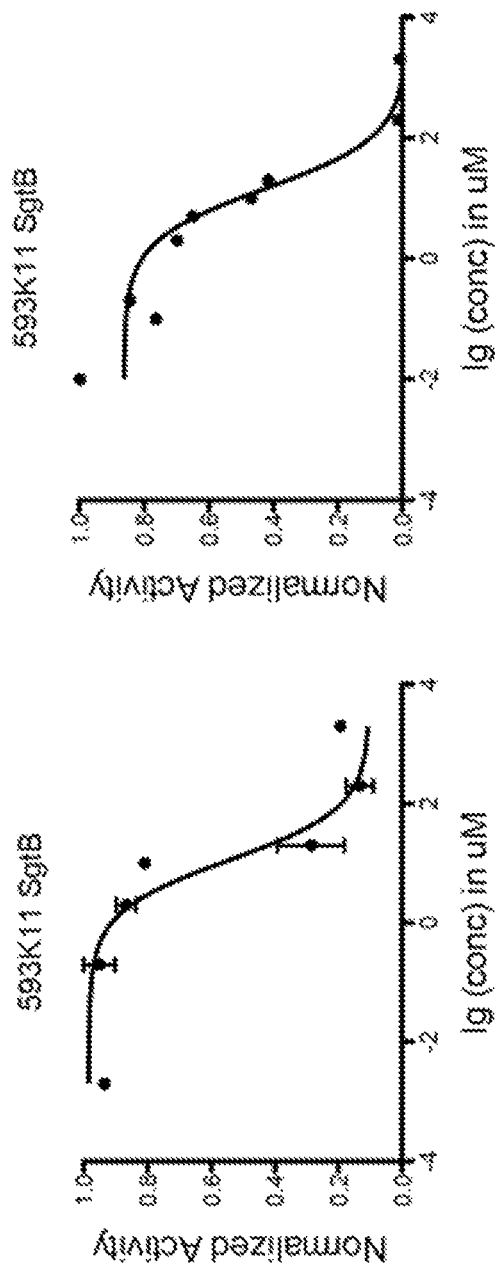
FIG. 14 shows dose-response curve for inhibition of PG formation by S. aureus SgtB (50 nM) from lipid II (4 µM). $IC_{50}$ for compound 593K11 were determined in independent experiments as 11.3 µM (left) and 14.4 µM (right).
Figure 15:
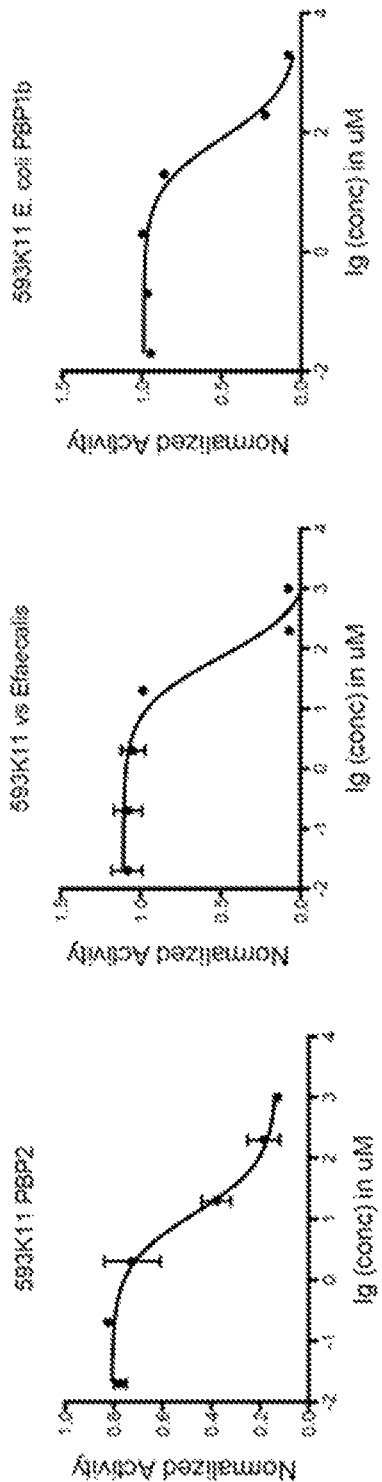
FIG. 15 shows dose-response curves for in vitro inhibition of PGTs (1.2 µM S. aureus PBP2, 50 nM E. faecalis PBP2a, 50 nM E. coli PBP1b, 4 µM lipid II). $IC_{50}$ (593K11 S. aureus PBP2)=12.0 µM; $IC_{50}$ (593K11 E. faecalis PBP2a)=70 µM; $IC_{50}$ (593K11 E. coli PBP1b)=79 µM.

The present invention provides methods and compositions for identifying inhibitors of glycosyltransferases, e.g., peptidoglycan glycosyltransferases. In one aspect, the present invention provides assays for glycosyltransferase inhibitors. In another aspect, the present invention provides moenomycin-based probe compounds for use in such assays. In another aspect, the present invention provides kits comprising one or more moenomycin-based probe compounds as described herein.

Probe Compounds

Moenomycin A is a natural product that inhibits peptidoglycan biosynthesis by binding to bacterial transglycosylases. Moenomycin A is a thousand times more potent than the antibiotic vancomycin, but poor pharmacokinetic properties related to the lipid side chain have prevented its use in humans. Removal of the natural lipid side chain completely abolishes biological activities. A comprehensive study of the effect of different side chains, optionally in combination with different sugar portions, on the anti-bacterial activity compared to natural moenomycin A, has been limited as most synthetic transformations employed in the removal of the natural lipid side chain and in the addition of other different side chains have also altered other structural features of the molecule. Recently, biosynthetic and semi-synthetic methodologies were disclosed which enabled SAR study of new moenomycins; e.g., see PCT Application Publication Nos. WO 2008/021367 and WO 2009/046314, incorporated herein by reference. In the '314 publication, the inventors explored groups of intermediate length and hydrophobicity, e.g., C15-farnesyl, in an effort to explore the optimal length for activity and bioavailability. The inventors have also found that groups with lengths greater than $C_{15}$, chains substituted with halogen atoms, and chains comprising multiple aryl moieties, provide potent anti-bacterial compounds; see U.S. Provisional Patent Application entitled "Moenomycin A Analogs, Methods of Synthesis, and Uses Thereof," filed on the same day as the present application and incorporated herein by reference. The inventors have also discovered new enzymatic methods for synthesizing moenomycin analogs; see U.S. Provisional Patent Application entitled "Chemoenzymatic Methods for Synthesizing Moenomycin Analogs," filed on the same day as the present application and incorporated herein by reference. The present invention provides probe compounds based on moenomycin for use in screening compounds that bind to bacterial glycosyltransferases.

In certain embodiments, the present invention provides a moenomcyin analog labeled with a detectable moiety. Such compounds are described herein as "probe compounds." In certain embodiments, the detectable moiety is fluorescent. The detectable moiety can be attached to the moenomycin analog, optionally through a linker, anywhere on the compound (e.g., on one of the saccharides, on the phosphoglycerate linker, or on the lipid tail). The probe compound may be moenomycin A labeled with a detectable moiety, or it may be an analog of moenomycin.

In certain embodiments, a probe compound of the present invention is a compound of Formula (I):

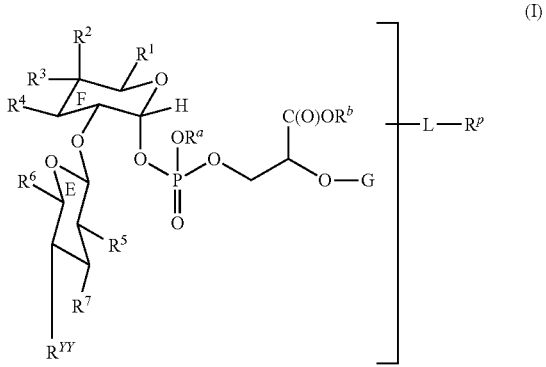

(I)

or a salt thereof, wherein $R^1$ is hydrogen, —C(O)NHR$^8$, —CH$_2$OR$^9$, or —C(O)OR$^9$;

$R^2$ and $R^3$ are independently hydrogen, optionally substituted aliphatic, —OR$^9$, —N(R$^8$)$_2$, or —C(O)NHR$^8$;

$R^4$ is hydrogen or —WR$^{4a}$;

W is —O— or —NH—;

$R^{4a}$ is hydrogen, a hydroxyl protecting group, optionally substituted aliphatic, —C(O)R$^{10}$, —C(O)NHR$^8$, —C(=NR$^8$)NHR$^8$, or —C(O)OR$^9$;

$R^5$ is hydrogen or —NHR$^8$;

$R^6$ is hydrogen, —CH$_3$, —CH$_2$OR$^9$, or —CH$_2$OR$^{CX}$; wherein R$^{CX}$ is a carbohydrate moiety;

$R^7$ is hydrogen, —OR$^9$, or —N(R$^8$)$_2$;

each $R^8$ is independently hydrogen, an amino protecting group, —C(O)R$^{10}$, optionally substituted aliphatic, optionally substituted aryl, optionally substituted heterocyclyl, or optionally substituted heteroaryl, or two R$^8$ groups on the same nitrogen may be taken together to form optionally substituted heterocyclyl;

each $R^9$ is independently hydrogen, a hydroxyl protecting group, —C(O)R$^{10}$, optionally substituted aliphatic, optionally substituted aryl, optionally substituted heterocyclyl, or optionally substituted heteroaryl;

each $R^{10}$ is independently optionally substituted aliphatic, optionally substituted heterocyclic, optionally substituted aryl, or optionally substituted heteroaryl;

$R^a$ and $R^b$ are independently hydrogen or a hydroxyl protecting group;

G is an optionally substituted $C_{1-30}$ aliphatic group, wherein 0 to 10 methylene units are optionally replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene; wherein each instance of R$^x$ is independently hydrogen, optionally substituted aliphatic, optionally substituted heterocyclyl, optionally substituted aryl, optionally substituted heteroaryl; or G is a group of Formula (a), (b), or (c):

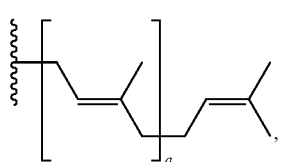

(a)

wherein a is 3, 4, or 5;

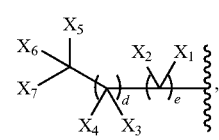

(b)

wherein
X$_1$, X$_2$, X$_3$, X$_4$, X$_5$, X$_6$, and X$_7$ are each independently hydrogen or halogen;
d is an integer between 1 and 25, inclusive; and
e is an integer of between 2 and 25, inclusive;
provided the sum of d and e is greater than 16; or

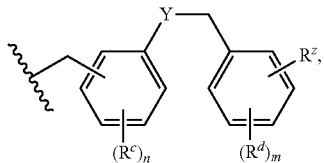
(c)

wherein
Y is —O—, —S—, —NR$^Y$—, or an optionally substituted methylene group, wherein R$^Y$ is hydrogen, optionally substituted aliphatic, or an amino protecting group;
each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring;
each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring;
R$^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring;
each instance of n is, independently, 0, 1, 2, 3, or 4;
each instance of m is, independently, 0, 1, 2, 3, or 4; and
x is 1, 2, 3, 4, 5, or 6;
R$^{YY}$ is hydrogen or —OR$^{XX}$;
R$^{XX}$ is hydrogen, a hydroxyl protecting group, or a group of formula:

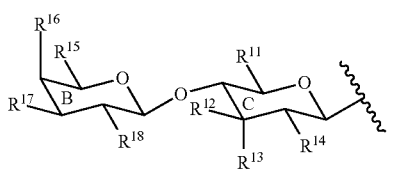 or

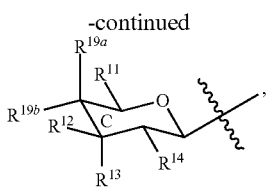

wherein
R$^{11}$ is hydrogen, optionally substituted aliphatic, —C(O)NHR$^8$, —CH$_2$OR$^9$, or —C(O)OR$^9$;
R$^{12}$ and R$^{13}$ are independently hydrogen, optionally substituted aliphatic, —OR$^9$, N(R$^8$)$_2$, or —C(O)NHR$^8$;
R$^{14}$ is hydrogen or —NHR$^8$;
R$^{15}$ is hydrogen, —C(O)NHR$^8$, —CH$_2$OR$^9$, or —C(O)OR$^9$;
R$^{16}$ is hydrogen or —OR$^9$;
R$^{17}$ is hydrogen or —OR$^9$;
R$^{18}$ is hydrogen or —OR$^9$;
R$^{19a}$ is hydrogen or —OR$^9$;
R$^{19b}$ is hydrogen or —OR$^9$;
wherein a hydrogen radical on the compound of Formula (I) is replaced with -L-R$^P$;
L is a covalent bond, —NR$^y$—, —N(R$^y$)C(O)—, —N(R$^y$)C(O)N(R$^y$)—, —N(R$^y$)C(S)N(R$^y$)—, —C(O)N(R$^y$)—, —N(R$^y$)SO$_2$—, —SO$_2$N(R$^y$)—, —O—, —C(O)—, —OC(O)—, —C(O)O—, —S—, —SO—, —SO$_2$—, optionally substituted cycloalkylene, optionally substituted heterocyclylene, optionally substituted arylene, optionally substituted heteroarylene, or an optionally substituted aliphatic linker, wherein one or more methylene units of the aliphatic linker are optionally replaced by —NR$^y$—, —N(R$^y$)C(O)—, —N(R$^y$)C(O)N(R$^y$)—, —N(R$^y$)C(S)N(R$^y$)—, —C(O)N(R$^y$)—, —N(R$^y$)SO$_2$—, —SO$_2$N(R$^y$)—, —O—, —C(O)—, —OC(O)—, —C(O)O—, —S—, —SO—, —SO$_2$—, cycloalkylene, heterocyclylene, arylene, or heteroarylene;
wherein R$^Y$ is hydrogen, C$_{1-6}$ alkyl, or —C(O)C$_{1-6}$ alkyl; and
R$^P$ is a detectable moiety.

In some embodiments, for Formula (I), R$^1$ is —C(O)NHR$^8$, —CH$_2$OR$^9$, or —C(O)OR$^9$; one of R$^2$ and R$^3$ is hydrogen, and the other is —OR$^9$; R$^4$ is —W—R$^{4a}$; R$^5$ is —NHR$^8$; R$^6$ is —CH$_3$, —CH$_2$OR$^9$, or —CH$_2$OR$^{CX}$; R$^7$ is —OR$^9$ or —N(R$^8$)$_2$; R$^{11}$ is —CH$_3$, —C(O)NHR$^8$, —CH$_2$OR$^9$, or —C(O)OR$^9$; one of R$^{12}$ and R$^{13}$ is hydrogen, and the other is —OR$^9$; R$^{14}$ is —NHR$^8$; R$^{15}$ is —C(O)NHR$^8$, —CH$_2$OR$^9$, or —C(O)OR$^9$; R$^{16}$ is —OR$^9$; R$^{17}$ is —OR$^9$; R$^{18}$ is —OR$^9$; and one of R$^{19a}$ and R$^{19b}$ is hydrogen, and the other is —OR$^9$.

In some embodiments, when R$^{YY}$ is —OH, a probe compound according to the present invention is of Formula (Ia):

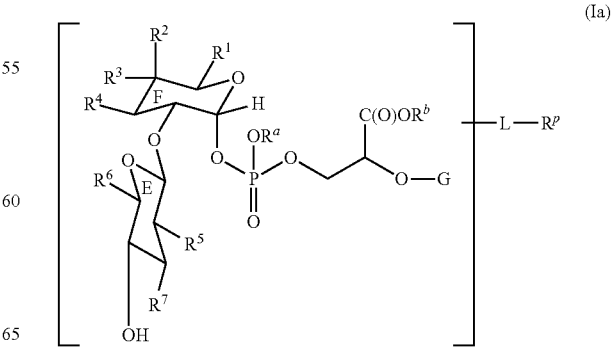
(Ia)

or a salt thereof, wherein $R^1$, $R^2$, $R^3$, $R^4$, $R^5$, $R^6$, $R^7$, $R^a$, $R^b$, G, L, and $R^P$ are as described herein. In some embodiments, for Formula (Ia), $R^1$ is —C(O)NHR$^8$, —CH$_2$OR$^9$, or —C(O)OR$^9$; one of $R^2$ and $R^3$ is hydrogen, and the other is —OR$^9$; $R^4$ is —W—R$^{4a}$; $R^5$ is —NHR$^8$; $R^6$ is —CH$_3$, —CH$_2$OR$^9$, or —CH$_2$OR$^{CX}$; and $R^7$ is —OR$^9$ or —N(R$^8$)$_2$.

In some embodiments, when $R^{XX}$ is

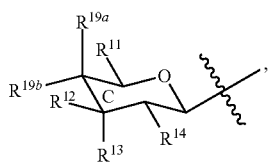

a probe compound according to the present invention is of Formula (Ib):

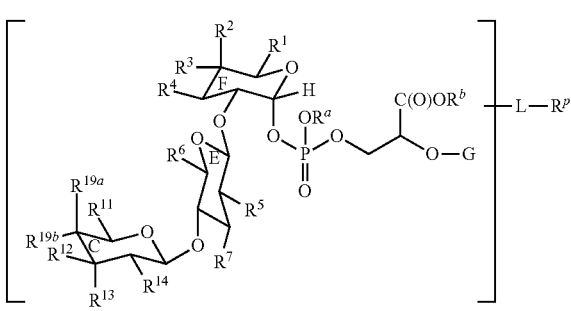

or a salt thereof, wherein $R^1$, $R^2$, $R^3$, $R^4$, $R^5$, $R^6$, $R^7$, $R^{11}$, $R^{12}$, $R^{13}$, $R^{14}$, $R^{19a}$, $R^{19b}$, $R^a$, $R^b$, G, L, and $R^P$ are as described herein. In some embodiments, for Formula (Ib), $R^1$ is —C(O)NHR$^8$, —CH$_2$OR$^9$, or —C(O)OR$^9$; one of $R^2$ and $R^3$ is hydrogen, and the other is —OR$^9$; $R^4$ is —W—R$^{4a}$; $R^5$ is —NHR$^8$; $R^6$ is —CH$_3$, —CH$_2$OR$^9$, or —CH$_2$OR$^{CX}$; $R^7$ is —OR$^9$ or —N(R$^8$)$_2$; $R^{11}$ is —CH$_3$, —C(O)NHR$^8$, —CH$_2$OR$^9$, or —C(O)OR$^9$; one of $R^{12}$ and $R^{13}$ is hydrogen, and the other is —OR$^9$; $R^{14}$ is —NHR$^8$; and one of $R^{19a}$ and $R^{19b}$ is hydrogen, and the other is —OR$^9$.

In some embodiments, when $R^{XX}$ is

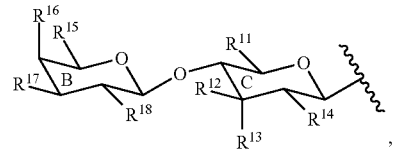

a probe compound according to the present invention is of Formula (Ic):

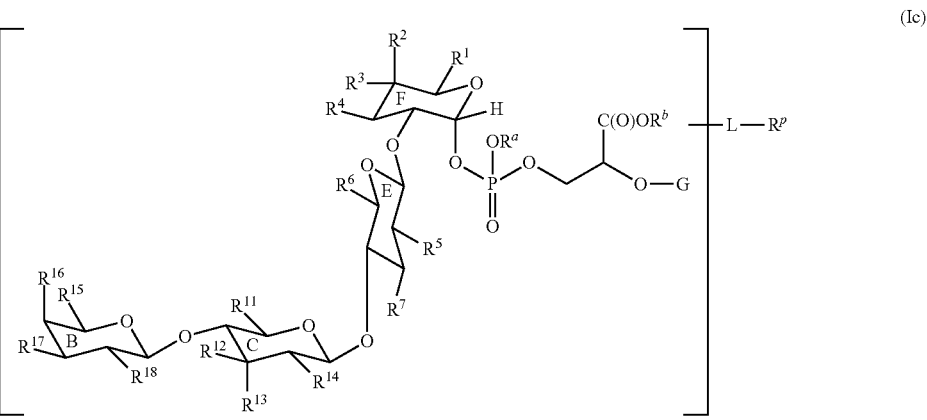

or a salt thereof, wherein $R^1$, $R^2$, $R^3$, $R^4$, $R^5$, $R^6$, $R^7$, $R^{11}$, $R^{12}$, $R^{13}$, $R^{14}$, $R^{15}$, $R^{16}$, $R^{17}$, $R^{18}$, $R^a$, $R^b$, G, L, and $R^P$ are as described herein. In some embodiments, for Formula (Ic), $R^1$ is —C(O)NHR$^8$, —CH$_2$OR$^9$, or —C(O)OR$^9$; one of $R^2$ and $R^3$ is hydrogen, and the other is —OR$^9$; $R^4$ is —W—R$^{4a}$; $R^5$ is —NHR$^8$; $R^6$ is —CH$_3$, —CH$_2$OR$^9$, or —CH$_2$OR$^{CX}$; $R^7$ is —OR$^9$ or —N(R$^8$)$_2$; $R^1$ is —CH$_3$, —C(O)NHR$^8$, —CH$_2$OR$^9$, or —C(O)OR$^9$; one of $R^{12}$ and $R^{13}$ is hydrogen, and the other is —OR$^9$; $R^{14}$ is —NHR$^8$; $R^{15}$ is —C(O)NHR$^8$, —CH$_2$OR$^9$, or —C(O)OR$^9$; $R^{16}$ is —OR$^9$; $R^{17}$ is —OR$^9$; and $R^{18}$ is —OR$^9$.

In some embodiments, when $R^6$ is —CH$_2$OR$^{CX}$; wherein $R^{CX}$ is of formula:

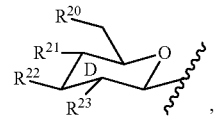

a probe compound according to the present invention is of Formula (Id):

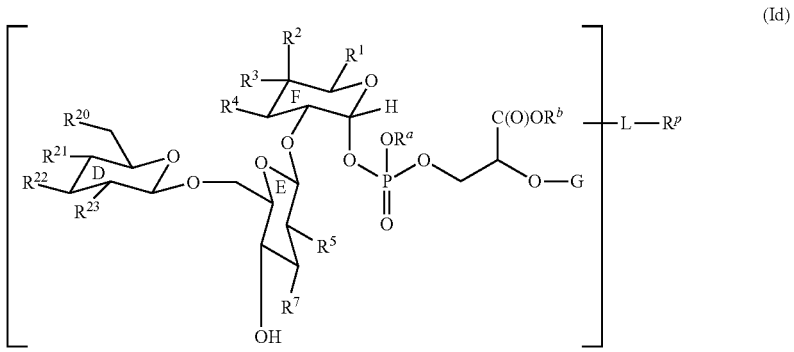

(Id)

or a salt thereof, wherein $R^1$, $R^2$, $R^3$, $R^4$, $R^5$, $R^7$, $R^{20}$, $R^{21}$, $R^{22}$, $R^{23}$, $R^a$, $R^b$, G, L, and $R^p$ are as described herein. In some embodiments, for Formula (Id), $R^1$ is —C(O)NHR$^8$, —CH$_2$OR$^9$, or —C(O)OR$^9$; one of $R^2$ and $R^3$ is hydrogen, and the other is —OR$^9$; $R^4$ is —W—R$^{4a}$; $R^5$ is —NHR$^8$; $R^7$ is —OR$^9$ or —N(R$^8$)$_2$; $R^1$ is —CH$_3$, —C(O)NHR$^8$, —CH$_2$OR$^9$, or —C(O)OR$^9$; $R^{20}$ is —OR$^9$; $R^{21}$ is —OR$^9$; $R^{22}$ is —OR$^9$; and $R^{23}$ is —OR$^9$ In some embodiments, a probe compound according to the present invention is of Formula (Ie):

are as described herein. In some embodiments, for Formula (Ie), $R^1$ is —C(O)NHR$^8$, —CH$_2$OR$^9$, or —C(O)OR$^9$; one of $R^2$ and $R^3$ is hydrogen, and the other is —OR$^9$; $R^4$ is —W—R$^{4a}$; $R^5$ is —NHR$^8$; $R^7$ is —OR$^9$ or —N(R$^8$)$_2$; $R^{11}$ is —CH$_3$, —C(O)NHR$^8$, —CH$_2$OR$^9$, or —C(O)OR$^9$; one of $R^{12}$ and $R^{13}$ is hydrogen, and the other is —OR$^9$; $R^{14}$ is —NHR$^8$; one of $R^{19a}$ and $R^{19b}$ is hydrogen, and the other is —OR$^9$; $R^{20}$ is —OR$^9$; $R^{21}$ is —OR$^9$; $R^{22}$ is —OR$^9$; and $R^{23}$ is —OR$^9$.

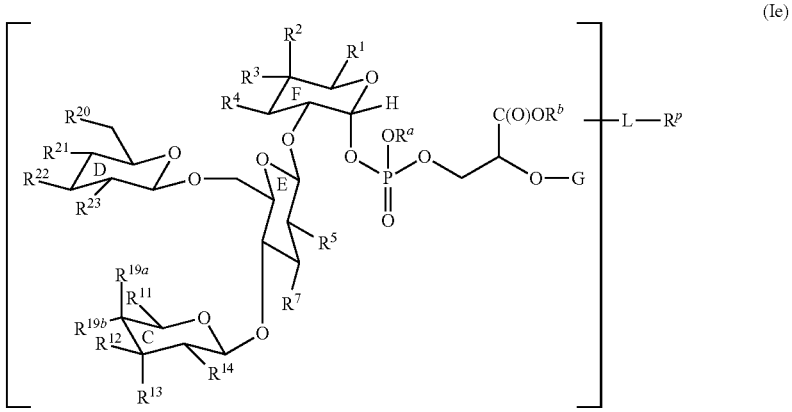

(Ie)

or a salt thereof, wherein $R^1$, $R^2$, $R^3$, $R^4$, $R^5$, $R^7$, $R^{11}$, $R^{12}$, $R^3$, $R^{14}$, $R^{19a}$, $R^{19b}$, $R^{20}$, $R^{21}$, $R^{22}$, $R^{23}$, $R^a$, $R^b$, G, L, and $R^p$ In some embodiments, a probe compound according to the present invention is of Formula (If):

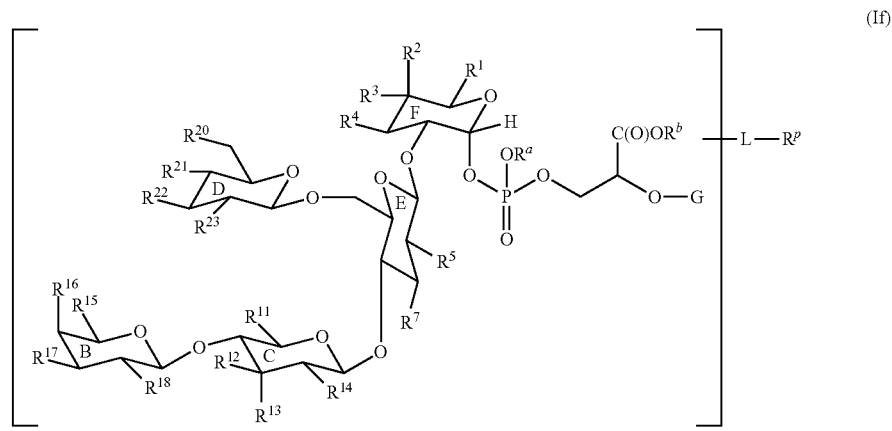

(If)

or a salt thereof, wherein $R^1$, $R^2$, $R^3$, $R^4$, $R^5$, $R^7$, $R^{11}$, $R^{12}$, $R^{13}$, $R^{14}$, $R^{15}$, $R^{16}$, $R^{17}$, $R^{18}$, $R^{20}$, $R^{21}$, $R^{22}$, $R^{23}$, $R^a$, $R^b$, G, L, and $R^p$ are as described herein. In some embodiments, for Formula (If), $R^1$ is —C(O)NHR$^8$, —CH$_2$OR$^9$, or —C(O)OR$^9$; one of $R^2$ and $R^3$ is hydrogen, and the other is —OR$^9$; $R^4$ is —W—R$^{4a}$; $R^5$ is —NHR$^8$; $R^7$ is —OR$^9$ or —N(R$^8$)$_2$; $R^{11}$ is —CH$_3$, —C(O)NHR$^8$, —CH$_2$OR$^9$, or —C(O)OR$^9$; one of $R^{12}$ and $R^{13}$ is hydrogen, and the other is —OR$^9$; $R^{14}$ is —NHR$^8$; $R^{15}$ is —C(O)NHR$^8$, —CH$_2$OR$^9$, or —C(O)OR$^9$; $R^{16}$ is —OR$^9$; $R^{17}$ is —OR$^9$; $R^{18}$ is —OR$^9$; $R^{20}$ is —OR$^9$; $R^{21}$ is —OR$^9$; $R^{22}$ is —OR$^9$; and $R^{23}$ is —OR$^9$ In some embodiments, a compound of Formula (I) is not of Formula (If).

In some embodiments, a compound of Formula (I) is not of formula:

As defined generally above, $R^1$ is hydrogen, —C(O)NHR$^8$, —CH$_2$R$^9$, or —C(O)OR$^9$; wherein $R^8$ is hydrogen, an amino protecting group, —C(O)R$^{10}$, optionally substituted aliphatic, optionally substituted aryl, optionally substituted heterocyclyl, or optionally substituted heteroaryl, or two $R^8$ groups on the same nitrogen may be taken together to form an optionally substituted heterocyclyl; and $R^9$ is hydrogen, a hydroxyl protecting group, —C(O)R$^{10}$, optionally substituted aliphatic, optionally substituted aryl, optionally substituted heterocyclyl, or optionally substituted heteroaryl. In some embodiments, $R^1$ is —C(O)NHR$^8$. In certain embodiments, $R^1$ is —C(O)NH$_2$. In certain embodiments, $R^1$ is —C(O)NH(alkyl). In some embodiments, $R^1$ is —CH$_2$OR$^9$. In certain embodiments, $R^1$ is —CH$_2$OH. In certain embodiments, $R^1$ is —CH$_2$O(protecting group) or

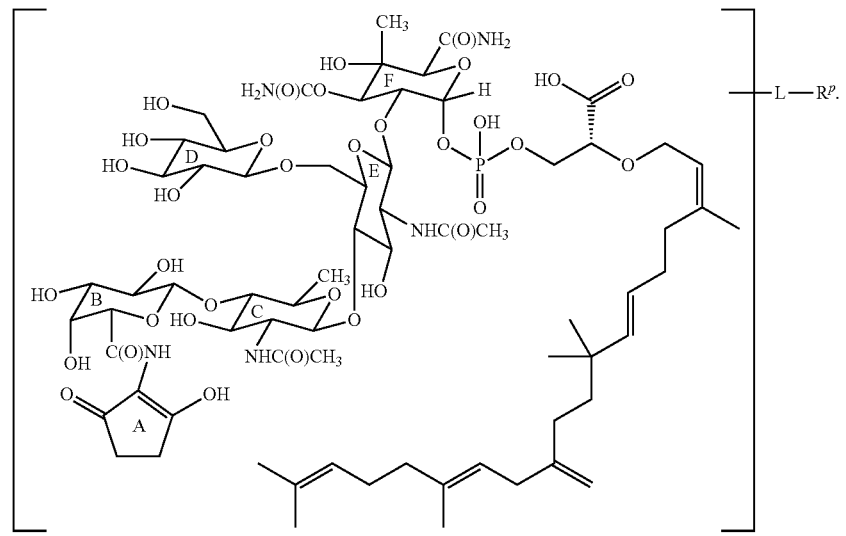

In some embodiments, a compound of Formula (I) is not

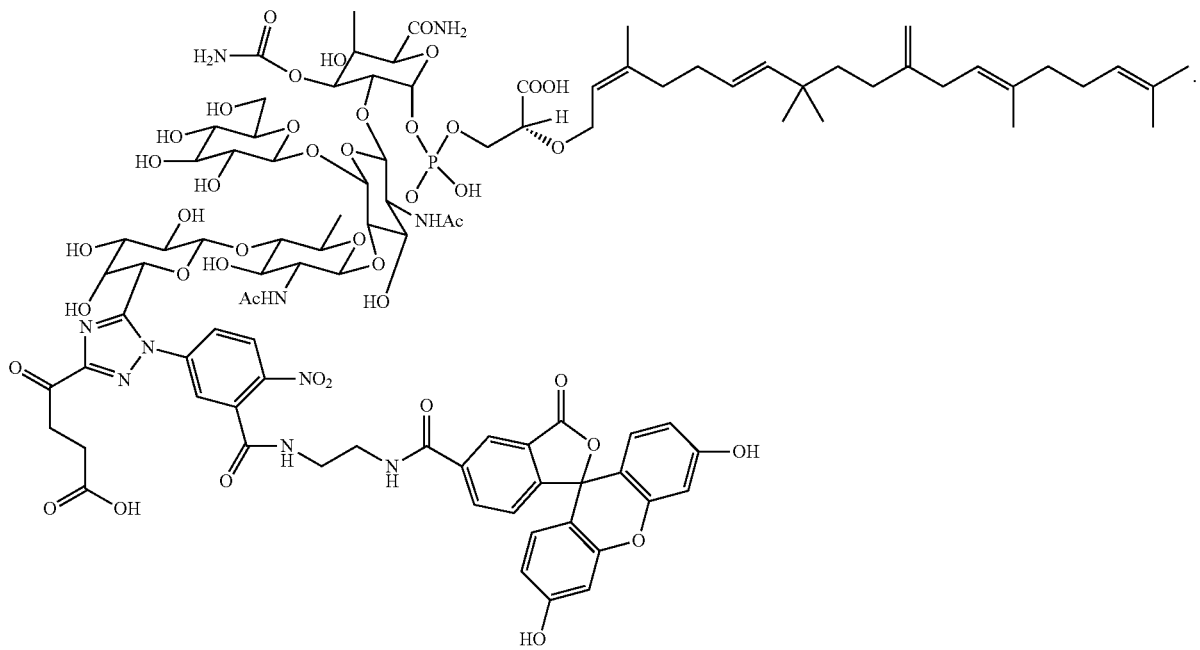

—CH$_2$O(alkyl). In some embodiments, R$^1$ is —C(O)OR$^9$. In certain embodiments, R$^1$ is —CO$_2$H.

As defined generally above, R$^2$ is hydrogen, optionally substituted aliphatic, —OR$^9$, —N(R$^8$)$_2$, or —C(O)NHR$^8$. In some embodiments, R$^2$ is hydrogen. In some embodiments, R$^2$ is optionally substituted aliphatic. In certain embodiments, R$^2$ is C$_{1-6}$ alkyl. In certain embodiments, R$^2$ is methyl. In some embodiments, R$^2$ is —OR$^9$. In certain embodiments, R$^2$ is —OH. In certain embodiments, R$^2$ is —O(alkyl) or —O(protecting group). In some embodiments, R$^2$ is —N(R$^8$)$_2$. In certain embodiments, R$^2$ is —NH$_2$. In certain embodiments, R$^2$ is —NH(alkyl) or —NH(protecting group). In some embodiments, R$^2$ is —C(O)NHR$^8$. In certain embodiments, R$^2$ is —C(O)NH$_2$. In certain embodiments, R$^2$ is —C(O)NH(alkyl).

As defined generally above, R$^3$ is hydrogen, optionally substituted aliphatic, —OR$^9$, —N(R$^8$)$_2$, or —C(O)NHR$^8$. In some embodiments, R$^3$ is hydrogen. In some embodiments, R$^3$ is optionally substituted aliphatic. In certain embodiments, R$^3$ is C$_{1-6}$ alkyl. In certain embodiments, R$^3$ is methyl. In some embodiments, R$^3$ is —OR$^9$. In certain embodiments, R$^3$ is —OH. In certain embodiments, R$^3$ is —O(alkyl) or —O(protecting group). In some embodiments, R$^3$ is —N(R$^8$)$_2$. In certain embodiments, R$^3$ is —NH$_2$. In certain embodiments, R$^3$ is —NH(alkyl) or —NH(protecting group). In some embodiments, R$^3$ is —C(O)NHR$^8$. In certain embodiments, R$^3$ is —C(O)NH$_2$. In certain embodiments, R$^3$ is —C(O)NH(alkyl).

In some embodiments, R$^2$ is hydrogen and R$^3$ is optionally substituted aliphatic, —OR$^9$, —N(R$^8$)$_2$, or —C(O)NHR$^8$. In some embodiments, R$^3$ is hydrogen and R$^2$ is optionally substituted aliphatic, —OR$^9$, —N(R$^8$)$_2$, or —C(O)NHR$^8$. In certain embodiments, R$^2$ is hydrogen and R$^3$ is —OH. In other embodiments, R$^3$ is hydrogen and R$^2$ is —OH.

As defined generally above, R$^4$ is hydrogen or —WR$^{4a}$, wherein W is —O— or —NH—, and R$^{4a}$ is hydrogen, a hydroxyl protecting group, optionally substituted aliphatic, —C(O)R$^{10}$, —C(O)NHR$^8$, —C(=NR$^8$)NHR$^8$, or —C(O)OR$^9$. In some embodiments, R$^4$ is —WR$^{4a}$. In certain embodiments, W is —O—. In certain embodiments, W is —NH—. In some embodiments, R$^{4a}$ is hydrogen. In some embodiments, R$^{4a}$ is a hydroxyl protecting group. In some embodiments, R$^{4a}$ is —C(O)R$^{10}$; wherein R$^{10}$ is optionally substituted aliphatic, optionally substituted heterocyclic, optionally substituted aryl, or optionally substituted heteroaryl. In certain embodiments, R$^{4a}$ is —C(O)R$^{10}$; wherein R$^{10}$ is optionally substituted alkyl. In certain embodiments, R$^{4a}$ is —C(O)C$_{1-6}$alkyl. In certain embodiments, R$^{4a}$ is acetyl. In some embodiments, R$^{4a}$ is —C(O)OR$^9$. In some embodiments, R$^{4a}$ is —C(O)OR$^9$; wherein R$^9$ is aryl. In certain embodiments, R$^{4a}$ is —C(O)OPh. In some embodiments, R$^{4a}$ is —C(O)NHR$^8$. In certain embodiments, R$^{4a}$ is —C(O)NH$_2$. In some embodiments, R$^{4a}$ is —C(=NR$^8$)NHR$^8$. In certain embodiments, R$^{4a}$ is —C(=NH)NH$_2$. In certain embodiments, —R$^4$ is —OH, —OC(O)NH$_2$, —NHC(O)NH$_2$, or —NHC(=NH)NH$_2$.

In certain embodiments, R$^1$ is —C(O)NH$_2$, R$^2$ is methyl, R$^3$ is —OH, and R$^4$ is —OC(O)NH$_2$. In certain embodiments, R$^1$ is —C(O)NH$_2$, R$^2$ is hydrogen, R$^3$ is —OH, and R$^4$ is —OC(O)NH$_2$. In certain embodiments, R$^1$ is —C(O)NH$_2$, R$^2$ is —OH, R$^3$ is hydrogen, and R$^4$ is —OH.

As defined generally above, R$^5$ is hydrogen or —NHR$^8$. In some embodiments, R$^5$ is —NH$_2$. In some embodiments, R$^5$ is —NH(protecting group). In some embodiments, R$^5$ is —NH(optionally substituted aliphatic). In certain embodiments, R$^5$ is —NH(optionally substituted alkyl). In certain embodiments, R$^5$ is —NH(C$_{1-6}$ alkyl). In some embodiments, R$^5$ is —NHC(O)R$^{10}$. In certain embodiments, R$^5$ is —NHC(O)R$^{10}$; wherein R$^{10}$ is optionally substituted alkyl. In certain embodiments, R$^5$ is —NHC(O)C$_{1-6}$alkyl. In certain embodiments, R$^5$ is —NHC(O)CH$_3$.

As defined generally above, R$^6$ is hydrogen, —CH$_3$, —CH$_2$OR$^9$, or —CH$_2$OR$^{CX}$; wherein R$^{CX}$ is a carbohydrate moiety. In certain embodiments, R$^6$ is —CH$_3$. In some embodiments, R$^6$ is —CH$_2$OR$^9$. In certain embodiments, R$^6$ is —CH$_2$OH. In certain embodiments, R$^6$ is —CH$_2$O(protecting group). In certain embodiments, R$^6$ is —CH$_2$OAc. In some embodiments, R$^6$ is —CH$_2$OR$^{CX}$. In certain embodiments, R$^6$ is —OR$^{CX}$; wherein R$^{CX}$ is of formula:

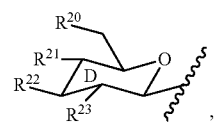

wherein R$^{20}$, R$^{21}$, R$^{22}$, and R$^{23}$ are independently hydrogen or —OR$^9$.

As defined generally above, R$^7$ is hydrogen, —OR$^9$ or —N(R$^8$)$_2$. In some embodiments, R$^7$ is —OR$^9$. In certain embodiments, R$^7$ is —OH. In certain embodiments, R$^7$ is —O(protecting group) or —O(alkyl). In some embodiments, R$^7$ is —N(R$^8$)$_2$. In certain embodiments, R$^7$ is —NH$_2$. In certain embodiments, R$^7$ is —NH(protecting group), —NH(alkyl), or —N(alkyl)$_2$.

In certain embodiments, R$^5$ is —NHC(O)CH$_3$, R$^6$ is —OCH$_2$R$^{CX}$, wherein R$^{CX}$ is

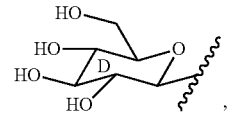

and R$^7$ is —OH. In certain embodiments, R$^5$ is —NHC(O)CH$_3$, R$^6$ is —CH$_2$OH, and R$^7$ is —OH.

As defined generally above, R$^{YY}$ is hydrogen or —OR$^{XX}$, wherein R$^{XX}$ is hydrogen, a hydroxyl protecting group, or a group of formula:

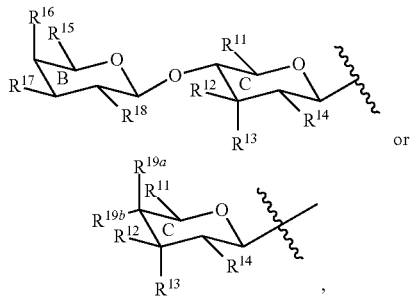

wherein

R$^{11}$ is hydrogen, optionally substituted aliphatic, —C(O)NHR$^8$, —CH$_2$OR$^9$, or —C(O)OR$^9$;

R$^{12}$ and R$^{13}$ are independently hydrogen, optionally substituted aliphatic, —OR$^9$, N(R$^8$)$_2$, or —C(O)NHR$^8$;

R$^{14}$ is hydrogen or —NHR$^8$;

R$^{15}$ is hydrogen, —C(O)NHR$^8$, —CH$_2$OR$^9$, or —C(O)OR$^9$;

$R^{16}$ is hydrogen or $-OR^9$;
$R^{17}$ is hydrogen or $-OR^9$;
$R^{18}$ is hydrogen or $-OR^9$;
$R^{19a}$ is hydrogen or $-OR^9$; and
$R^{19b}$ is hydrogen or $-OR^9$;
wherein $R^8$ and $R^9$ are as described herein.

In some embodiments, $R^{YY}$ is $-OR^{XX}$.

In some embodiments, $R^x$ is hydrogen. In some embodiments, $R^{XX}$ is

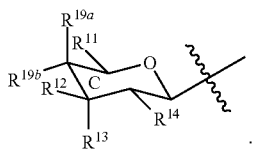

In some embodiments, $R^{XX}$ is

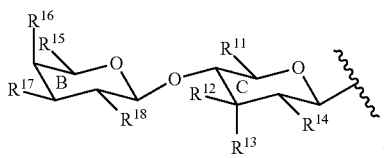

As defined generally above, $R^{11}$ is hydrogen, optionally substituted aliphatic, $-C(O)NHR^8$, $-CH_2OR^9$, or $-C(O)OR^9$. In some embodiments, $R^1$ is optionally substituted aliphatic. In certain embodiments, $R^{11}$ is optionally substituted alkyl. In certain embodiments, $R^{11}$ is $C_{1-6}$ alkyl. In certain embodiments, $R^{11}$ is methyl. In some embodiments, $R^{11}$ is $-C(O)NHR^8$. In certain embodiments, $R^{11}$ is $-C(O)NH_2$. In certain embodiments, $R^{11}$ is $-C(O)NH(alkyl)$. In some embodiments, $R^{11}$ is $-CH_2OR^9$. In certain embodiments, $R^1$ is $-CH_2OH$. In certain embodiments, $R^1$ is $-CH_2O(protecting\ group)$ or $-CH_2O(alkyl)$. In some embodiments, $R^1$ is $-C(O)OR^9$. In certain embodiments, $R^1$ is $-CO_2H$.

As defined generally above, $R^{12}$ is hydrogen, optionally substituted aliphatic, $-OR^9$, $-N(R^8)_2$, or $-C(O)NHR^8$. In some embodiments, $R^{12}$ is hydrogen. In some embodiments, $R^{12}$ is optionally substituted aliphatic. In certain embodiments, $R^{12}$ is $C_{1-6}$ alkyl. In certain embodiments, $R^{12}$ is methyl. In some embodiments, $R^{12}$ is $-OR^9$. In certain embodiments, $R^{12}$ is $-OH$. In certain embodiments, $R^{12}$ is $-O(alkyl)$ or $-O(protecting\ group)$. In some embodiments, $R^{12}$ is $-N(R^8)_2$. In certain embodiments, $R^{12}$ is $-NH_2$. In certain embodiments, $R^{12}$ is $-NH(alkyl)$ or $-NH(protecting\ group)$. In some embodiments, $R^{12}$ is $-C(O)NHR^8$. In certain embodiments, $R^{12}$ is $-C(O)NH_2$. In certain embodiments, $R^{12}$ is $-C(O)NH(alkyl)$.

As defined generally above, $R^{13}$ is hydrogen, optionally substituted aliphatic, $-OR^9$, $-N(R^8)_2$, or $-C(O)NHR^8$. In some embodiments, $R^{13}$ is hydrogen. In some embodiments, $R^{13}$ is optionally substituted aliphatic. In certain embodiments, $R^{13}$ is $C_{1-6}$ alkyl. In certain embodiments, $R^{13}$ is methyl. In some embodiments, $R^{13}$ is $-OR^9$. In certain embodiments, $R^{13}$ is $-OH$. In certain embodiments, $R^{13}$ is $-O(alkyl)$ or $-O(protecting\ group)$. In some embodiments, $R^{13}$ is $-N(R^8)_2$. In certain embodiments, $R^{13}$ is $-NH_2$. In certain embodiments, $R^{13}$ is $-NH(alkyl)$ or $-NH(protecting\ group)$. In some embodiments, $R^{13}$ is $-C(O)NHR^8$. In certain embodiments, $R^{13}$ is $-C(O)NH_2$. In certain embodiments, $R^{13}$ is $-C(O)NH(alkyl)$.

In some embodiments, $R^{12}$ is hydrogen and $R^{13}$ is optionally substituted aliphatic, $-OR^9$, $-N(R^8)_2$, or $-C(O)NHR^8$. In some embodiments, $R^{12}$ is hydrogen and $R^{13}$ is optionally substituted aliphatic, $-OR^9$, $-N(R^8)_2$, or $-C(O)NHR^8$. In certain embodiments, $R^{12}$ is hydrogen and $R^3$ is $-OH$. In other embodiments, $R^3$ is hydrogen and $R^{12}$ is $-OH$.

As defined generally above, $R^{14}$ is hydrogen or $-NHR^8$. In some embodiments, $R^{14}$ is $-NH_2$. In some embodiments, $R^{14}$ is $-NH(amino\ protecting\ group)$. In some embodiments, $R^{14}$ is $-NH(optionally\ substituted\ aliphatic)$. In certain embodiments, $R^{14}$ is $-NH(optionally\ substituted\ alkyl)$. In certain embodiments, $R^{14}$ is $-NH(C_{1-6}\ alkyl)$. In some embodiments, $R^{14}$ is $-NHC(O)R^{10}$. In certain embodiments, $R^{14}$ is $-NHC(O)R^{10}$; wherein $R^{10}$ is optionally substituted alkyl. In certain embodiments, $R^{14}$ is $-NHC(O)C_{1-6}alkyl$. In certain embodiments, $R^{14}$ is $-NHC(O)CH_3$.

As defined generally above, $R^5$ is hydrogen, $-C(O)NHR^8$, $-CH_2OR^9$, or $-C(O)OR^9$. In some embodiments, $R^{15}$ is $-C(O)NHR^8$. In certain embodiments, $R^{15}$ is $-C(O)NH_2$. In certain embodiments, $R^{15}$ is $-C(O)NH(alkyl)$. In some embodiments, $R^{15}$ is $-CH_2OR^9$. In certain embodiments, $R^5$ is $-CH_2OH$. In certain embodiments, $R^5$ is $-CH_2O(protecting\ group)$ or $-CH_2O(alkyl)$. In some embodiments, $R^{15}$ is $-C(O)OR^9$. In certain embodiments, $R^{15}$ is $-CO_2H$. In certain embodiments, $R^{15}$ is $-C(O)NHR^8$, wherein $R^8$ is

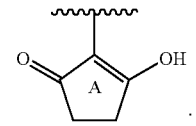

As defined generally above, $R^{16}$ is hydrogen or $-OR^9$. In certain embodiments, $R^{16}$ is $-OR^9$. In some embodiments, $R^{16}$ is $-OH$. In some embodiments, $R^{16}$ is a $-O(protecting\ group)$. In certain embodiments, $R^{16}$ is $-O(optionally\ substituted\ aliphatic)$. In certain embodiments, $R^{16}$ is $-O(C_{1-6}\ alkyl)$. In certain embodiments, $R^{16}$ is $-OCH_3$.

As defined generally above, $R^7$ is hydrogen or $-OR^9$. In certain embodiments, $R^{17}$ is $-OR^9$. In some embodiments, $R^7$ is $-OH$. In some embodiments, $R^7$ is a $-O(protecting\ group)$. In certain embodiments, $R^{17}$ is $-O(optionally\ substituted\ aliphatic)$. In certain embodiments, $R^7$ is $-O(C_{1-6}\ alkyl)$. In certain embodiments, $R^7$ is $-OCH_3$.

As defined generally above, $R^8$ is hydrogen or $-OR^9$. In certain embodiments, $R^{18}$ is $-OR^9$. In some embodiments, $R^{18}$ is $-OH$. In some embodiments, $R^{18}$ is a $-O(protecting\ group)$. In certain embodiments, $R^{18}$ is $-O(optionally\ substituted\ aliphatic)$. In certain embodiments, $R^{18}$ is $-O(C_{1-6}\ alkyl)$. In certain embodiments, $R^{18}$ is $-OCH_3$.

As defined generally above, $R^{19a}$ is hydrogen or $-OR^9$. In some embodiments, $R^{19a}$ is hydrogen. In some embodiments, $R^{19a}$ is $-OR^9$. In certain embodiments, $R^{19a}$ is $-OH$. In certain embodiments, $R^{19a}$ is $-O(alkyl)$ or $-O(protecting\ group)$.

As defined generally above, $R^{19b}$ is hydrogen or $-OR^9$. In some embodiments, $R^{19b}$ is hydrogen. In some embodiments, $R^{19b}$ is $-OR^9$. In certain embodiments, $R^{19b}$ is $-OH$. In certain embodiments, $R^{19b}$ is $-O(alkyl)$ or $-O(protecting\ group)$.

In certain embodiments, $R^{19a}$ is hydrogen, and $R^{19b}$ is —OH. In other embodiments, $R^{19b}$ is hydrogen, and $R^{19a}$ is —OH.

As defined generally above, $R^{20}$ is hydrogen or —$OR^9$. In certain embodiments, $R^{20}$ is —$OR^9$. In some embodiments, $R^{20}$ is —OH. In some embodiments, $R^{20}$ is a —O(protecting group). In some embodiments, $R^{20}$ is —O(optionally substituted aliphatic). In certain embodiments, $R^{20}$ is —O($C_{1-6}$ alkyl). In certain embodiments, $R^{20}$ is —$OCH_3$.

As defined generally above, $R^{21}$ is hydrogen or —$OR^9$. In certain embodiments, $R^{21}$ is —$OR^9$. In some embodiments, $R^{21}$ is —OH. In some embodiments, $R^{21}$ is a —O(protecting group). In some embodiments, $R^{21}$ is —O(optionally substituted aliphatic). In certain embodiments, $R^{21}$ is —O($C_{1-6}$ alkyl). In certain embodiments, $R^{21}$ is —$OCH_3$.

As defined generally above, $R^{22}$ is hydrogen or —$OR^9$. In certain embodiments, $R^{22}$ is —$OR^9$. In some embodiments, $R^{22}$ is —OH. In some embodiments, $R^{22}$ is a —O(protecting group). In some embodiments, $R^{22}$ is —O(optionally substituted aliphatic). In certain embodiments, $R^{22}$ is —O($C_{1-6}$ alkyl). In certain embodiments, $R^{22}$ is —$OCH_3$.

As defined generally above, $R^{23}$ is hydrogen or —$OR^9$. In certain embodiments, $R^{23}$ is —$OR^9$. In some embodiments, $R^{23}$ is —OH. In some embodiments, $R^{23}$ is a —O(protecting group). In some embodiments, $R^{23}$ is —O(optionally substituted aliphatic). In certain embodiments, $R^{23}$ is —O($C_{1-6}$ alkyl). In certain embodiments, $R^{23}$ is —$OCH_3$.

In certain embodiments, $R^1$ is —$CH_2OH$, $R^{12}$ is —OH, $R^{13}$ is hydrogen, $R^{19a}$ is —OH, and $R^{19b}$ is hydrogen.

In certain embodiments, $R^{20}$, $R^{21}$, $R^{22}$, and $R^{23}$ are all —OH.

As defined generally above, $R^a$ is hydrogen or a hydroxyl protecting group. In certain embodiments, $R^a$ is hydrogen. In certain embodiments, $R^a$ is a hydroxyl protecting group.

As defined generally above, $R^b$ is hydrogen or a hydroxyl protecting group. In certain embodiments, $R^b$ is hydrogen. In certain embodiments, $R^b$ is a hydroxyl protecting group.

As defined generally above, G is an optionally substituted $C_{1-30}$ aliphatic group, wherein 0 to 10 methylene units are optionally replaced with —O—, —$NR^x$—, —S—, —C(O)—, —C(=$NR^x$)—, —S(O)—, —$SO_2$—, —N=N—, —C=N—, —N—O—, an optionally substituted arylene, an optionally substituted heterocyclylene, or an optionally substituted heteroarylene; wherein each instance of $R^x$ is independently hydrogen, optionally substituted aliphatic, optionally substituted heterocyclyl, optionally substituted aryl, optionally substituted heteroaryl; or G is a group of Formula (a), (b), or (c):

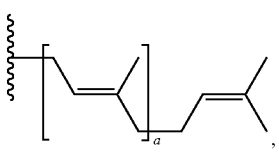

(a)

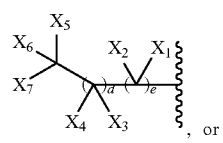

(b)

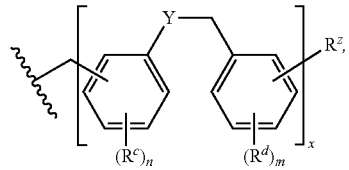

(c)

wherein a, $X_1$, $X_2$, $X_3$, $X_4$, $X_5$, $X_6$, $X_7$, d, e, Y, $R^c$, $R^d$, $R^z$, x, m, and n are as described herein.

In certain embodiments, G is an optionally substituted $C_{1-30}$ aliphatic group, wherein 0 to 10 methylene units are optionally replaced with —O—, —$NR^x$—, —S—, —C(O)—, —C(=$NR^x$)—, —S(O)—, —$SO_2$—, —N=N—, —C=N—, —N—O—, an optionally substituted arylene, an optionally substituted heterocyclylene, or an optionally substituted heteroarylene. In certain embodiments, G is an optionally substituted $C_{1-10}$, $C_{5-20}$, $C_{10-20}$, $C_{12-18}$, or $C_{15-20}$ aliphatic group, wherein 0, 1, 2, 3, 4, 5, 6, 7, 8, 9, or 10 methylene units are optionally replaced with —O—, —$NR^x$—, —S—, —C(O)—, —C(=$NR^x$)—, —S(O)—, —$SO_2$—, —N=N—, —C=N—, —N—O—, an optionally substituted arylene, an optionally substituted heterocyclylene, or an optionally substituted heteroarylene. In some embodiments, $R^x$ is hydrogen, optionally substituted aliphatic, optionally substituted heterocyclyl, optionally substituted aryl, optionally substituted heteroaryl. In some embodiments, $R^x$ is hydrogen. In some embodiments, $R^x$ is optionally substituted aliphatic. In some embodiments, $R^x$ is $C_{1-6}$ alkyl. In some embodiments, $R^x$ is methyl.

Exemplary aliphatic moieties include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), hexadecyl ($C_{16}$), heptadecyl ($C_{17}$), octadecyl ($C_{18}$), nonadecyl ($C_{19}$), eicosyl ($C_{20}$), and so on, up to ($C_{30}$). In certain embodiments, the aliphatic moiety is a straight chain alkyl moiety, including, but not limited to, methyl ($C_1$), ethyl ($C_2$), n-propyl ($C_3$), n-butyl ($C_4$), n-pentyl ($C_5$), n-hexyl ($C_6$), n-heptyl ($C_7$), n-octyl ($C_8$), n-nonyl ($C_9$), n-decyl ($C_{10}$), n-undecyl ($C_{11}$), n-dodecyl ($C_{12}$), n-tridecyl ($C_{13}$), n-tetradecyl ($C_{14}$), n-pentadecyl ($C_{15}$), n-hexadecyl ($C_{16}$), n-heptadecyl ($C_{17}$), n-octadecyl ($C_{18}$), n-nonadecyl ($C_{19}$), n-eicosyl ($C_{20}$), and so on, up to ($C_{30}$).

Exemplary substituents include are described throughout, and include optionally substituted aliphatic (e.g., alkyl, alkenyl, alkynyl), optionally substituted heteroaliphatic, optionally substituted aryl, optionally substituted heteroaryl, halogen, —$OR^v$, —$N(R^v)_2$, —$SR^v$, —$NO_2$, —NC, —CN, —$N_3$, —$N(R^v)$=$NR^v$, —CHO, —C(=O)$R^v$, —C(=S)$R^v$, —C(=NR)$R^v$, —C(=O)$OR^q$, —C(=$NR^q$)$OR^q$, —C(=$NR^v$)N($R^v$)$_2$, —C(=O)N($R^v$)$_2$, —C(=S)$OR^v$, —C(=O)$SR^v$, —C(=S)$SR^v$, —P(=O)($OR^v$)$_2$, —P(=O)$_2$($OR^v$), —S(=O)($OR^v$), —S(=O)$_2$($OR^v$), —P(=O)N($R^v$)$_2$, —P(=O)$_2$N($R^v$)$_2$, —S(=O)N($R^v$)$_2$, or —S(=O)$_2$N($R^v$)$_2$; wherein each instance of $R^v$ is H, optionally substituted aliphatic, optionally substituted heteroaliphatic, optionally substituted aryl, optionally substituted heteroaryl or a protecting group. In certain embodiments, the G hydrocarbon chain is substituted with one or more optionally substituted aliphatic moieties, optionally substituted heteroaliphatic moieties, optionally substituted aryl moieties, optionally substituted heteroaryl moieties, halogen moieties, —$OR^v$ moieties, —$N(R^v)_2$ moieties, or —$SR^v$ moieties. In certain embodiments, the G hydrocarbon chain is substituted with one or more optionally substituted aliphatic moieties or —OR$^v$ moieties. In certain embodiments, the G hydrocarbon chain is substituted with one or more optionally substituted aliphatic moieties. In certain embodiments, the G hydrocarbon chain is substituted with one or more optionally substituted $C_{1-6}$ alkyl moieties. In certain embodiments, the G hydrocarbon chain is substituted with one or more —CH$_3$ moieties.

In certain embodiments, G is an optionally substituted, optionally unsaturated, $C_{5-20}$ hydrocarbon chain, wherein 0 to 10 methylene units are optionally replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene.

In certain embodiments, G is an optionally substituted, optionally unsaturated, $C_{10-20}$ hydrocarbon chain, wherein 0 to 8 methylene units are optionally replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene.

In certain embodiments, G is an optionally substituted, optionally unsaturated, C10-18 hydrocarbon chain, wherein 0 to 6 methylene units are optionally replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene.

In certain embodiments, G is an unsubstituted, optionally unsaturated hydrocarbon chain.

In certain embodiments, G is an unsubstituted and saturated hydrocarbon chain. In certain embodiments, G is an unsubstituted hydrocarbon and saturated hydrocarbon chain wherein 0 to 10 methylene units are replaced with —O—, —NR$^x$—, —S—, —C(=O)—, —C(=NR$^x$)—, —S(=O)—, —S(=O)$_2$— or —N—O—.

In certain embodiments, G is an unsubstituted and unsaturated hydrocarbon chain. In certain embodiments, G is an unsubstituted hydrocarbon and unsaturated hydrocarbon chain, wherein 1 to 10 methylene units are replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene.

In certain embodiments, G is a substituted and saturated hydrocarbon chain. In certain embodiments, G is a substituted and saturated hydrocarbon chain, wherein 0 to 10 methylene units are replaced with —O—, —NR$^x$—, —S—, —C(=O)—, —C(=NR$^x$)—, —S(=O)—, —S(=O)$_2$— or —N—O—.

In certain embodiments, G is a substituted, optionally unsaturated hydrocarbon chain. In certain embodiments, G is a substituted and unsaturated hydrocarbon chain. In certain embodiments, G is a substituted hydrocarbon and unsaturated hydrocarbon chain wherein 1 to 10 methylene units are replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene.

In certain embodiments, G is an optionally substituted, optionally unsaturated, $C_{10}$-$C_{16}$ aliphatic moiety. In certain embodiments, G is an optionally substituted, $C_8$-$C_{16}$ alkyl moiety. In certain embodiments, G is an optionally substituted, $C_{10}$-$C_{14}$ alkyl moiety.

In certain embodiments, G is:

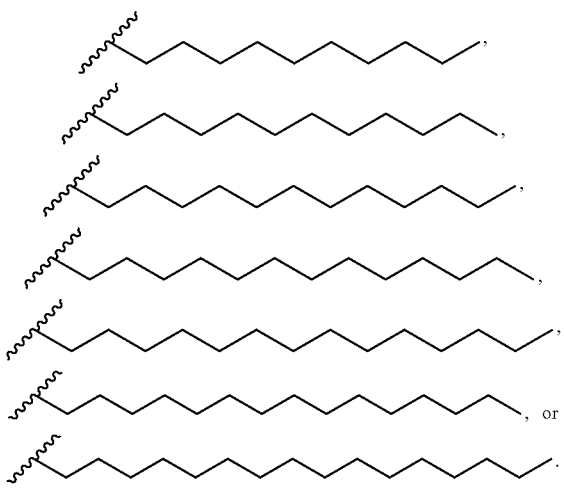

In certain embodiments, G is:

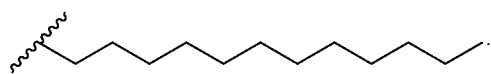 [SMILES: *CCCCCCCCCCCC]

In certain embodiments, G is fluorinated. G may be perfluorinated or partially fluorinated. In certain embodiments, all the hydrogen atoms of G are replaced with fluorine atoms. In certain embodiments, only a portion of the hydrogen atoms of G are replaced with fluorine atoms. In certain embodiments, at least 10%, at least 20%, at least 30%, at least 40%, at least 50%, at least 60%, at least 70%, at least 80%, or at least 80% of the hydrogen atoms are replaced with fluorine atoms. In certain embodiments, G comprises at least 1, 2, 3, 4, 5, 6, 7, 8, 9, 10, 15, 20, or more fluorine atoms. In certain embodiments, G may include substituents that are or are not fluorinated. In certain embodiments, G is a fluorinated, optionally unsaturated, $C_{10}$-$C_{16}$ aliphatic moiety. In certain embodiments, G is a perfluorinated, optionally unsaturated, $C_{10}$-$C_{16}$ aliphatic moiety. In certain embodiments, G is a partially fluorinated, optionally unsaturated, $C_{10}$-$C_{16}$ aliphatic moiety. In certain embodiments, G is a fluorinated, $C_8$-$C_{16}$ alkyl moiety. In certain embodiments, G is a perfluorinated, $C_8$-$C_{16}$ alkyl moiety. In certain embodiments, G is a partially fluorinated, $C_8$-$C_{16}$ alkyl moiety. In certain embodiments, G is a fluorinated, $C_{10}$-$C_{14}$ alkyl moiety. In certain embodiments, G is a perfluorinated, $C_{10}$-$C_{14}$ alkyl moiety. In certain embodiments, G is a partially fluorinated, $C_{10}$-$C_{14}$ alkyl moiety.

In certain embodiments, G is a perfluorinated, optionally unsaturated $C_{10}$-$C_{16}$ alkyl moiety. In certain embodiments, G is:

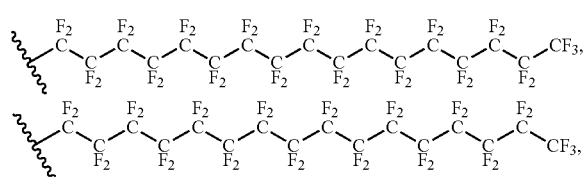

-continued

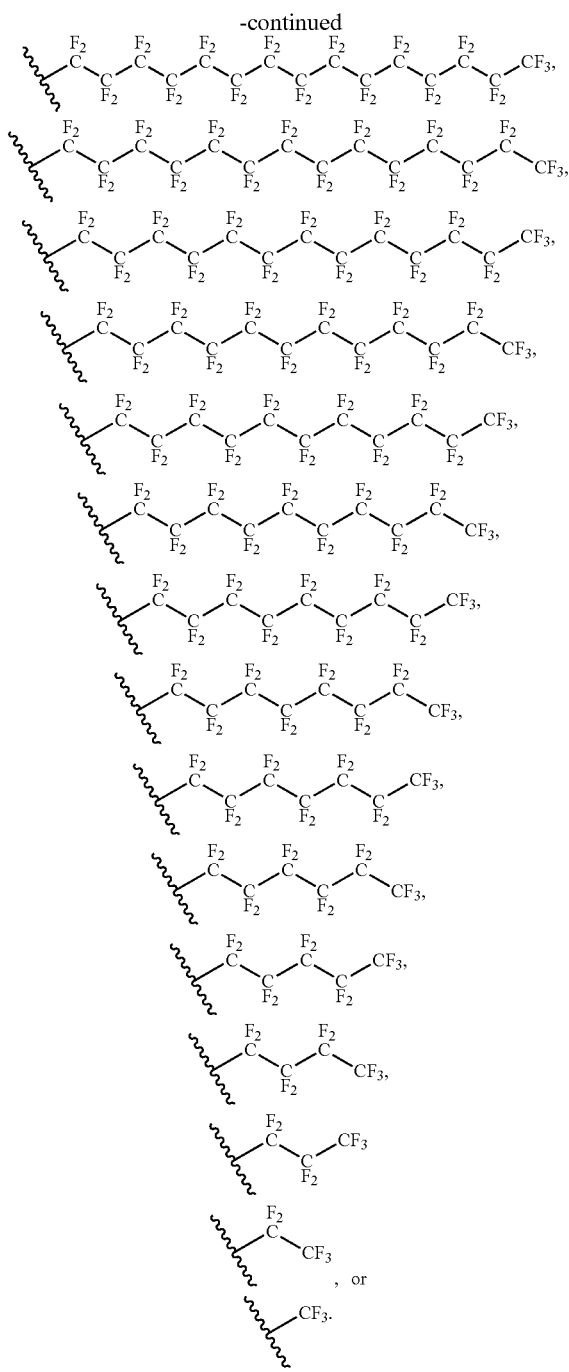

In certain embodiments, G is:

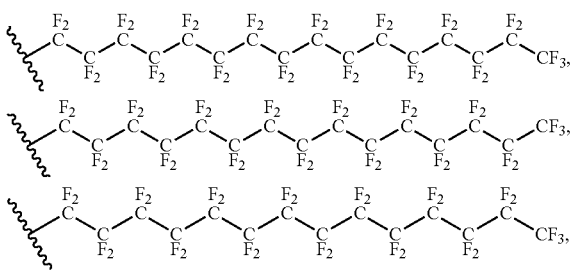

-continued

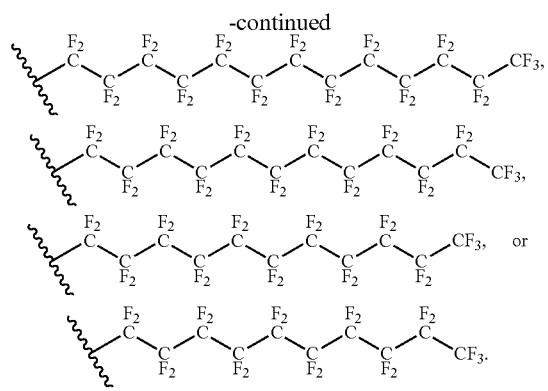

In certain embodiments, G is:

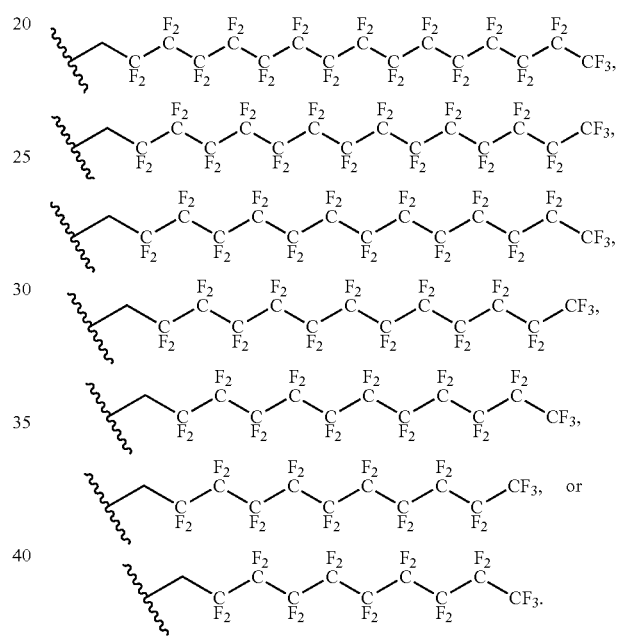

In certain embodiments, G is a substituted or unsubstituted optionally unsaturated $C_{2-30}$ hydrocarbon chain of the formulae:

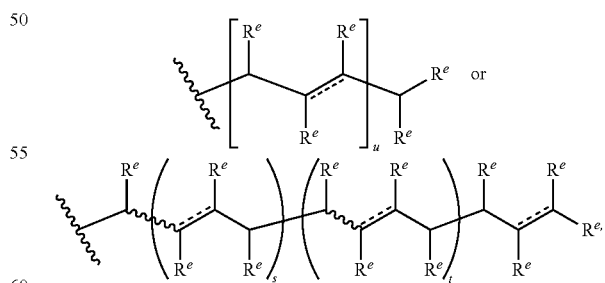

wherein ⚌ is a single or double bond, and each instance of $R^e$ is, independently, H, optionally substituted aliphatic, optionally substituted heteroaliphatic, optionally substituted aryl, optionally substituted heteroaryl, halogen, —$OR^v$, —$N(R^v)_2$, —$SR^v$, —$NO_2$, —NC, —CN, —$N_3$, —$N(R^v)$ =NR$^v$, —CHO, —C(=O)R$^v$, —C(=S)R$^v$, —C(=NR)R$^v$, —C(=O)OR$^v$, —C(=NR$^q$)OR$^q$, —C(=NR$^v$)N(R$^v$)$_2$, —C(=O)N(R$^v$)$_2$, —C(=S)OR$^v$, —C(=O)SR$^v$, —C(=S)SR$^v$, —P(=O)(OR$^v$)$_2$, —P(=O)$_2$(OR$^v$), —S(=O)(OR$^v$), —S(=O)$_2$(OR$^v$), —P(=O)N(R$^v$)$_2$, —P(=O)$_2$N(R$^v$)$_2$, —S(=O)N(R$^v$)$_2$, or —S(=O)$_2$N(R$^v$)$_2$; wherein each instance of R$^v$ is H, optionally substituted aliphatic, optionally substituted heteroaliphatic, optionally substituted aryl, optionally substituted heteroaryl or a protecting group; and each instance of u, s and t is, independently, 0, 1, 2, 3, 4, or 5.

In certain embodiments, R$^e$ is, independently, H or optionally substituted aliphatic, optionally substituted heteroaliphatic, optionally substituted aryl, optionally substituted heteroaryl, halogen, —OR$^v$ or —N(R$^v$)$_2$. In certain embodiments, R$^e$ is, independently, H, optionally substituted aliphatic, optionally substituted heteroaliphatic, optionally substituted aryl or optionally substituted heteroaryl. In certain embodiments, R$^e$ is, independently, optionally substituted aliphatic or optionally substituted heteroaliphatic. In certain embodiments, R$^e$ is, independently, H or optionally substituted aliphatic. In certain embodiments, R$^e$ is, independently, H or —CH$_3$.

In certain embodiments, G is a fully saturated hydrocarbon group of the formula:

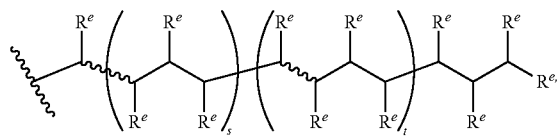

wherein R$^e$, s and t are as defined above and herein.

In certain embodiments, G is a fully saturated hydrocarbon group of the formulae:

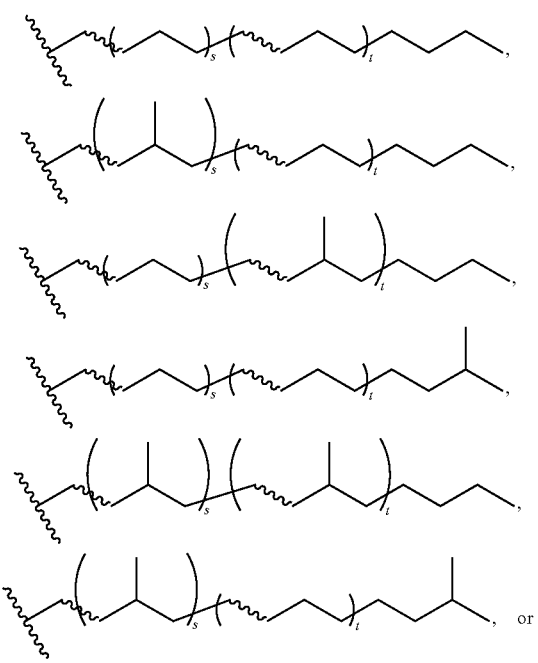

wherein s and t are as defined above and herein.

In certain embodiments, G is an unsaturated group of the formulae:

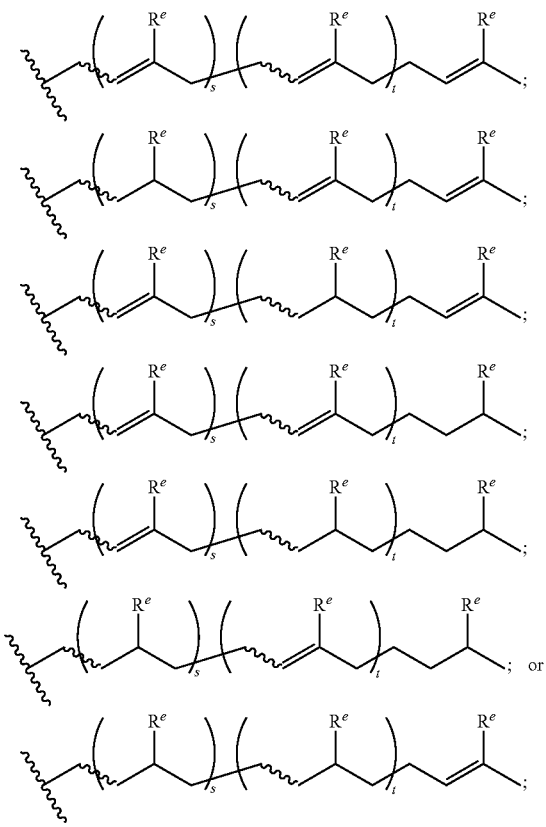

wherein R$^e$, s, and t are as defined herein.

In certain embodiments, G is a group of the formula:

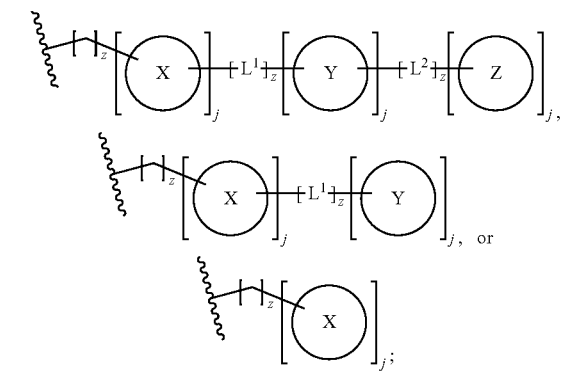

wherein Ring X, Ring Y and Ring Z are, independently, an optionally substituted arylene or an optionally substituted heteroarylene moiety;

z is 0 to 3;

each instance of j is, independently, 1 or 2; and each instance of L¹ and L² are, independently, —(C(R°)₂—, —O—, —NR$^{x1}$—, —S—, —C(=O)—, —C(=O)O—, —C(=O)NR$^{x1}$—, —C(=O)S—, —C(=NR$^x$)—, —C(=NR$^{x1}$)O—, —C(=NR$^{x1}$)NR$^{x1}$—, —C(=NR$^{x1}$)S—, —S(=O)—, —S(=O)₂—, —N=N—, —C=N—, —C(R$^{y1}$)=C(R$^{y1}$)—, or —N—O—, wherein R° is H, optionally substituted aliphatic, optionally substituted heteroaliphatic, optionally substituted aryl, optionally substituted heteroaryl, each instance of R$^{x1}$ is, independently, H, optionally substituted aliphatic, optionally substituted heteroaliphatic, optionally substituted aryl, optionally substituted heteroaryl or an amino protecting group, and each instance of R$^{y1}$ is, independently, H, optionally substituted aliphatic, optionally substituted heteroaliphatic, optionally substituted aryl, or optionally substituted heteroaryl.

Exemplary optionally substituted arylene groups include, but are not limited to:

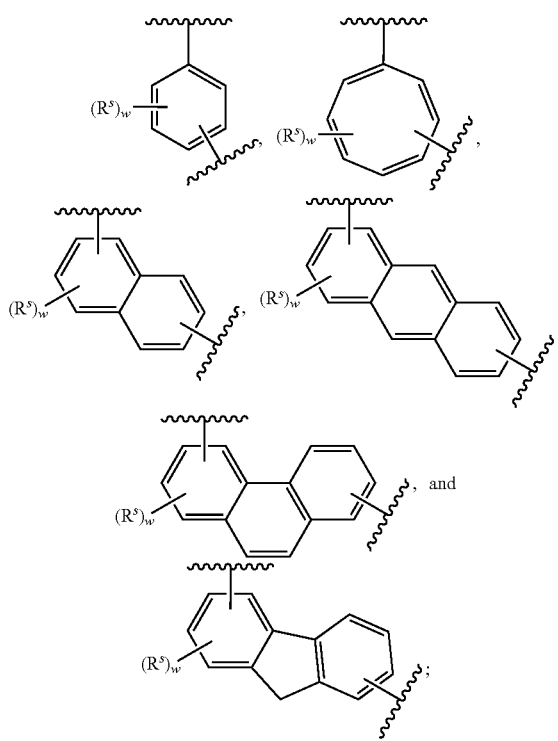

wherein each instance of R$^s$ is, independently, optionally substituted aliphatic, optionally substituted heteroaliphatic, optionally substituted aryl, optionally substituted heteroaryl, halogen, —OR$^v$, —N(R$^v$)₂, —SR$^v$, —NO₂, —NC, —CN, —N₃, —N(R$^v$)=NR$^v$, —CHO, —C(=O)R$^v$, —C(=S)R$^v$, —C(=NR$^v$)R$^v$, —C(=O)OR$^q$, —C(=NR$^v$)OR$^v$, —C(=NR$^v$)N(R$^v$)₂, —C(=O)N(R$^v$)₂, —C(=S)OR$^v$, —C(=O)SR$^v$, —C(=S)SR$^v$, —P(=O)(OR$^v$)₂, —P(=O)₂(OR$^v$), —S(=O)(OR$^v$), —S(=O)₂(OR$^v$), —P(=O)N(R$^v$)₂, —P(=O)₂N(R$^v$)₂, —S(=O)N(R$^v$)₂, or —S(=O)₂N(R$^v$)₂; wherein each instance of R$^v$ is H, optionally substituted aliphatic, optionally substituted heteroaliphatic, optionally substituted aryl, optionally substituted heteroaryl or a protecting group; and w is an integer between 0 to 10, inclusive.

Exemplary optionally substituted heteroarylene groups include, but are not limited to:

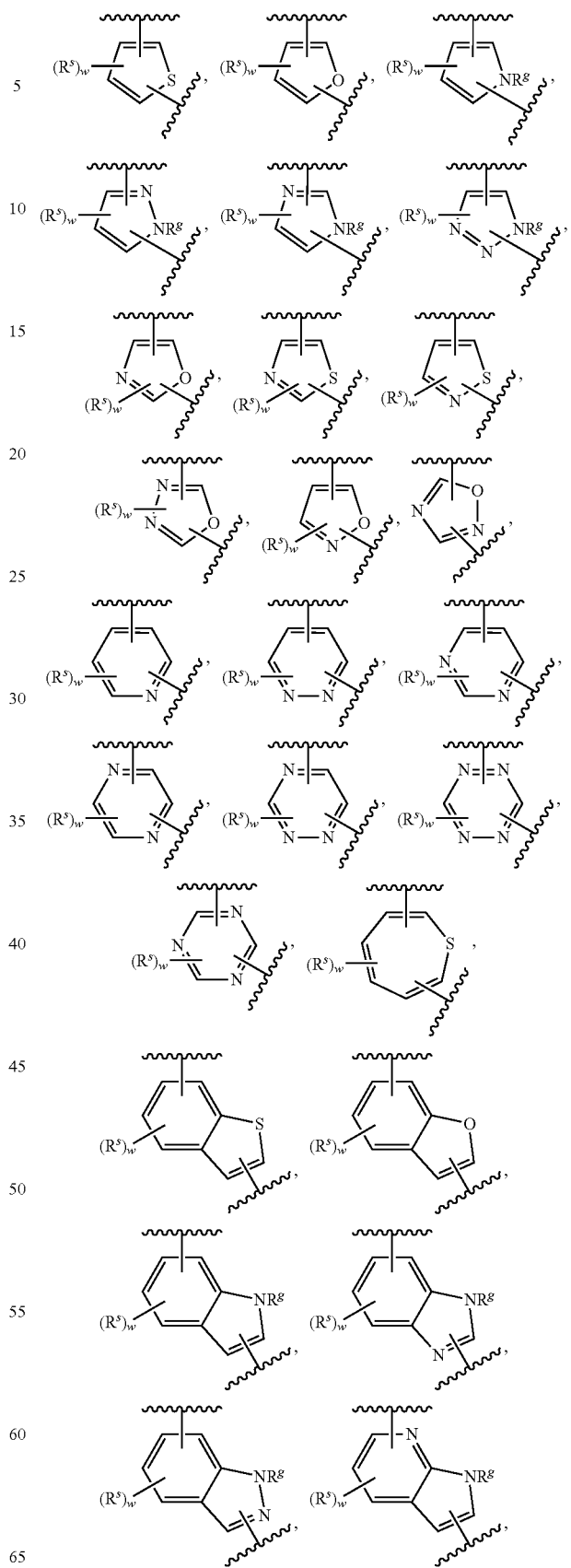

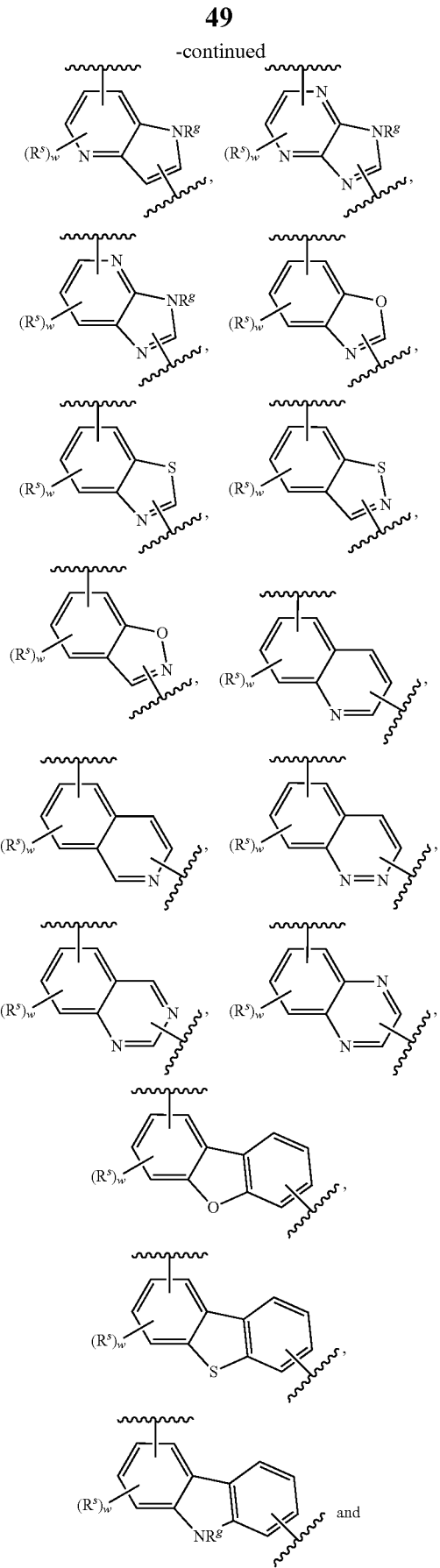

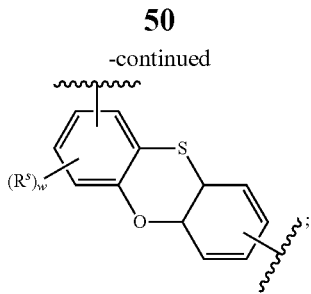

wherein each instance of $R^s$ is, independently, optionally substituted aliphatic, optionally substituted heteroaliphatic, optionally substituted aryl, optionally substituted heteroaryl, halogen, —$OR^v$, —$N(R^v)_2$, —$SR^v$, —$NO_2$, —NC, —CN, —$N_3$, —$N(R^v)$=$NR^v$, —CHO, —C(=O)$R^v$, —C(=S)$R^v$, —C(=$NR^v$)$R^v$, —C(=O)$OR^q$, —C(=$NR^q$)$OR^q$, —C(=$NR^v$)N($R^v$)$_2$, —C(=O)N($R^v$)$_2$, —C(=S)$OR^v$, —C(=O)$SR^v$, —C(=S)$SR^v$, —P(=O)($OR^v$)$_2$, —P(=O)$_2$($OR^v$), —S(=O)($OR^v$), —S(=O)$_2$($OR^v$), —P(=O)N($R^v$)$_2$, —P(=O)$_2$N($R^v$)$_2$, —S(=O)N($R^v$)$_2$, or —S(=O)$_2$N($R^v$)$_2$; wherein each instance of $R^v$ is H, optionally substituted aliphatic, optionally substituted heteroaliphatic, optionally substituted aryl, optionally substituted heteroaryl or a protecting group; and w is an integer between 0 to 10, inclusive, and each instance of $R^g$ is, independently, H, optionally substituted aliphatic, optionally substituted heteroaliphatic, optionally substituted aryl, optionally substituted heteroaryl or an amino protecting group.

In certain embodiments, Ring X, Ring Y and Ring Z are, independently, an optionally substituted arylene moiety. In certain embodiments, Ring X, Ring Y and Ring Z are, independently, an optionally substituted phenylene moiety. For example, in certain embodiments, G is an group of the formulae:

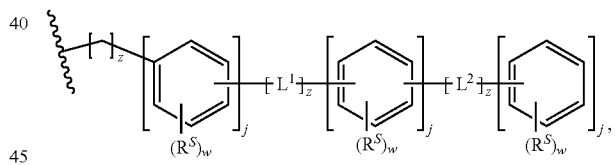

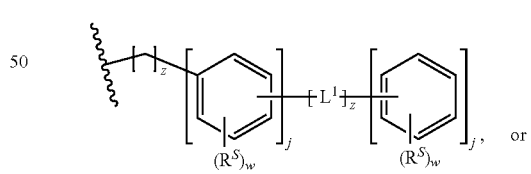

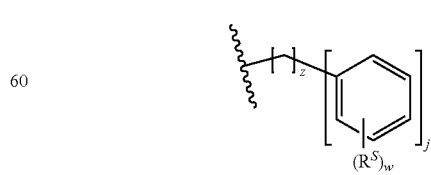

wherein z, w, j, $L^1$, $L^2$, and $R^s$ are as defined above and herein.

In certain embodiments, G is of one of the formulae:
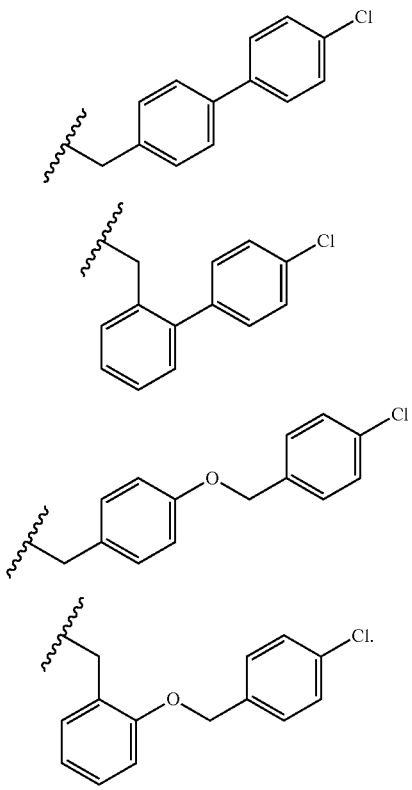
In certain embodiments, G is any one of the following groups:
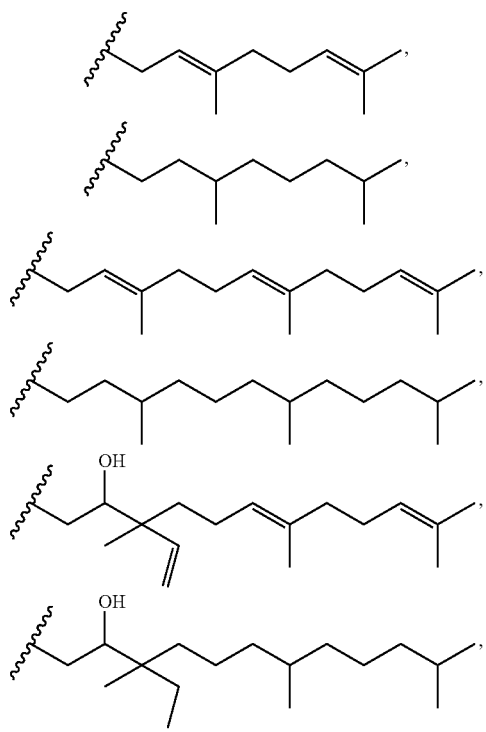
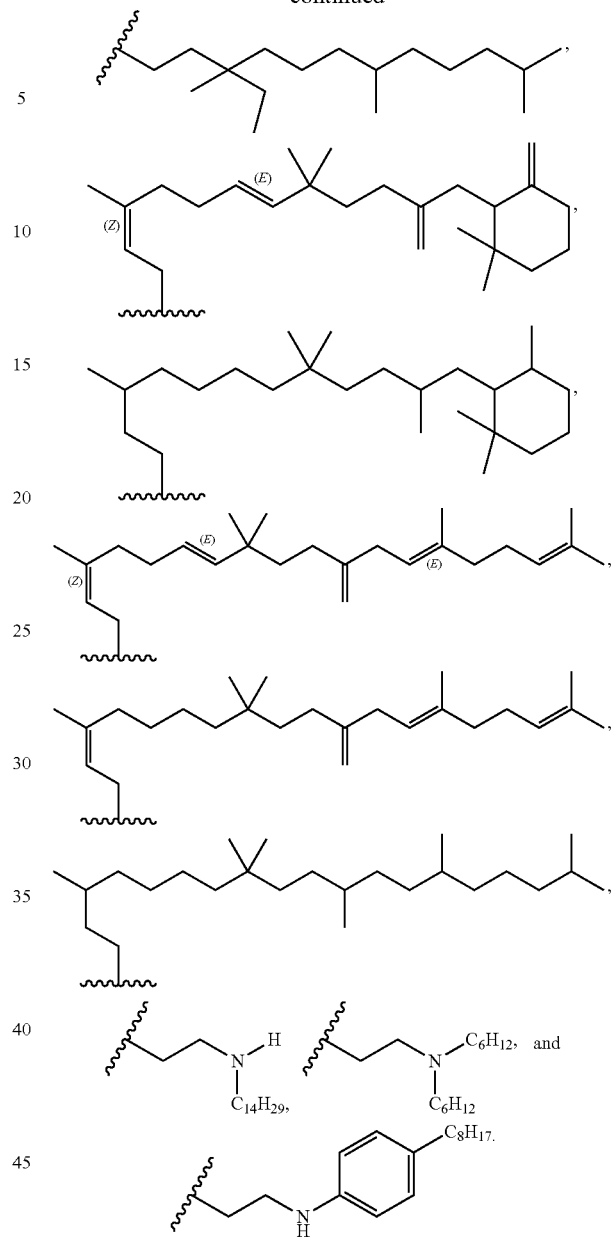
In certain embodiments, G is the geranyl group:
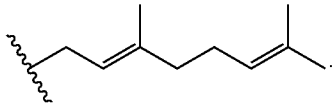 [SMILES: *C/C=C(\C)CCC=C(C)C]
In certain embodiments, G is the farnesyl group:
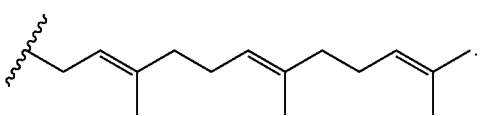 [SMILES: *C/C=C(\C)CC/C=C(\C)CCC=C(C)C]

In certain embodiments, G is C$_{12}$ alkyl of the formula:

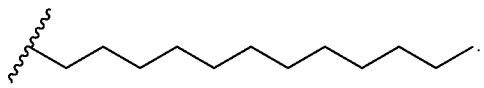 [SMILES: *CCCCCCCCCCCC]

In certain embodiments, G is the nerolyl group:

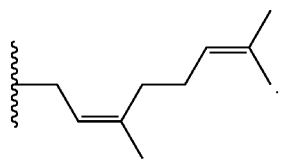

In certain embodiments, G is of the formula:

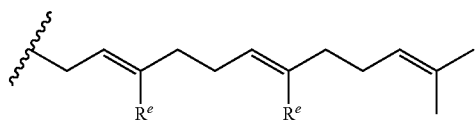

wherein each occurrence of R$^e$ is independently hydrogen or an optionally substituted aliphatic moiety. In certain embodiments, R$^e$ is hydrogen or C$_1$-C$_6$ aliphatic. In certain embodiments, R$^e$ is hydrogen, C$_1$-C$_6$ alkyl, or C$_1$-C$_6$ alkenyl. In certain embodiments, R$^e$ is vinyl. In certain embodiments, R$^e$ is allyl. In certain embodiments, R$^e$ is isopropyl. In certain embodiments, R$^e$ is n-propyl. In certain embodiments, R$^e$ is isobutyl. In certain embodiments, R$^e$ is n-butyl. In certain embodiments, R$^e$ is t-butyl. In certain embodiments, R$^e$ is n-pentyl. In certain embodiments, R$^e$ is isopentyl. In certain embodiments, R$^e$ is neopentyl. In certain embodiments, R$^e$ is 3-methyl-but-2-enyl. Exemplary G groups include:

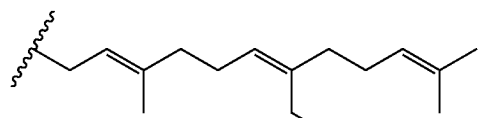

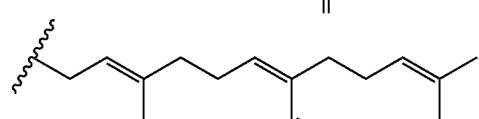

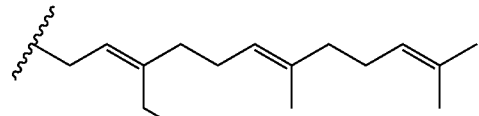

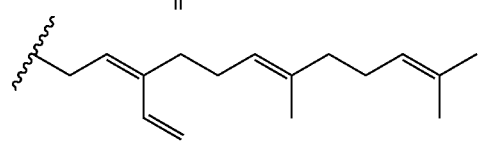

-continued

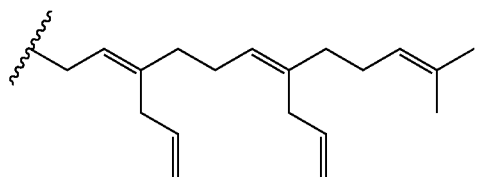

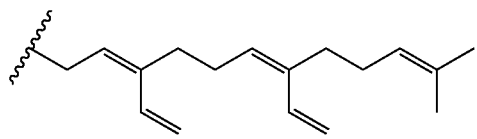

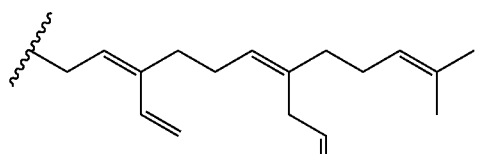

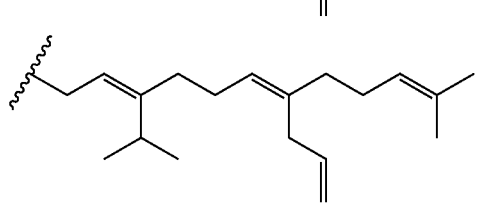

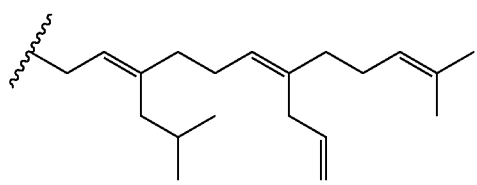

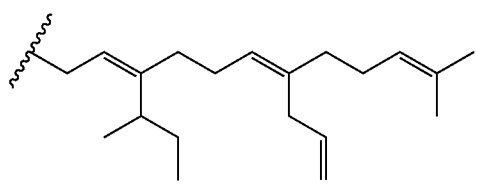

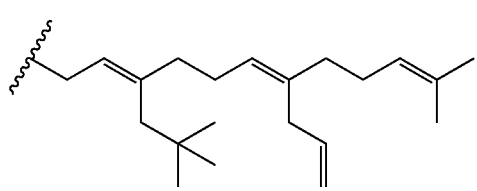

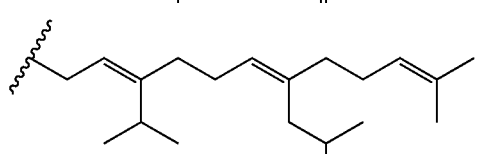

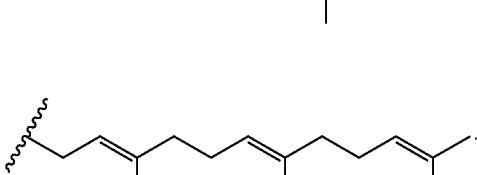

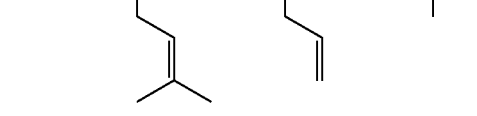

In certain embodiments, G is of the formula:

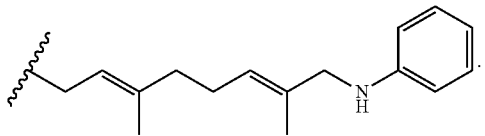 [SMILES: *C/C=C(\C)CC/C=C(\C)CNc1ccccc1]

In some embodiments, G is of Formula (a):

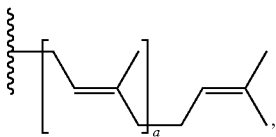 (a)

wherein a is 3, 4, or 5.
For example, in certain embodiments, G is:

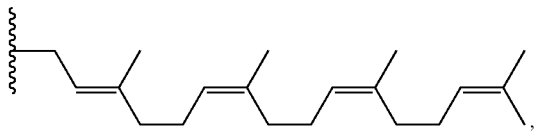

wherein a is 3;

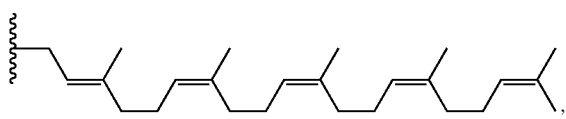

wherein a is 4; or

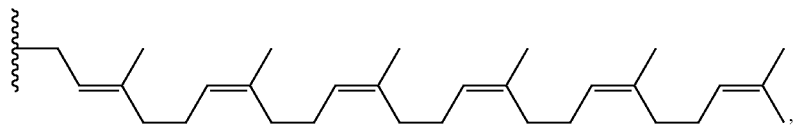

wherein a is 5.
In some embodiments, G is of Formula (b):

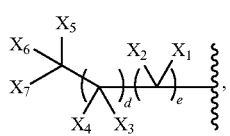 (b)

wherein:
$X_1$, $X_2$, $X_3$, $X_4$, $X_5$, $X_6$, and $X_7$ are each independently hydrogen or halogen;
d is an integer between 1 and 25, inclusive; and
e is an integer of between 2 and 25, inclusive;
provided the sum of d and e is greater than 16.

In certain embodiments, e is 2, 3, 4, 5, 6, 7, 8, 9, 10, 11, 12, 13, 14, 15, 16, 17, 18, 19, 20, 21, 22, 23 24, or 25. In certain embodiments, d is 1, 2, 3, 4, 5, 6, 7, 8, 9, 10, 11, 12, 13, 14, 15, 16, 17, 18, 19, 20, 21, 22, 23 24, or 25. Any particular combination of e or d is contemplated, provided the sum of d and e is greater than 16.

For example, in certain embodiments, e is 16 or an integer greater than 16, and d is 1 or an integer greater than 1. In certain embodiments, e is 15, and d is 2 or an integer greater than 2. In certain embodiments, e is 14, and d is 3 or an integer greater than 3. In certain embodiments, e is 13, and d is 4 or an integer greater than 4. In certain embodiments, e is 12, and d is 5 or an integer greater than 5. In certain embodiments, e is 11, and d is 6 or an integer greater than 6. In certain embodiments, e is 10, and d is 7 or an integer greater than 7. In certain embodiments, e is 9, and d is 8 or an integer greater than 8. In certain embodiments, e is 8, and d is 9 or an integer greater than 9. In certain embodiments, e is 7, and d is 10 or an integer greater than 10. In certain embodiments, e is 6, and d is 11 or an integer greater than 11. In certain embodiments, e is 5, and d is 12 or an integer greater than 12. In certain embodiments, e is 4, and d is 13 or an integer greater than 13. In certain embodiments, e is 3, and d is 14 or an integer greater than 14. In certain embodiments, e is 2, and d is 15 or an integer greater than 15.

In certain embodiments, e is 10, and d is 7 or an integer greater than 7, e.g., d is 7, 8, 9, 10, 11, 12, 13, 14, 15, 16, 17, 18, 19, 20, 21, 22, 23 24, or 25. In certain embodiments, e is 10 and d is 7. In certain embodiments, e is 10 and d is 8. In certain embodiments, e is 10 and d is 9. In certain embodiments, e is 10 and d is 10. In certain embodiments, e is 10 and d is 11. In certain embodiments, e is 10 and d is 12. In certain embodiments, e is 10 and d is 13. In certain embodiments, e is 10 and d is 14. In certain embodiments, e is 10 and d is 15.

In certain embodiments, each instance of $X_1$ and $X_2$ is hydrogen. In certain embodiments, each instance of $X_1$ and $X_2$ is halogen, e.g., fluoro.

In certain embodiments, each instance of $X_3$ and $X_4$ is hydrogen. In certain embodiments, each instance of $X_3$ and $X_4$ is halogen, e.g., fluoro.

In certain embodiments, each instance of $X_5$, $X_6$, and $X_7$ is hydrogen. In certain embodiments, each instance of $X_5$, $X_6$, and $X_7$ is halogen, e.g., fluoro.

In certain embodiments, each instance of $X_1$, $X_2$, $X_3$, $X_4$, $X_5$, $X_6$, and $X_7$ is hydrogen, i.e., to provide an n-alkyl group. Exemplary n-alkyl groups of Formula (b) include, but are not limited to:

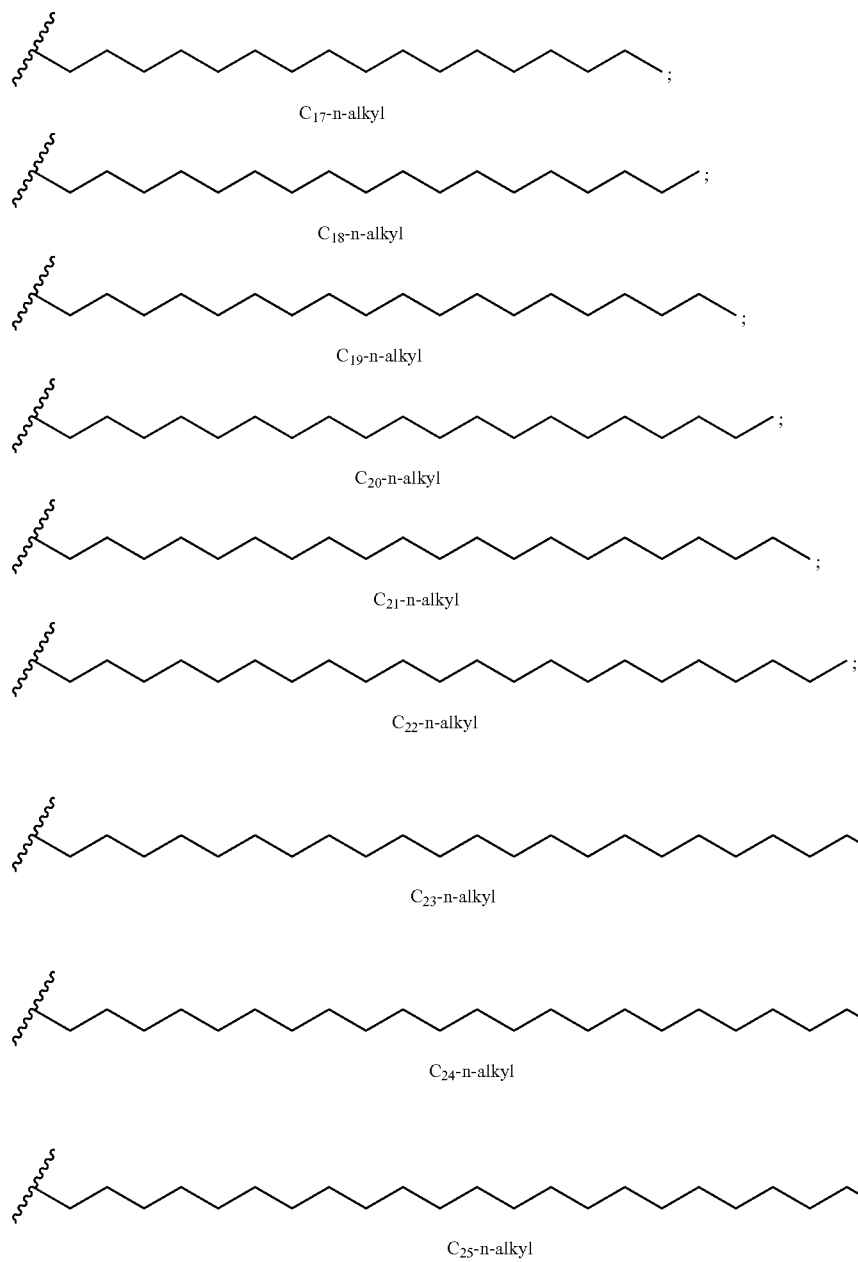

In certain embodiments, each instance of $X_1$ and $X_2$ is fluoro, optionally wherein each instance of $X_3$ and $X_4$ is fluoro and/or each instance of $X_5$, $X_6$, and $X_7$ is fluoro. Alternatively, each instance of $X_3$ and $X_4$ is fluoro, optionally wherein each instance of $X_1$ and $X_2$ is fluoro and/or each instance of $X_5$, $X_6$, and $X_7$ is fluoro. In certain embodiments, $X_1$ and $X_2$ are each hydrogen, $X_3$ and $X_4$ are each fluoro, and $X_5$, $X_6$, and $X_7$ are each fluoro. In certain embodiments, $X_1$, $X_2$ are each fluoro, $X_3$ and $X_4$ are each hydrogen, and $X_5$, $X_6$, and $X_7$ are each hydrogen.

Exemplary fluoroalkyl groups of Formula (b), wherein $X_1$ and $X_2$ are hydrogen and $X_3$, $X_4$, $X_5$, $X_6$, and $X_7$ are each fluoro include, but are not limited to:

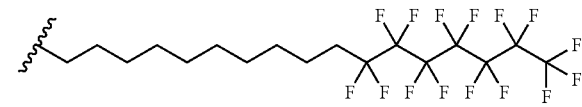

wherein e is 10, and d is 7;

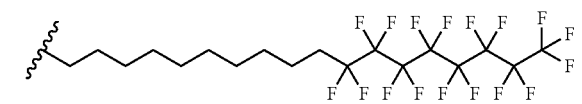

wherein e is 10, and d is 8;

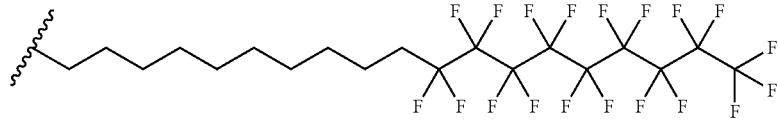
wherein e is 10, and d is 9;
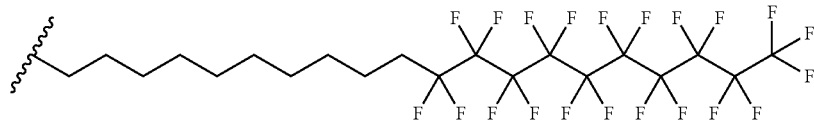
wherein e is 10, and d is 10;
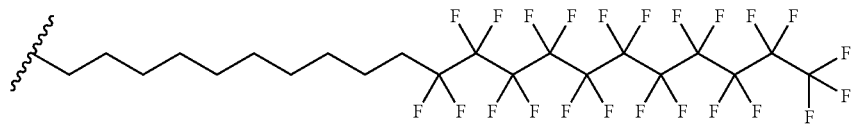
wherein e is 10, and d is 11;
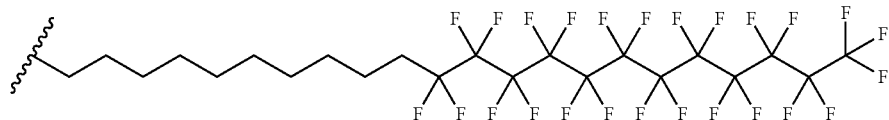
wherein e is 10, and d is 12:
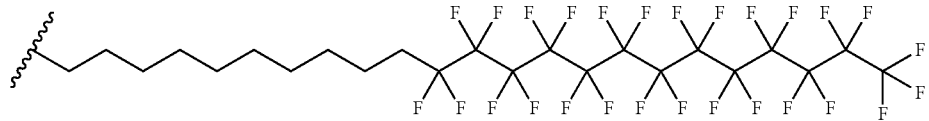
wherein e is 10, and d is 13;
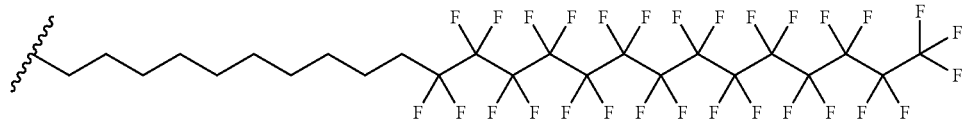
wherein e is 10, and d is 14; and
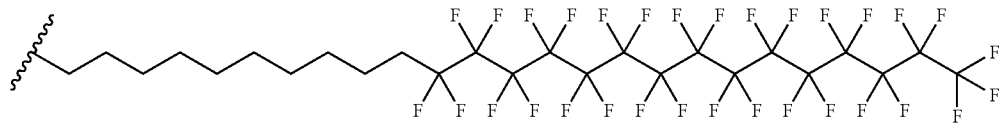
wherein e is 10, and d is 15.

Exemplary fluoroalkyl groups of formula (b), wherein each instance of $X_1$, $X_2$, $X_3$, $X_4$, $X_5$, $X_6$, and $X_7$ is fluoro, include but are not limited to:
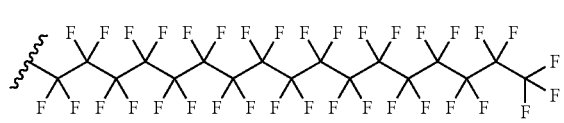
wherein e is 10, and d is 7;
wherein e is 10, and d is 8;
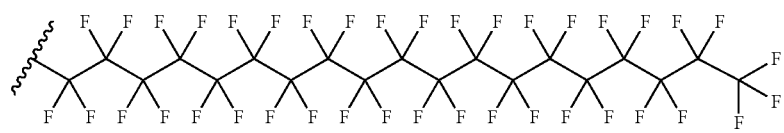
wherein e is 10, and d is 9;
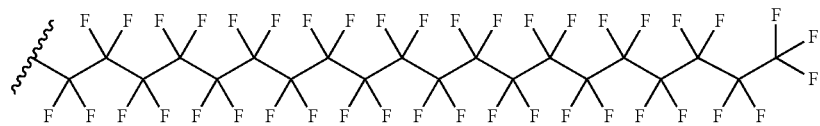
wherein e is 10, and d is 10;
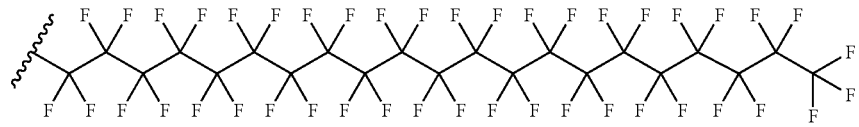
wherein e is 10, and d is 11;
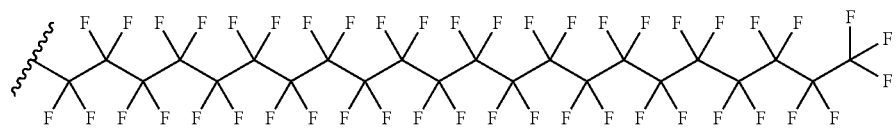
wherein e is 10, and d is 12;
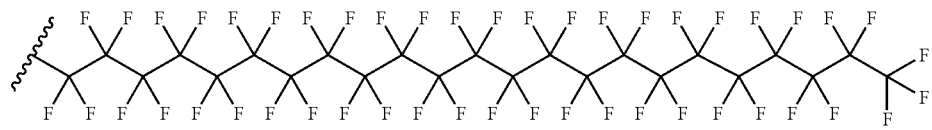
wherein e is 10, and d is 13;

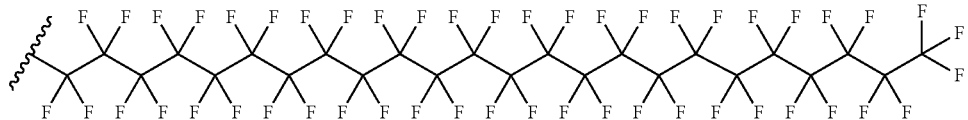

wherein e is 10, and d is 14; and

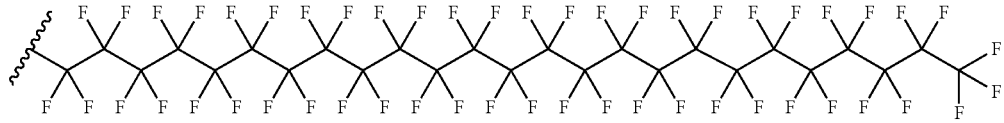

wherein e is 10, and d is 15.

In some embodiments, G is of Formula (c):

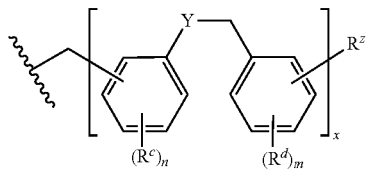

wherein:

Y is —O—, —S—, —NR$^Y$—, or an optionally substituted methylene group, wherein R$^Y$ is hydrogen, optionally substituted aliphatic, or an amino protecting group;

each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, and —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring;

each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring;

R$^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring;

each instance of n is, independently, 0, 1, 2, 3, or 4;

each instance of m is, independently, 0, 1, 2, 3, or 4; and x is 1, 2, 3, 4, 5, or 6.

As generally defined above, Y is —O—, —S—, —NR$^Y$—, or an optionally substituted methylene group, wherein R$^Y$ is hydrogen, optionally substituted aliphatic, or an amino protecting group. In certain embodiments, Y is —O—. In certain embodiments, Y is —S—. In certain embodiments, Y is —NR$^Y$—. In certain embodiments, Y is an optionally substituted methylene group, e.g., —CH$_2$—.

As generally defined above, each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, heterocycyl, optionally substituted aryl, or optionally substituted heteroaryl, or two R$^e$ groups are joined to form a 5- to 6-membered optionally substituted heterocycyl or optionally substituted heteroaryl ring; and n is 0, 1, 2, 3, or 4.

In certain embodiments, each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring; wherein each instance of aliphatic, heteroaliphatic, carbocycyl, heterocycyl, aryl and heteroaryl is independently unsubstituted or substituted with 1, 2, 3, 4, 5, 6, 7, 8, 9, 10, or more substituents, as defined herein. In certain embodiments, each instance of aliphatic, heteroaliphatic, carbocycyl, heterocycyl, aryl and heteroaryl is independently unsubstituted or substituted with C$_{1-6}$alkyl, C$_{1-6}$-fluoroalkyl or halogen.

In certain embodiments, each instance of R$^c$ is independently —F, aliphatic, heteroaliphatic, carbocycyl, heterocycyl, aryl, or heteroaryl, wherein each instance of aliphatic, heteroaliphatic, carbocycyl, heterocycyl, aryl and heteroaryl is independently unsubstituted or substituted with $C_{1-6}$alkyl, $C_{1-6}$-fluoroalkyl or halogen.

In certain embodiments, each instance of $R^c$ is independently —F or alkyl, wherein each instance of alkyl is independently unsubstituted or substituted with $C_{1-6}$alkyl, $C_{1-6}$fluoroalkyl or halogen.

In certain embodiments, n is 0 or 1. In certain embodiments, n is 0. In certain embodiments, n is 1. In certain embodiments, n is 2.

As generally defined above, each instance of $R^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^f$, —$SR^f$, —$NHR^f$, or —$N(R^f)_2$, wherein each instance of $R^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^f$ groups are joined to form a 5- to 6-membered optionally substituted heterocycyl or optionally substituted heteroaryl ring; and m is 0, 1, 2, 3, or 4.

In certain embodiments, each instance of $R^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^f$, —$SR^f$, —$NHR^f$, or —$N(R^f)_2$, wherein each instance of $R^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^f$ groups are joined to form a 5- to 6-membered optionally substituted heterocycyl or optionally substituted heteroaryl ring; wherein each instance of aliphatic, heteroaliphatic, carbocycyl, heterocycyl, aryl and heteroaryl is independently unsubstituted or substituted with 1, 2, 3, 4, 5, 6, 7, 8, 9, 10, or more substituents, as defined herein. In certain embodiments, each instance of aliphatic, heteroaliphatic, carbocycyl, heterocycyl, aryl and heteroaryl is independently unsubstituted or substituted with $C_{1-6}$alkyl, $C_{1-6}$fluoroalkyl or halogen.

In certain embodiments, each instance of $R^d$ is independently —F, aliphatic, heteroaliphatic, carbocycyl, heterocycyl, aryl, or heteroaryl, wherein each instance of aliphatic, heteroaliphatic, carbocycyl, heterocycyl, aryl, and heteroaryl is independently unsubstituted or substituted with $C_{1-6}$alkyl, $C_{1-6}$fluoroalkyl or halogen.

In certain embodiments, each instance of $R^d$ is independently —F or alkyl, wherein each instance of alkyl is independently unsubstituted or substituted with $C_{1-6}$alkyl, $C_{1-6}$fluoroalkyl, or halogen.

In certain embodiments, m is 0 or 1. In certain embodiments, m is 0. In certain embodiments, m is 1. In certain embodiments, m is 2.

In certain embodiments, $R^z$ is an ortho, meta, or para substituent to the —$OCH_2$-linking group. In certain embodiments, $R^z$ is a meta substituent.

As generally defined above, $R^z$ is hydrogen, —F, —Br, —I, —Cl, optionally substituted aliphatic, heteroaliphatic, optionally substituted carbocycyl, optionally substituted heterocycyl, optionally substituted aryl, optionally substituted heteroaryl, —$OR^g$, —$SR^g$, —$NHR^g$, or —$N(R^g)_2$, wherein each instance of $R^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two $R^g$ groups are joined to form a 5- to 6-membered optionally substituted heterocycyl or optionally substituted heteroaryl ring.

In certain embodiments, $R^z$ is hydrogen, —F, —Br, —I, —Cl, optionally substituted aliphatic, heteroaliphatic, optionally substituted carbocycyl, optionally substituted heterocycyl, optionally substituted aryl, optionally substituted heteroaryl, —$OR^g$, —$SR^g$, —$NHR^g$, or —$N(R^g)_2$, wherein each instance of $R^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two $R^g$ groups are joined to form a 5- to 6-membered optionally substituted heterocycyl or optionally substituted heteroaryl ring, wherein each instance of aliphatic, heteroaliphatic, carbocycyl, heterocycyl, aryl and heteroaryl is independently unsubstituted or substituted with 1, 2, 3, 4, 5, 6, 7, 8, 9, 10, or more substituents, as defined herein. In certain embodiments, each instance of aliphatic, heteroaliphatic, carbocycyl, heterocycyl, aryl and heteroaryl is independently unsubstituted or substituted with $C_{1-6}$alkyl, $C_{1-6}$fluoroalkyl or halogen.

In certain embodiments, $R^z$ is hydrogen, alkyl, alkenyl, alkynyl, carbocycyl, heterocycyl, aryl, heteroaryl, —$OR^g$, —$SR^g$, —$NHR^g$, or —$N(R^g)_2$, wherein each instance of $R^g$ is independently hydrogen, alkyl, alkenyl, alkynyl, carbocycyl, heterocycyl, aryl, heteroaryl, or two $R^g$ groups are joined to form a 5- to 6-membered heterocycyl or heteroaryl ring, and wherein each instance of alkyl, alkenyl, alkynyl, carbocycyl, heterocycyl, aryl, and heteroaryl, is independently unsubstituted or substituted with $C_{1-6}$alkyl, $C_{1-6}$fluoroalkyl or halogen.

In certain embodiments, $R^z$ is hydrogen or aryl, wherein aryl is unsubstituted or substituted with $C_{1-6}$alkyl, $C_{1-6}$fluoroalkyl or halogen.

As generally depicted above, x is 1, 2, 3, 4, 5, or 6. In certain embodiments, x is 1 or 2. In certain embodiments, x is 1. In certain embodiments, x is 2.

It will be understood by one skilled in the art that each repeat unit of formula (c), when x is greater than 1, can optionally differ from one another, arising from differences in the independent variables Y, $R^c$, $R^d$, n and m, as well as different substitution patterns on and between each repeating unit. Thus, in further defining the compounds of the present invention, it is also generally helpful to further designate Y, $R^c$, $R^d$, n and m, with a sequential number corresponding to the first, second, third, fourth, fifth or sixth sequential group from which it is formally a member, e.g., Y, $R^c$, $R^d$, n, m and x can also be referred to as $Y^1$, $R^{c1}$, $R^{d1}$, n1 and m1 for the first group in the sequence; $Y^2$, $R^{c2}$, $R^{d2}$, n2 and m2 for the second optional repeating unit in the sequence; $Y^3$, $R^{c3}$, $R^{d3}$, n3 and m3 for the third optional repeating unit in the sequence; $Y^4$, $R^{c4}$, $R^{d4}$, n4 and m4 for the fourth optional repeating unit in the sequence; Y, $R^{c5}$, $R^{d5}$, n5 and m5 for the fifth optional repeating unit in the sequence; and $Y^6$, $R^{c6}$, $R^{d6}$, n6 and m6 for the sixth optional repeating unit in the sequence.

For example, in certain embodiments, the group of Formula (c) is of the formula:

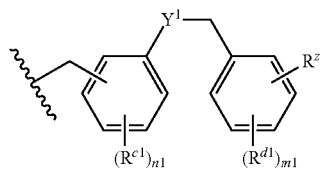

wherein x is 1;

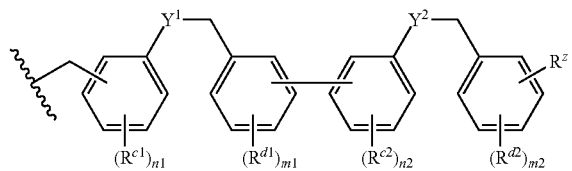
wherein x is 2;
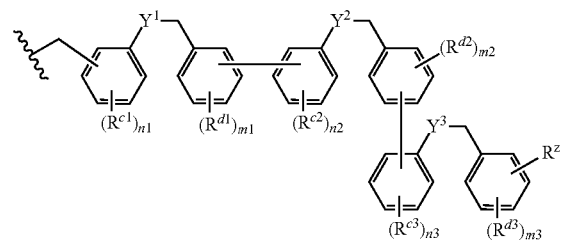
wherein x is 3;
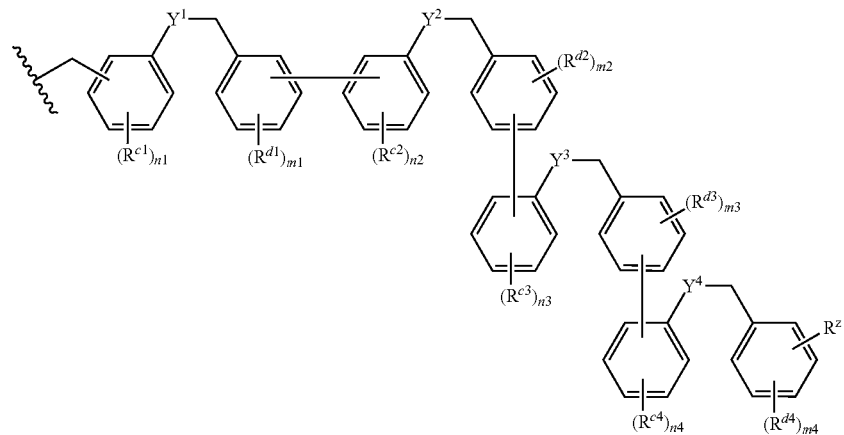
wherein x is 4;
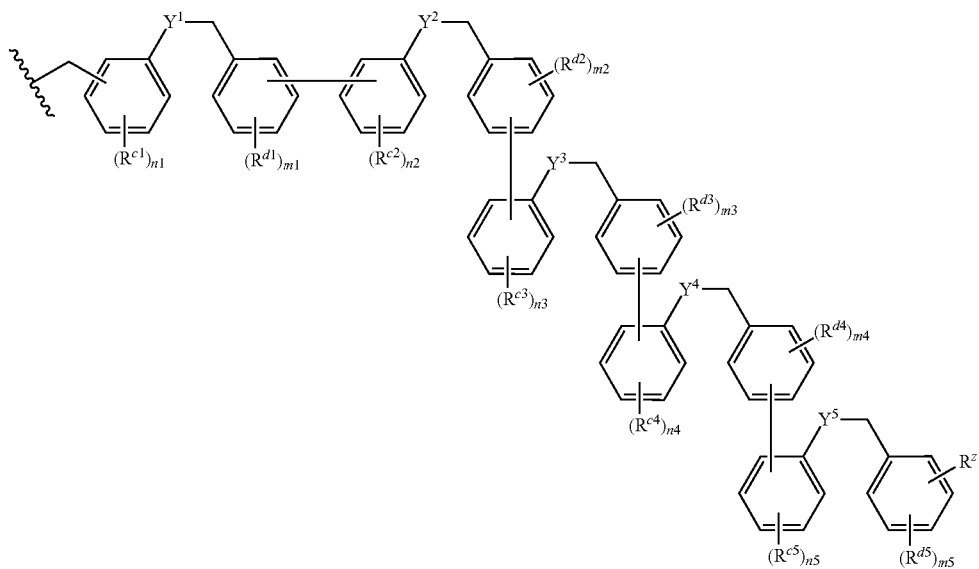
wherein x is 5;

or

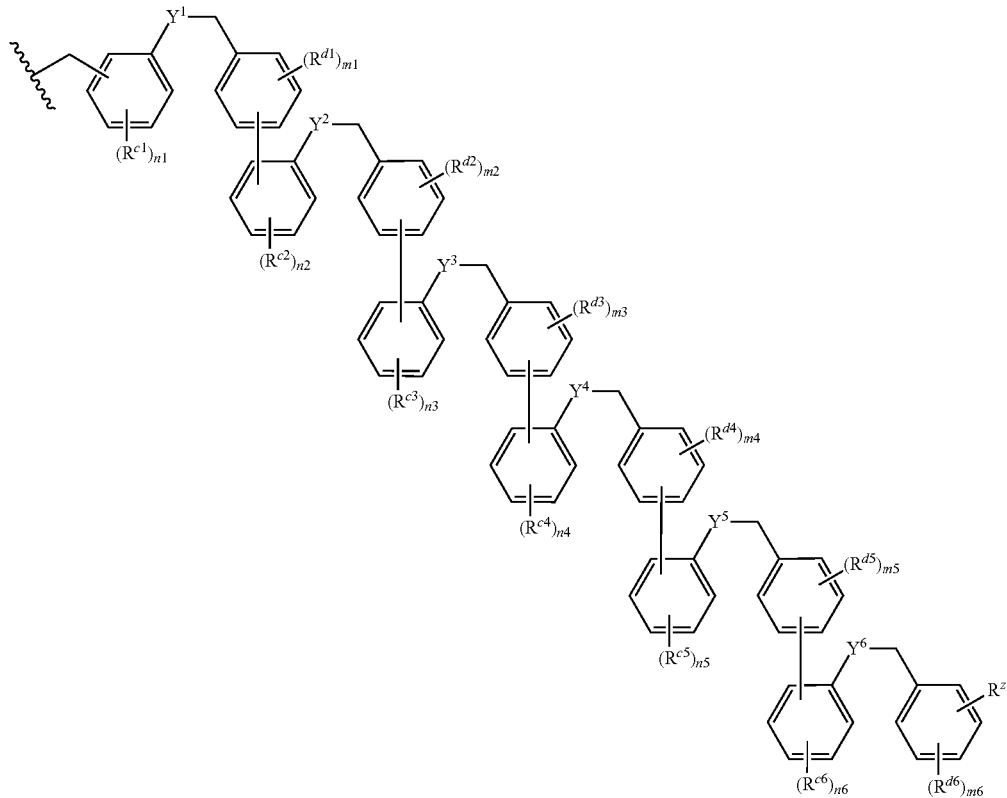

wherein x is 6;
wherein:

$R^{c1}$, $R^{c2}$, $R^{c3}$, $R^{c4}$, $R^{c5}$, and $R^{c6}$ each independently correspond to the definition and various embodiments of $R^c$;

$R^{d1}$, $R^{d2}$, $R^{d3}$, $R^{d4}$, $R^{d5}$, and $R^{d6}$ each independently correspond to the definition and various embodiments of $R^d$;

n1, n2, n3, n4, n5, and n6 each independently correspond to the definition and various embodiments of n;

m1, m2, m3, m4, m5, and m6 each independently correspond to the definition and various embodiments of m;

$Y^1$, $Y^2$, $Y^3$, $Y^4$, $Y^5$, and $Y^6$, each independently correspond to the definition and various embodiments of Y; and $R^z$ is as defined herein.

In certain embodiments, the group of Formula (c) is of the formula:

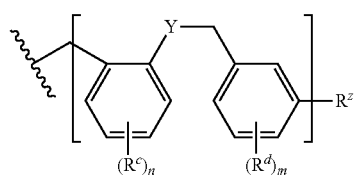

wherein Y, $R^z$, $R^c$, $R^d$, m, n, and x are as defined herein.

In certain embodiments, the group of Formula (c) is:

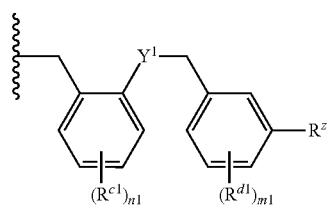

wherein x is 1;

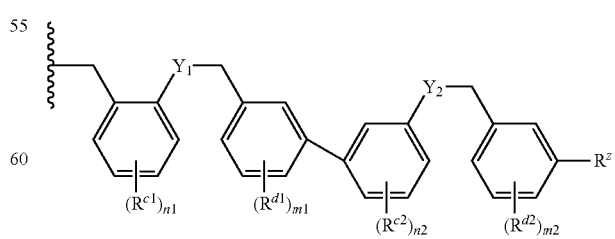

wherein x is 2;

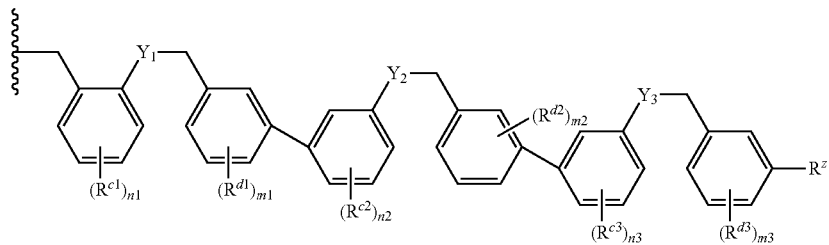
wherein x is 3;
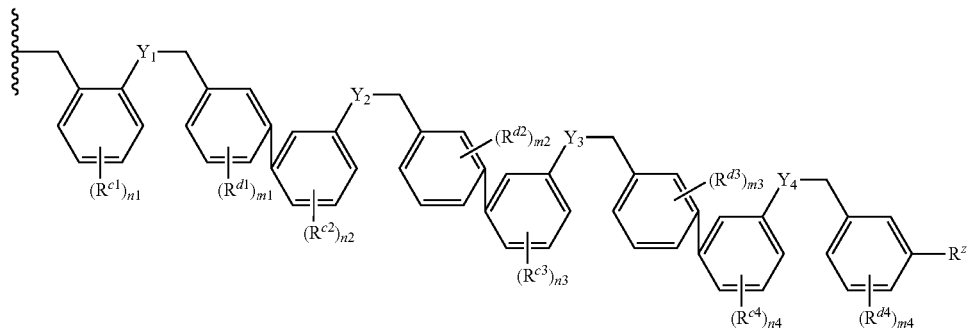
wherein x is 4;
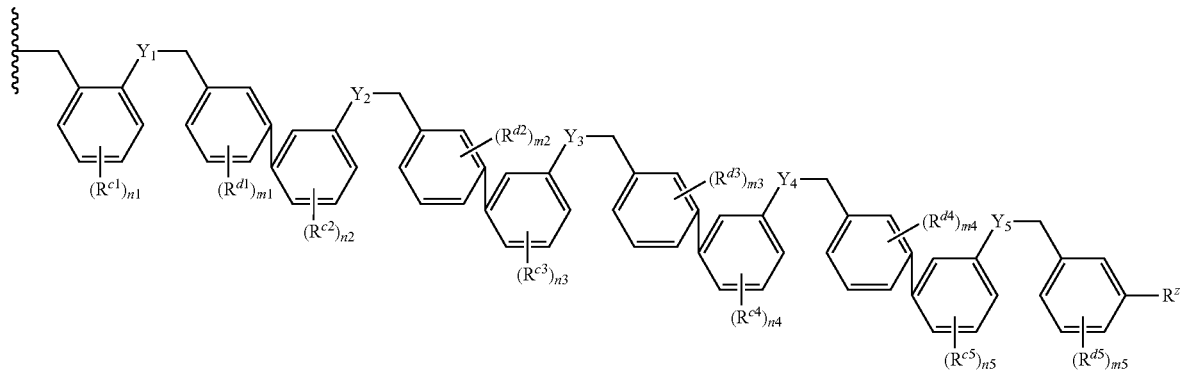
wherein x is 5;
or
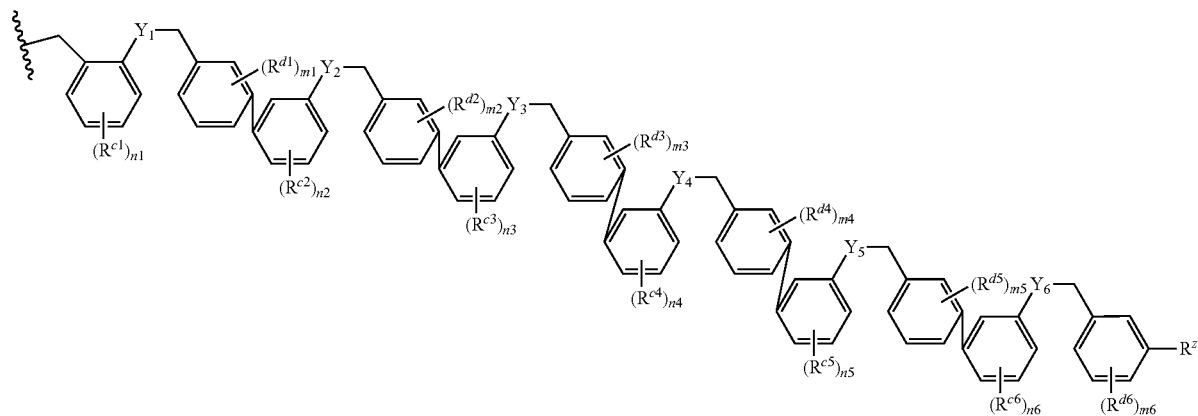
wherein x is 6;

wherein:

$R^{c1}$, $R^{c2}$, $R^{c3}$, $R^{c4}$, $R^{c5}$, and $R^{c6}$ each independently correspond to the definition and various embodiments of $R^c$;

$R^{d1}$, $R^{d2}$, $R^{d3}$, $R^{d4}$, $R^{d5}$, and $R^{d6}$ each independently correspond to the definition and various embodiments of $R^d$;

n1, n2, n3, n4, n5, and n6 each independently correspond to the definition and various embodiments of n;

m1, m2, m3, m4, m5, and m6 each independently correspond to the definition and various embodiments of m;

$Y^1$, $Y^2$, $Y^3$, $Y^4$, $Y^5$, and $Y^6$, each independently correspond to the definition and various embodiments of Y; and $R^z$ is as defined herein.

In certain embodiments, each of n, n1, n2, n3, n4, n5, and n6 is 0.

In certain embodiments, each of m, m1, m2, m3, m4, m5, and m6 is 0.

In certain embodiments, each of Y, $Y^1$, $Y^2$, $Y^3$, $Y^4$, $Y^5$, and $Y^6$ is —O—.

As described generally above, a hydrogen radical on a compound of Formula (I) is replaced with -L-$R^P$. The -L-$R^P$ group can reside at any position on a compound of Formula (I). In certain embodiments, $R^1$ is -L-$R^P$, —C(O)NH-L-$R^P$, —CH$_2$O-L-$R^P$, or —C(O)O-L-$R^P$. In certain embodiments, $R^2$ is -L-$R^P$, —O-L-$R^P$, —N($R^8$)-L-$R^P$, or —C(O)NH-L-$R^P$. In certain embodiments, $R^3$ is -L-$R^P$, —O-L-$R^P$, —N($R^8$)-L-$R^P$, or —C(O)NH-L-$R^P$. In certain embodiments, $R^4$ is -L-$R^P$ or —O-L-$R^P$. In certain embodiments, $R^5$ is -L-$R^P$ or —NH-L-$R^P$. In certain embodiments, $R^6$ is —O-L-$R^P$. In certain embodiments, $R^6$ is —O—$R^{CX}$, wherein $R^{CX}$ is a carbohydrate moiety substituted with -L-$R^P$. In certain embodiments, $R^7$ is -L-$R^P$, —O-L-$R^P$, or —N($R^8$)-L-$R^P$. In certain embodiments, $R^8$ is -L-$R^P$. In certain embodiments, $R^9$ is -L-$R^P$. In certain embodiments, $R^{10}$ is -L-$R^P$. In certain embodiments, $R^a$ is -L-$R^P$. In certain embodiments, $R^b$ is -L-$R^P$. In certain embodiments, $R^{11}$ is -L-$R^P$, —C(O)NH-L-$R^P$, —CH$_2$O-L-$R^P$, or —C(O)O-L-$R^P$. In certain embodiments, $R^{12}$ is -L-$R^P$, —O-L-$R^P$, —N($R^8$)-L-$R^P$, or —C(O)NH-L-$R^P$. In certain embodiments, $R^{13}$ is -L-$R^P$, —O-L-$R^P$, —N($R^8$)-L-$R^P$, or —C(O)NH-L-$R^P$. In certain embodiments, $R^{14}$ is -L-$R^P$ or —NH-L-$R^P$. In certain embodiments, $R^{14}$ is —NHC(O)CH$_2$-L-$R_P$. In certain embodiments, $R^{15}$ is -L-$R^P$, —C(O)NH-L-$R^P$, —CH$_2$O-L-$R^P$, or —C(O)O-L-R. In certain embodiments, $R^{16}$ is -L-$R^P$ or —O-L-$R^P$. In certain embodiments, $R^{17}$ is -L-$R^P$ or —O-L-$R^P$. In certain embodiments, $R^{18}$ is -L-$R^P$ or —O-L-$R^P$. In certain embodiments, $R^{19a}$ is -L-$R^P$ or —O-L-$R^P$. In certain embodiments, $R^{19b}$ is -L-$R^P$ or —O-L-$R^P$ In certain embodiments, the G group is substituted with -L-$R^P$.

For example, in certain embodiments, a compound of Formula (I) can be any one of the following formulae:

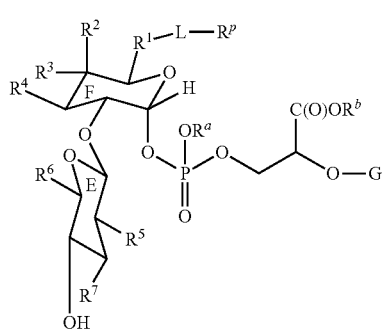

(Ia-i)

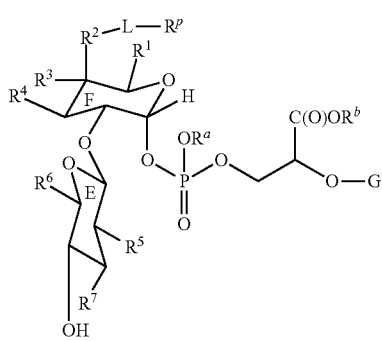

(Ia-ii)

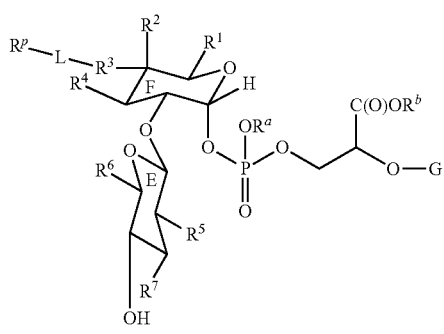

(Ia-iii)

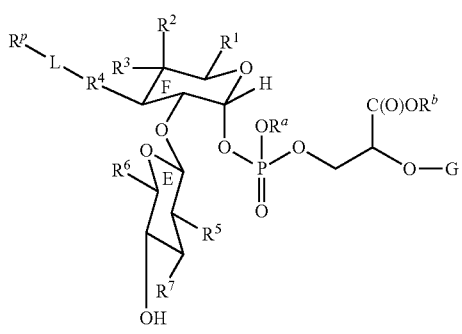

(Ia-iv)

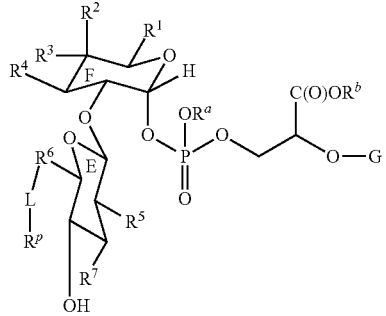

(Ia-v)

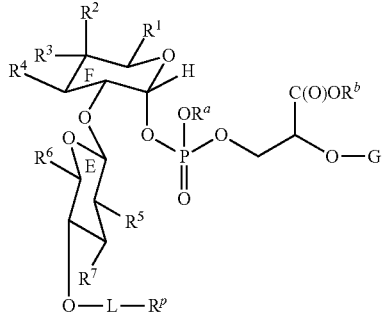

(Ia-vi)

-continued
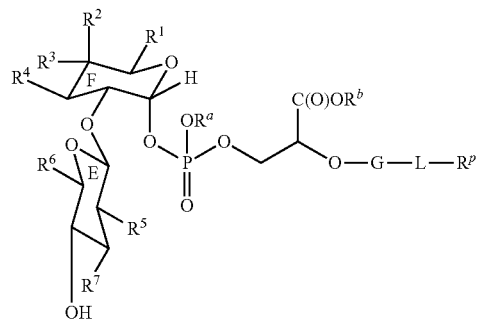
(Ia-vii)
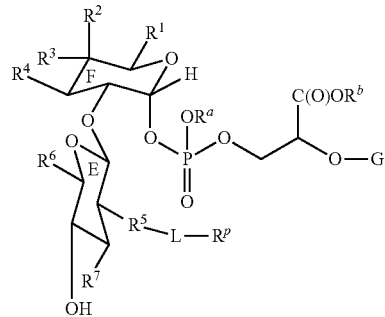
(Ia-viii)
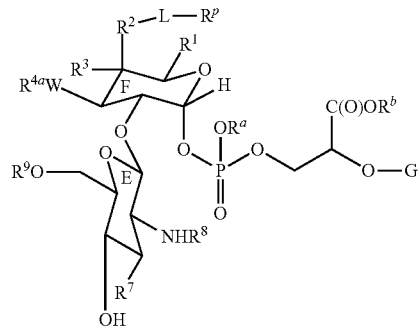
(Ia-ix)
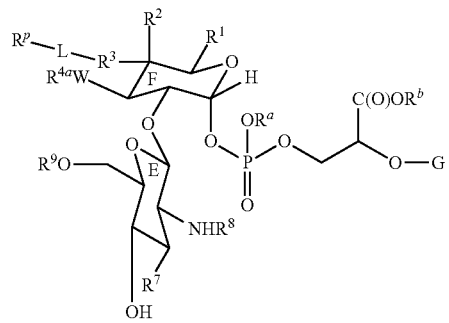
(Ia-x)
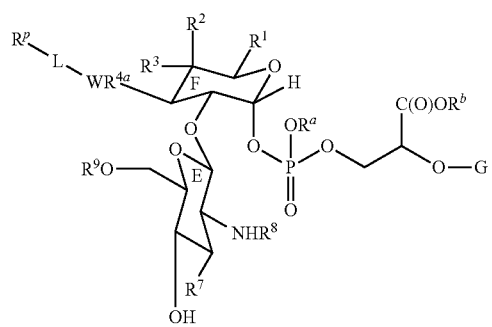
(Ia-xi)
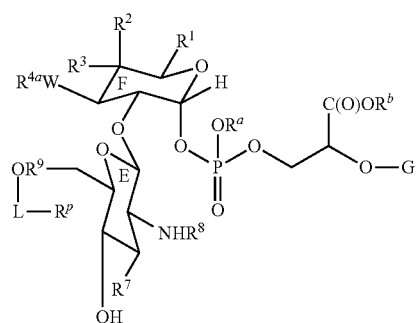
(Ia-xii)
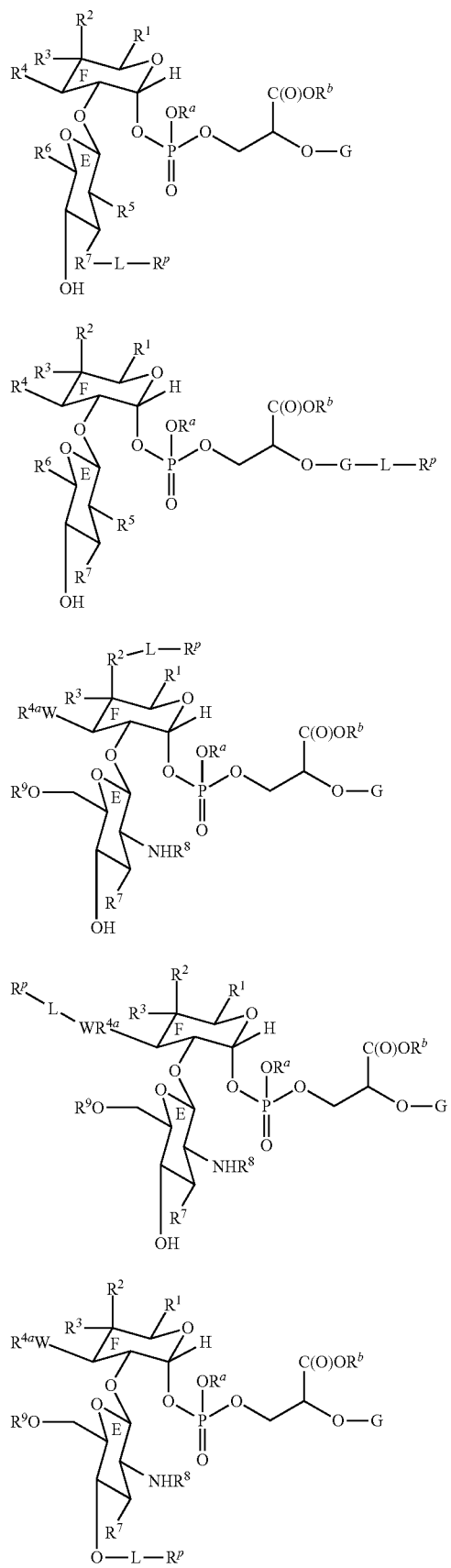
(Ia-xiii)
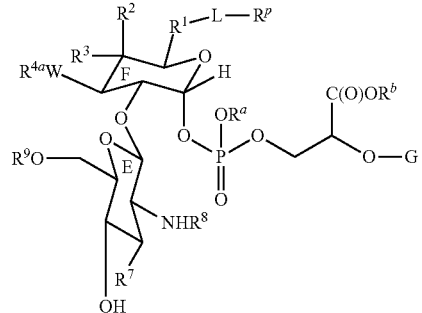
(Ia-xiv)
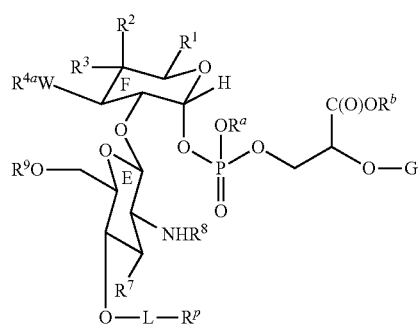
(Ia-xv)
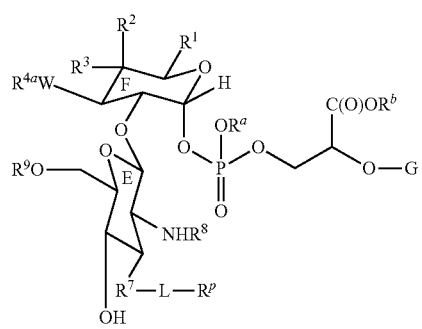
(Ia-xvi)

-continued
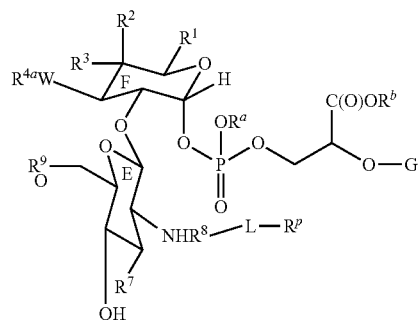
(Ia-xvii)
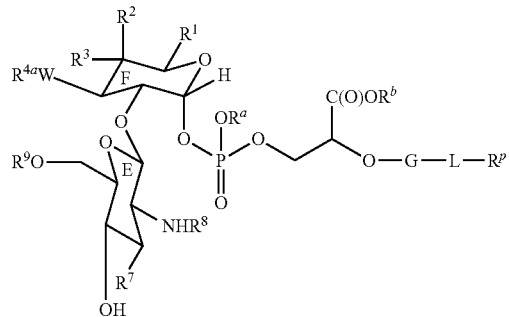
(Ia-xviii)
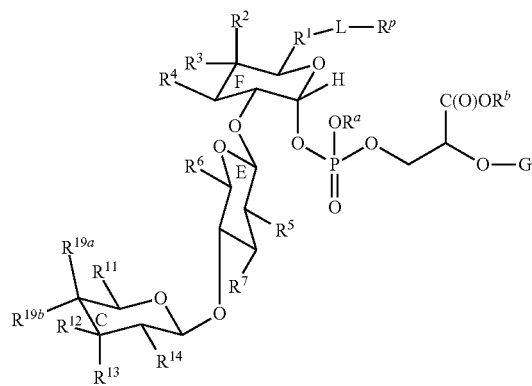
(Ib-i)
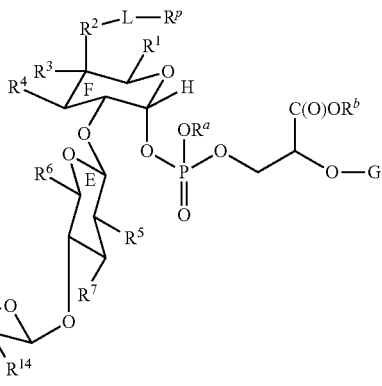
(Ib-ii)
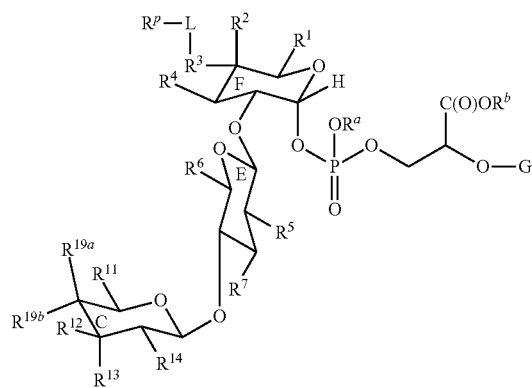
(Ib-iii)
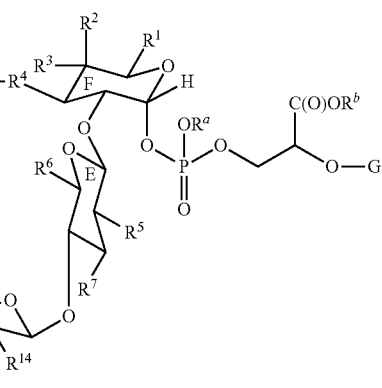
(Ib-iii)
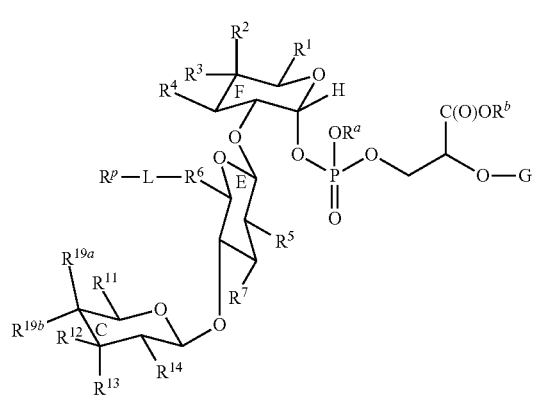
(Ib-iv)
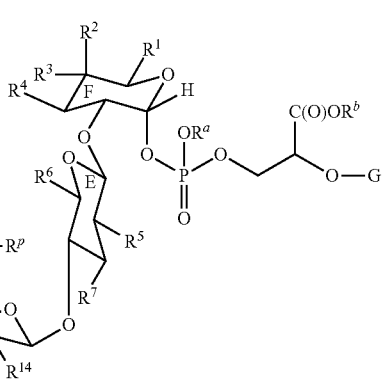
(Ib-v)

-continued
(Ib-vi)
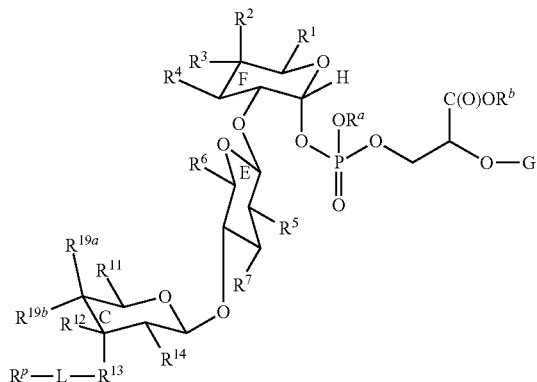
(Ib-vii)
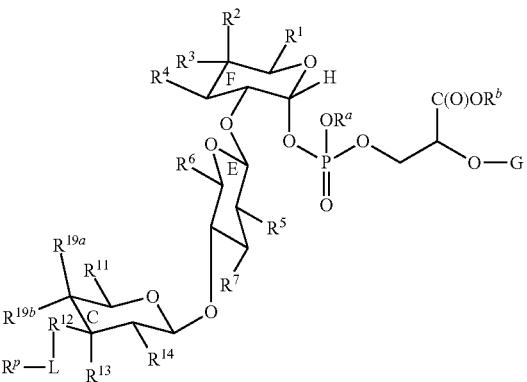
(Ib-viii)
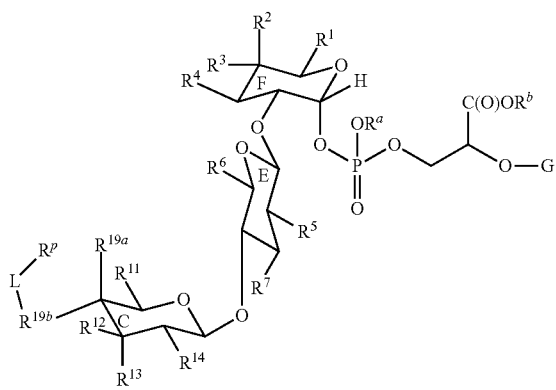
(Ib-ix)
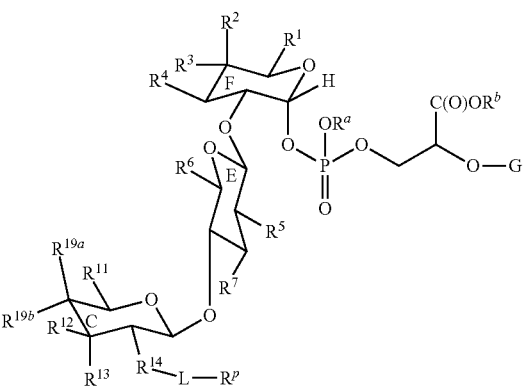
(Ib-x)
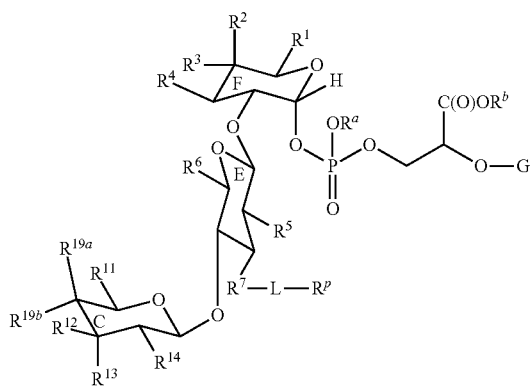
(Ib-xi)
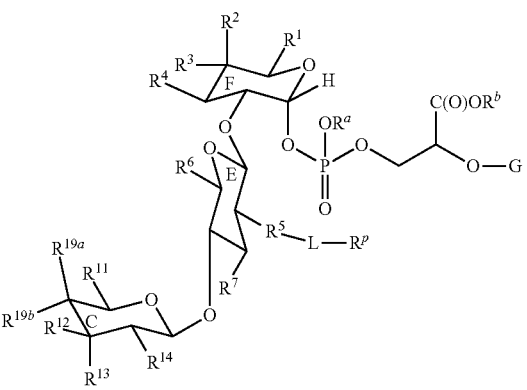
(Ib-xii)
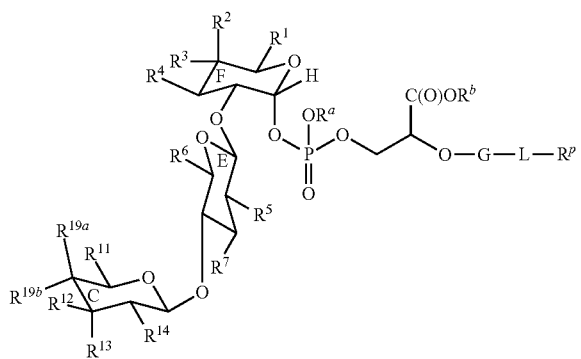
(Xb-xiii)
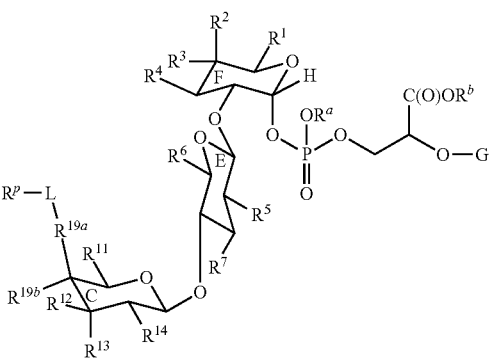

(Ib-xiv)
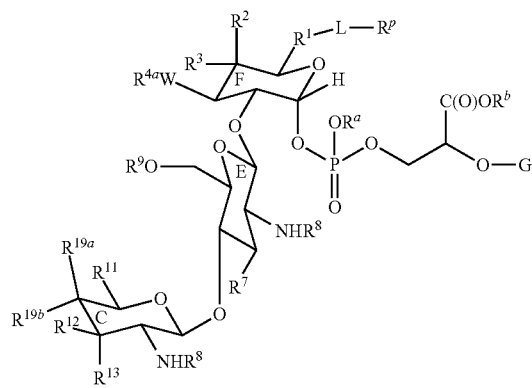
(Ib-xv)
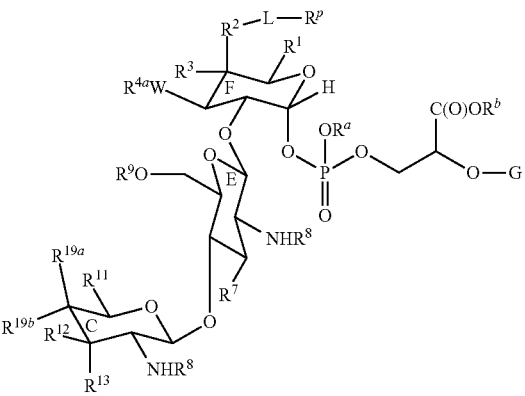
(Ib-xvi)
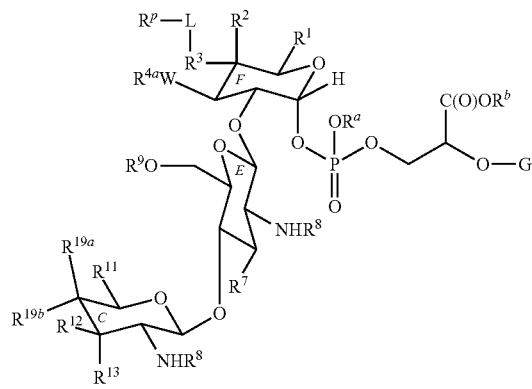
(Ib-xvii)
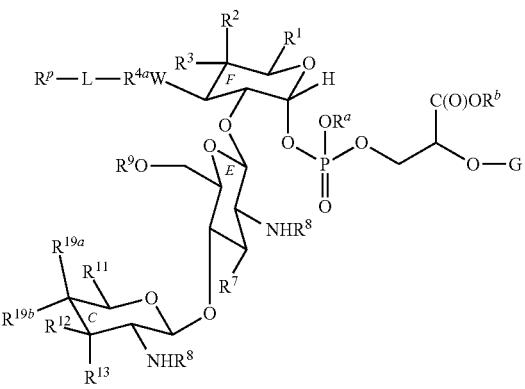
(Ib-xviii)
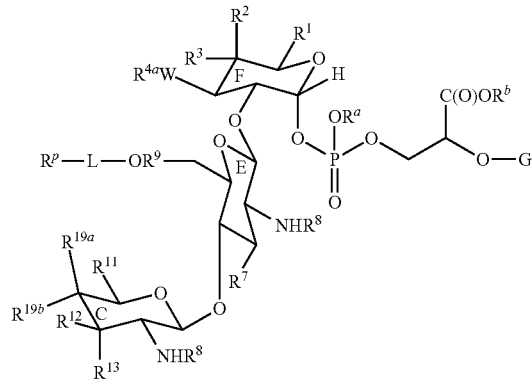
(Ib-xix)
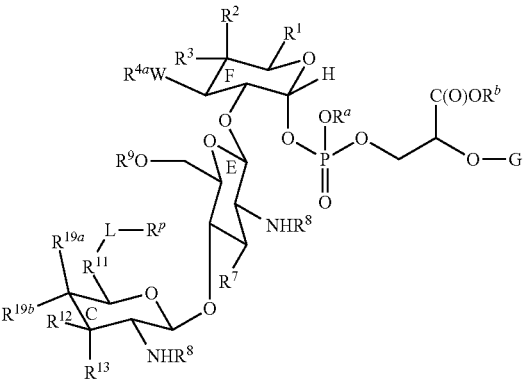
(Ib-xx)
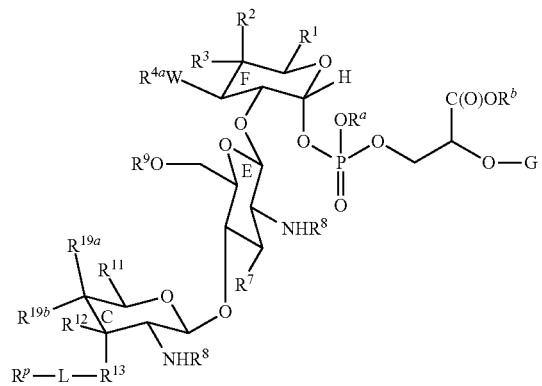
(Ib-xxii)
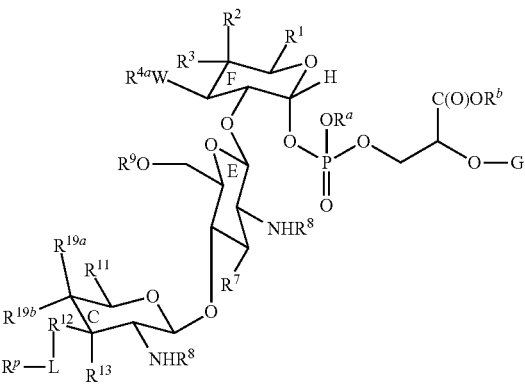

-continued
(Ib-xxiii)
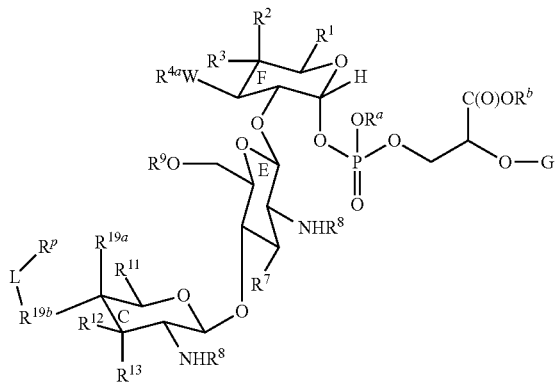
(Ib-xxiv)
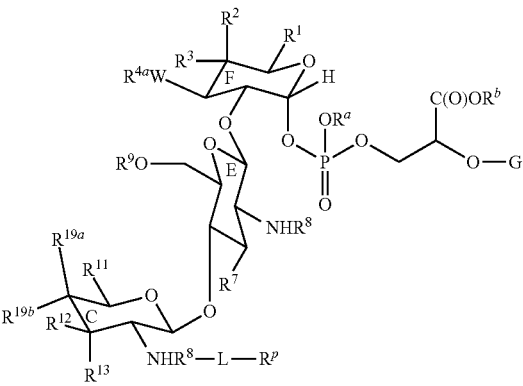
(Ib-xxv)
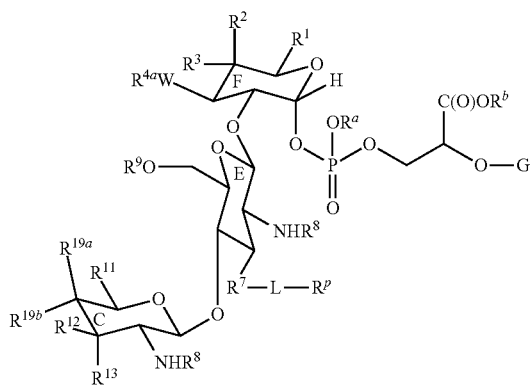
(Ib-xxvi)
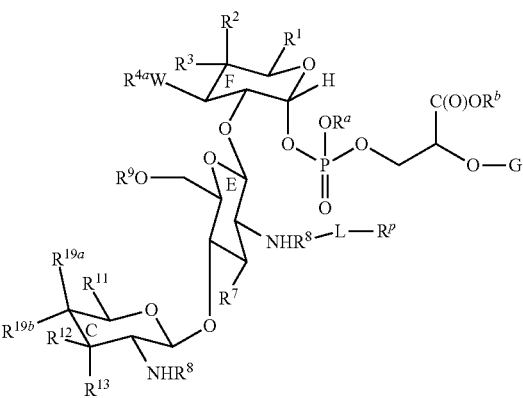
(Ib-xxvii)
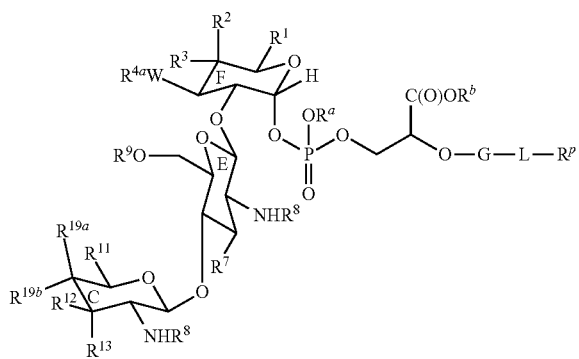
(Ib-xxviii)
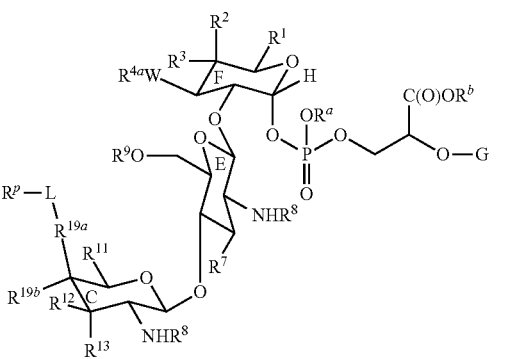
(Ic-i)
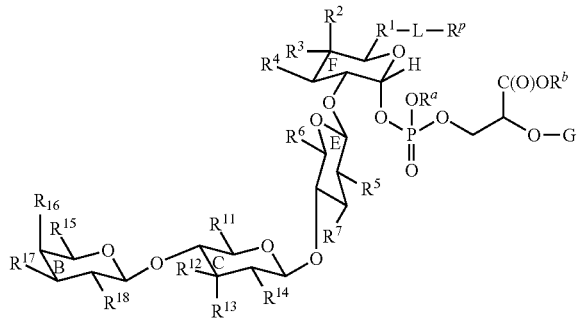
(Ic-ii)
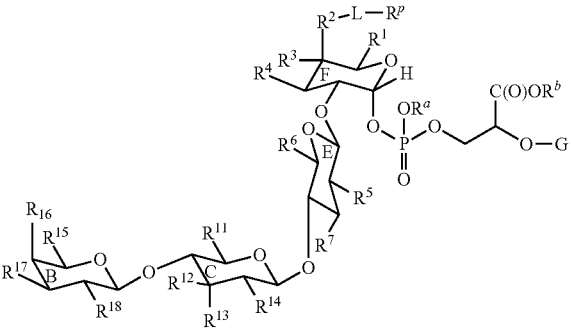

(Ic-iii)
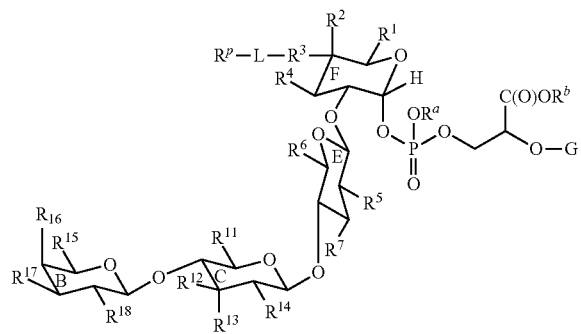
(Ic-iv)
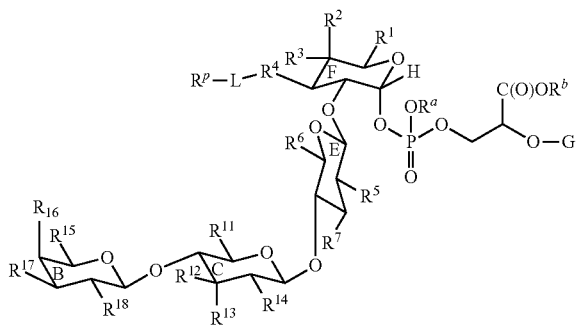
(Ic-v)
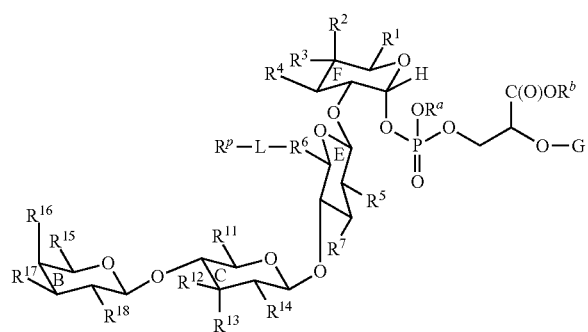
(Ic-vi)
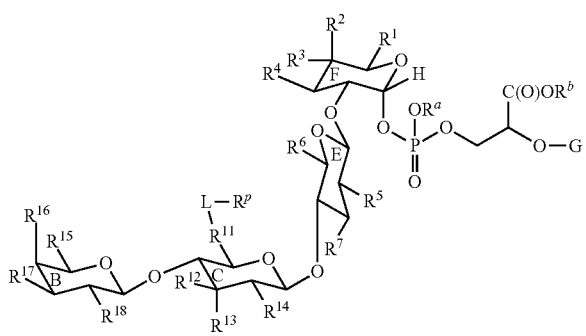
(Ic-vii)
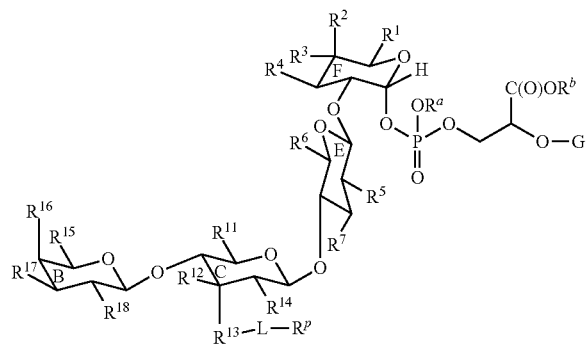
(Ic-viii)
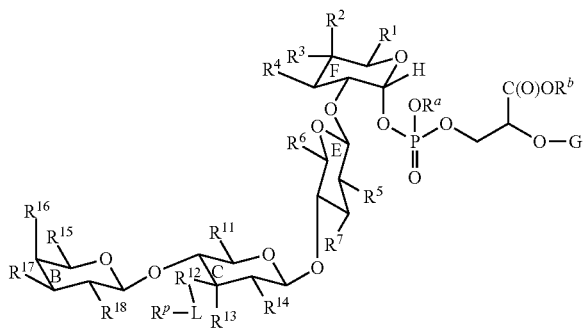
(Ic-ix)
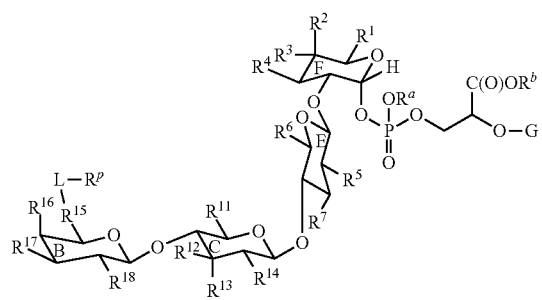
(Ic-x)
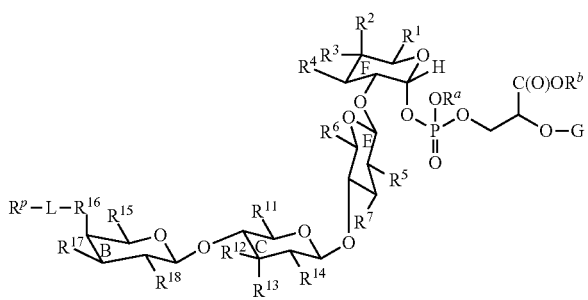

(Ic-xi)
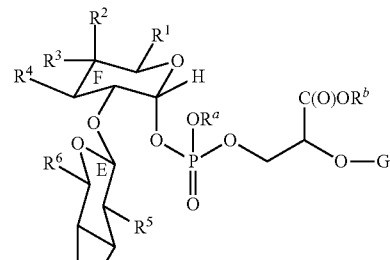
(Ic-xii)
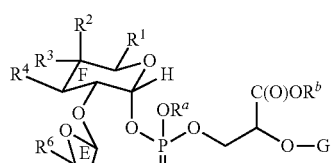
(Ic-xiii)
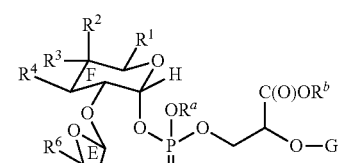
(Ic-xiv)
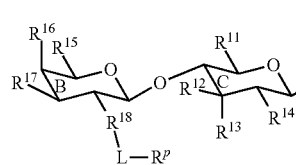
(Ic-xv)
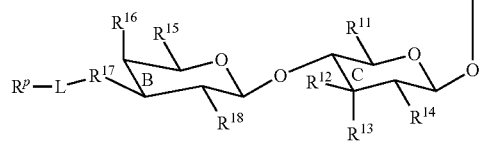
(Ic-xvi)
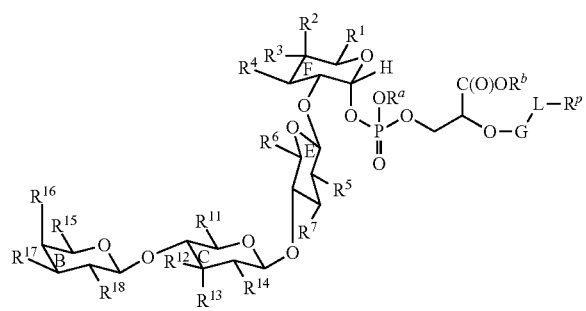
(Ic-xvii)
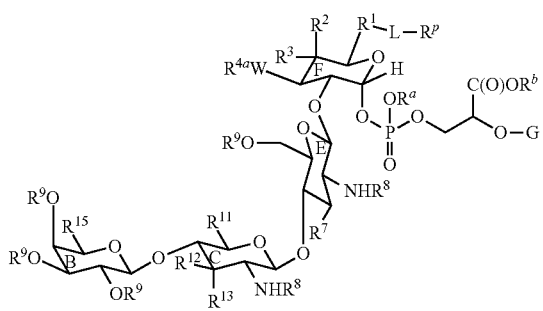
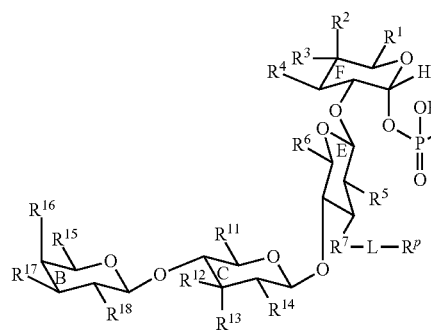

(Ic-xviii)
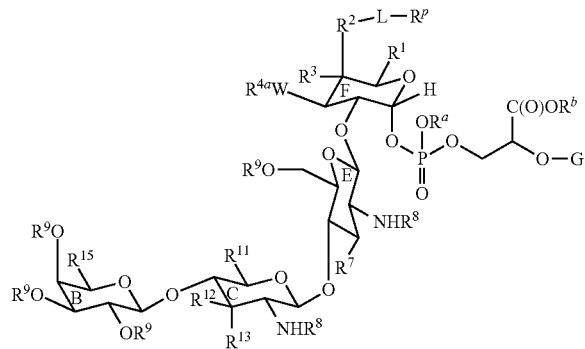
(Ic-xix)
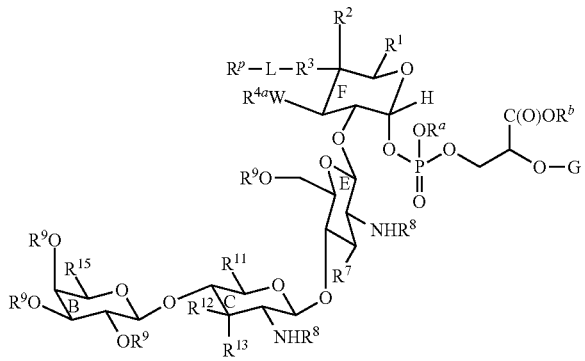
(Ic-xx)
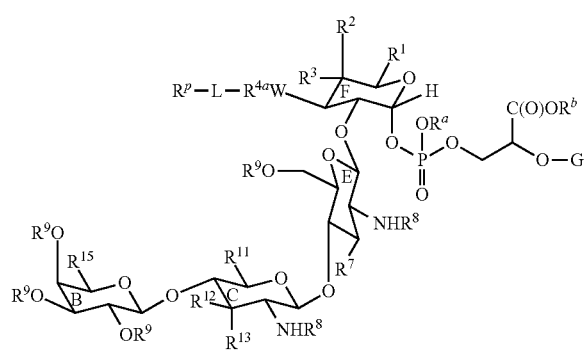
(Ic-xxi)
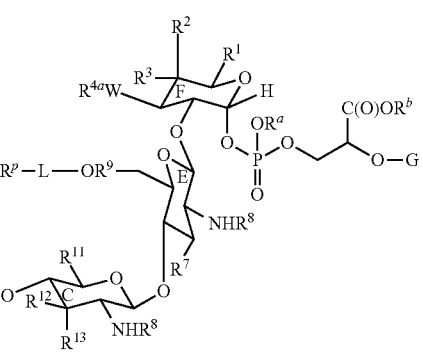
(Ic-xxii)
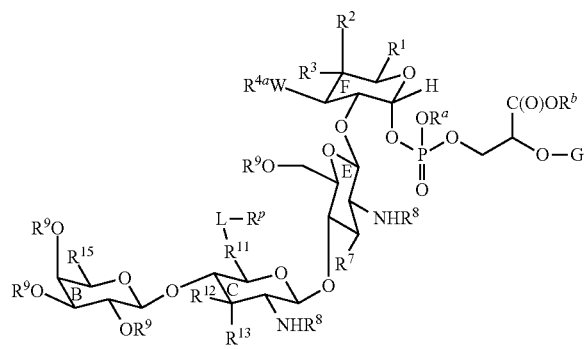
(Ic-xxiii)
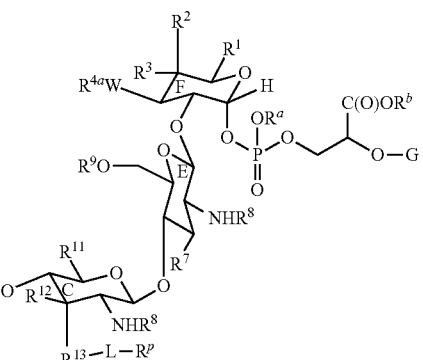
(Ic-xxiv)
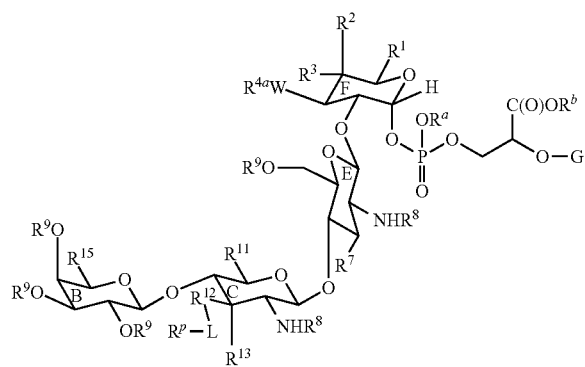
(Ic-xxv)
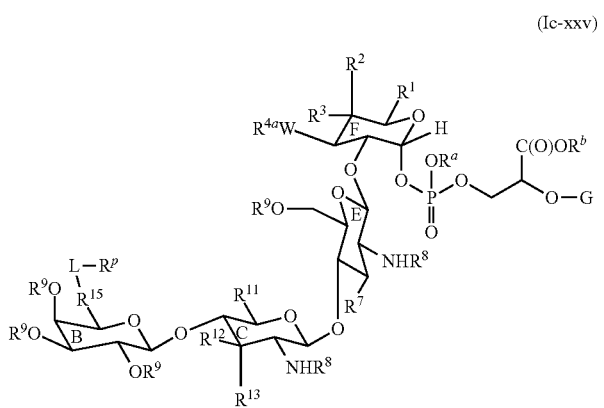

-continued
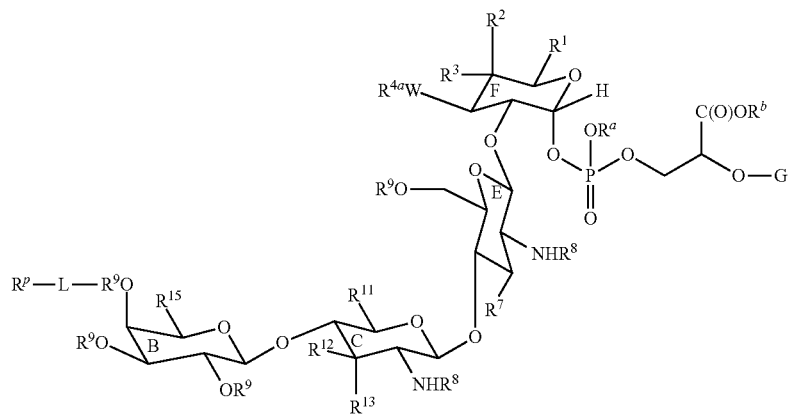
(Ic-xxvi)
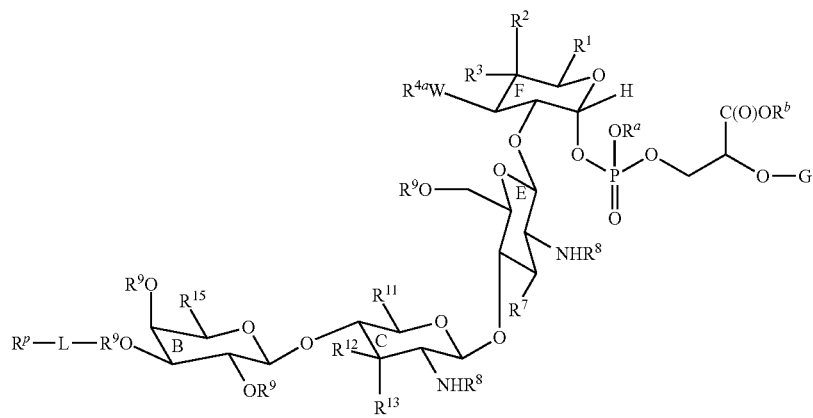
(Ic-xxvii)
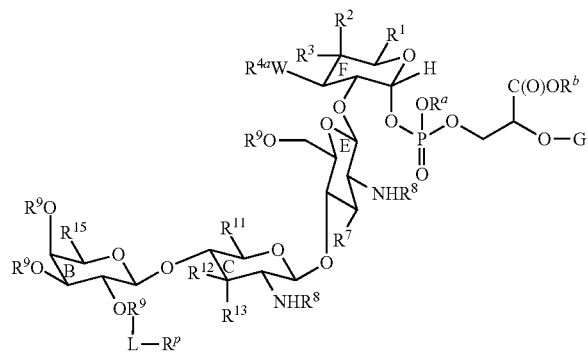
(Ic-xxviii)
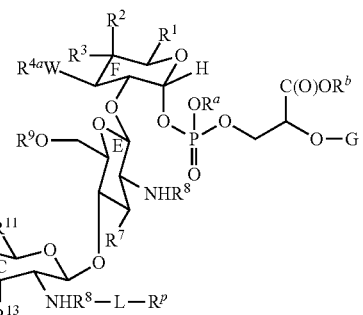
(Ic-xxix)
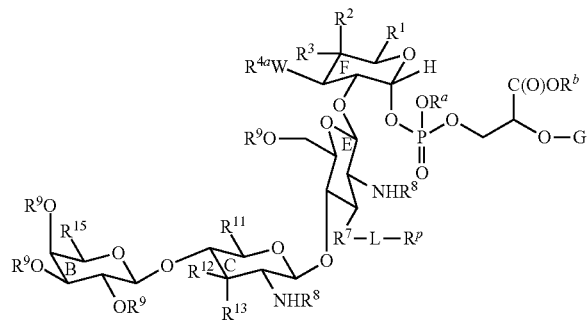
(Ic-xxx)
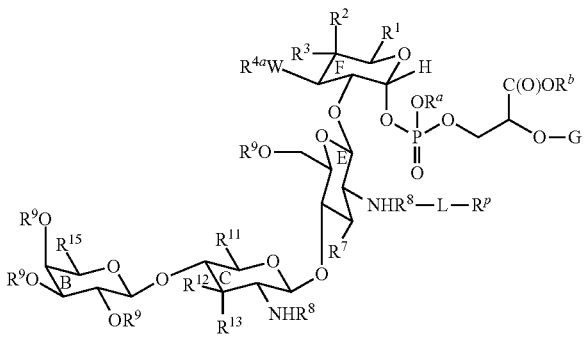
(Ic-xxxi)

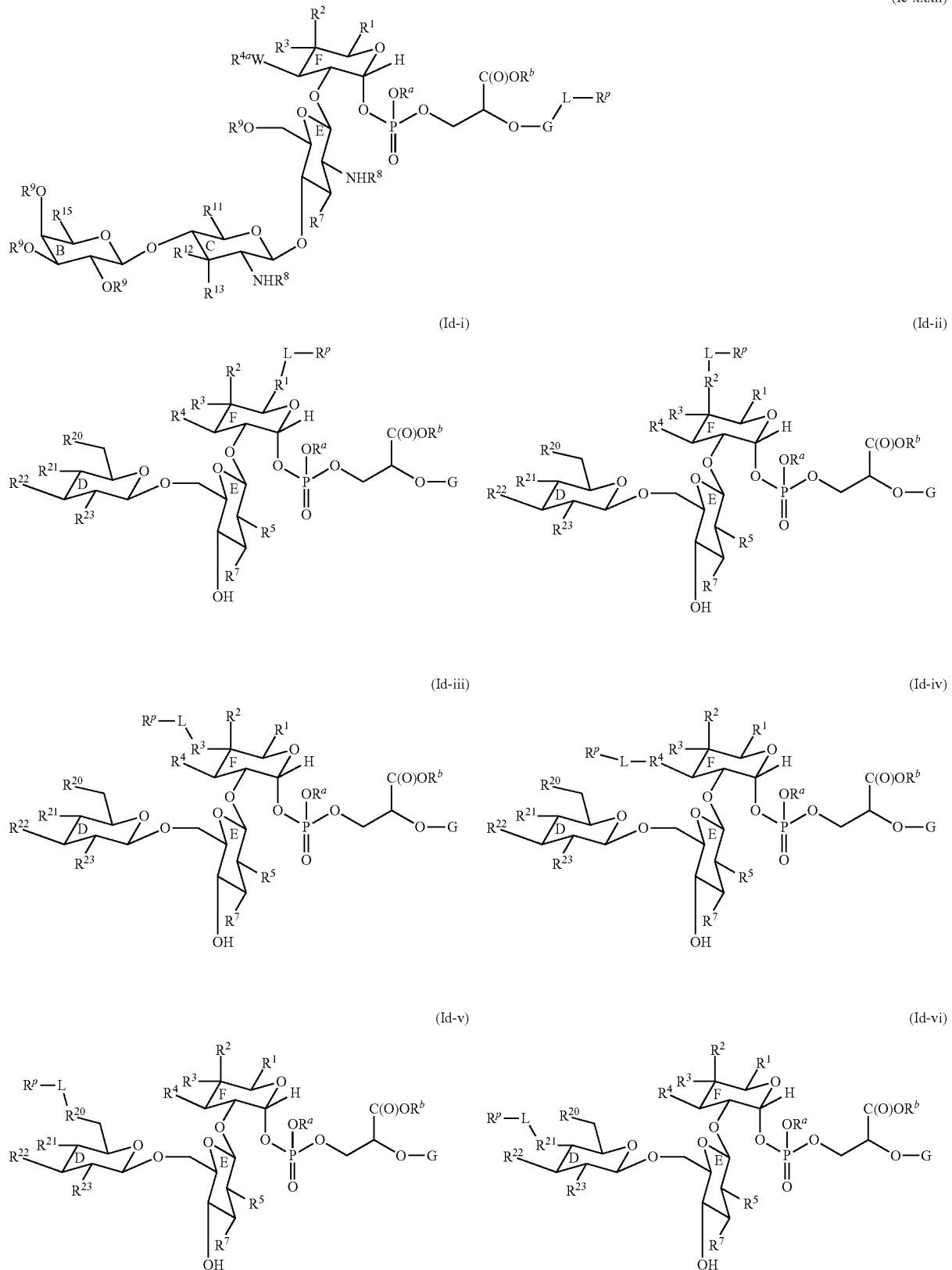

-continued
(Id-vii)
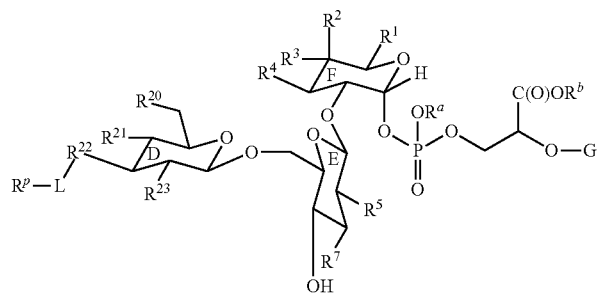
(Id-viii)
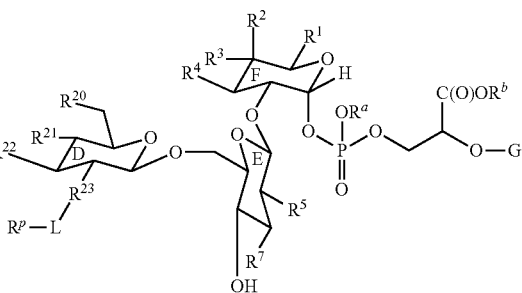
(Id-ix)
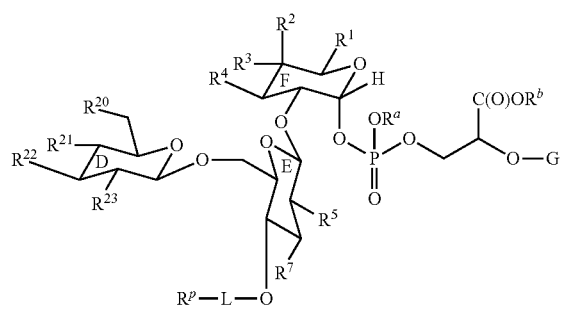
(Id-x)
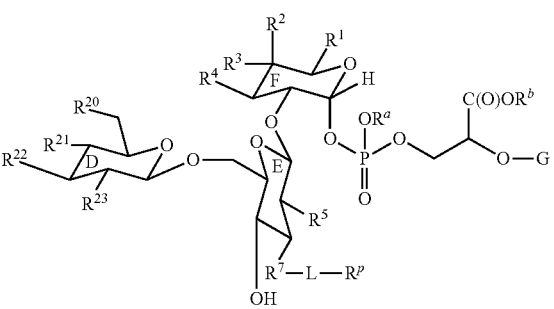
(Id-xi)
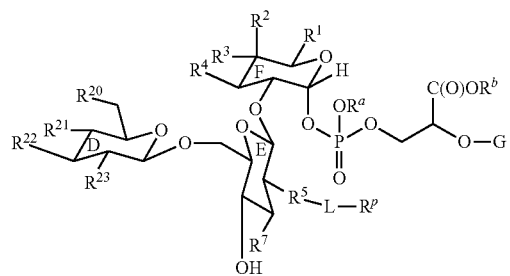
(Id-xii)
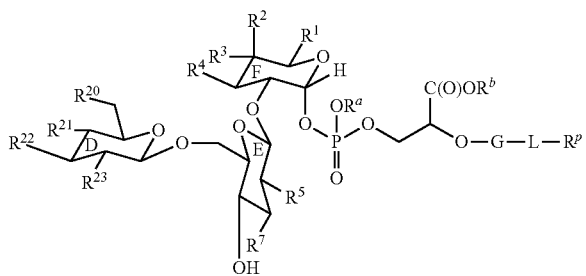
(Id-xiii)
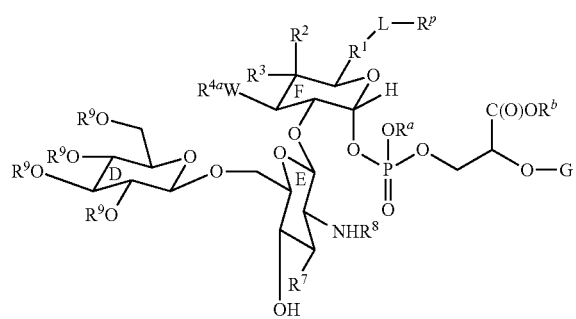
(Id-xiv)
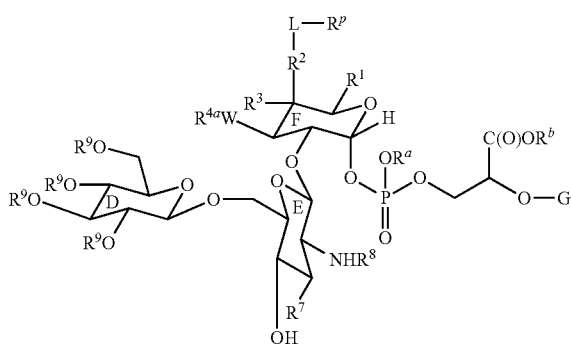
(Id-xv)
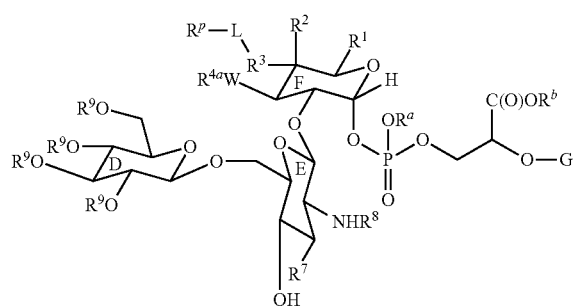
(Id-xvi)
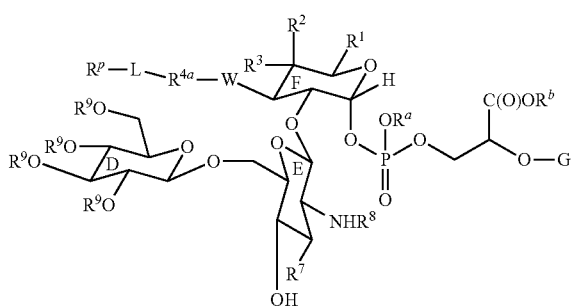

-continued
(Id-xvii)
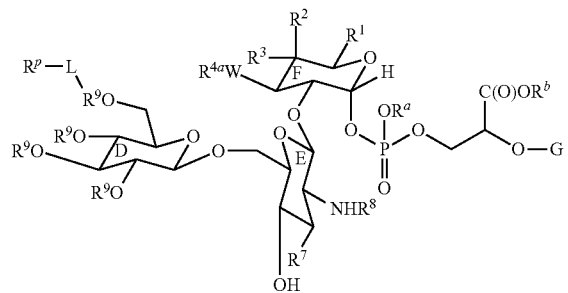
(Id-xviii)
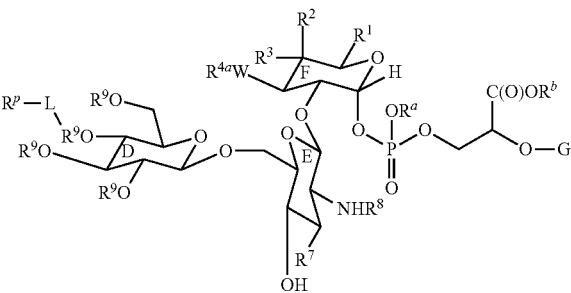
(Id-xix)
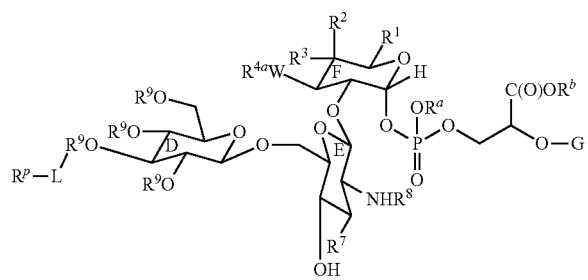
(Id-xx)
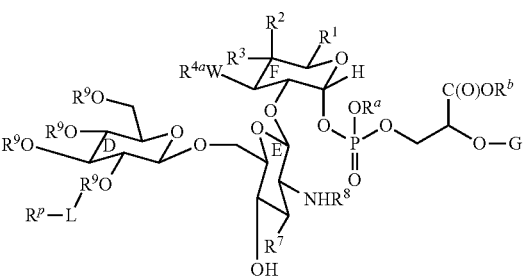
(Id-xxi)
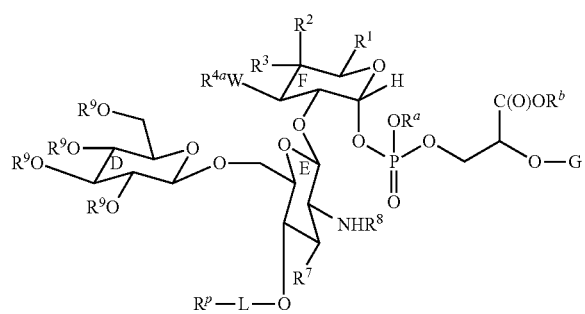
(Id-xxii)
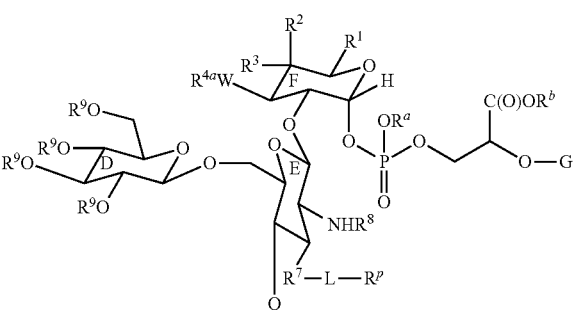
(Id-xxiii)
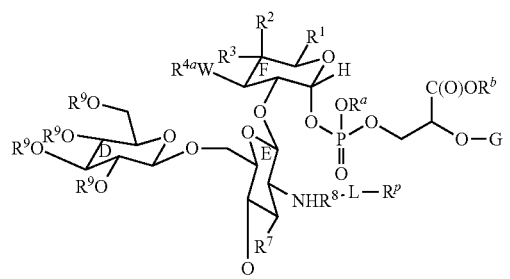
(Id-xxiv)
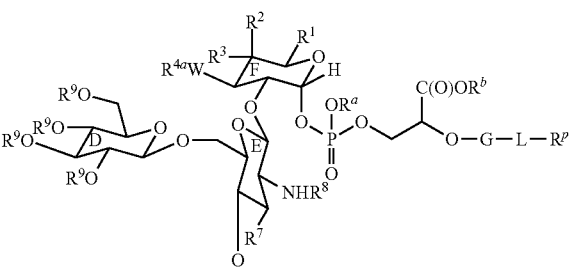
(Ie-i)
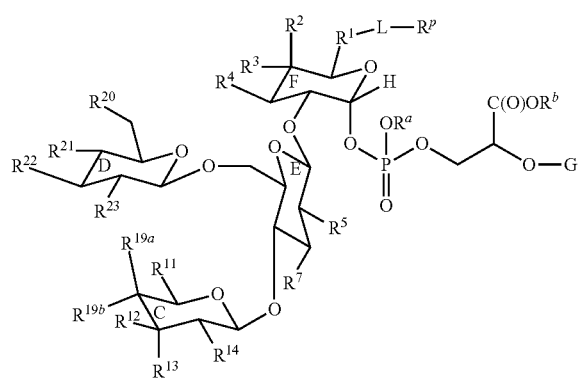
(Ie-ii)
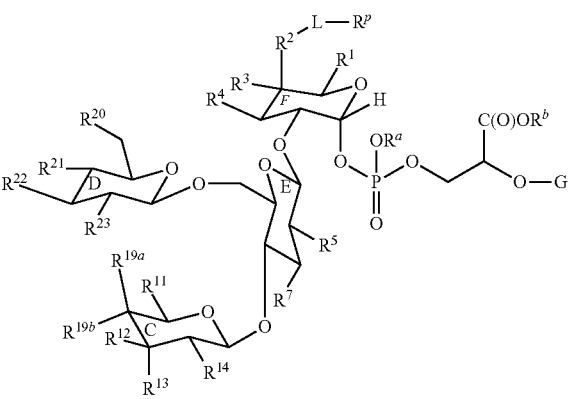

-continued
(Ie-iii)
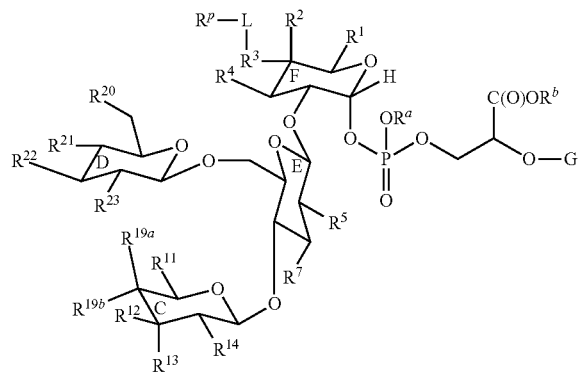
(Ie-iv)
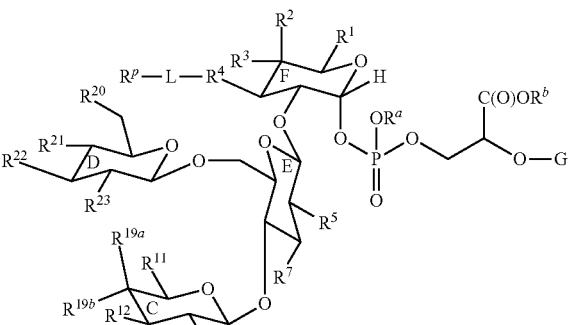
(Ie-v)
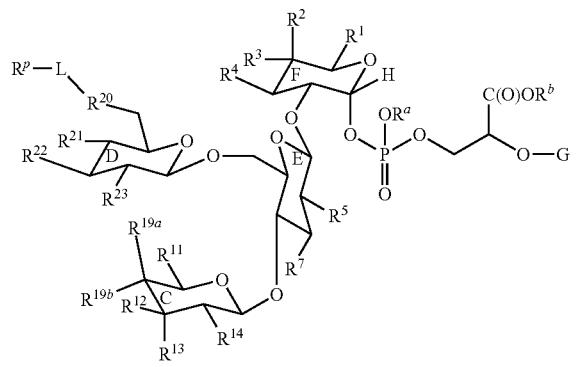
(Ie-vi)
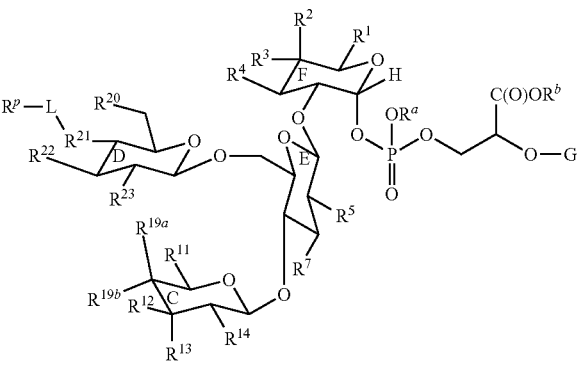
(Ie-vii)
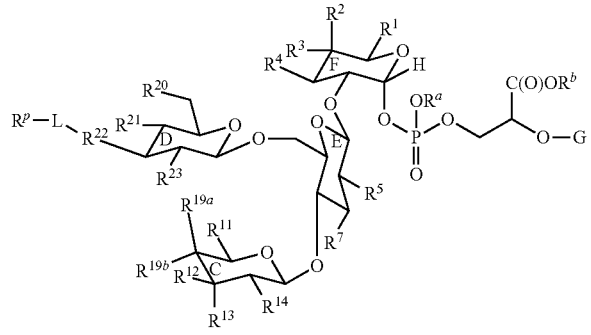
(Ie-viii)
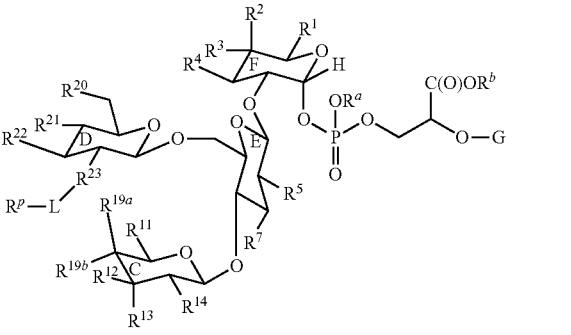
(Ie-ix)
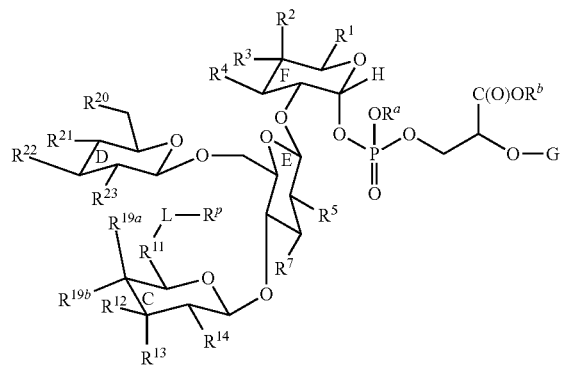
(Ie-x)
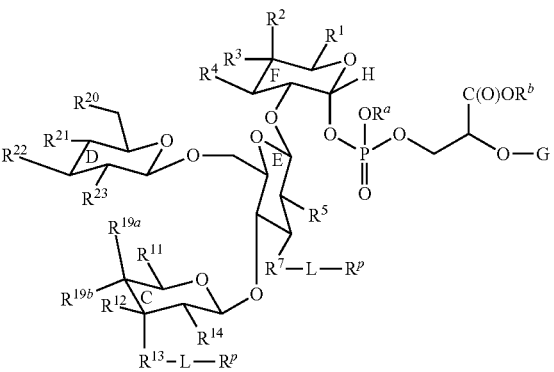

-continued
(Ie-xi)
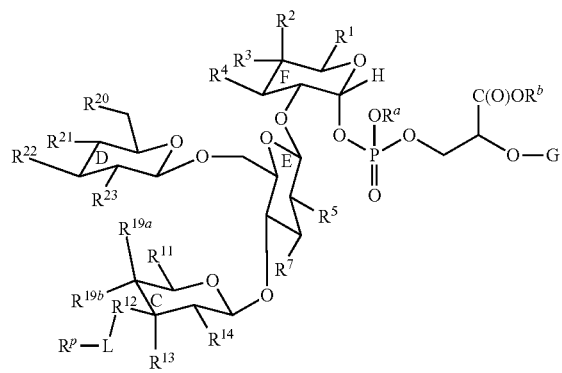
(Ie-xii)
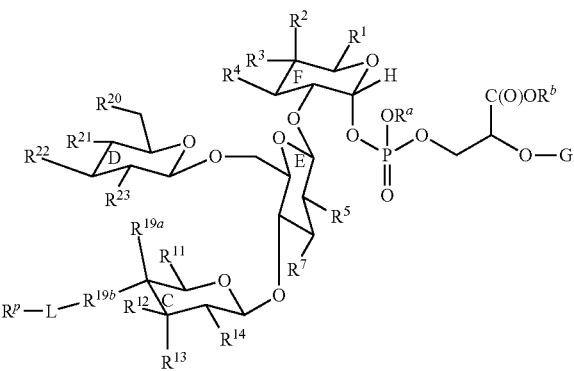
(Ie-xiii)
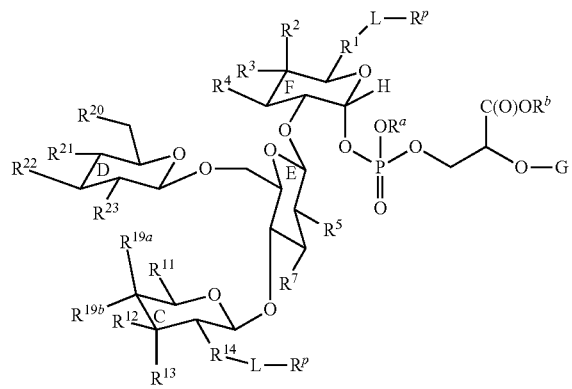
(Ie-xiv)
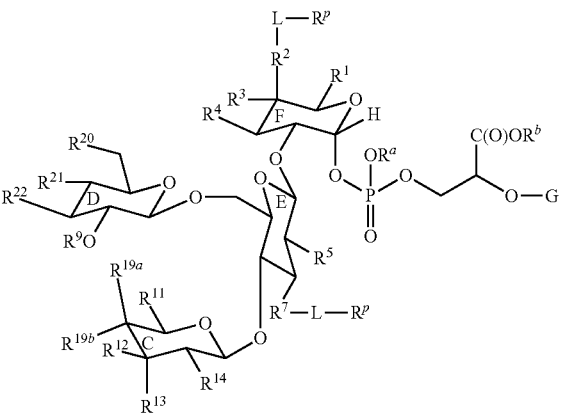
(Ie-xv)
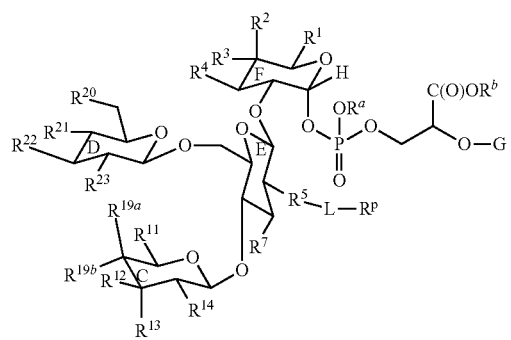
(Ie-xvi)
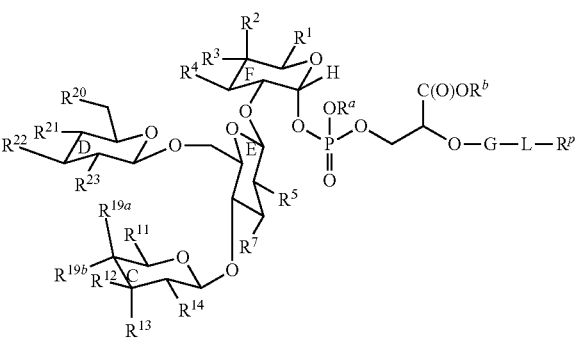
(Ie-xvii)
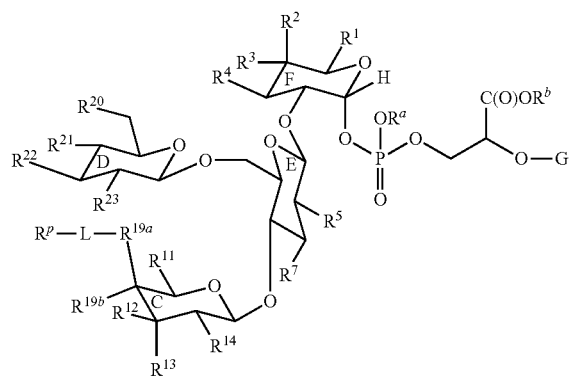
(Ie-xviii)
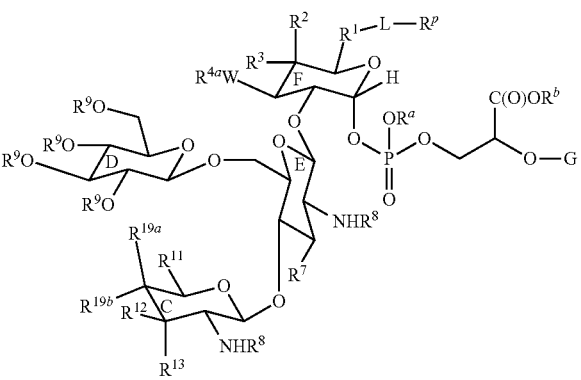

-continued
(Ie-xix)
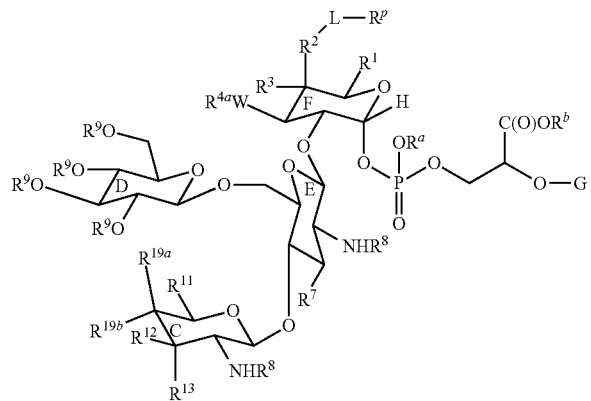
(Ie-xx)
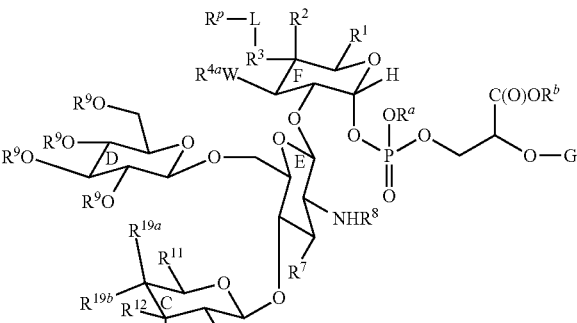
(Ie-xxi)
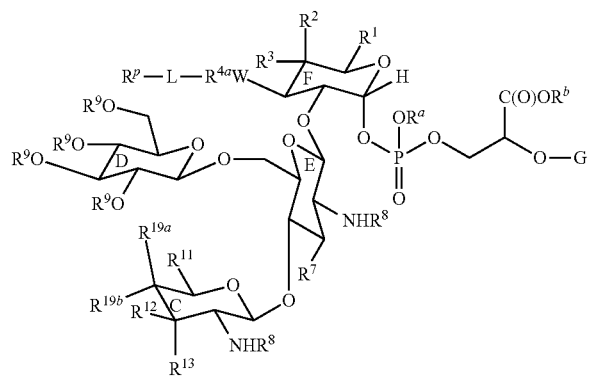
(Ie-xxii)
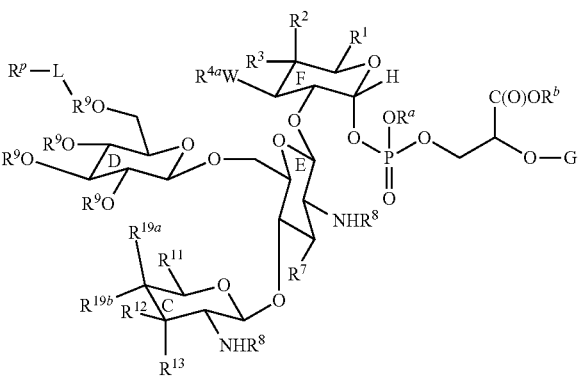
(Ie-xxiii)
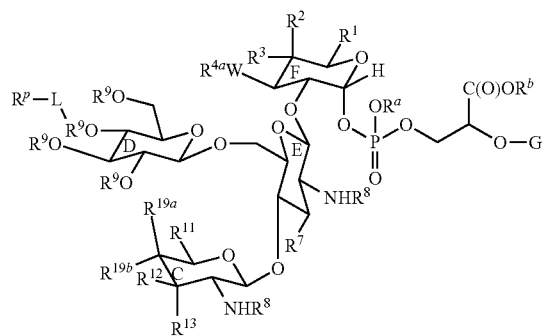
(Ie-xxiv)
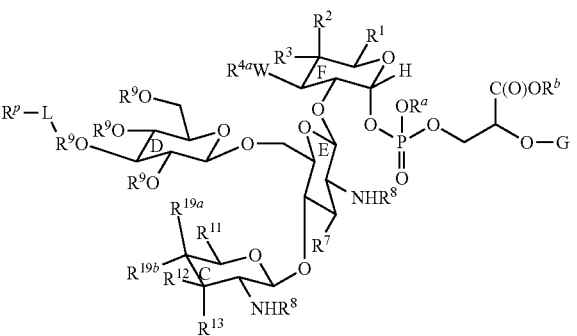
(Ie-xxv)
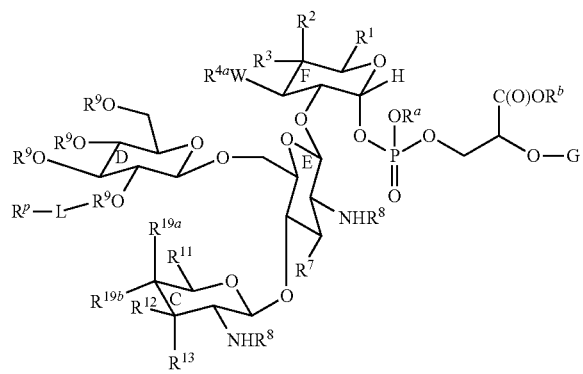
(Ie-xxvi)
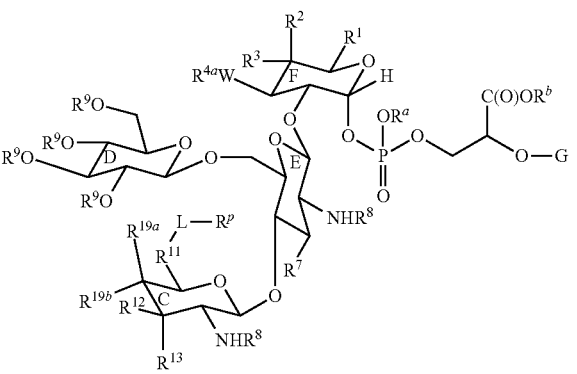

(Ie-xxvii)
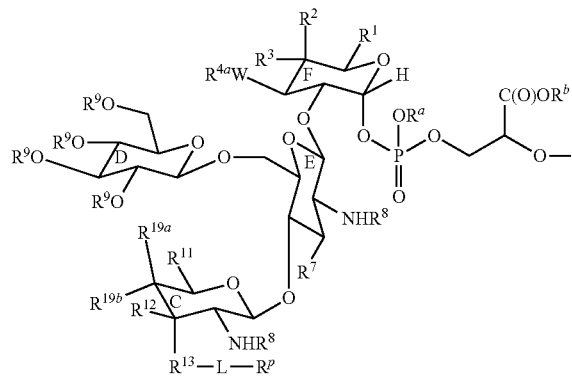
(Ie-xxviii)
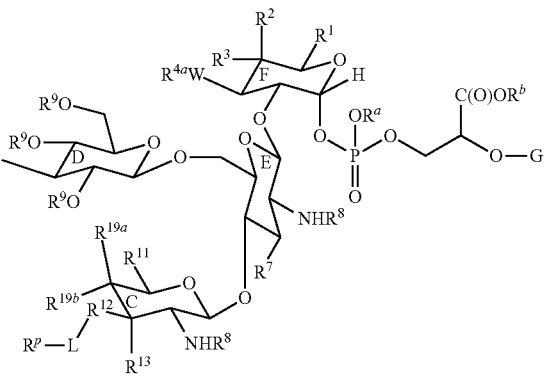
(Ie-xxix)
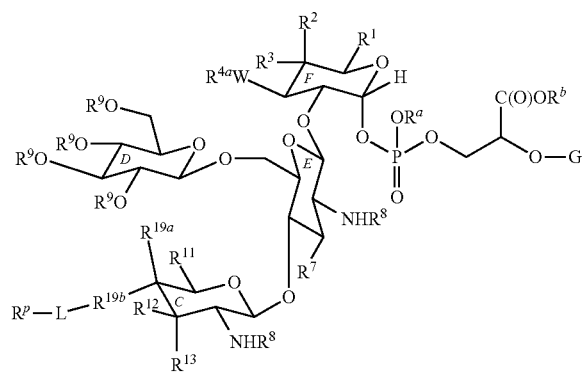
(Ie-xxx)
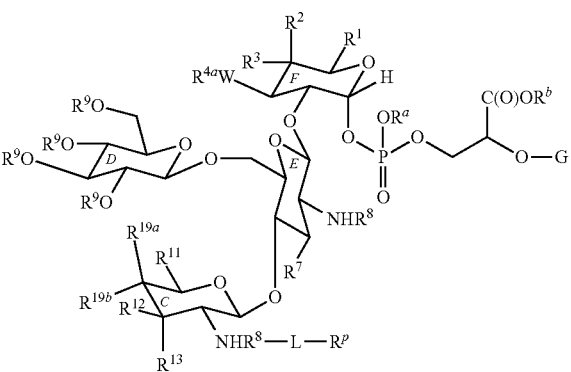
(Ie-xxxi)
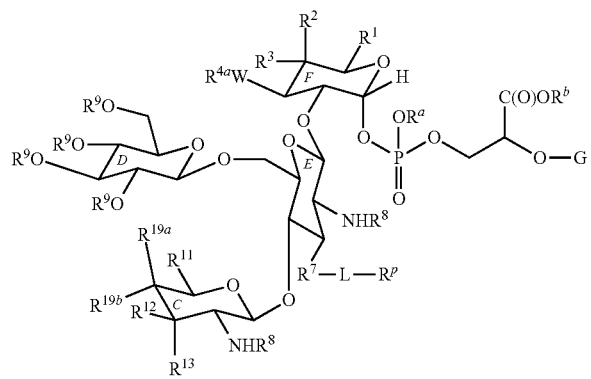
(Ie-xxxii)
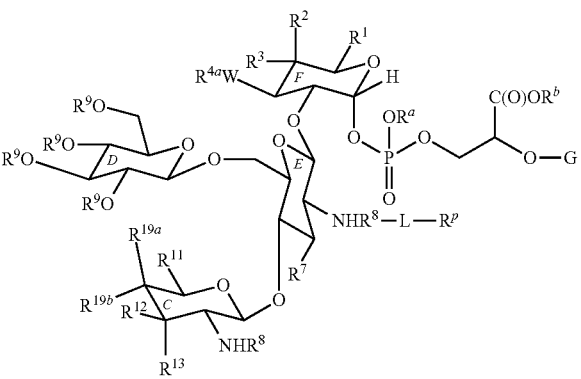
(Ie-xxxiii)
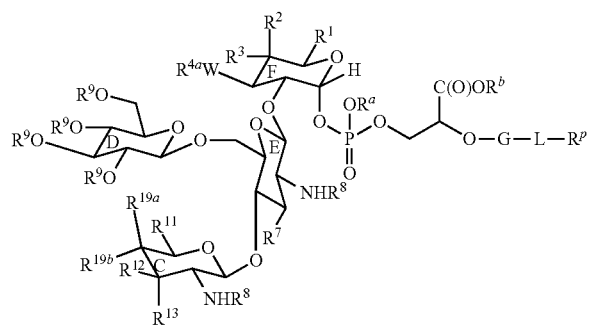
(Ie-xxxiv)
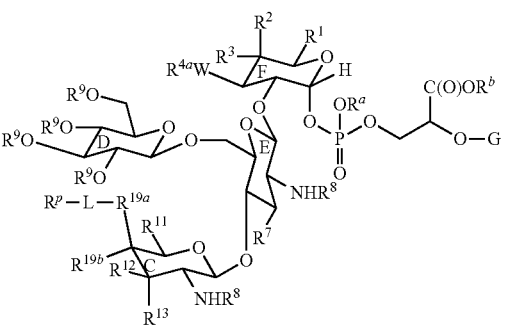

-continued
(If-i)
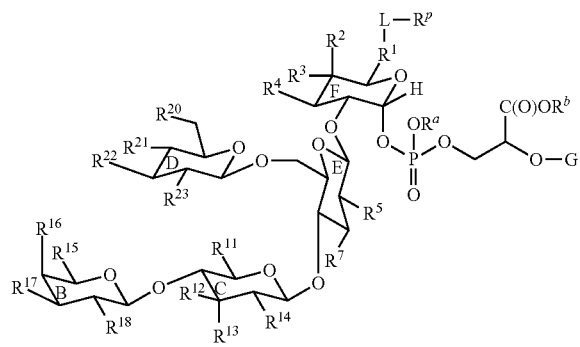
(If-ii)
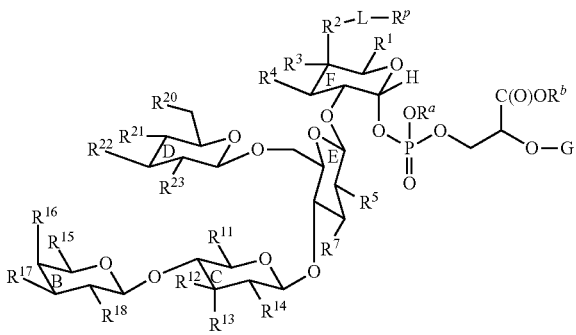
(If-iii)
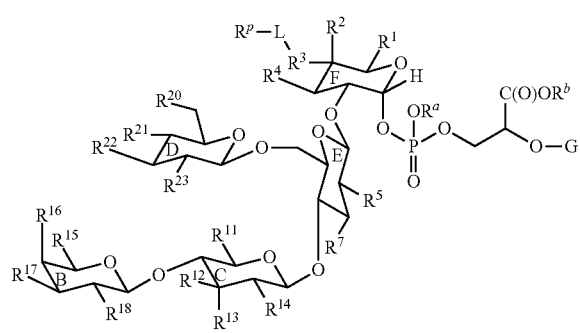
(If-iv)
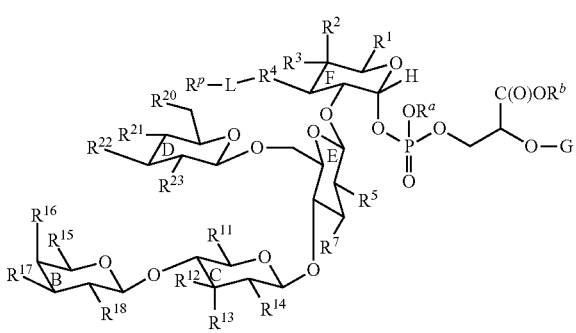
(If-v)
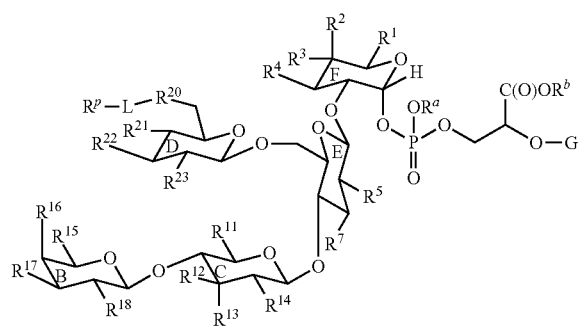
(If-vi)
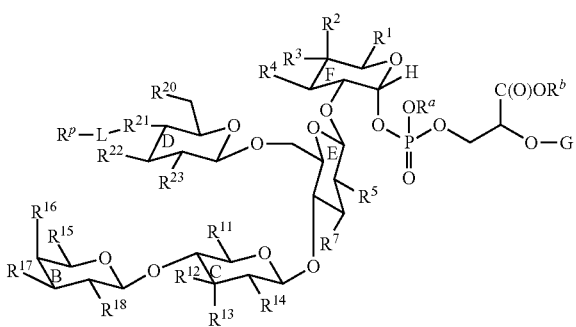
(If-vii)
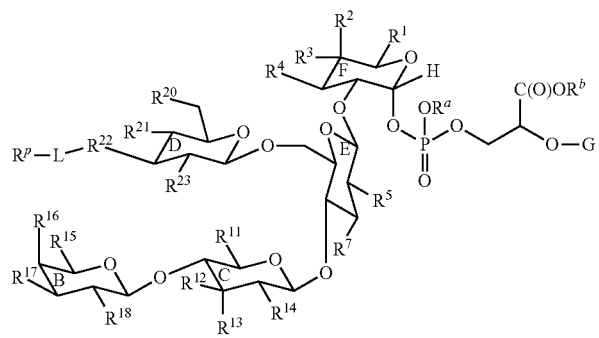
(If-viii)
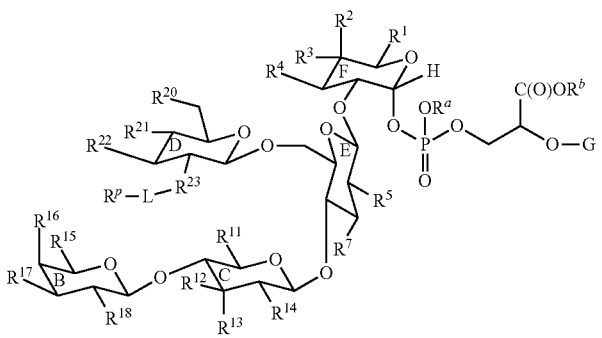

-continued
(If-ix)
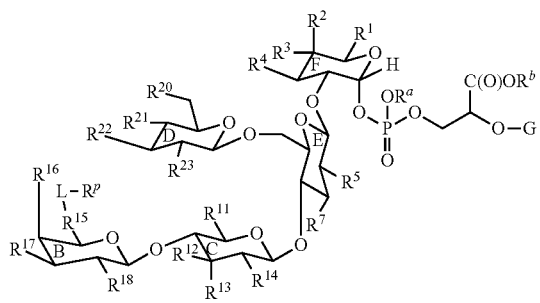
(If-x)
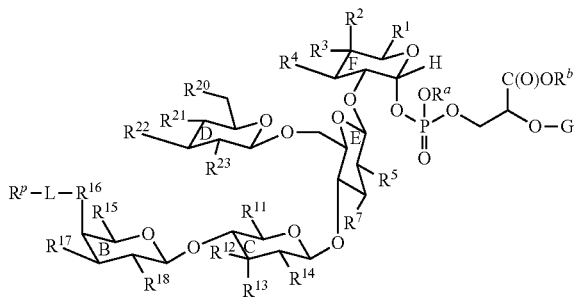
(If-xi)
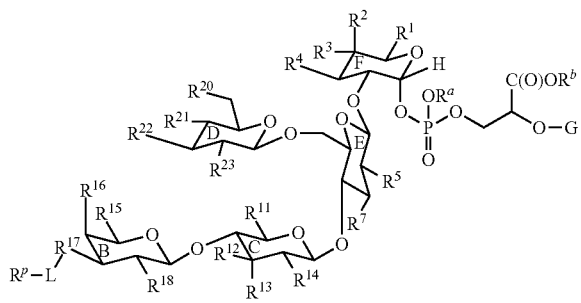
(If-xii)
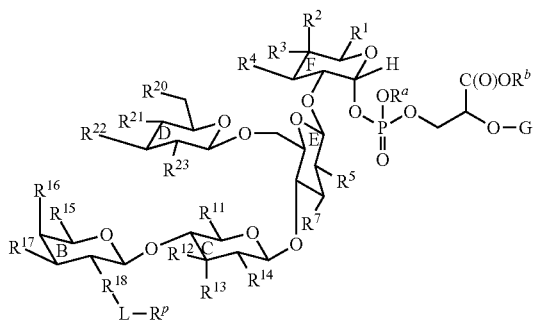
(If-xiii)
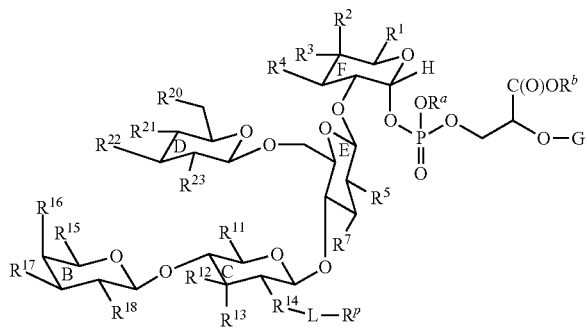
(If-xiv)
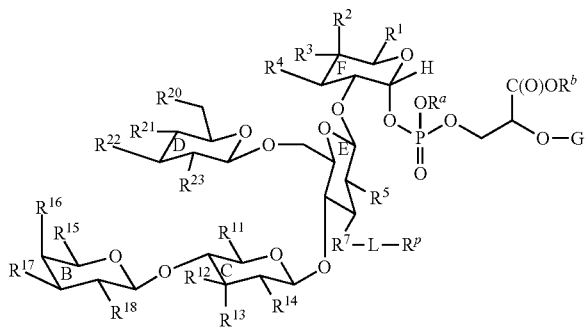
(If-xv)
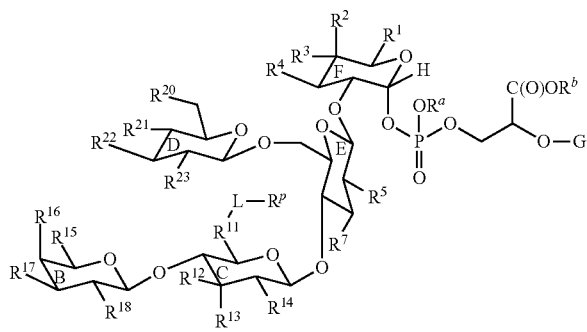
(If-xvi)
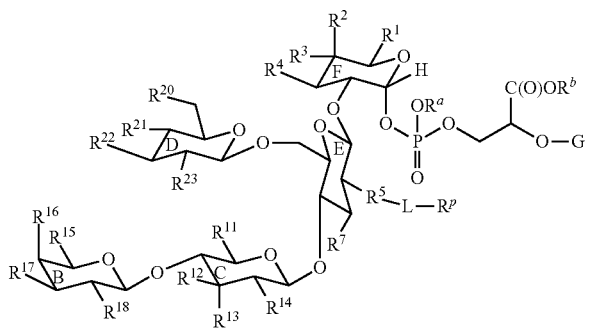

-continued
(If-xvii)
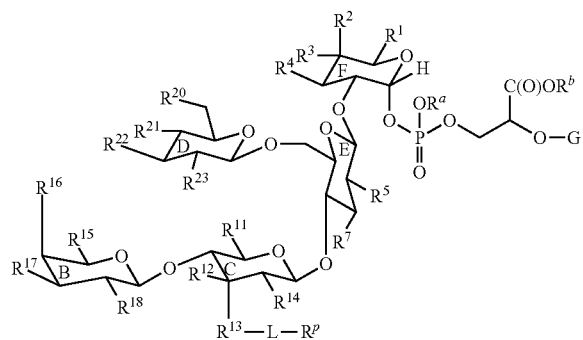
(If-xviii)
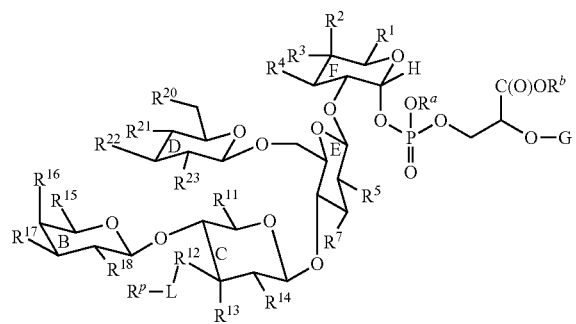
(If-xix)
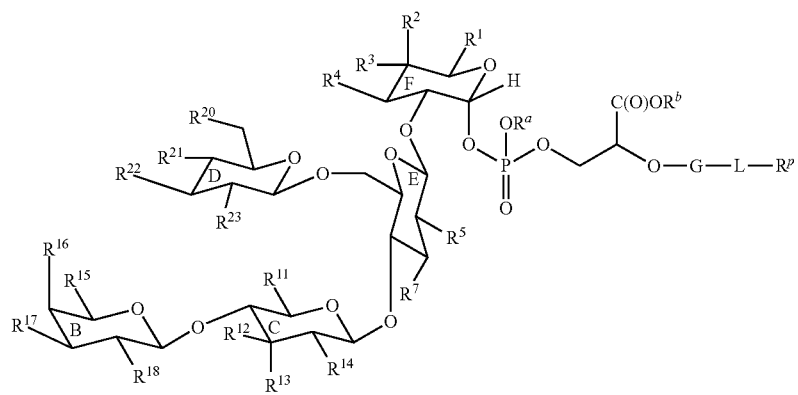
(If-xx)
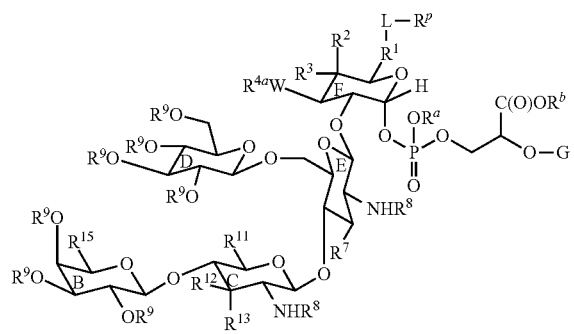
(If-xxi)
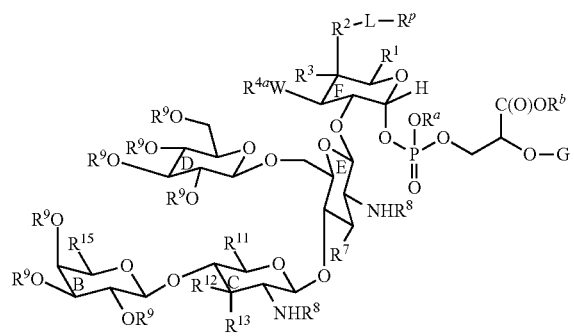
(If-xxii)
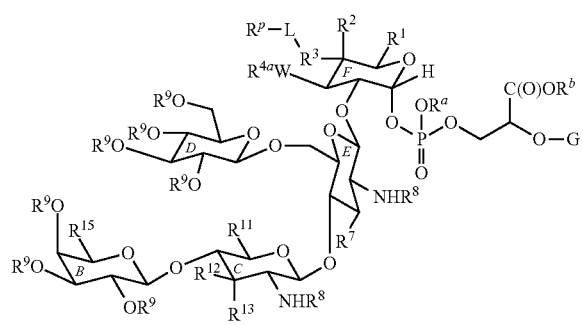
(If-xxiii)
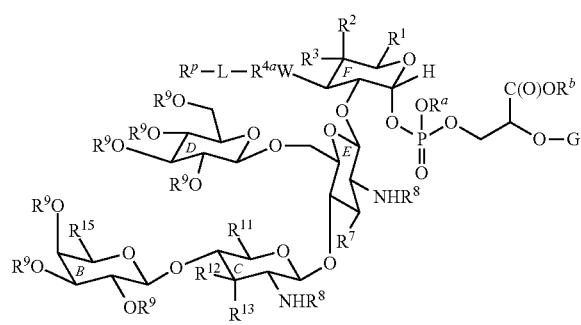

(If-xxiv)
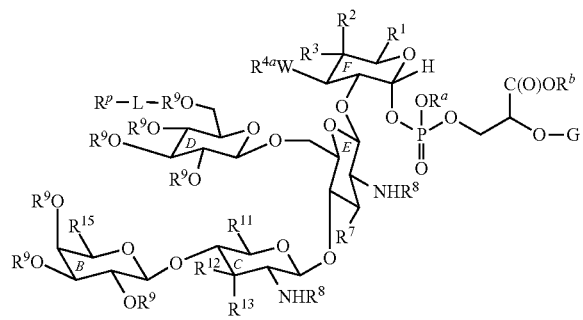
(If-xxv)
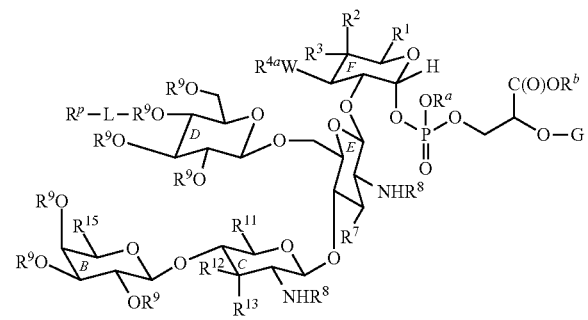
(If-xxvi)
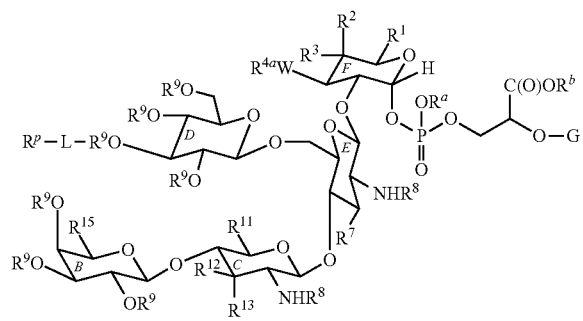
(If-xxvii)
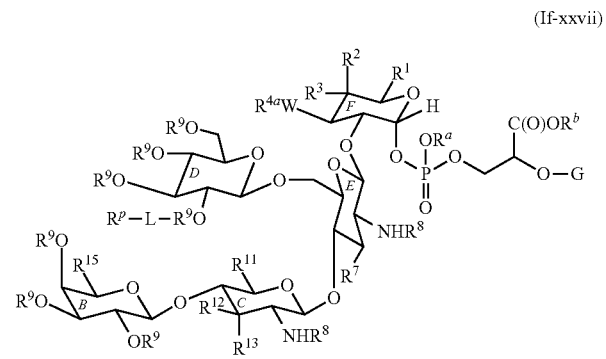
(If-xxviii)
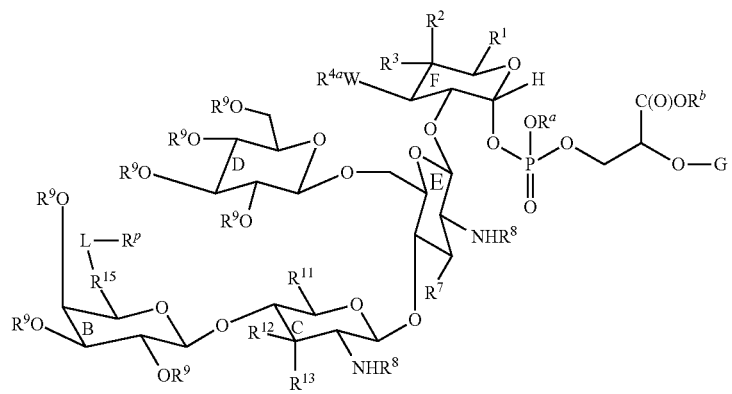
(If-xxix)
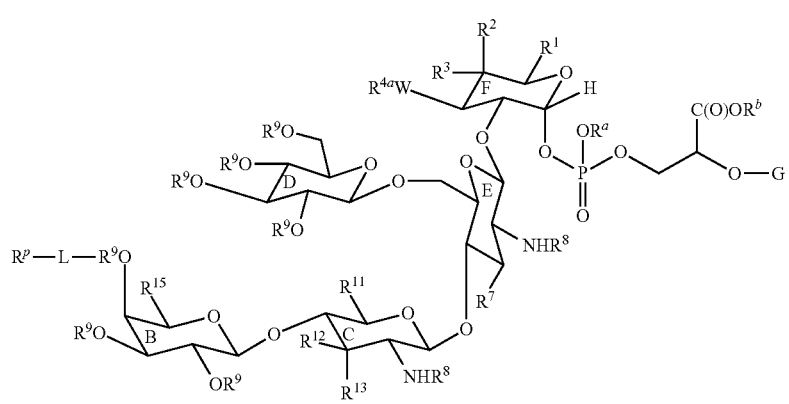

(If-xxx)
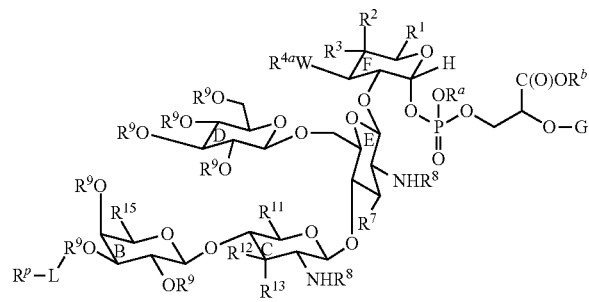
(If-xxxi)
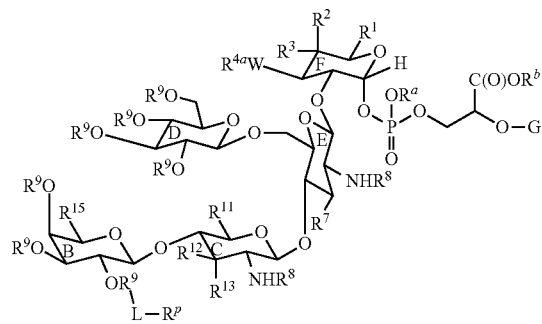
(If-xxxii)
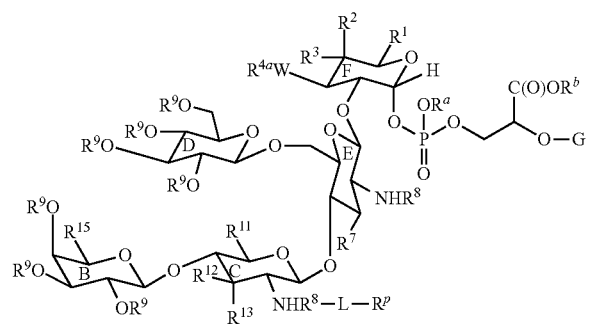
(If-xxxiii)
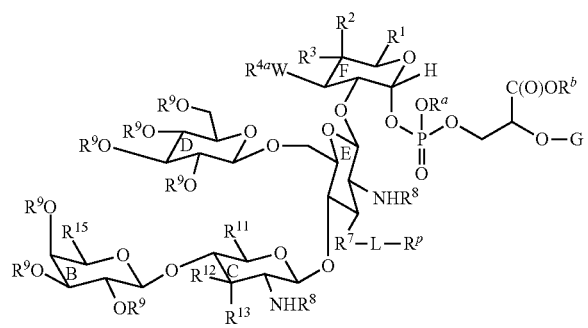
(If-xxxiv)
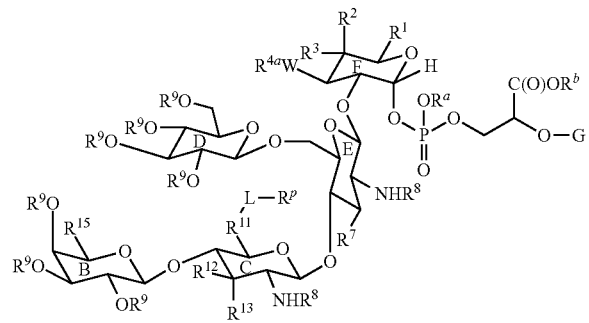
(If-xxxv)
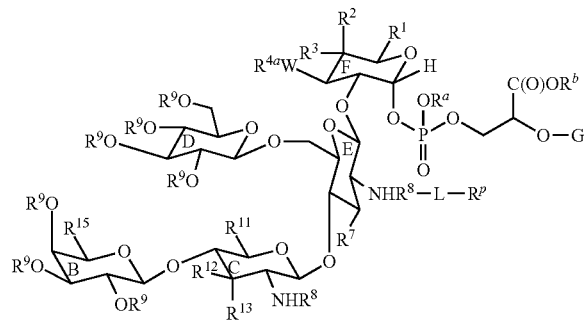
(If-xxxvi)
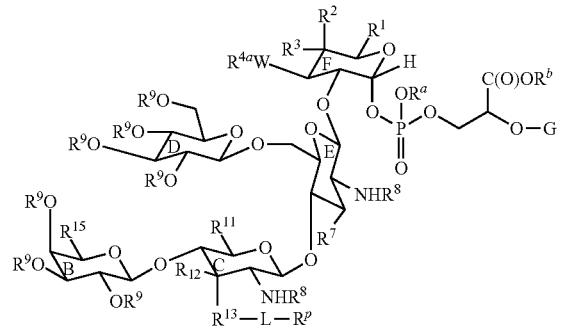
(If-xxxvii)
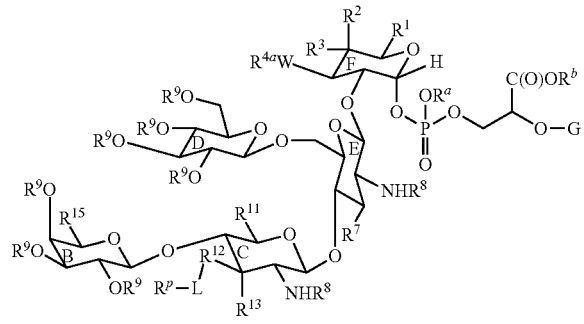

(If-xxxviii)

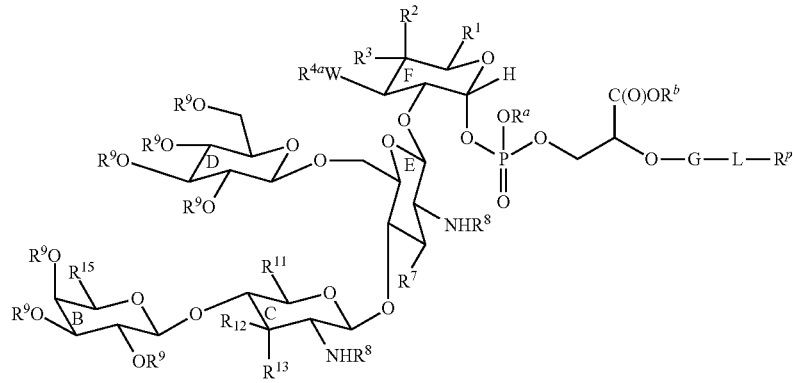

or a salt thereof, wherein $R^1$, $R^2$, $R^3$, $R^4$, $R^5$, $R^6$, $R^7$, $R^8$, $R^9$, $R^{11}$, $R^{12}$, $R^{13}$, $R^{14}$, $R^{15}$, $R^{16}$, $R^{17}$ $R^{18}$, $R^{19a}$, $R^{19b}$, $R^{20}$, $R^{21}$, $R^{22}$, $R^{23}$, $R^a$, $R^b$, G, L, and $R^P$ are as described herein.

As defined generally above, L is a covalent bond, —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, optionally substituted cycloalkylene, optionally substituted heterocyclylene, optionally substituted arylene, optionally substituted heteroarylene, or an optionally substituted aliphatic linker, wherein one or more methylene units of the aliphatic linker are optionally replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, cycloalkylene, heterocyclylene, arylene, or heteroarylene; wherein $R^y$ is hydrogen, $C_{1-6}$ alkyl, or —$C(O)C_{1-6}$ alkyl. In some embodiments, L is a covalent bond. In some embodiments, L is —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, or —$SO_2$—. In certain embodiments, L is —NHC(S)NH—. In certain embodiments, L is —NHC(O)NH—, —NHC(O)—, or —C(O)NH—. In some embodiments, L is optionally substituted cycloalkylene, optionally substituted heterocyclylene, optionally substituted arylene, or optionally substituted heteroarylene. In certain embodiments, L is heteroarylene. In certain embodiments, L is triazolylene. In certain embodiments, L is 1,2,3-triazolylene. In some embodiments, L is an optionally substituted aliphatic linker, wherein one or more methylene units of the aliphatic linker are optionally replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, cycloalkylene, heterocyclylene, arylene, or heteroarylene; wherein $R^y$ is hydrogen, $C_{1-6}$ alkyl, or —$C(O)C_{1-6}$ alkyl. In some embodiments, L is an optionally substituted $C_{1-20}$ aliphatic linker, wherein one or more methylene units of the aliphatic linker are optionally replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, cycloalkylene, heterocyclylene, arylene, or heteroarylene. In some embodiments, L is an optionally substituted $C_{1-10}$ aliphatic linker, wherein one or more methylene units of the aliphatic linker are optionally replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, cycloalkylene, heterocyclylene, arylene, or heteroarylene. In some embodiments, L is an optionally substituted $C_{1-6}$ aliphatic linker, wherein one or more methylene units of the aliphatic linker are optionally replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, cycloalkylene, heterocyclylene, arylene, or heteroarylene. In some embodiments, L is an optionally substituted $C_{1-6}$ alkylene linker, wherein one or more methylene units of the alkylene linker are optionally replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, cycloalkylene, heterocyclylene, arylene, or heteroarylene. In certain embodiments, 1, 2, 3, 4, or 5 methylene units of L are replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, cycloalkylene, heterocyclylene, arylene, or heteroarylene. In certain embodiments, one methylene unit of L is replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, cycloalkylene, heterocyclylene, arylene, or heteroarylene. In certain embodiments, two methylene units of L are replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, —$SO_2$—, cycloalkylene, heterocyclylene, arylene, or heteroarylene. In certain embodiments, one methylene unit of L is replaced by heteroarylene and one methylene unit of L is replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)O—, —S—, —SO—, or —$SO_2$—. In certain embodiments, L is an optionally substituted aliphatic linker wherein one methylene unit is replaced by tetrazolyl and one or more additional methylene units are optionally replaced by —$NR^y$—, —$N(R^y)C(O)$—, —$N(R^y)C(O)N(R^y)$—, —$N(R^y)C(S)N(R^y)$—, —$C(O)N(R^y)$—, —$N(R^y)SO_2$—, —$SO_2N(R^y)$—, —O—, —C(O)—, —OC(O)—, —C(O)

O—, —S—, —SO—, or —SO₂—. In certain embodiments, L is an optionally substituted aliphatic linker wherein one methylene unit is replaced by —NHC(S)NH— and one or more additional methylene units are optionally replaced by —NR$^{y'}$—, —N(R$^{y'}$)C(O)—, —N(R$^{y'}$)C(O)N(R$^{y'}$)—, —N(R$^{y'}$)C(S)N(R$^{y'}$)—, —C(O)N(R$^{y'}$)—, —N(R$^{y'}$)SO₂—, —SO₂N(R$^{y'}$)—, —O—, —C(O)—, —OC(O)—, —C(O)O—, —S—, —SO—, —SO₂—, cycloalkylene, heterocyclylene, arylene, or heteroarylene. In certain embodiments, one methylene unit of L is replaced by heteroarylene and one methylene unit of L is replaced by —NHC(O)— or —C(O)NH—. In certain embodiments, L is —C(O)CH₂—NHC(S)NH—. In certain embodiments, L is

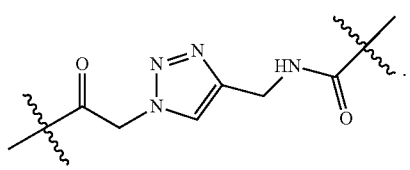 [SMILES: *C(=O)Cn1cc(CNC(*)=O)nn1]

In certain embodiments, L is

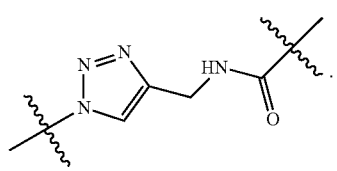 [SMILES: *C(=O)NCc1cn(*)nn1]

In certain embodiments, L is C$_{1-10}$ alkylene. In certain embodiments, L is C$_{1-6}$ alkylene. In certain embodiments, L is —CH₂— or —CH₂CH₂—. In certain embodiments, L is a PEG linker. In certain embodiments, L is a peptide linker. In certain embodiments, L is an amino acid linker.

As defined generally above, R$^P$ is a detectable moiety. In some embodiments, R$^P$ is a ligand, radionuclide, fluorescent dye, chemiluminescent agent, microparticle, enzyme, calorimetric label, magnetic label, or hapten.

In some embodiments, R$^P$ is a fluorophore. In some embodiments, R$^P$ is Alexa Fluor 350, Alexa Fluor 488, Alexa Fluor 500, Alexa Fluor 532, Alexa Fluor 546, Alexa Fluor 568, Alexa Fluor 594, Alexa Fluor 633, Alexa Fluor 660 and Alexa Fluor 680, AMCA, AMCA-S, BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665, aminomethylcoumarin, carbocyanine, carboxyrhodamine 6G, carboxy-X-rhodamine (ROX), Cascade Blue, Cascade Yellow, coumarin, coumarin 343, cyanine dyes, dansyl, dapoxyl, dialkylaminocoumarin, 4',5'-dichloro-2',7'-dimethoxyfluorescein, DM-NERF, eosin, erythrosin, fluorescein, FAM, hydroxycoumarin, IRD40, IRD 700, IRD 800, 6-carboxy-4',5'-dichloro-2',7'-dimethoxyfluorescein (6-JOE), lissamine rhodamine B, Marina Blue, merocyanine, methoxycoumarin, naphthofluorescein, Oregon Green 488, Oregon Green 500, Oregon Green 514, oxonol dyes, Pacific Blue, phycoerythrin, PyMPO, pyrene, rhodamine B, rhodamine 6G, rhodamine green, rhodamine red, rhodol green, styryl dyes, 2',4',5',7'-tetrabromosulfonefluorescein, tetramethyl-rhodamine (TMR), carboxytetramethylrhodamine (TAMRA), Texas Red, Texas Red-X, 5(6)-carboxyfluorescein, 2,7-dichlorofluorescein, N,N-bis(2,4,6-trimethylphenyl)-3,4,9,10-perylenebis(dicarboximide), HPTS, ethyl eosin, DY-490XL MegaStokes, DY-485XL MegaStokes, Adirondack Green 520, ATTO 465, ATTO 488, ATTO 495, Y0Y0-1,5-FAM, BCECF, dichlorofluorescein, rhodamine 110, rhodamine 123, YO-PRO-I, SYTOX Green, Sodium Green, SYBR Green I, Alexa Fluor 500, FITC, Fluo-3, Fluo-4, fluoro-emerald, YoYo-I ssDNA, YoYo-I dsDNA, YoYo-I, SYTO RNASelect, Diversa Green-FP, Dragon Green, EvaGreen, Surf Green EX, Spectrum Green, Spectrum Red, NeuroTrace 500525, NBD-X, MitoTracker Green FM, LysoTracker Green DND-26, CBQCA, PA-GFP (post-activation), WEGFP (post-activation), FLASH-CCXXCC, Azami Green monomeric, Azami Green, green fluorescent protein (GFP), EGFP, Kaede Green, 7-benzylamino-4-nitrobenz-2-oxa-1,3-diazole, BexI, doxorubicin, Lumio Green, or SuperGlo GFP. In certain embodiments, R$^P$ is Alexa Fluor 350, Alexa Fluor 488, Alexa Fluor 500, Alexa Fluor 532, Alexa Fluor 546, Alexa Fluor 568, Alexa Fluor 594, Alexa Fluor 633, Alexa Fluor 660, or Alexa Fluor 680. In certain embodiments, R$^P$ is AMCA or AMCA-S. In certain embodiments, R$^P$ is BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, or BODIPY 650/665. In certain embodiments, R$^P$ is aminomethylcoumarin, coumarin, coumarin 343, dialkylaminocoumarin, or hydroxycoumarin. In certain embodiments, R$^P$ is carbocyanine, carboxyrhodamine 6G, carboxy-X-rhodamine (ROX), Cascade Blue, Cascade Yellow, cyanine dyes, dansyl, dapoxyl, DM-NERF, eosin, or erythrosine. In certain embodiments, R$^P$ is IRD40, IRD 700, or IRD 800. In certain embodiments, R$^P$ is Oregon Green 488, Oregon Green 500, or Oregon Green 514. In certain embodiments, R$^P$ is Marina Blue, merocyanine, oxonol dyes, Pacific Blue, phycoerythrin, PyMPO, pyrene, or styryl dyes. In certain embodiments, R$^P$ is lissamine rhodamine B, rhodamine B, rhodamine 6G, rhodamine green, rhodamine red, rhodol green, tetramethylrhodamine (TMR), carboxytetramethylrhodamine (TAMRA), rhodamine 110, or rhodamine 123. In certain embodiments, R$^P$ is fluorescein, naphthofluorescein, 4',5'-dichloro-2',7'-dimethoxy-fluorescein, 2',4',5',7'-tetrabromosulfone-fluorescein, 2,7-dichlorofluorescein, 6-carboxy-4',5'-dichloro-2',7'-dimethoxyfluorescein, or 5(6)-carboxyfluorescein. In certain embodiments, R$^P$ is fluorescein.

In certain embodiments, the stereochemistry of the phosphoglycerate linker of a compound of Formula (I), (Ia), (Ib), (Ic), (Id), (Ie), (If), or any embodiment or subformula described herein is

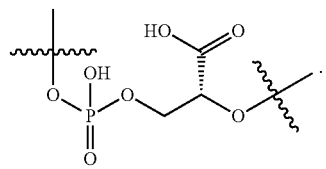 [SMILES: *O[C@H](COP(=O)(O)O*)C(=O)O]

In certain embodiments, the stereochemistry of the phosphoglycerate linker of a compound of Formula (I), (Ia), (Ib), (Ic), (Id), (Ie), (If), or any embodiment or subformula described herein is

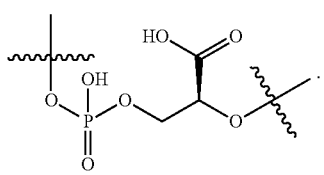 [SMILES: *O[C@@H](COP(=O)(O)O*)C(=O)O]

In certain embodiments, a compound of Formula (I) is:

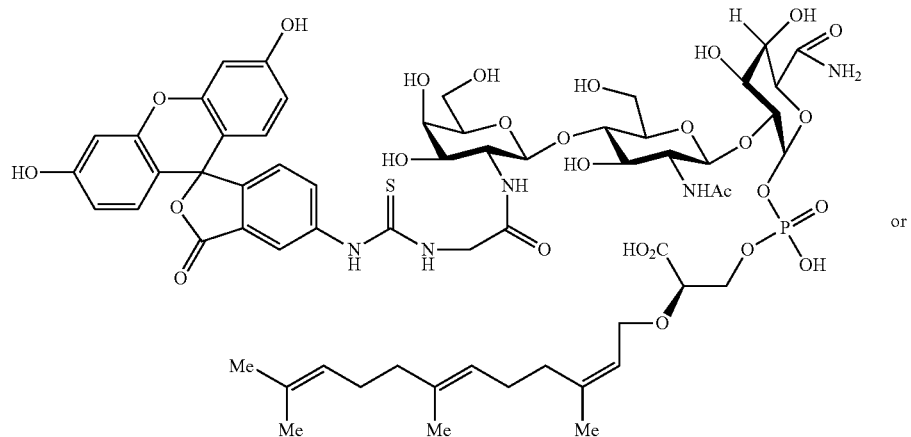

or

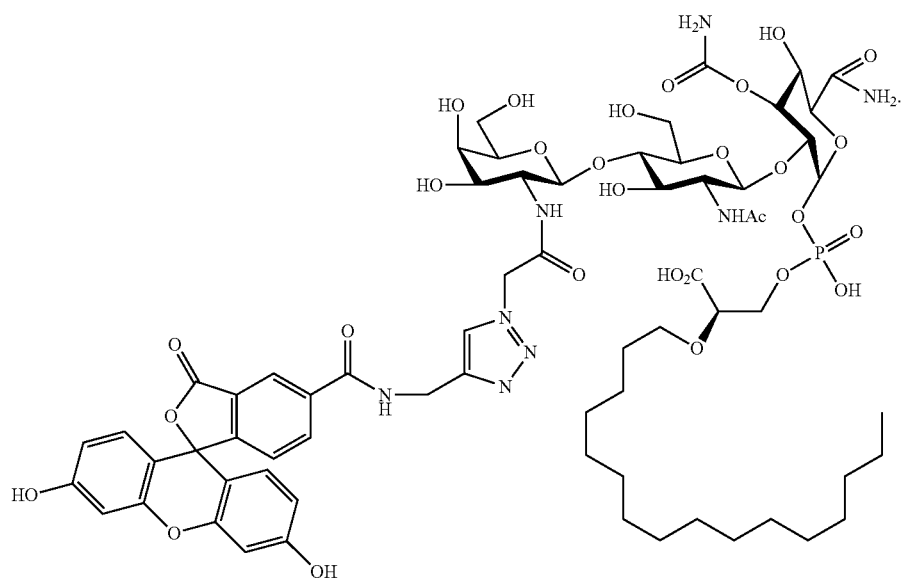

Glycosyltransferase Assay

In another aspect, the present invention provides an assay to determine the inhibitory effect of a test compound on a glycosyltransferase protein. Efforts have been made by others to provide such as an assay (see Cheng et al., *Proc. Natl. Acad. Sci. USA* 105:431 (2008)), but the present inventors have found that the fluorescent probe compound used in that assay binds too tightly to the glycosyltransferase protein, resulting in false negatives when screening test compounds. To overcome high false negative rates, compounds of formula (I) were prepared. The dissociation constant of the probe compound of formula (I) can be tuned by varying lengths of the G group, number of sugars, etc., allowing the operator of the assay to regulate the activity threshold for hit screening.

In some embodiments, an assay of the present invention comprises the steps of incubating a glycosyltransferase protein with a probe compound of formula (I) or a salt thereof; measuring fluorescence polarization of the compound of formula (I) in the presence of the glycosyltransferase protein; adding a test compound; and measuring a change in fluorescence polarization of the probe compound after addition of the test compound. In certain embodiments, a decrease in fluorescence polarization indicates that the probe compound has been liberated from the glycosyltransferase.

In certain embodiments, a probe compound for use in a provided assay is of formula (I), (Ia), (Ib), (Ic), (Id), (Ie), (If), or any subformula or embodiment described herein.

In certain embodiments, a probe compound for use in a provided assay is of formula:

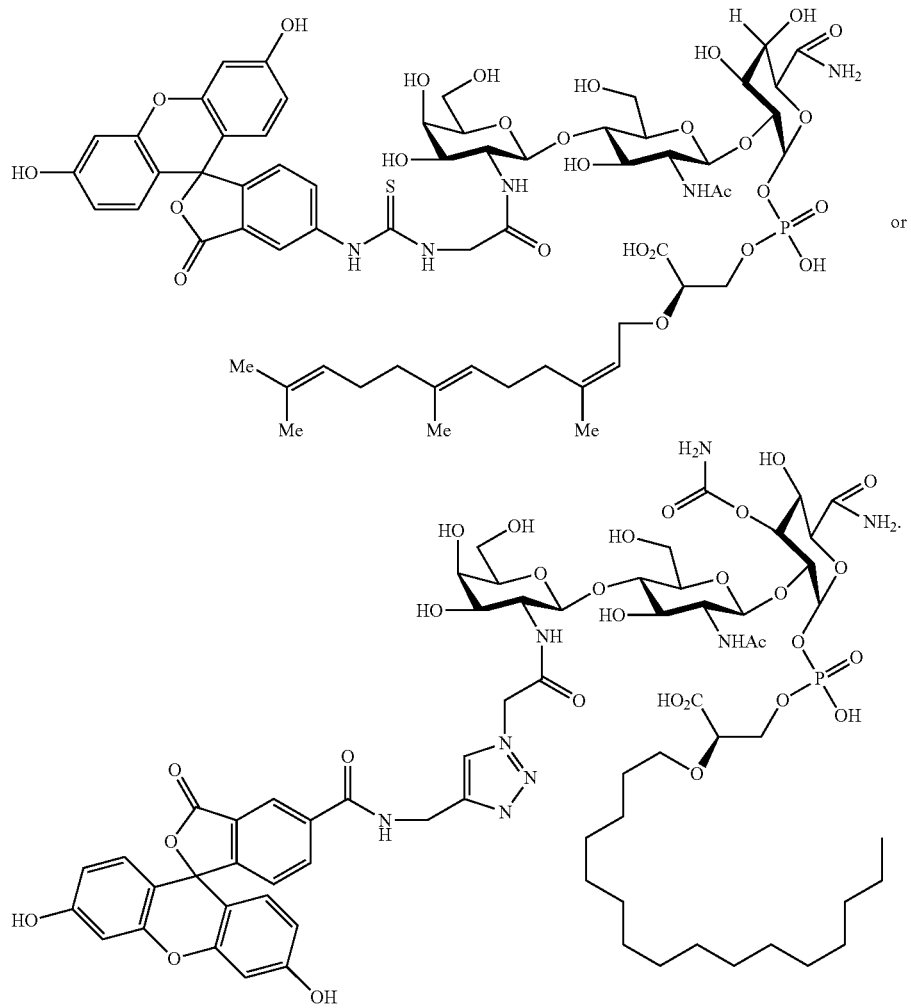

In certain embodiments, the glycosyltransferase protein is a recombinant, full length glycosyltransferase protein. In certain embodiments, the glycosyltransferase protein is a bacterial glycosyltransferase. In other embodiments, the glycosyltransferase protein is a purified glycosyltransferase protein. In still other embodiments, the glycosyltransferase protein is a crude glycosyltransferase protein. In further embodiments, the glycosyltransferase protein is purified from natural sources. In other embodiments, the glycosyltransferase protein is a modified form of a glycosyltransferase protein. In other embodiments, the glycosyltransferase protein is a mutant form of a glycosyltransferase protein. In other embodiments, the glycosyltransferase protein is a truncated form of a glycosyltransferase protein. In still other embodiments, the glycosyltransferase protein is a truncated form of a glycosyltransferase protein which includes at least an active site.

In certain embodiments, the assay is carried out at a concentration of the substrate greater than the substrate $K_d$. In other embodiments, the assay is carried out at a concentration of the substrate approximately equivalent to the substrate $K_d$.

In certain embodiments, the glycosyltransferase protein is a peptidoglycan glycosyltransferase. In certain embodiments, the glycosyltransferase protein is *B. pertussis* PBP1a, *C. freudii* PBP1b, *E. coli* PBP1b, *H. influenzae* PBP1b, *H. pylori* PBP1a, *K. pneumoniae* PBP1b, *P. aeruginosa* PBP1b, *S. enterica* PBP1b, *S. flexneri* PBP2, *B. subtilis* PBP1a/1b, *C. difficile* PBP, *E. faecalis* PBP2a, *E. faecium* PBP1, *S. aureus* PBP2, *S. pneumoniae* PBP1b, or *S. aureus* SgtB. In certain embodiments, the glycosyltransferase protein is PGT, PBP1b, PBP2a, or SgtB. In certain embodiments, the glycosyltransferase protein is *Aquifex aeolicus* PGT, *E. coli* PBP1b, *E. faecalis* PBP2a, and *S. aureus* SgtB. In certain embodiments, the glycosyltransferase protein is *E. coli* PBP1b. In certain embodiments, the glycosyltransferase protein is *E. faecalis* PBP2a. In certain embodiments, the glycosyltransferase protein is *S. aureus* SgtB.

The inventive assay is suitable for high-throughput screening, and multiple assays may be run in parallel. This aspect of the assay allows for the screening of many test compounds at multiple concentrations at once optionally using more than one glycosyltransferase protein. In certain embodiments, multiple assays are run in parallel. In other embodiments, at least 10 assays are run in parallel. In still other embodiments, at least 50 assays are run in parallel. In further embodiments, at least 100 assays are run in parallel. In certain embodiments, at least 500 assays are run in parallel. In other embodiments, at least 1000 assays are run in parallel.

In certain embodiments, the assay is performed at approximately room temperature. In other embodiments, the assay is performed at approximately 25° C. In still other embodiments, the assay is performed at approximately 37° C. In further embodiments, the assay is performed at approximately 20-40° C. In certain embodiments, the assay is performed below 25° C. In other embodiments, the assay is performed above 25° C. In still other embodiments, the assay is performed at approximately 10-15° C. In further other embodiments, the assay is performed at approximately 15-20° C. In certain embodiments, the assay is performed at approximately 20-25° C. In other embodiments, the assay is performed at approximately 25-30° C. In still other embodiments, the assay is performed at approximately 30-35° C. In further embodiments, the assay is performed at approximately 35-40° C. In certain embodiments, the assay is performed at approximately 40-45° C. In other embodiments, the assay is performed at approximately 45-50° C. In still other embodiments, the assay is performed at approximately 50-60° C. In further embodiments, the assay is performed above 60° C. In certain embodiments, the assay is performed at any temperature at which a glycosyltransferase enzyme functions. In other embodiments, the assay is performed at a temperature optimum for a glycosyltransferase enzyme to function.

In certain embodiments, the assay is performed for approximately 30 seconds to 12 hours. In other embodiments, the assay is performed for approximately 30 seconds to 5 minutes. In still other embodiments, the assay is performed for approximately 5 minutes to 15 minutes. In further embodiments, the assay is performed for approximately 15 minutes to 30 minutes. In certain embodiments, the assay is performed for approximately 30 minutes to 1 hour. In other embodiments, the assay is performed for approximately 1 hour to 3 hours. In still other embodiments, the assay is performed for approximately 3 hours to 6 hours. In further embodiments, the assay is performed for approximately 6 hours to 9 hours. In certain embodiments, the assay is performed for approximately 9 hours to 12 hours. In certain embodiments, the assay is performed for less than 3 hours. In certain embodiments, the assay is performed for approximately 3 hours. In certain embodiments, the assay is performed for less than 12 hours. In other embodiments, the assay is performed for greater than 12 hours.

In certain embodiments, the assay is performed in water. In other embodiments, the assay is performed in an organic solvent. In still other embodiments, the assay in performed in a buffer. In certain embodiments, the buffer is an assay buffer. In other embodiments, the assay buffer comprises TRIS and NaCl. In further embodiments, the assay buffer is 10 mM TRIS pH 8, 100 mM NaCl. In certain embodiments, the assay is performed at approximately pH 5.0-6.0. In other embodiments, the assay is performed at approximately pH 6.0-6.5. In still other embodiments, the assay is performed at approximately pH 6.5-7.0. In further embodiments, the assay is performed at approximately pH 7.0-7.5. In certain embodiments, the assay is performed at approximately pH 7.4. In other embodiments, the assay is performed at approximately pH 7.5-8.0. In certain embodiments, the assay is performed at approximately pH 8.0. In still other embodiments, the assay is performed at approximately pH 8.0-9.0. In certain embodiments, the assay is performed at a pH optimum for a glycosyltransferase enzyme to function.

In certain embodiments, the concentration of the probe compound of formula (I) is 1-1000 nM. In certain embodiments, the concentration of the probe compound is 0.01-100 µM. In further embodiments, the concentration of the probe compound is 1-500 nM. In other embodiments, the concentration of the probe compound is 1-100 nM. In still other embodiments, the concentration of the probe compound is 5-10 nM. In yet other embodiments, the concentration of the probe compound is 10-15 nM. In further embodiments, the concentration of the probe compound is 15-20 nM. In other embodiments, the concentration of the probe compound is 10-20 nM. In further embodiments, the concentration of the probe compound is 20-30 nM. In certain embodiments, the concentration of the probe compound is 30-40 nM. In other embodiments, the concentration of the probe compound is 40-50 nM. In still other embodiments, the concentration of the probe compound is 50-60 nM. In further embodiments, the concentration of the probe compound is 60-70 nM. In certain embodiments, the concentration of the probe compound is 70-80 nM. In other embodiments, the concentration of the probe compound is 80-90 nM. In still other embodiments, the concentration of the probe compound is 90-100 nM. In certain embodiments, the concentration of the probe compound is less than 100 nM. In other embodiments, the concentration of the probe compound is greater than 100 nM.

In certain embodiments, the concentration of the glycosyltransferase protein is less than 1 µM. In other embodiments, the concentration of the glycosyltransferase protein is greater than 1 µM. In certain embodiments, the concentration of the glycosyltransferase protein is less than 5 µM. In other embodiments, the concentration of the glycosyltransferase protein is greater than 5 µM. In certain embodiments, the concentration of the glycosyltransferase protein is 0.01-5 µM. In other embodiments, the concentration of the glycosyltransferase protein is 0.01-0.05 µM. In still other embodiments, the concentration of the glycosyltransferase protein is 0.05-0.1 µM. In further embodiments, the concentration of the glycosyltransferase protein is 0.1-0.5 µM. In certain embodiments, the concentration of the glycosyltransferase protein is 0.5-5 µM. In certain embodiments, the concentration of the glycosyltransferase protein is 0.1 µM. In certain embodiments, the concentration of the glycosyltransferase protein is 0.2 µM. In certain embodiments, the concentration of the glycosyltransferase protein is 0.4 µM. In certain embodiments, the concentration of the glycosyltransferase protein is 0.15 µM.

In some embodiments, the probe compound employed in a provided assay is of intermediate activity with respect to binding to a glycosyltransferase of interest. If the probe compound associates with a glycosyltransferase of interest with very high affinity, then the assay may not identify test compounds of lower affinity. On the other hand, if the probe compound only associates with a glycosyltransferase of interest with very low affinity, then the assay may not discriminate among various test compounds of varying affinities to the glycosyltransferase. Assays provided by the present invention in conjunction with the probe compounds of formula (I) provide the opportunity to tune the assay to the desired activity threshold.

In some embodiments, a probe compound used in a provided assay has a $K_d$ in the range of 0.1-10 µM with respect to a glycosyltransferase of interest. In certain embodiments, a probe compound used in a provided assay has a $K_d$ in the range of 0.1-1 µM. In certain embodiments, a probe compound used in a provided assay has a $K_d$ in the range of 1-10 µM. In certain embodiments, a probe compound used in a provided assay has a $K_d$ in the range of 0.1-0.5 µM. In certain embodiments, a probe compound used in a provided assay has a $K_d$ in the range of 0.5-1 µM.

In certain embodiments, a probe compound used in a provided assay has a $K_d$ of about 0.1, 0.2, 0.3, 0.4, 0.5, 0.6, 0.7, 0.8, 0.9, or 1 μM.

In some embodiments, a probe compound used in a provided assay has an $IC_{50}$ in the range of 0.01-10 μM with respect to a glycosyltransferase of interest. In certain embodiments, a probe compound used in a provided assay has an $IC_{50}$ in the range of 0.1-10 μM. In certain embodiments, a probe compound used in a provided assay has an $IC_{50}$ in the range of 0.1-1 μM. In certain embodiments, a probe compound used in a provided assay has an $IC_{50}$ in the range of 1-10 μM. In certain embodiments, a probe compound used in a provided assay has an $IC_{50}$ in the range of 0.5-5 μM. In certain embodiments, a probe compound used in a provided assay has an $IC_{50}$ in the range of 0.1-0.5 μM. In certain embodiments, a probe compound used in a provided assay has an $IC_{50}$ in the range of 0.5-1 μM. In certain embodiments, a probe compound used in a provided assay has an $IC_{50}$ in the range of 0.2-0.8 μM. In certain embodiments, a probe compound used in a provided assay has an $IC_{50}$ in the range of 0.4-0.8 μM. In certain embodiments, a probe compound used in a provided assay has an $IC_{50}$ of about 0.6 μM. In certain embodiments, a probe compound used in a provided assay has an $IC_{50}$ of about 0.1, 0.2, 0.3, 0.4, 0.5, 0.6, 0.7, 0.8, 0.9, or 1 μM.

In certain embodiments, the assay is performed at the same concentration per test compound. In other embodiments, the assay is performed at multiple concentrations per test compound.

In certain embodiments, an assay of the present invention measures a change in fluorescence polarization after addition of a test compound. In certain embodiments, the change in fluorescence polarization is a decrease in polarization. Such a decrease in fluorescence polarization indicates that a test compound competes with the probe compound for binding to the glycosyltransferase protein.

In certain embodiments, the present invention provides a kit comprising a probe compound as described herein and glycosyltransferase protein. In some embodiments, a provided kit comprises a probe compound as described herein and a peptidoglycan glycosyltransferase, such as for example *B. pertussis* PBP1a, *C. freudii* PBP1b, *E. coli* PBP1b, *H. influenzae* PBP1b, *H. pylori* PBP1a, *K. pneumoniae* PBP1b, *P. aeruginosa* PBP1b, *S. enterica* PBP1b, *S. flexneri* PBP2, *B. subtilis* PBP1a/1b, *C. difficile* PBP, *E. faecalis* PBP2a, *E. faecium* PBP1, *S. aureus* PBP2, *S. pneumoniae* PBP1b, or *S. aureus* SgtB. In some embodiments, the kit further comprises a buffer. In some embodiments, the kit further comprises instructions for use.

These and other aspects of the present invention will be further appreciated upon consideration of the following Examples, which are intended to illustrate certain particular embodiments of the invention but are not intended to limit its scope, as defined by the claims.

EXAMPLES

Chemical Syntheses

All reactions in non-aqueous reaction medium were carried out under an atmosphere of argon, unless otherwise noted. Commercial chemicals were used without prior purification. Solvents were dried by passage over columns filled with activated aluminum oxide (Glass Contour Solvent Systems, SG Water USA, Nashua, N.H., USA).

In addition to the exemplary syntheses described below, also see the following patent applications incorporated herein by reference for methods of synthesizing moenomycin analogs: WO 2008/021367; WO 2009/046314; U.S. Provisional Patent Application entitled "Moenomycin A Analogs, Methods of Synthesis, and Uses Thereof," filed on the same day as the present application; and U.S. Provisional Patent Application entitled "Chemoenzymatic Methods for Synthesizing Moenomycin Analogs."

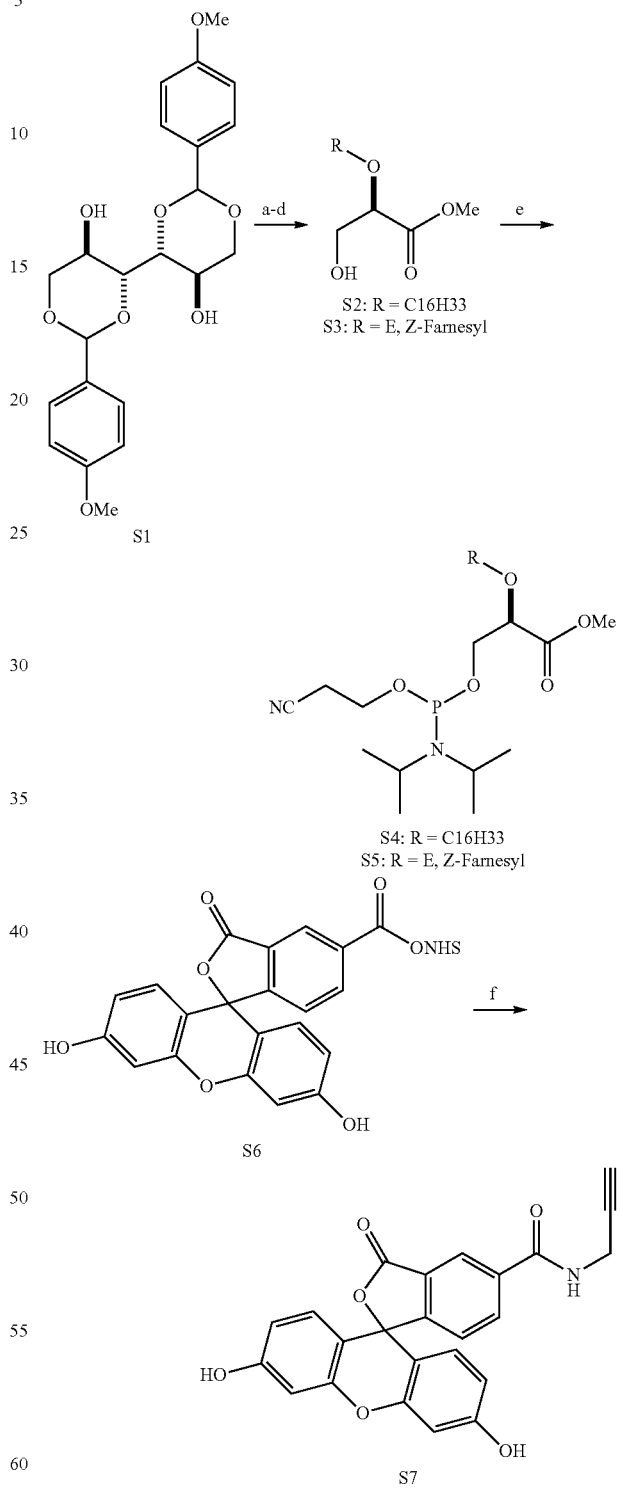

a R—Br, DMF, NaH then: AcOH;
b NaIO4, THF, H2O;
c NaClO2, NaH2PO4, H2O, 2-methyl-2-butene;
d TMSCHN2, MeOH, THF;
e ClP(CEO)N'Pr2;
f propargyl amine, NEt3, DMF.

Synthesis of S2 and S3

General Procedure for Preparation of 2,5-Di-O-alkyl-D-Mannitol

To a stirred suspension of 60% NaH (3 equiv.), washed twice with petroleum ether, in anhydrous DMF (8 mL/mmol-starting material (SM)) was added 1,3:4,6-di-O,O-(4-methoxybenzylidene)-D-mannitol (1 equiv., SM) at room temperature. After being stirred for 30 min, the mixture was treated with a 1.2 M solution of alkylating reagents (2.4 equiv., Br, and methane- or p-toluene-sulfonate for R=allyl, and n-alkyl groups, respectively) in anhydrous DMF and a catalytic amount of tetrabutylammonium iodide for allyl-Br, or 15-Crown-5 for n-alkyl sulfonates. The resulting mixture was stirred for 18 h at rt for allyl-Br and 70° C. for n-alkyl sulfonates, and then poured into sat. aq. $NH_4Cl$ (8 mL/mmol-SM). The immiscible mixture was extracted twice with $Et_2O$ and the combined organic phases were washed with water, brine, dried over $MgSO_4$, and then concentrated in vacuo. The crude ether was used for the next reaction without further purification.

For allyl derivatives, a stirred solution of the residue in THF-$H_2O$ (4:1, 8 mL/mmol-SM) was treated with AcOH (170 equiv.) at room temperature. After being stirred at 55° C. for 2 d, the mixture was cooled to 0° C. and basified with 4 M aq. $K_2CO_3$ (90 equiv.). The immiscible mixture was extracted twice with $CHCl_3$ and the combined organic phases were washed with brine, dried over $MgSO_4$, and then concentrated in vacuo. The residue was purified by silica gel chromatography (petroleum ether:EtOAc=1:3 to 0:1) to give 2,5-di-O-allyl-D-mannitol.

For n-alkyl derivatives, a stirred solution of the residue in EtOH (12 mL/mmol-SM) was treated with 3 M aq. HCl (12 equiv.) at room temperature. After being stirred at 70° C. for 3 h, the mixture was cooled to room temperature and basified with 4 M aq. $K_2CO_3$ (16 equiv.). The immiscible mixture was extracted twice with $CHCl_3$ and the combined organic phases were washed with brine, dried over $MgSO_4$, and then concentrated in vacuo. The residue was purified by recrystallization from $Et_2O$/EtOAc to give 2,5-di-O-n-alkyl-D-mannitol.

Preparation of Methyl 2-O-Alkyl-D-Glycerate

To a 5.5 M solution of 2,5-di-O-alkyl-D-mannitol (1 equiv., SM) in THF-$H_2O$ (9:1) was added $NaIO_4$ (1.2 equiv.) at room temperature, and the mixture was stirred at 50° C. for 1 h. The resulting inorganic salt was removed by filtration through a pad of silica gel and washed with EtOAc. The filtrate was concentrated in vacuo and the crude aldehyde was used for the next reaction.

To a stirred solution of the residue in t-BuOH (20 mL/mmol-SM) were added 2-methyl-2-butene (100 equiv.) and a solution of 80% $NaClO_2$ (12 equiv.) and $NaH_2PO_4$·$H_2O$ (10 equiv.) in $H_2O$ (8 mL/mmol —SM) at 0° C. successively. The resulting yellow mixture was allowed to warm to room temperature for 6 h, during which it turned into clear. Then, the mixture was cooled to 0° C. again and treated with 2.5 M aq. $Na_2SO_3$ (25 equiv.) to reduce an excess of $NaClO_2$. The mixture was acidified with 10% aq. citric acid (10 mL/mmol-SM) and extracted twice with $CHCl_3$ and the combined organic phases were washed with brine, dried over $MgSO_4$, and then concentrated in vacuo. The crude acid was used for the next reaction without further purification.

To a stirred solution of the residue in anhydrous THF-MeOH (1:1, 10 mL/mmol-SM) was treated with 2 M $TMSCHN_2$ solution in hexanes (3.2 equiv.) at 0° C. After being stirred for 10 min, the resulting yellow mixture was decolorized by an addition of AcOH (3.2 equiv.) to consume an excess of $TMSCHN_2$. The mixture was concentrated in vacuo and the residue was purified by silica gel chromatography (petroleum ether:EtOAc=4:1 to 3:2) to give methyl 2-O-alkyl-D-glycerate.

Analytical data for S2: $^1$H-NMR (500 MHz; $CDCl_3$): δ 3.99 (dd, J=6.1, 3.8 Hz, 1H), 3.99 (dd, J=6.1, 3.8 Hz, 1H), 3.79 (d, J=14.1 Hz, 4H), 3.73 (q, J=7.9 Hz, 1H), 3.43 (t, J=11.3 Hz, 1H), 1.65-1.62 (m, 2H), 1.35-1.26 (m, 28H), 0.89 (t, J=7.0 Hz, 3H); $^{13}$C NMR (125 MHz, $CDCl_3$): δ 171.6, 79.8, 71.7, 63.7, 52.3, 32.2, 29.9 (multiple peaks), 29.8, 29.7, 29.6, 26.2, 22.9, 14.4; HRMS (ESI) calcd for $C_{20}H_{40}O_4Na^+$ [M+Na]$^+$ 367.2819, found 367.2823.

Analytical data for S3: $^1$H NMR (500 MHz; $CDCl_3$): δ 5.66 (dd, J=6.0, 2.1, 1H), 5.12-5.07 (m, 2H), 4.26-4.22 (m, 1H), 4.10 (d, J=6.5, 1H), 4.05 (m, 1H), 3.96 (m, 1H), 3.86 (m, 1H), 3.77 (s, 3H), 2.08-1.77 (m, 8H), 1.77 (s, 3H), 1.68 (s, 3H), 1.60 (s, 6H); $^{13}$C NMR (125 MHz, $CDCl_3$): δ 171.6, 142.5, 136.0, 131.6, 124.5, 123.7, 120.8, 67.2, 63.7, 52.3, 39.9, 32.7, 29.8, 29.7, 26.9, 25.7, 24.1, 23.6, 16.2; HRMS (ESI) calcd for $C_{19}H_{32}O_4Na^+$ [M+Na]$^+$ 347.2193, found 347.2206.

Preparation of 0.2 M Phosphoramidite Solution (S4 and S5)

To a 0.2 M solution of methyl 2-O-alkyl-D-glycerate (1 equiv.) in anhydrous $CH_3CN$ were added N,N-diisopropylethylamine (1.5 equiv.) and ClP(OCE)Ni—Pr$_2$ (1.2 equiv.) at room temperature successively. The reaction mixture was stirred for 1 h and directly used for the next coupling reaction.

Preparation of S7

To as solution of N-hydroxysuccinimide fluorescein (S6, 15 mg, 21 µmol) in DMF (300 µL) was added NEt$_3$ (20 µL) and propargyl amine (3.0 mg, 48 µmol). After stirring the solution for 24 h the solvent was removed in vacuo and the residue was purified by column chromatography ($SiO_2$, hexane/EtOAc=2/8) to obtain S7 (11 mg, 27 µmol, 84%) as bright orange solid.

$^1$H NMR (500 MHz, $CD_3OD$) δ 8.43 (s, 1H), 8.20 (d, J=9.50 Hz, 1H), 7.31 (d, J=8.0 Hz, 1H), 6.69 (s, 1H), 6.61 (d, J=8.5 Hz, 2H), 6.54 (d, J=9.0 Hz, 2H), 4.59 (s, 1H), 4.21 (d, J=2.0 Hz, 1H), 2.65 (d, J=2.5 Hz, 1H); $^{13}$C NMR (500 MHz, $CD_3OD$) δ 169.4, 166.8, 152.9, 136.2, 134.4, 129.1, 129.0, 124.7, 123.9, 112.6, 112.2, 109.7, 102.5, 79.3, 78.1, 77.8, 71.2, 29.1.

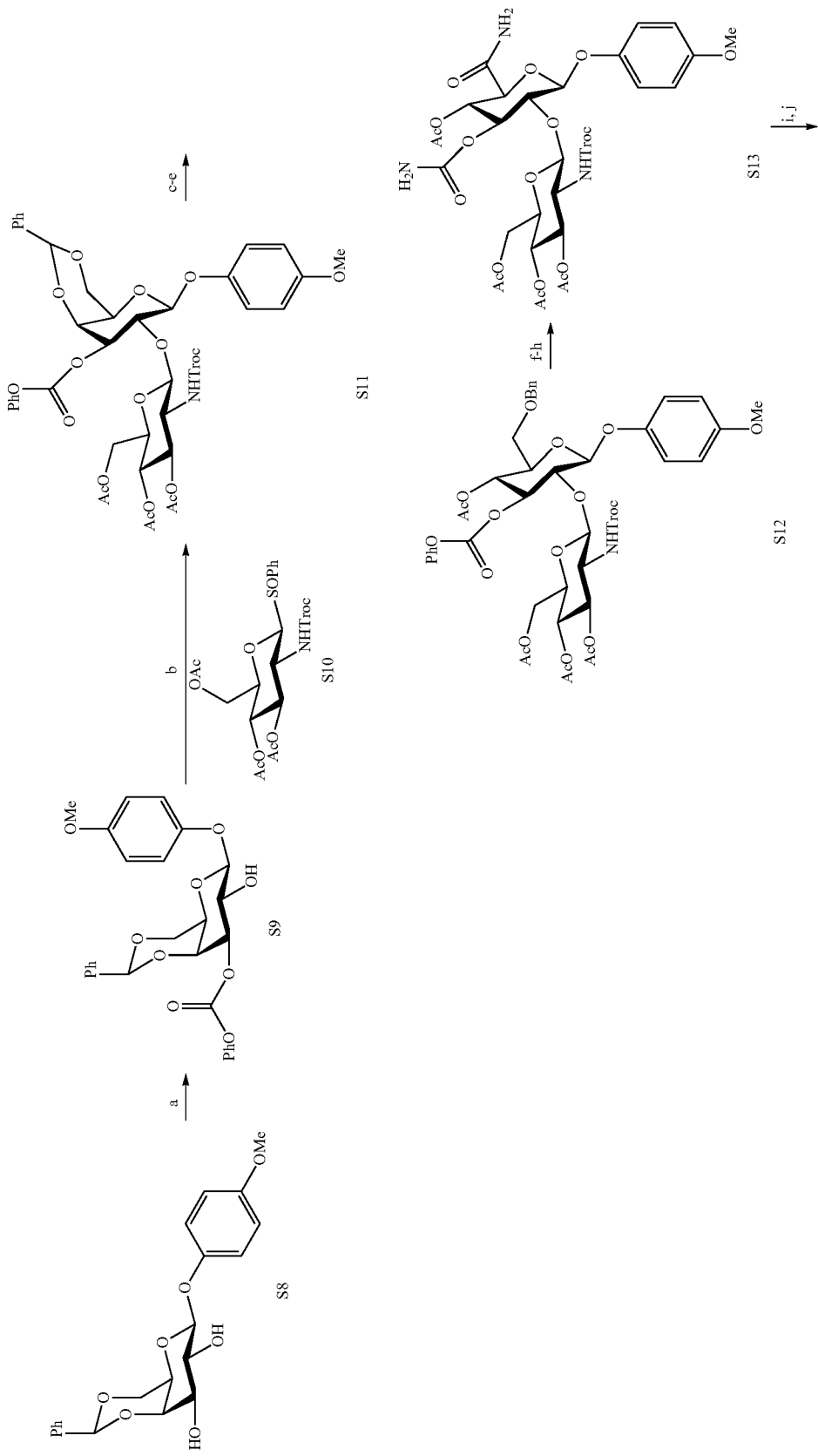

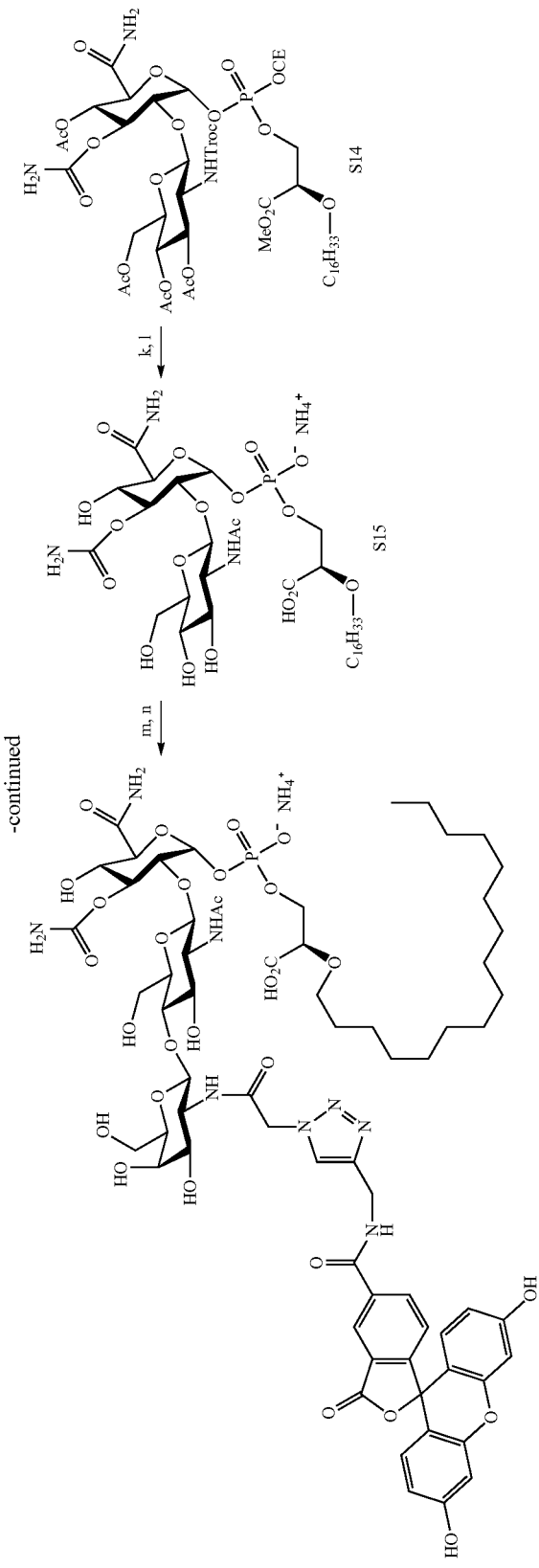
-continued
a ClCO$_2$Ph, Py;
b Tf$_2$O, DTBMP, ADMB, MS-4A, DCM;
c Et$_3$SiH, TfOH, MS-4A, DCM;
d Tf$_2$O, Py, DCM;
e CsOAc, 18-Crown-6, PhMe;
f H$_2$, 10% Pd-C, 1 wt % Cl$_3$CCO$_2$H/MeOH;
g TEMPO, PhI(OAc)$_2$, DCM-H$_2$O (2:1);
h ClCO$_2$iBu, NMM, THF then NH$_3$, i-PrOH;
i CAN, ACN—H$_2$O (4:1);
j S2, tetrazole, MS-3A, ACN, then t-BuO$_2$H;
k Zn, Ac$_2$O, AcOH, THF;
l LiOH, THF—H$_2$O$_2$ (8:1);
m UDP-GalNAz, β1,4-GalT;
n DMF, H$_2$O, CuSO$_4$, Na-ascorbate.

Synthesis of S9

Saccharide S8 (18.7 g, 49.9 mmol, CAS: 176299-96-0) was dissolved in pyridine (160 mL) and cooled to −40° C. Phenylchlorocarbonate (11 mL) was added drop wise to the stirred solution. After 2 h, methanol (11 mL) and toluene (100 mL) were added and the solvent was removed in vacuum. The residue was taken up in EtOAc and washed with HCl (1 M) and NaCl (sat.). The organic layer was dried over $MgSO_4$ and the solvent was removed in vacuum. Recrystallization from $Et_2O$ yielded the title compound as colorless solid (18.5 g, 75%).

$^1$H NMR (500 MHz; $CDCl_3$): δ 7.54 (d, J=7.6 Hz, 2H), 7.37-3.35 (d, J=1.9 Hz, 5H), 7.22-7.21 (m, 3H), 7.07 (d, J=9.1 Hz, 2H), 6.83 (d, J=9.1 Hz, 2H), 5.55 (s, 1H), 4.91 (dd, J=10.2 Hz, 3.7 Hz, 1H), 4.85 (d, J=7.8 Hz, 1H), 4.53 (d, J=3.3 Hz, 1H), 4.34-4.31 (m, 2H), 4.05 (d, J=11.5 Hz, 1H), 3.76 (s, 3H), 3.51 (s, 1H), 2.89 (d, J=2.8 Hz, 1H); $^{13}$C NMR (125 MHz, $CDCl_3$): δ 155.9, 153.6, 151.3, 137.8, 129.7, 129.4, 128.4, 126.6, 126.4, 122.0, 121.3, 119.5, 114.8, 102.8, 101.1, 73.2, 69.1, 68.6, 66.5, 55.9; HRMS (ESI) calcd for $C_{27}H_{26}O_9Na^+$ $[M+Na]^+$ 517.1469, found 517.1506.

Synthesis of S10

Sulfoxide S10 was obtained by oxidation of peracyl-N-Troc-phenyl-(S,O)-glucosamine (CAS: 187022-49-7; 9.00 g, 15.1 mmol) with Selectfluor (6.00 g, 16.8 mmol) in MeCN (105 mL) and water (10.5 mL) at room temperature. The reaction was carried out in an open flask. After 1 h the solvent was removed in vacuum, and the residue was taken up in chloroform, washed with NaCl (sat.) and dried over $NaSO_4$. After concentration in vacuo the residue was recrystallized from EtOAc/hexane to yield sulfoxide S10 as an off-white solid (9.10 g, 15.5 mmol, 98%; 1/1 mixture of diastereomers).

Synthesis of S11

In a 100 mL round bottom flask, gylcosyl donor S10 (1.50 g, 2.55 mmol), gylcosyl acceptor S9 (840 mg, 1.70 mmol), 2,6-di-tert-butylpyridine (478 mg, 2.50 mmol), and a 4-allyl-1,2-dimethoxybenzene (2.73 g, 15.3 mmol) were combined and dried by azeotropic distillation with benzene. The residue was further dried in vacuum for 30 min before dichloromethane (17 mL) and molecular sieves 3 A (ca. 500 mg) were added. The suspension was stirred at room temperature for 30 min and then cooled to −78° C. Triflic anhydride (285 μL, 479 mg, 1.70 mmol) was slowly added and the resulting green solution was stirred for 1.5 h at −78° C. $NaHCO_3$ (sat., 1 volume) was added, and the mixture was allowed to reach room temperature. The phases were separated, and the organic phase was washed with NaCl (sat.) and dried over $Na_2SO_4$. Removal of the solvent in vacuum was followed by column chromatography ($SiO_2$, toluene/EtOAc 8/2→7/3) to yield the title compound as colorless solid (910 mg, 0.951 mmol, 56%).

$^1$H NMR (500 MHz; $CDCl_3$): δ 7.54 (d, J=7.6 Hz, 2H), 7.39-3.37 (d, J=1.9 Hz, 5H), 7.29-7.26 (m, 3H), 7.02 (d, J=9.1 Hz, 2H), 6.80 (d, J=9.1 Hz, 2H), 5.57 (s, 1H), 5.20-5.00 (m, 4H), 5.85-5.78 (m, 3H), 4.59 (br s, 1H), 4.40-4.22 (m, 3H), 4.21-4.19 (m, 1H), 4.16-4.12 (m, 1H), 3.86-3.75 (m, 2H), 3.77 (s, 3H), 3.59 (br s, 1H), 2.01 (s, 3H), 2.01 (s, 3H), 2.00 (s, 3H); $^{13}$C NMR (125 MHz, $CDCl_3$): δ 170.99, 170.88, 169.6, 155.63, 154.34, 152.75, 151.5, 151.2, 137.6, 128.9, 129.5, 128.5, 126.6, 121.3, 121.2, 118.8, 118.7, 114.7, 101.9, 101.3, 100.9, 76.2, 74.6, 72.9, 72.4, 72.0, 69.1, 68.4, 66.1, 61.8, 55.9, 20.91, 20.86; HRMS (ESI) calcd for $C_{42}H_{44}Cl_3NO_{18}Na^+$ $[M+Na]^+$ 978.1516, found 978.1472.

Synthesis of S12

Disaccharide S11 (1.06 g, 1.11 mmol) was dissolved in dichloromethane (22.2 mL) and HSiEt3 (530 μL, 387 mg, 3.33) and molecular sieves 3 Å (ca. 500 mg) were added. The suspension was stirred for 30 min at room temperature and then cooled to −78° C. before triflic acid (333 μL, 566 mg, 3.77 mmol) was added dropwise. After 2.5 h at −78° C., $NaHCO_3$ (sat.) was added and the mixture was allowed to reach room temperature. The phases were parted and the aqueous layer was extracted once with dichloromethane. The combined organic layers were washed with brine and dried over $Na_2SO_4$. Removal of the solvent in vacuum provided the corresponding C6-benzyl ether of S11 in high purity, which was used in the next step without further purification.

The C6-benzyl ether previously obtained (1.15 g, 1.20 mmol) was dissolved in dichloromethane (12 mL) and pyridine (290 μL, 284 mg, 3.59 mmol), and the solution was cooled to −40° C. Triflic anhydride (242 μL, 406 mg, 1.44 mmol) was slowly added and the mixture was allowed to reach room temperature over 2 h. The reaction mixture was washed with 2 volumes of 0.5 M HCl, water, $NaHCO_3$ (sat.), and NaCl (sat), and then dried over $Na_2SO_4$. The solvent was removed in vacuum and the residue was dissolved in toluene (30 mL), and CsOAc (830 mg, 5.48 mmol) and 18-crown-6 (1.21 g, 4.58 mmol) were added. The resulting mixture was vigorously stirred for 14 h and then washed with $NaHCO_3$ (sat.) and NaCl (sat.). The residue obtained after drying of the solution over $Na_2SO_4$ and removal of the solvent in vacuum was purified by column chromatography ($SiO_2$, toluene/EtOAc 85/15) to obtain S12 as colorless solid (668 mg, 667 μmol, 55% over 3 steps).

$^1$H NMR (500 MHz; $CDCl_3$): δ 7.41-7.38 (m, 2H), 7.27 (s, 8H), 7.00 (d, J=9.0 Hz, 2H), 6.80 (d, J=8.50 Hz, 2H), 5.31 (t, J=9.6, 1H), 5.20-5.18 (m, 2H), 5.14-5.05 (m, 4H), 5.01 (d, J=8.1, 1H), 4.68 (d, J=12.0, 1H), 4.56 (d, J=11.8, 1H), 4.47 (d, J=11.9, 1H), 4.27 (d, J=12.2, 1H), 4.18 (dd, J=11.9, 3.4, 1H), 4.07 (td, J=8.2, 1.4, 1H), 3.77 (s, 3H), 3.67-3.60 (m, 3H), 3.59-3.57 (m, 1H), 2.01 (s, 3H), 2.01 (s, 3H), 2.00 (s, 3H), 1.95 (s, 3H); $^{13}$C NMR (125 MHz, $CDCl_3$): δ 170.93, 170.86, 170.11, 169.7, 155.69, 154.21, 153.32, 151.23, 151.12, 138.10, 137.91, 129.84, 129.27, 128.61, 128.46, 128.03, 127.98, 126.55, 125.52, 121.27, 118.12, 114.82, 114.79, 101.14, 100.44, 95.67, 79.60, 78.88, 74.53, 73.81, 73.22, 72.13, 72.00, 69.56, 68.81, 68.46, 61.72, 56.72, 55.91, 21.70, 20.91, 20.85, 20.81; HRMS (ESI) calcd for $C_{44}H_{48}Cl_3NO_{19}Na^+$ $[M+Na]^+$ 1022.1779, found 1022.1766.

Synthesis of S13

In a 100 ml round bottom flask, disaccharide S12 (283 mg, 283 μmol) was dissolved in methanol (20 mL), and 10% Pd/C (100 mg) was added. The atmosphere above the solution was exchanged to $H_2$, and the solution was stirred vigorously. After 45 min the suspension was filtered through celite and the filtrate was concentrated in vacuo. The residue was dissolved in dichloromethane (3.4 mL) and water (1.7 mL), and PhI(OAc)$_2$ (237 mg, 756 μmol) and TEMPO (9.0 mg, 57 μmol) were added. After stirring the mixture for 2 h, the reaction was quenched by addition of $Na_2S_2O_3$ (sat.) and the solution was partitioned between dichloromethane and water. The organic layer was washed with NaCl (sat.) and dried over Na$_2$SO$_4$. The solvent was removed in vacuo, and the residue was taken up in THF (5.7 mL). This solution was cooled to −40° C., N-methylmorpholine (78 μL, 72 mg, 0.71 mmol) was added and the mixture was treated with isobutyl chloroformate (93 μL, 97 mg, 0.71 mmol). After 5 min, NH$_3$ (2.0 M in $^i$PrOH) was added and the mixture was stirred at room temperature for 24 h. Removal of the solvent in vacuum and column chromatography (SiO$_2$, CHCl$_3$/EtOH 99/1→95/5→9/1) yielded the title compound as colorless flakes (111 mg, 131 μmol, 46% over 3 steps).

$^1$H NMR (500 MHz; CDCl$_3$/CD$_3$OD 9/1): δ 6.92 (d, J=8.9, 2H), 6.76 (d, J=9.0, 2H), 5.22 (t, J=9.9, 1H), 5.16-5.12 (m, 2H), 4.98 (dd, J=10.0, 2H), 4.90 (d, J=8.4, 1H), 4.87 (d, J=12.1, 1H), 4.49 (d, J=12.1, 1H), 4.09 (dd, J=12.3, 3.7, 1H), 3.99 (d, J=8.9, 1H), 3.88 (t, J=7.1, 1H), 3.78 (d, J=11.6, 1H), 3.71 (s, 3H), 3.62 (d, J=9.9, 1H), 3.55-3.48 (m, 5H), 2.00 (s, 3H), 1.94 (s, 3H), 1.93 (s, 3H), 1.92 (s, 3H); $^{13}$C NMR (125 MHz, CDCl$_3$/CD$_3$OD 9/1): δ 171.20, 170.92, 170.6, 170.3, 170.0, 156.4, 155.8, 154.8, 150.7, 118.3, 114.9, 101.1, 100.1, 95.8, 79.4, 74.5, 73.9, 72.4, 71.8, 69.6, 68.7, 61.9, 56.5, 55.8, 49.7, 49.5, 49.4, 49.2, 48.9, 48.7, 20.7, 20.7; HRMS (ESI) calcd for C$_{31}$H$_{38}$Cl$_3$N$_3$O$_{18}$Na$^+$ [M+Na]$^+$ 868.1109, found 868.1067.

Synthesis of S14

Disaccharide S13 (167 mg, 187 μmol) was dissolved in MeCN (8 mL) and water (2 mL), and cerium(IV) ammonium nitrate (542 mg, 989 μmol) was added. The mixture was stirred at room temperature for 1.5 h and then concentrated in vacuo. Purification of the residue by column chromatography (SiO$_2$, CHCl$_3$/EtOH 9/1->4/1) gave the lactol of S13 as colorless solid (115 mg, 79%). This lactol (42.9 mg, 57.9 μmol) was further dried by azeotropic distillation with toluene (2×), dissolved in tetrazole solution (0.34 M in MeCN, 1.0 mL), and stirred with molecular sieves 3 Å for 30 min at room temperature and 30 min at 0° C. A solution of S4 (0.2 M in MeCN, 0.58 mL) was added and the mixture was stirred at 0° C. for 2 h before $^t$BuOOH (5.5 M in decane, 127 μL, 699 μmol) was added. After 1 h at 0° C. P(OMe)$_3$ (82 μL, 86 mg, 695 μmol) was added and the suspension was filtered through a pad of celite. Evaporation of the solvent in vacuo and column chromatographic purification (C18, gradient 30-100% MeCN/H$_2$O) of the residue gave phosphoglycerate S14 (32.5 mg, 27.1 μmol, 47%) as colorless solid as a 1/1 mixture of phosphate diastereomers.

analytical data for one diastereomer: $^1$H NMR (500 MHz; CD$_3$OD): δ 6.03 (dd, J=6.3, 3.2, 1H), 5.27-5.20 (m, 3H), 5.07 (t, J=9.7, 1H), 5.02 (d, J=12.3, 1H), 4.78 (d, J=8.5, 1H), 4.61 (d, J=12.3, 1H), 4.46-4.42 (m, 4H), 4.45-4.41 (m, 4H), 4.22 (dd, J=12.3, 2.2, 1H), 4.00 (dd, J=6.9, 3.3, 1H), 3.87-3.83 (m, 2H), 3.82 (s, 3H), 3.72-3.65 (m, 2H), 3.59-3.55 (m, 1H), 3.01 (t, J=6.0, 2H), 2.10 (s, 3H), 2.04 (s, 3H), 2.01 (s, 3H), 1.96 (s, 3H), 1.66 (t, J=7.2, 2H), 1.30 (s, 28H), 0.91 (t, J=7.0, 3H); HSQC ($^{13}$C signals, 125 MHz, CD$_3$OD): δ 102.7, 97.2; 77.9, 77.6, 74.2, 74.1, 72.2, 72.0, 71.5, 71.4, 70.4, 70.3, 69.5, 68.8, 68.2, 68.1, 63.6, 61.9, 61.8, 55.6, 51.8, 48.1, 31.6, 29.6 (multiple peaks), 25.8, 22.5, 19.6, 19.3, 19.3, 19.3, 18.9, 13.2; $^{31}$P (162 MHz; CD$_3$OD): δ −3.16; HRMS (ESI) calcd for C$_{47}$H$_{74}$Cl$_3$N$_4$O$_{23}$PNa$^+$ [M+Na]$^+$ 1223.3410, found 1223.3337.

Synthesis of S15

To a solution of phosphoglycerate S14 (113 mg, 94.2 μmol) in THF (3 mL), Ac$_2$O (1 mL), and AcOH (2 mL) was added activated Zn (653 mg, 9.99 mmol), and the solution was stirred at room temperature for 10 h. The slurry was filtered through a pad of SiO$_2$ and the residue was thoroughly washed with CHCl$_3$/EtOH 2/1 (100 mL). The filtrate was concentrated, and the residue was dissolved in THF (19 mL), H$_2$O$_2$(30%, 4.8 mL) LiOH solution (1 M, 1.9 mL). After stirring the solution at 0° C. for 2 h, DOWEX50WX$_2$-100 resin (HPy+ form, 0.8 g) was added, and the mixture was stirred for 2 h. The resin was filtered off by passing the reaction mixture through a cotton plug. Chromatographic purification (C18, gradient 20-50% MeCN in 0.2% NH$_4$HCO$_3$) of the residue obtained after concentration of the filtrate yielded disaccharide S15 (50.7 mg, 61.0 μmol, 63%).

HPLC/MS retention time: 11.9 min (Phenomenex Luna, 3u-C18 50×2 mm$^2$ 3 micron, 0.3 mL/min, gradient 30-75% MeCN+0.1% HCO$_2$H in H$_2$O+0.1% HCO$_2$H over 6 min, then to 99% MeCN+0.1% HCO$_2$H over 5 min) LRMS (ESI) calcd for C$_{34}$H$_{61}$N$_3$O$_{18}$P$^-$ [M−H]$^-$ 830.4, found 830.3; $^1$H NMR (500 MHz; CD$_3$OD): δ 5.98 (dd, J=7.1, 3.1, 1H), 5.05 (t, J=9.7, 1H), 4.58 (d, J=8.4, 1H), 4.36 (d, J=10.0, 1H), 4.26-4.22 (m, 1H), 4.18-4.08 (m, 1H), 4.00-3.96 (m, 1H), 3.87-3.84 (m, 1H), 3.76-3.71 (m, 3H), 3.71 (s, 3H), 3.68-3.64 (m, 3H), 3.53-3.47 (m, 3H), 3.36-3.29 (m, 4H), 2.04 (s, 3H), 1.66-1.64 (m, 2H), 1.30 (s, 28H), 0.91 (t, J=7.0, 3H); $^{13}$C NMR (125 MHz, CD$_3$OD): δ; 175.6, 173.0, 158.2, 103.0, 95.5, 79.6, 76.9, 74.5, 73.2, 71.4, 70.8, 70.6, 70.5, 70.2, 66.9, 66.8, 61.6, 61.1, 59.9, 56.1, 31.9, 29.6, 29.6, 29.5, 29.3, 26.0, 22.6, 22.2, 13.3; $^{31}$P (162 MHz; D$_6$-DMSO): δ −2.31; HRMS (ESI) calcd for C$_{34}$H$_{63}$N$_3$O$_{18}$P$^+$ [M+H]$^+$ 832.3839, found 832.7735.

Synthesis of S16 (CMG121)

To a solution of TRIS (50 mM in H$_2$O, pH=8.0, 2.5 mL) were sequentially added MnCl$_2$ (50 mM in H$_2$O, 2.5 mL), H$_2$O (5 mL), GalT Y289L (Ramakrishanan et al. *J. Biol. Chem.* 2002, 277, 20833; 1 mg/mL in 50 mM TRIS buffer, pH=8.0, 1.88 mL,), UDP-N-azidoacetylgalactosamine (UDP-GalNAz, prepared according to Hang et al. *J. Am. Chem. Soc.* 2003, 126, 6; 20 mM in H$_2$O, 500 μL), disaccharide S15 (10 mM in H$_2$O, 125 μL), and calf intestinal alkaline phosphatase (CIP, 1000 U, 25 μL, Roche Diagnostics GmbH, Mannheim, Germany). The mixture was gently mixed and kept at 37° C. for 60 h. MeOH (7.5 mL) was added, and the mixture was vortexed and centrifuged (15 min at 5000×g) to pellet precipitated proteins. The supernatant was concentrated in vacuo, and the residue obtained was loaded onto a Phenomenex Strata C-18 column pre-equilibrated with H$_2$O. The column was eluted with H$_2$O to obtain unreacted UDP-GalNAz. Elusion with H$_2$O/MeOH 1/9 provided the desired trisaccharide in near quantitative yield.

HPLC retention time: 11.0 min (Phenomenex Luna, 3u-C18 50×2 mm$^2$ 3 micron, 0.3 mL/min, gradient 30-75% MeCN+0.1% HCO$_2$H in H$_2$O+0.1% HCO$_2$H over 6 min, then to 99% MeCN+0.1% HCO$_2$H over 5 min) LRMS (ESI) calcd for C$_{42}$H$_{73}$N$_7$O$_{23}$P$^-$ [M−H]$^-$ 1074.5, found 1074.3.

The GalNAz-trisaccharide previously obtained (4.0 mg, 3.8 μmol) was dissolved in DMF (400 μL) and CuSO$_4$ (0.9 M in H$_2$O, 4.0 μL, 3.6 μmol) and Na-ascorbate (1.8 M in H$_2$O, 4.0 μL, 7.2 μmol) were added. The mixture was stirred at room temperature, and after 24 h another portion of CuSO$_4$ (0.9 M in H$_2$O, 4.0 μL, 3.6 μmol) and Na-ascorbate (1.8 M in H$_2$O, 4.0 μL, 7.2 μmol) was added. After 48 h the solution was concentrated in vacuo and the residue was purified by column chromatography (C-18, gradient 30-90%

MeOH in H₂O; then 10% 2M NH₃ in MeOH to elute the product) to obtain the title compound (4.9 mg, 3.3 μmol, 87%).

HPLC/MS retention time: 10.8 min (Phenomenex Luna, 3u-C18 50×2 mm² 3 micron, 0.3 mL/min, gradient 30-75% MeCN+0.1% HCO₂H in H₂O+0.1% HCO₂H over 6 min, then to 99% MeCN+0.1% HCO₂H over 5 min); LRMS (ESI) calcd for $C_{66}H_{88}N_8O_{29}P^-$ [M−H]⁻ 1487.5, found 1487.3; ¹H NMR (600 MHz; CD₃OD): δ 8.51 (s, 1H), 8.28-8.27 (m, 1H), 8.11 (s, 1H), 7.35 (d, J=7.5, 1H), 6.72 (m, 2H), 6.65 (d, J=8.5, 2H), 6.60-6.59 (m, 2H), 6.01 (br s, 1H), 5.29 (br s, 1H), 5.05 (t, J=6.8, 1H), 4.77 (m, 2H), 4.61-4.56 (m, 2H), 4.38 (d, J=7.5, 1H), 4.29-4.25 (m, 2H), 4.15-4.05 (m, 2H), 4.05-3.99 (m, 2H), 3.86-3.76 (m, 4H), 3.76-3.60 (m, 13H), 3.48 (br s, 1H), 2.02 (s, 3H), 1.65-1.64 (m, 6H), 1.48-1.42 (m, 12H), 1.31 (m, 38H), 0.92 (t, J=5.4, 3H); HSQC (¹³C signals, 125 MHz, CD₃OD): δ 129.1, 124.1, 112.9, 102.4, 102.3, 79.5, 75.8, 75.0, 73.3, 73.0, 71.5, 71.2, 70.5, 70.0, 68.3, 67.0, 61.2, 53.4, 52.0, 35.1, 31.8, 29.5, 26.0, 23.5, 22.6, 21.9, 13.1; HRMS (ESI) calcd for $C_{66}H_{90}N_8O_{29}P^+$ [M+H]⁺ 1489.5546, found 1489.5420.

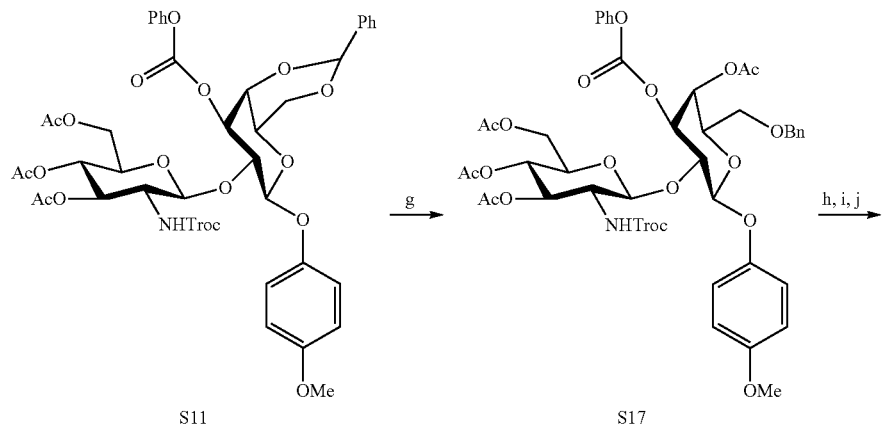

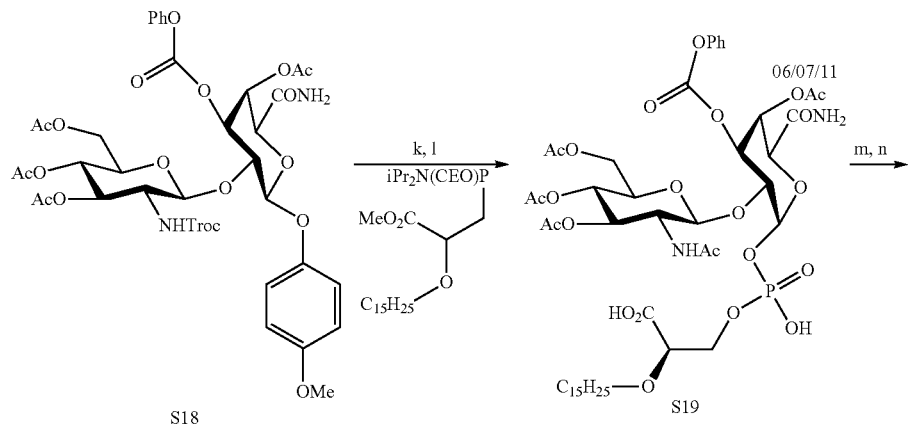

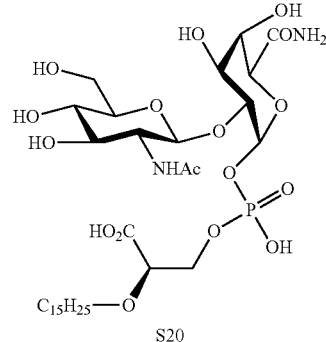

-continued

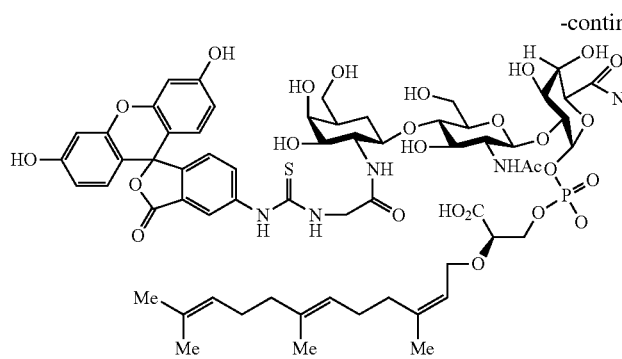

S22 or CMG54

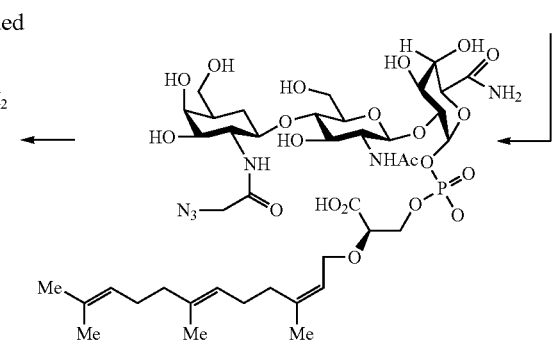

S21 g Et$_3$SiH, triflic acid, then: Ac$_2$O, Py., cat. DMAP, DCM;
) H$_2$, 10% Pd-C, 1 wt % Cl$_3$CCO$_2$H/MeOH;
i TEMPO, PhI(OAc)$_2$, DCM-H$_2$O (2:1);
j ClCO$_2$/Bu, NMM, THF then NH$_3$, i-PrOH;
k CAN, ACN-H$_2$O (4:1);
l S5, tetrazole, MS-3A, ACN, then t-BuO$_2$H;
m Zn, Ac$_2$O, AcOH, THF;
n LiOH, THF—MeOH—H$_2$O (3:3:1);
o UDP-GalNAz, β1,4-GalT;
p Pd(OH)$_2$/C, MeOH, H$_2$;
q fluoresceinisothiocyanate

Synthesis of S17

Disaccharide S11 (650 mg, 679 mol) was dissolved in dichloromethane (13.6 mL) and HSiEt$_3$ (325 μL, 237 mg, 2.04 mmol) and molecular sieves 3 Å (ca. 250 mg) were added. The suspension was stirred for 30 min at room temperature and then cooled to −78° C. before triflic acid (204 μL, 347 mg, 2.31 mmol) was added dropwise. After 2.5 h at −78° C., NaHCO$_3$ (sat.) was added and the mixture was allowed to reach room temperature. The phases were parted and the aqueous layer was extracted once with dichloromethane. The combined organic layers were washed with brine and dried over Na$_2$SO$_4$. Removal of the solvent in vacuo provided the corresponding C6-benzyl ether of S11 in high purity, which was dissolved in dichloromethane (3.4 mL), and pyridine (164 μL, 161 mg, 2.04 mmol), DMAP (8.3 mg, 0.07 mmol), and Ac$_2$O (94 μL, 104 mg, 1.02 mmol) were added. After 3 h at room temperature the reaction was diluted with dichloromethane and washed with HCl (1 M), H$_2$O, NaHCO$_3$ (sat.), and NaCl (sat.). The organic layers were dried over Na$_2$SO$_4$ and then concentrated in vacuo. Purification of the residue yielded acetate S17 (539 mg, 538 μmol, 79% over 2 steps) as colorless solid.

$^1$H NMR (500 MHz; CDCl$_3$): δ 7.39 (t, J=7.8, 2H), 7.34-7.25 (m, 8H), 7.01 (d, J=9.0, 2H), 6.79 (d, J=9.0, 2H), 5.64 (d, J=2.5, 1H), 5.26 (t, J=10.1, 1H), 5.14-5.10 (m, 2H), 5.01 (d, J=7.2, 1H), 4.90-4.88 (m, 2H), 4.81 (d, J=12.2, 1H), 4.56 (d, J=12.0, 1H), 4.44 (d, J=12.0, 1H), 4.29 (d, J=12.2, 1H), 4.23 (dd, J=12.2, 3.3, 1H), 4.11 (dd, J=9.8, 7.7, 1H), 3.94 (t, J=6.4, 1H), 3.90-3.86 (m, 2H), 3.77 (s, 3H), 3.70-3.66 (m, 2H), 3.59-3.55 (m, 2H), 2.11 (s, 3H), 2.03 (s, 3H), 2.02 (s, 3H), 2.01 (s, 3H); $^{13}$C NMR (125 MHz, CDCl$_3$): δ 171.1, 170.9, 170.5, 169.6, 155.7, 154.2, 152.7, 151.5, 151.2, 138.1, 137.7, 129.8, 129.3, 128.7, 128.5, 128.2, 128.1, 126.6, 125.6, 121.5, 118.3, 114.8, 101.9, 100.8, 95.7, 74.5, 73.8, 72.0, 68.4, 67.7, 67.2, 61.8, 56.9, 55.9, 21.0, 20.9, 20.8, 20.8; HRMS (ESI) calcd for C$_{44}$H$_{48}$Cl$_3$NO$_{19}$Na$^+$ [M+Na]$^+$ 1022.1779, found 1022.1707.

Synthesis of S18

In a 10 mL roundbottom flask S17 (56.4 mg, 56.3 μmol) was dissolved in a solution of 1% trichloroacetic acid in methanol (2.8 mL, 2.4 equiv. of TCA), 10% Pd/C (11.9 mg) was added and the atmosphere above the solution was exchanged to H$_2$. After stirring for 15 min the solution was filtered through a pad of Celite and poured into NaHCO$_3$ (sat.). The mixture was extracted with EtOAc (2×), washed with NaCl (sat.), and dried over MgSO$_4$. Evaporation of the solvent in vacuum yielded the free C6-alcohol in quantitative yield.

The alcohol previously obtained (51.3 mg, 56.3 μmol) was dissolved in dichloromethane (0.2 mL) and water (0.1 mL). After addition of TEMPO (1.8 mg, 1.2 μmol) and diacetoxy iodobenzene (45.0 mg, 140 μmol) the mixture was stirred at room temperature for 1.5 h. Na$_2$S$_2$O$_3$ (sat.) solution was added, and the reaction mixture was extracted with EtOAc (2×). The combined organic layers were washed with NaCl (sat.) and dried over MgSO$_4$. The residue obtained after concentration of the solution in vacuum was purified by column chromatography (SiO$_2$, petrol ether/EtOAc/1% AcOH 2/1→1/4) to obtain pure C6-carboxylic acid (36.8 mg, 39.8 μmol, 71% over 2 steps).

The C6-carboxylic acid (22.0 mg, 23.8 μmol) was dissolved in THF (0.6 mL) and N-methyl-morpholine (5.2 μL, 47 μmol), and the solution was cooled to −30° C. before isobutylchloroformate (6.2 μL, 47 μmol) was added. After 30 min the turbid mixture was treated with 7M NH$_3$ solution in MeOH (14 μL) and stirred at 0° C. for another 30 min. The mixture was poured into NH$_4$Cl and extracted with EtOAc (2×). The organic layers were washed with NaCl (sat.) and dried over MgSO$_4$ before they were concentrated in vacuo. Column chromatographic purification of the residue (SiO$_2$, petroleum ether/EtOAc 2/1→1/4) gave S18 as colorless solid (21.8 mg, 23.6 μmol, 99%).

Synthesis of S19

Deprotection of the PMP group was achieved by treatment of a solution of S18 (21.8 mg, 23.8 μmol) in MeCN (1.2 mL) and water (0.3 mL) with cerium (IV) ammonium nitrate (40.2 mg, 73.3 μmol). After stirring at room temperature for 1 h the mixture was concentrated in vacuo, and the residue was purified by column chromatography (SiO$_2$, CHCl$_3$/MeOH 98/2→95/5) to give the free lactol as colorless solid (12.8 mg, 15.6 μmol, 66%). This material was dried by azeotropic distillation with toluene (2×), dissolved in a solution of tetrazole in MeCN (0.34 M, 0.28 mL), and molecular sieves 3 Å (43 mg) were added. The mixture was stirred at room temperature for 15 min and then cooled to 0° C. before a solution of S5 was added (0.2 M in MeCN, 0.15 mL). After 1 h at 0° C., $^t$BuOOH (5.5 M in decane, 23 μL) was added, and the suspension was stirred for another hour before P(OMe)$_3$ (22 μL, 186 μmol) was added. The mixture was filtered over Celite, and the residue was concentrated in vacuo. Purification of the residue by column chromatography (SiO$_2$, CHCl$_3$/MeOH 97/3→96/4) gave S19 as colorless solid as a mixture of phosphate diastereomers (16.0 mg, 12.7 mol, 81%).

Synthesis of S20

Phosphoglycerate S19 (7.6 mg, 6.0 mol) was dissolved in a mixture of THF (0.3 mL), Ac$_2$O (0.1 mL), and AcOH (0.2 mL) and activated zinc (70.1 mg) was added in portions over the course of 1.5 d. The suspension was filtered through a pad of Celite, concentrated in vacuo, and subjected to column chromatography (SiO$_2$, CHCl$_3$/MeOH 96/4). The product obtained was dissolved in a mixture of THF (0.66 mL), MeOH (0.22 mL), and H$_2$O (0.22 mL) and LiOH (1 M in H$_2$O, 66 μL, 66 μmol) was added. After stirring at room temperature for 1.5 h, AcOH (4 μL, 7 μmol) was added, and the solution was concentrated in vacuo. Purification of the residue by column chromatography (C18, gradient 25-75% MeOH in H$_2$O+0.1% AcOH) gave S20 (3.3 mg, 4.3 μmol, 71% over 2 steps) as colorless solid.

Synthesis of S21

To a solution (2 mL) containing HEPES (50 mM, pH=7.5), NaCl (100 mM), MnCl$_2$ (1 mM), S20 (1 mM), UDP-N-azidoacetylgalactosamine (UDP-GalNAz, prepared according to Hang et al. J. Am. Chem. Soc. 2003, 126, 6; 2 mM) were added calf intestinal alkaline phosphatase (1000 U, 5 μL, Roche Diagnostics GmbH, Mannheim, Germany) and GalT Y289L (Ramakrishanan et al. J. Biol. Chem. 2002, 277, 20833, 150 μg), and the mixture was incubated at 37° C. for 2 h. The reaction was quenched by precipitation of the proteins by addition of MeOH (4 mL), was centrifuged, and the supernatant was passed over a 30 mg Strata-X C18 column (Phenomenex). The column was eluted with water (2 mL) to rinse off salts, UMP, and UDP-GalNAz, and the desired trisaccharide S21 was eluted with MeOH/H$_2$O 8/2. The material obtained was directly used in the next reaction.

Synthesis of S22

Azide S21 (3.8 mg, 3.8 μmol) was dissolved in a mixture of MeOH (210 μL), water (10 μL), and HOAc (2 M, 2 μL) and Pd(OH)$_2$/C (1 mg) was added. The atmosphere above the solution was exchanged for H$_2$, and the mixture was stirred vigorously for 48 h. The mixture was filtered over a plug of celite, the residue was thoroughly washed with MeOH/H$_2$O 4/1, and the filtrate was concentrated in vacuo. The residue obtained was suspended in DMF (76 μL) and treated with diisopropylethylamine (5.3 μL) and fluorescein isothiocyanate (1.7 mg, 4.6 μmol). After 16 h at room temperature, the solution was concentrated in vacuum, and the residue was purified by column chromatography (SiO$_2$, CHCl$_3$/MeOH+0.1% AcOH 9/1→8/2; then CHCl$_3$/MeOH/ H$_2$O 60/40/8) to obtain the title compound (2.0 mg, 1.5 μmol, 40% over 2 steps) as orange solid.

HPLC/MS retention time: 11.6 min (Phenomenex Luna, 3u-C18 50×2 mm$^2$ 3 micron, 0.3 mL/min, gradient 25-45% MeCN+0.1% HCO$_2$H in H$_2$O+0.1% HCO$_2$H over 6 min, then to 99% MeCN+0.1% HCO$_2$H over 6.5 min); LRMS (ESI) calcd for C$_{61}$H$_{77}$N$_5$O$_{27}$PS$^-$ [M−H]$^-$ 1374.4, found 1374.3; HRMS (ESI) calcd for C$_{61}$H$_{79}$N$_5$O$_{27}$PS$^+$ [M+H]$^+$ 1376.4416, found 1376.4224.

Assay Development
Enzyme Titration with Probe S16 (CMG121)

Solution containing 10 mM TRIS (pH=8.0), 100 mM NaCl, 0.3% DMSO, 75 nM S16, and bacterial glycosyltransferase (E. coli PBP1b c=2.2 uM; E. faecalis PBP2a c=5.1 uM; S. aureus SgtB c=2.1 uM) were allowed to equilibrate for 30 min at 0° C. and then serially diluted (1/1 dilutions) into buffer containing 10 mM TRIS (pH=8.0), 100 mM NaCl, 0.3% DMSO, and 75 nM S16. After equilibration at 0° C. for 30 min the 20 μL of the solutions were transferred to a black 384 well plate (Corning NBS Low Volume) and fluorescence polarization (FP, ex: 480 nm; em: 535 nm) was measured using a Perkin Elmer Envision microplate reader. Each series was performed in duplicate and the data was plotted FP vs. concentration of enzyme. For determination of the KD, the average FP values were converted to fluorescence anisotropy and fitted to the standard equation describing an equilibrium L+E<->LE (L=ligand; E=enzyme; LE=ligand enzyme complex) using GraphPad Prism 5.0 (GraphPad Software, Inc.; La Jolla, Calif., USA). The K$_D$ values for probe S16 are: E. coli PBP1b: 0.15; E. faecalis PBP2a: 0.38;
S. aureus SgtB: 0.18. Probe CMG121 (75 nM) is displaced from S. aureus SgtB (0.2 μM) by addition of either moenomycin or the weaker PGT inhibitor disaccharide S15, as evidenced by reduction of FP. Ki (1)=0.64 μM; Ki (3)=3.17 μM. As used herein, mP: millipolarization; KD: dissociation constant; Ki: inhibitor constant. The IC$_{50}$ values for probe S16 are E. coli PBP1b: 600 nM; S. aureus SgtB: 31 nM.

Solution containing 10 mM TRIS (pH=8.0), 100 mM NaCl, 0.3% DMSO, 75 nM Probe CMG121, and bacterial glycosyltransferase (E. coli PBP1b c=2.2 uM; E. faecalis PBP2a c=5.1 uM; S. aureus SgtB c=2.1 uM) were allowed to equilibrate for 30 min at 0° C. and then serially diluted (1/1 dilutions) into buffer containing 10 mM TRIS (pH=8.0), 100 mM NaCl, 0.3% DMSO, and 75 nM Probe CMG121. After equilibration at 0° C. for 30 min the 20 μL of the solutions were transferred to a black 384 well plate (Corning NBS Low Volume) and fluorescence polarization (FP, ex: 480 nm; em: 535 nm) was measured using a Perkin Elmer Envision microplate reader. Each series was performed in duplicate and the data was plotted FP vs. concentration of enzyme. For determination of the KD, the average FP values were converted to fluorescence anisotropy and fitted to the standard equation describing an equilibrium L+E<->LE (L=ligand; E=enzyme; LE=ligand enzyme complex) using GraphPad Prism 5.0 (GraphPad Software, Inc.; La Jolla, Calif., USA). The K$_D$ values for probe S16 are
Validation of the Essay To equilibrated solutions containing 10 mM TRIS (pH=8.0), 100 mM NaCl, 75 nM S16, and bacterial glycosyltransferase (E. coli PBP1b c=0.1-0.15 uM; E. faecalis PBP2a c=0.38-0.46 uM; S. aureus SgtB c=0.2-0.25 uM) was added the test compound in DMSO or DMSO/H$_2$O solutions (stock solutions were typically 2 mM) to obtain a final concentration of test compound of ca. 200 uM. These solutions were serially diluted (1/1 dilutions) into buffer containing 10 mM TRIS (pH=8.0), 100 mM NaCl, 75 nM Probe CMG121, and bacterial glycosyl transferase (*E. coli* PBP1b c=0.1-0.15 uM; *E. faecalis* PBP2a c=0.38-0.46 uM; *S. aureus* SgtB c=0.2-0.25 uM). After equilibration at 0° C. for 30 min the 20 µL of the solutions were transferred to a black 384 well plate (Corning NBS Low Volume) and fluorescence polarization (FP, ex: 480 nm; em: 535 nm) was measured using a Perkin Elmer Envision microplate reader. Each series was performed in duplicate and the data was plotted FP vs. concentration of test compound.

Determination of Z'-value (Zhang et al. *J. Biomol. Screen* 1999, 4, 67-73.)

Using a Matrix WellMate, a black 384 well plate (Corning NBS Low Volume) was filled (10 µL per well) with equilibrated solutions containing 10 mM TRIS (pH=8.0), 100 mM NaCl, 75 nM S16, and bacterial glycosyltransferase (*E. coli* PBP1b c=0.2 uM; *E. faecalis* PBP2a c=0.46 uM; *S. aureus* SgtB c=0.25 uM). From a second 384 well plate, filled half with DMSO and half with 10 mM disaccharide S15, 100 nL were transferred to the test plate by pin transfer. After 10 min at room temperature fluorescence polarization (FP, ex: 480 nm; em: 535 nm) was measured using a Perkin Elmer Envision microplate reader. The following Z'-values were obtained and were stable over a period of at least 30 min:
*E. coli* PBP1b: 0.70
*E. faecalis* PBP2a: 0.58
*S. aureus* SgtB: 0.64

Protocol for High-Throughput Screening

Assay solutions consisted of: 1.0-1.5 µM *S. aureus* ΔTM SgtB (depending on protein batch), 75 nM probe CMG121, 10 mM Tris pH 8.0, 100 mM NaCl. The assay was carried out in 384-well plates (Corning 3820) dispensing 10 µL of assay solution per well, followed by pin transfer of 100 nL of each experimental compound from library plates by a stainless steel pin array. The assay was subsequently adapted to 1536-well plates (Greiner 782076), which were filled with 3 µL assay solution per well, followed by a 33 nL pin transfer of experimental compounds. The final concentration of pertubator was ca. 100 µM. A solution containing 1.0-1.5 µM *S. aureus* ΔTM SgtB (depending on protein batch), 75 nM probe CMG121, 10 mM Tris pH 8.0, 100 mM NaCl and 20 µM moenomycin A was used as positive control. All wells in row 24 (384-well plate) or rows 47 and 48 (1536-well plate) were filled with 10 µL (384-well plate) or 3 µL (384-well plate) of this solution, respectively. Assay plates were incubated for 30 minutes at 4° C. after the addition of experimental compounds and then read on a PerkinElmer EnVision microplate reader (Excitation: 480 nm, Emission: 535 nm). Library plates were screened in duplicate, with both assay plates in a given set prepared on the same day.

For each plate, an adjusted FP threshold value was calculated using the formula: [plate average negative control FP−0.9*(average negative control FP−average positive control FP)]. Wells were considered positive if FP for both replicates was <threshold value (10% of the adjusted plate average negative control FP) and fluorescence intensity was below detector saturation.

Protocol for Secondary Assay

A black 384 well plate (Corning NBS Low Volume No. 3820) was filled (10 µL per well) with an equilibrated solution containing 10 mM TRIS (pH=8.0), 100 mM NaCl, 75 nM disaccharide S15, and 1.0-1.5 µM *S. aureus* SgtB (depending on protein batch). Using an HP D300 Digital Dispenser, for each compound a 1/1 dilution series (12 wells) of the primary hit compound in DMSO (normalized to 1 µL with DMSO) was prepared and added to the aforementioned assay solution. The plate was incubated at 4° C. for 30 min and read with an Perkin Elmer EnVision microplate reader as described above. The dilution series was performed in duplicate.

For determination of the $K_i$, the average FP values were first converted to fluorescence anisotropy. Using GraphPad Prism 5.0 (GraphPad Software, Inc.; La Jolla, Calif., USA), this data was fitted to the equation describing the competition for two ligands for a common binding site:

$$\frac{[RL]}{[R]} = \frac{1}{1 + \frac{K_D}{[L]}\left(1 + \frac{[A]}{K_i}\right)}$$

[RL]: conc. of receptor-ligand complex; [A]: conc. of test compound; [L]: conc. of probe=75 nM; $K_D$: dissociation constant for the probe compound (determined above)

In vitro PGT Inhibition Assays (Chen et al., *Proc. Natl. Acad. Sci. USA* 2003, 100, 5658-5663; Wang et al., *J. Am. Chem. Soc.* 2011, 133, 8528-8530)

In Vitro Inhibition of *S. aureus* SgtB:

A solutions of *S. aureus* SgtB (50 nM) in 12.5 mM HEPES (pH=7.5), 2 mM $MnCl_2$, and 250 µM tween-80 (8 µL) were incubated with DMSO solutions containing the inhibitor of interest in different concentrations (1 µL) for 20 min. Then $^{14}C$-labelled lipid II (1 µL, 40 µM, $^{14}C/^{12}C$ 1/3) was added and the polymerization reaction was allowed to proceed for 25 min at room temperature. The reaction was quenched with 10 µL of a solution of moenomycin (1 µM) in 10% triton-X reduced and the remaining lipid II was separated from peptidoglycan (PG) using paper strip chromatography (isobutyric acid/1M $NH_4OH$ 5/3). Using a scintillation counter the ratio of radioactivity in PG to total radioactivity was determined and plotted vs. inhibitor concentration. $IC_{50}$s were determined using the curve fitting program GraphPad Prism 5.0 (GraphPad Software, Inc.; La Jolla, Calif., USA).

In Vitro Inhibition of *S. aureus* PBP2:

Solutions of *S. aureus* PBP2 (1.2 µM) in 50 mM HEPES (pH=5.0), 50 mM CHES, 50 mM AcOH, 10 mM $CaCl_2$, 50 mM MES, and 1000 U/min PenG (8 µL) were incubated with DMSO solutions containing the inhibitor of interest in different concentrations (1 µL) for 20 min. Then $^{14}C$-labelled lipid II (1 µL, 40 µM, $^{14}C/^{12}C$ 1/3) was added and the polymerization reaction was allowed to proceed for 25 min at room temperature. The reaction was quenched and processed as described above.

In Vitro Inhibition of *E. coli* PBP1b and *E. faecalis* PBP2a

Solutions of the PGT (50 nM) in 50 mM HEPES (pH=7.5), 10 mM $CaCl_2$, and 1000 U/min PenG (8 µL) were incubated with DMSO solutions containing the inhibitor of interest in different concentrations (1 µL) for 20 min. Then $^{14}C$-labelled lipid II (1 µL, 40 µM, $^{14}C/^{12}C$ 1/3) was added and the polymerization reaction was allowed to proceed for 25 min at room temperature. The reaction was quenched and processed as described above.

Other Embodiments

This application refers to various issued patents, published patent applications, journal articles, books, manuals, and other publications, all of which are incorporated herein by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:
1. A compound of Formula (I):

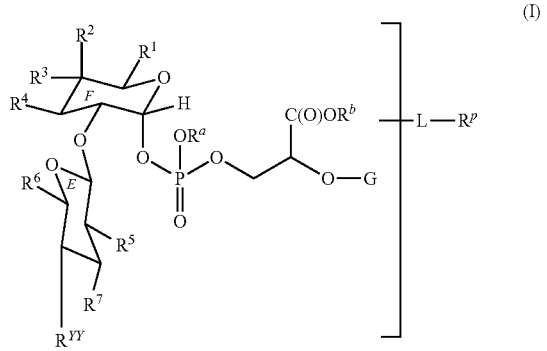

or a salt thereof,
wherein
  $R^1$ is -L-$R^P$, —C(O)NH-L-$R^P$, —CH$_2$O-L-$R^P$, or —C(O)O-L-$R^P$;
  $R^2$ and $R^3$ are independently hydrogen, optionally substituted aliphatic, —OR$^9$, —N(R$^8$)$_2$, or —C(O)NHR$^8$;
  $R^4$ is hydrogen or —WR$^{4a}$;
  W is —O— or —NH—;
  $R^{4a}$ is hydrogen, a hydroxyl protecting group, optionally substituted aliphatic, —C(O)R$^{10}$, —C(O)NHR$^8$, —C(=NR$^8$)NHR$^8$, or —C(O)OR$^9$;
  $R^5$ is hydrogen or —NHR$^8$;
  $R^6$ is hydrogen, —CH$_3$, —CH$_2$OR$^9$, or —CH$_2$OR$^{CX}$; wherein $R^{CX}$ is a carbohydrate moiety;
  $R^7$ is hydrogen, —OR$^9$, or —N(R$^8$)$_2$;
  each $R^8$ is independently hydrogen, an amino protecting group, —C(O)R$^{10}$, optionally substituted aliphatic, optionally substituted aryl, optionally substituted heterocyclyl, or optionally substituted heteroaryl, or two $R^8$ groups on the same nitrogen may be taken together to form an optionally substituted heterocyclyl;
  each $R^9$ is independently hydrogen, a hydroxyl protecting group, —C(O)R$^{10}$, optionally substituted aliphatic, optionally substituted aryl, optionally substituted heterocyclyl, or optionally substituted heteroaryl;
  each $R^{10}$ is independently optionally substituted aliphatic, optionally substituted heterocyclic, optionally substituted aryl, or optionally substituted heteroaryl;
  $R^a$ and $R^b$ are independently hydrogen or a hydroxyl protecting group;
  G is an optionally substituted C$_{1-16}$ aliphatic group, wherein 0 to 10 methylene units are optionally replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene; wherein each instance of $R^x$ is independently hydrogen, optionally substituted aliphatic, optionally substituted heterocyclyl, optionally substituted aryl, optionally substituted heteroaryl; or
  G is a group of Formula (a), (b), or (c):

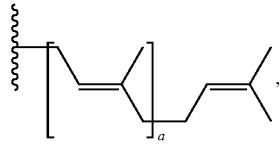

(a)

wherein a is 3, 4, or 5;

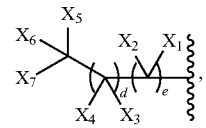

(b)

wherein
  $X_1$, $X_2$, $X_3$, $X_4$, $X_5$, $X_6$, and $X_7$ are each independently hydrogen or halogen;
  d is an integer between 1 and 25, inclusive; and
  e is an integer of between 2 and 25, inclusive;
  provided the sum of d and e is greater than 16; or

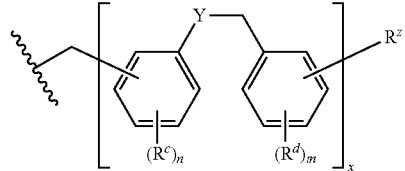

(c)

wherein
  Y is —O—, —S—, —NR$^Y$—, or an optionally substituted methylene group, wherein $R^Y$ is hydrogen, optionally substituted aliphatic, or an amino protecting group;
  each instance of $R^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of $R^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^e$ groups are joined to form a 5- to 6-membered optionally substituted heterocycyl or optionally substituted heteroaryl ring;
  each instance of $R^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of $R^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^f$ groups are joined to form a 5- to 6-membered optionally substituted heterocycyl or optionally substituted heteroaryl ring;

$R^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^g$, —$SR^g$, —$NHR^g$, or —$N(R^g)_2$, wherein each instance of $R^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two $R^g$ groups are joined to form a 5- to 6-membered optionally substituted heterocycyl or optionally substituted heteroaryl ring;

each instance of n is, independently, 0, 1, 2, 3, or 4;
each instance of m is, independently, 0, 1, 2, 3, or 4; and
x is 1, 2, 3, 4, 5, or 6;
$R^{YY}$ is hydrogen or —$OR^{XX}$;
$R^{XX}$ is hydrogen, a hydroxyl protecting group, or a group of formula:

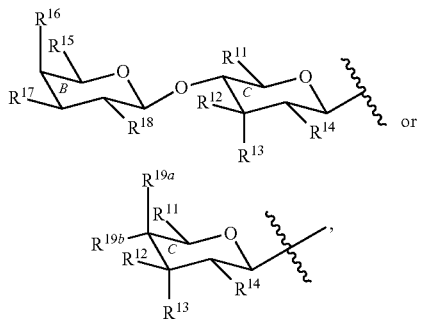

wherein
$R^{11}$ is hydrogen, optionally substituted aliphatic, —C(O)NHR$^8$, —CH$_2$OR$^9$, or —C(O)OR$^9$;
$R^{12}$ and $R^{13}$ are independently hydrogen, optionally substituted aliphatic, —OR$^9$, —N(R$^8$)$_2$, or —C(O)NHR$^8$;
$R^{14}$ is hydrogen or —NHR$^8$;
$R^{15}$ is hydrogen, —C(O)NHR$^8$, —CH$_2$OR$^9$, or —C(O)OR$^9$;
$R^{16}$ is hydrogen or —OR$^9$;
$R^{17}$ is hydrogen or —OR$^9$;
$R^{18}$ is hydrogen or —OR$^9$;
$R^{19a}$ is hydrogen or —OR$^9$;
$R^{19b}$ is hydrogen or —OR$^9$;

wherein a hydrogen radical on the compound of Formula (I) is replaced with -L-R$^P$;

L is a covalent bond, —NR$^y$—, —N(R$^y$)C(O)—, —N(R$^y$)C(O)N(R$^y$)—, —N(R$^y$)C(S)N(R$^y$)—, —C(O)N(R$^y$)—, —N(R$^y$)SO$_2$—, —SO$_2$N(R$^y$)—, —O—, —C(O)—, —OC(O)—, —C(O)O—, —S—, —SO—, —SO$_2$—, optionally substituted cycloalkylene, optionally substituted heterocyclylene, optionally substituted arylene, optionally substituted heteroarylene, or an optionally substituted aliphatic linker, wherein one or more methylene units of the aliphatic linker are optionally replaced by —NR$^y$—, —N(R$^y$)C(O)—, —N(R$^y$)C(O)N(R$^y$)—, —N(R$^y$)C(S)N(R$^y$)—, —C(O)N(R$^y$)—, —N(R$^y$)SO$_2$—, —SO$_2$N(R$^y$)—, —O—, —C(O)—, —OC(O)—, —C(O)O—, —S—, —SO—, —SO$_2$—, cycloalkylene, heterocyclylene, arylene, or heteroarylene; wherein R$^y$ is hydrogen, C$_{1-6}$ alkyl, or —C(O)C$_{1-6}$ alkyl; and R$^P$ is selected from the group consisting of ligands, radionuclides, fluorescent dyes, chemiluminescent agents, microparticles, enzymes, calorimetric labels, magnetic labels, and haptens.

2. A compound of Formula (I):

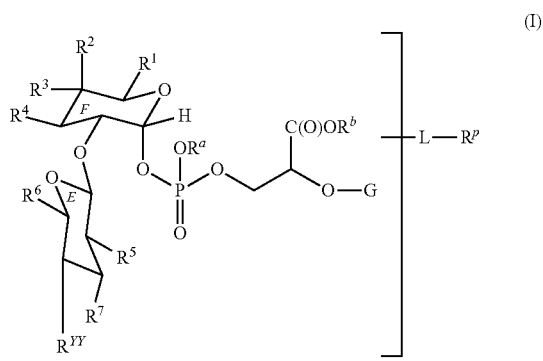

or a salt thereof,
wherein
$R^1$ is hydrogen, —C(O)NHR$^8$, —CH$_2$OR$^9$, or —C(O)OR$^9$;
$R^2$ and $R^3$ are independently hydrogen, optionally substituted aliphatic, —OR$^9$, —N(R$^8$)$_2$, or —C(O)NHR$^8$;
$R^4$ is hydrogen or —WR$^{4a}$;
W is —O— or —NH—;
$R^{4a}$ is hydrogen, a hydroxyl protecting group, optionally substituted aliphatic, —C(O)R$^{10}$, —C(O)NHR$^8$, —C(=NR$^8$)NHR$^8$, or —C(O)OR$^9$;
$R^5$ is hydrogen or —NHR$^8$;
$R^6$ is hydrogen, —CH$_3$, —CH$_2$OR$^9$, or —CH$_2$OR$^{CX}$; wherein R$^{CX}$ is a carbohydrate moiety;
$R^7$ is hydrogen, —OR$^9$, or —N(R$^8$)$_2$;
each $R^8$ is independently hydrogen, an amino protecting group, —C(O)R$^{10}$, optionally substituted aliphatic, optionally substituted aryl, optionally substituted heterocyclyl, or optionally substituted heteroaryl, or two R$^8$ groups on the same nitrogen may be taken together to form an optionally substituted heterocyclyl;
each $R^9$ is independently hydrogen, a hydroxyl protecting group, —C(O)R$^{10}$, optionally substituted aliphatic, optionally substituted aryl, optionally substituted heterocyclyl, or optionally substituted heteroaryl;
each $R^{10}$ is independently optionally substituted aliphatic, optionally substituted heterocyclic, optionally substituted aryl, or optionally substituted heteroaryl;
$R^a$ and $R^b$ are independently hydrogen or a hydroxyl protecting group;
G is an optionally substituted C$_{1-16}$ aliphatic group, wherein 0 to 10 methylene units are optionally replaced with —O—, —NR$^x$—, —S—, —C(O)—, —C(=NR$^x$), —S(O)—, —SO$_2$—, —N=N—, —C=N—, —N—O—, an optionally substituted arylene, an optionally substituted heterocyclylene, or an optionally substituted heteroarylene; wherein each instance of R$^x$ is independently hydrogen, optionally substituted aliphatic, optionally substituted heterocyclyl, optionally substituted aryl, optionally substituted heteroaryl; or G is a group of Formula (a), (b), or (c):

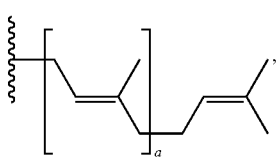

wherein a is 3, 4, or 5;

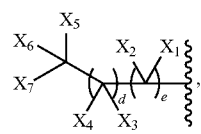

wherein
$X_1$, $X_2$, $X_3$, $X_4$, $X_5$, $X_6$, and $X_7$ are each independently hydrogen or halogen;
d is an integer between 1 and 25, inclusive; and
e is an integer of between 2 and 25, inclusive;
provided the sum of d and e is greater than 16; or

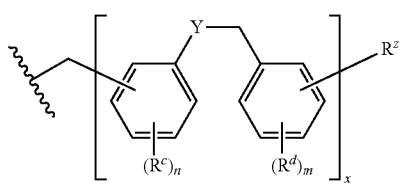

wherein
Y is —O—, —S—, —NR$^Y$—, or an optionally substituted methylene group, wherein R$^Y$ is hydrogen, optionally substituted aliphatic, or an amino protecting group;
each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring;
each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring;

R$^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring;

each instance of n is, independently, 0, 1, 2, 3, or 4;
each instance of m is, independently, 0, 1, 2, 3, or 4; and
x is 1, 2, 3, 4, 5, or 6;
R$^{YY}$ is hydrogen or —OR$^{XX}$;
R$^{XX}$ is hydrogen, a hydroxyl protecting group, or a group of formula:

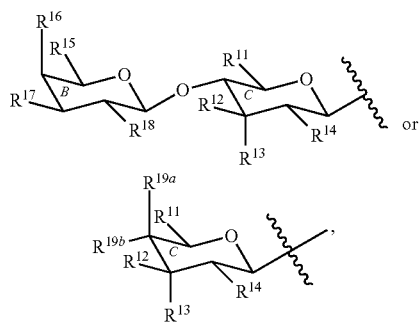

wherein
R$^{11}$ is hydrogen, optionally substituted aliphatic, —C(O)NHR$^8$, —CH$_2$OR$^9$, or —C(O)OR$^9$;
R$^{12}$ and R$^{13}$ are independently hydrogen, optionally substituted aliphatic, —OR$^9$, —N(R$^8$)$_2$, or —C(O)NHR$^8$;
R$^{14}$ is hydrogen or —NHR$^8$;
R$^{15}$ is hydrogen, —C(O)NHR$^8$, —CH$_2$OR$^9$, or —C(O)OR$^9$;
R$^{16}$ is hydrogen or —OR$^9$;
R$^{17}$ is hydrogen or —OR$^9$;
R$^{18}$ is hydrogen or —OR$^9$;
R$^{19a}$ is hydrogen or —OR$^9$;
R$^{19b}$ is hydrogen or —OR$^9$;
wherein a hydrogen radical on the compound of Formula (I) is replaced with -L-R$^P$:
L is —NHC(S)NH—, —C(O)CH$_2$—NHC(S)NH—,

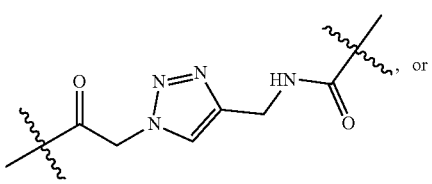

-continued

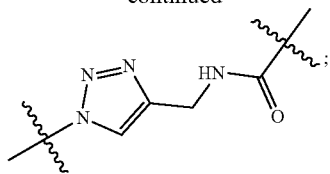

and
R$^P$ is selected from the group consisting of ligands, radionuclides, fluorescent dyes, chemiluminescent agents, microparticles, enzymes, calorimetric labels, magnetic labels, and haptens.

3. The compound of claim 2, wherein R$^{YY}$ is —OH or —OR$^{XX}$, and R$^{XX}$ is a group of formula:

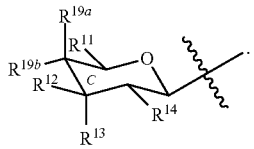

4. The compound of claim 2, wherein R$^{XX}$ is a group of formula:

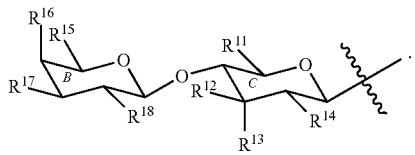

5. The compound of claim 2, wherein R$^6$ is —CH$_2$OH or —CH$_2$OR$^{CX}$; wherein R$^{CX}$ is a carbohydrate moiety.

6. The compound of claim 2, wherein G is

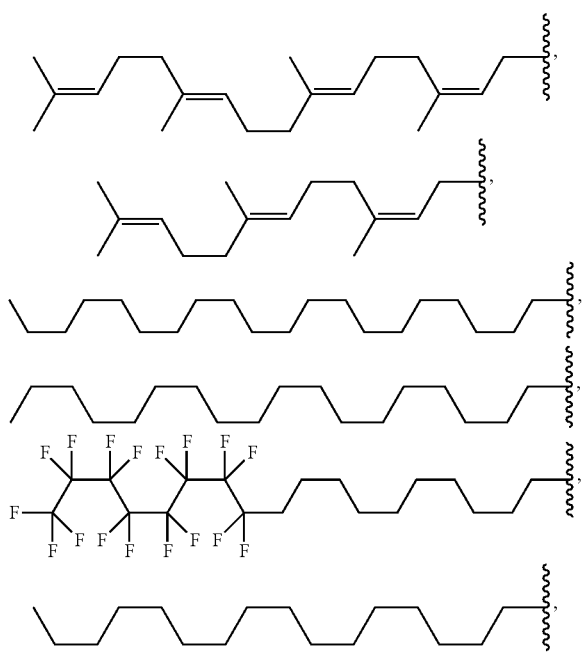

-continued

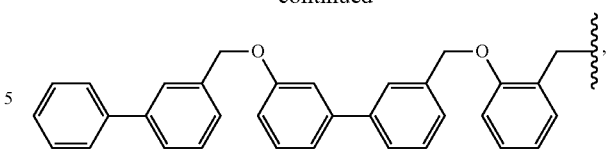

7. The compound of claim 2, wherein R$^P$ is selected from the group consisting of Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680, AMCA, AMCA-S, BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665, aminomethylcoumarin, carbocyanine, carboxyrhodamine 6G, carboxy-X-rhodamine (ROX), Cascade Blue, Cascade Yellow, coumarin, coumarin 343, cyanine dyes, dansyl, dapoxyl, dialkylaminocoumarin, 4',5'-dichloro-2',7'-dimethoxyfluorescein, DM-NERF, eosin, erythrosin, fluorescein, FAM, hydroxycoumarin, IRD40, IRD 700, IRD 800, 6-carboxy-4',5'-dichloro-2',7'-dimethoxyfluorescein (6-JOE), lissamine rhodamine B, Marina Blue, merocyanine, methoxycoumarin, naphthofluorescein, Oregon Green 488, Oregon Green 500, Oregon Green 514, oxonol dyes, Pacific Blue, phycoerythrin, PyMPO, pyrene, rhodamine B, rhodamine 6G, rhodamine green, rhodamine red, rhodol green, styryl dyes, 2',4',5',7'-tetrabromosulfone-fluorescein, tetramethyl-rhodamine (TMR), carboxytetramethylrhodamine (TAMRA), Texas Red, Texas Red-X, 5(6)-carboxyfluorescein, 2,7-dichlorofluorescein, N,N-bis(2,4,6-trimethylphenyl)-3,4,9,10-perylenebis(dicarboximide), HPTS, ethyl eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-I, SYTOX Green, Sodium Green, SYBR Green I, Alexa Fluor 500, FITC, Fluo-3, Fluo-4, fluoro-emerald, YoYo-I ssDNA, YoYo-I dsDNA, YoYo-I, SYTO RNASelect, Diversa Green-FP, Dragon Green, EvaGreen, Surf Green EX, Spectrum Green, Spectrum Red, NeuroTrace 500525, NBD-X, MitoTracker Green FM, LysoTracker Green DND-26, CBQCA, PA-GFP (post-activation), WEGFP (post-activation), FLASH-CCXXCC, Azami Green monomeric, Azami Green, green fluorescent protein (GFP), EGFP, Kaede Green, 7-benzylamino-4-nitrobenz-2-oxa-1,3-diazole, BexI, doxorubicin, Lumio Green, and SuperGlo GFP.

8. The compound of claim 2 of formula:

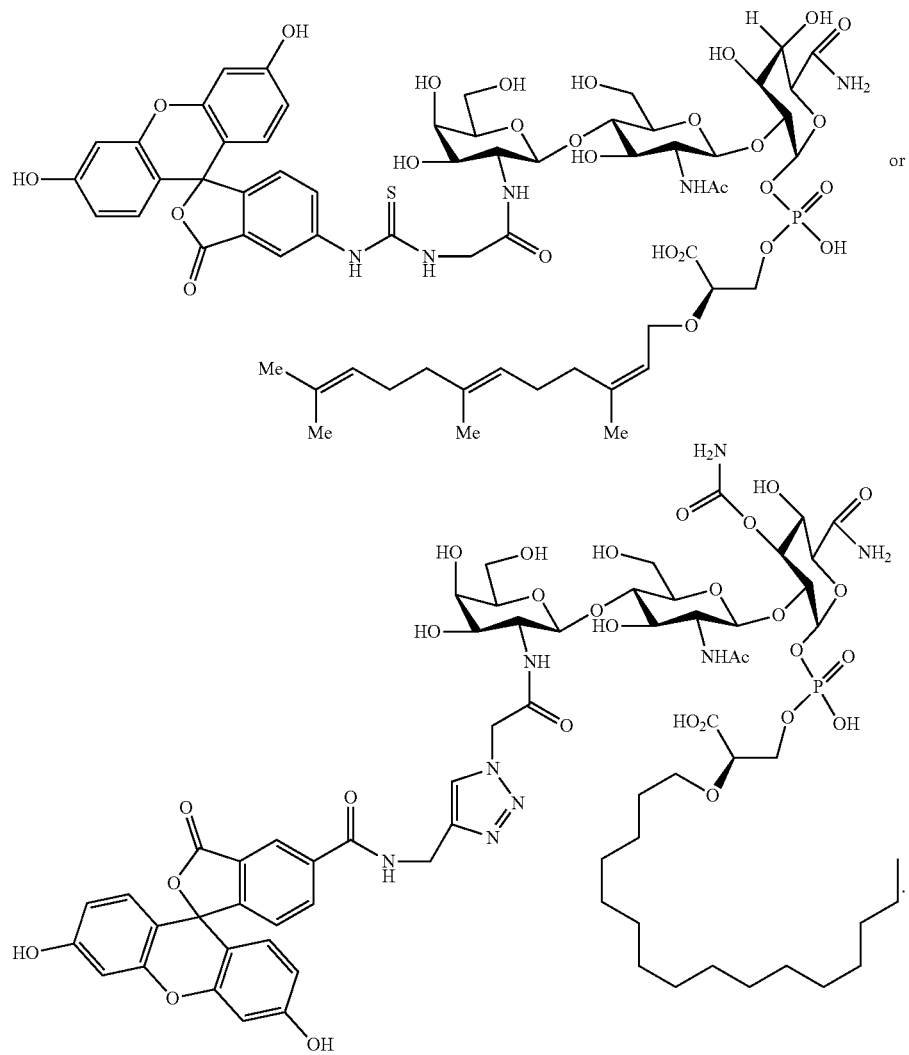

9. The compound of claim 2, wherein:
R$^1$ is —C(O)NHR$^8$, —CH$_2$OR$^9$, or —C(O)OR$^9$;
one of R$^2$ and R$^3$ is hydrogen, and the other is —OR$^9$;
R$^4$ is —W—R$^{4a}$;
R$^5$ is —NHR$^8$;
R$^6$ is —CH$_3$, —CH$_2$OR$^9$, or —CH$_2$OR$^{CX}$;
R$^7$ is —OR$^9$ or —N(R$^8$)$_2$;
R$^{11}$ is —CH$_3$, —C(O)NHR$^8$, —CH$_2$OR$^9$, or —C(O)OR$^9$;
one of R$^{12}$ and R$^{13}$ is hydrogen, and the other is —OR$^9$;
R$^{14}$ is —NHR$^8$; and
one of R$^{19a}$ and R$^{19b}$ is hydrogen, and the other is —OR$^9$.

10. The compound of claim 3, wherein R$^{11}$ is —CH$_2$OH.

11. The compound of claim 2, wherein R$^P$ is selected from the group consisting of fluorescein, naphthofluorescein, 4',5'-dichloro-2',7'-dimethoxy-fluorescein, 2',4',5',7'-tetrabromosulfone-fluorescein, 2,7-dichlorofluorescein, 6-carboxy-4',5'-dichloro-2',7'-dimethoxyfluorescein, and 5(6)-carboxyfluorescein.

12. The compound of claim 11, wherein R$^P$ is fluorescein.

13. The compound of claim 3, wherein R$^{11}$ is —CH$_3$.

14. The compound of claim 2, wherein R$^{12}$ is hydrogen; and R$^{13}$ is —OH.

15. The compound of claim 2, wherein G is of Formula (a).

16. The compound of claim 2, wherein G is of Formula (b).

17. A compound of Formula (I):

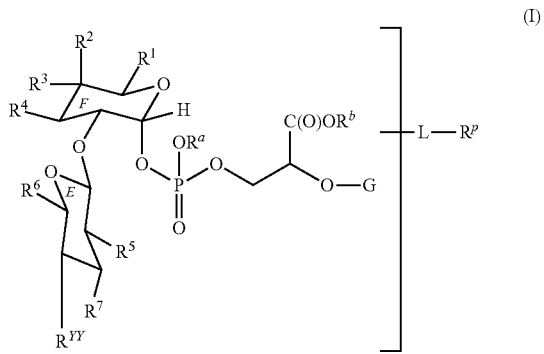

or a salt thereof, wherein

R¹ is hydrogen, —C(O)NHR⁸, —CH₂OR⁹, or —C(O)OR⁹;

R² and R³ are independently hydrogen, optionally substituted aliphatic, —OR⁹, —N(R⁸)₂, or —C(O)NHR⁸;

R⁴ is hydrogen or —WR⁴ᵃ;

W is —O— or —NH—;

R⁴ᵃ is hydrogen, a hydroxyl protecting group, optionally substituted aliphatic, —C(O)R¹⁰, —C(O)NHR⁸, —C(=NR⁸)NHR⁸, or —C(O)OR⁹;

R⁵ is hydrogen or —NHR⁸;

R⁶ is hydrogen, —CH₃, —CH₂OR⁹, or —CH₂OR^{CX}; wherein R^{CX} is a carbohydrate moiety;

R⁷ is hydrogen, —OR⁹, or —N(R⁸)₂;

each R⁸ is independently hydrogen, an amino protecting group, —C(O)R¹⁰, optionally substituted aliphatic, optionally substituted aryl, optionally substituted heterocyclyl, or optionally substituted heteroaryl, or two R⁸ groups on the same nitrogen may be taken together to form an optionally substituted heterocyclyl;

each R⁹ is independently hydrogen, a hydroxyl protecting group, —C(O)R¹⁰, optionally substituted aliphatic, optionally substituted aryl, optionally substituted heterocyclyl, or optionally substituted heteroaryl;

each R¹⁰ is independently optionally substituted aliphatic, optionally substituted heterocyclic, optionally substituted aryl, or optionally substituted heteroaryl;

Rᵃ and Rᵇ are independently hydrogen or a hydroxyl protecting group;

G is an optionally substituted C₁₋₁₆ aliphatic group, wherein 0 to 10 methylene units are optionally replaced with —O—, —NRˣ—, —S—, —C(O)—, —C(=NRˣ)—, —S(O)—, —SO₂—, —N=N—, —C=N—, —N—O—, an optionally substituted arylene, an optionally substituted heterocyclylene, or an optionally substituted heteroarylene; wherein each instance of Rˣ is independently hydrogen, optionally substituted aliphatic, optionally substituted heterocyclyl, optionally substituted aryl, optionally substituted heteroaryl; or G is a group of Formula (a), (b), or (c):

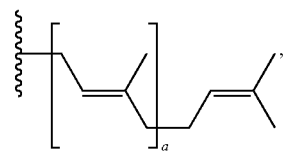

(a)

wherein a is 3, 4, or 5;

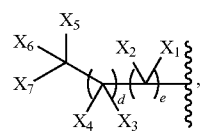

(b)

wherein

X₁, X₂, X₃, X₄, X₅, X₆, and X₇ are each independently hydrogen or halogen;

d is an integer between 1 and 25, inclusive; and e is an integer of between 2 and 25, inclusive; provided the sum of d and e is greater than 16; or

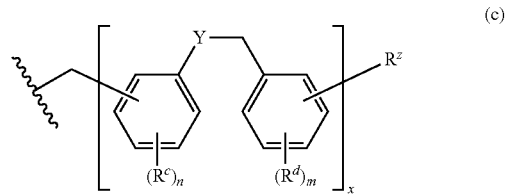

(c)

wherein

Y is —O—, —S—, —NRʸ—, or an optionally substituted methylene group, wherein Rʸ is hydrogen, optionally substituted aliphatic, or an amino protecting group;

each instance of Rᶜ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —ORᵉ, —SRᵉ, —NHRᵉ, or —N(Rᵉ)₂, wherein each instance of Rᵉ is independently hydrogen, optionally substituted aliphatic, optionally substituted heteroaliphatic, optionally substituted carbocycyl, optionally substituted heterocycyl, optionally substituted aryl, or optionally substituted heteroaryl, or two Rᵉ groups are joined to form a 5- to 6-membered optionally substituted heterocycyl or optionally substituted heteroaryl ring;

each instance of Rᵈ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —ORᶠ, —SRᶠ, —NHRᶠ, or —N(Rᶠ)₂, wherein each instance of Rᶠ is independently hydrogen, optionally substituted aliphatic, optionally substituted heteroaliphatic, optionally substituted carbocycyl, optionally substituted heterocycyl, optionally substituted aryl, or optionally substituted heteroaryl, or two Rᶠ groups are joined to form a 5- to 6-membered optionally substituted heterocycyl or optionally substituted heteroaryl ring;

Rᶻ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —ORᵍ, —SRᵍ, —NHRᵍ, or —N(Rᵍ)₂, wherein each instance of Rᵍ is independently hydrogen, optionally substituted aliphatic, optionally substituted heteroaliphatic, optionally substituted carbocycyl, optionally substituted heterocycyl, optionally substituted aryl, or optionally substituted heteroaryl or two Rᵍ groups are joined to form a 5- to 6-membered optionally substituted heterocycyl or optionally substituted heteroaryl ring;

each instance of n is, independently, 0, 1, 2, 3, or 4;

each instance of m is, independently, 0, 1, 2, 3, or 4; and x is 1, 2, 3, 4, 5, or 6;

R^{YY} is hydrogen or —OR^{XX};

R^{XX} is hydrogen, a hydroxyl protecting group, or a group of formula:

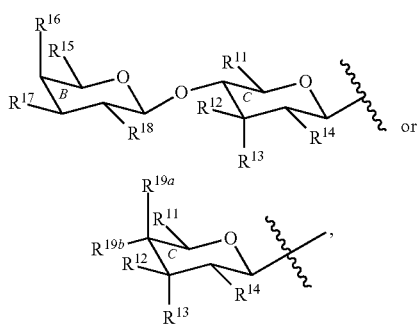

wherein
- $R^{11}$ is hydrogen, optionally substituted aliphatic, —C(O)NHR$^8$, —CH$_2$OR$^9$, or —C(O)OR$^9$;
- $R^{12}$ and $R^{13}$ are independently hydrogen, optionally substituted aliphatic, —OR$^9$, —N(R$^8$)$_2$, or —C(O)NHR$^8$;
- $R^{14}$ is hydrogen or —NHR$^8$;
- $R^{15}$ is hydrogen, —C(O)NHR$^8$, —CH$_2$OR$^9$, or —C(O)OR$^9$;
- $R^{16}$ is hydrogen or —OR$^9$;
- $R^{17}$ is hydrogen or —OR$^9$;
- $R^{18}$ is hydrogen or —OR$^9$;
- $R^{19a}$ is hydrogen or —OR$^9$;
- $R^{19b}$ is hydrogen or —OR$^9$;

wherein a hydrogen radical on the compound of Formula (I) is replaced with -L-R$^P$;

- L is an optionally substituted aliphatic linker wherein one methylene unit is replaced by tetrazolyl or NHC(S)NH—; and one or more additional methylene units are optionally replaced by —NR$^y$—, —N(R$^y$)C(O)—, —N(R$^y$)C(O)N(R$^y$)—, —N(R$^y$)C(S)N(R$^y$)—, —C(O)N(R$^y$)—, —N(R$^y$)SO$_2$—, —SO$_2$N(R$^y$)—, —O—, —C(O)—, —OC(O)—, —C(O)O—, —S—, —SO—, or —SO$_2$—; wherein R$^y$ is hydrogen, C$_{1-6}$ alkyl, or —C(O)C$_{1-6}$ alkyl; and
- R$^P$ is selected from the group consisting of ligands, radionuclides, fluorescent dyes, chemiluminescent agents, microparticles, enzymes, calorimetric labels, magnetic labels, and haptens.

* * * * *

UNITED STATES PATENT AND TRADEMARK OFFICE
CERTIFICATE OF CORRECTION

| | |
|---|---|
| PATENT NO. | : 10,106,833 B2 |
| APPLICATION NO. | : 14/390857 |
| DATED | : October 23, 2018 |
| INVENTOR(S) | : Daniel Evan Kahne et al. |

Page 1 of 1

It is certified that error appears in the above-identified patent and that said Letters Patent is hereby corrected as shown below:

In the Specification

Please replace the paragraph at Column 1, Lines 15-19, with the following paragraph:
-- This invention was made with government support under GM066174 and GM076710 awarded by the National Institutes of Health (NIH). The government has certain rights in the invention. --

Signed and Sealed this
Twelfth Day of May, 2020

Andrei Iancu
*Director of the United States Patent and Trademark Office*